US010435400B2

(12) United States Patent
Lan et al.

(10) Patent No.: US 10,435,400 B2
(45) Date of Patent: *Oct. 8, 2019

(54) 2,4-DISUBSTITUTED PHENYLENE-1,5-DIAMINE DERIVATIVES AND APPLICATIONS THEREOF, AND PHARMACEUTICAL COMPOSITIONS AND PHARMACEUTICALLY ACCEPTABLE COMPOSITIONS PREPARED THEREFROM

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Jiong Lan, Shanghai (CN); Yunzhou Jin, Shanghai (CN); Fusheng Zhou, Shanghai (CN); Jing Xie, Shanghai (CN); Sida Shen, Shanghai (CN); Yi Hu, Shanghai (CN); Wei Liu, Shanghai (CN); Qiang Lv, Shanghai (CN)

(73) Assignees: SHANGHAI HAIYAN PHARMACEUTICAL TECHNOLOGY CO. LTD., Shanghai (CN); YANGTZE RIVER PHARMACEUTICAL GROUP CO., LTD., Jiangsu (CN)

( * ) Notice: Subject to any disclaimer, the term of this patent is extended or adjusted under 35 U.S.C. 154(b) by 46 days.

This patent is subject to a terminal disclaimer.

(21) Appl. No.: 15/121,320

(22) PCT Filed: Feb. 13, 2015

(86) PCT No.: PCT/CN2015/073044
§ 371 (c)(1),
(2) Date: Aug. 24, 2016

(87) PCT Pub. No.: WO2015/127872
PCT Pub. Date: Sep. 3, 2015

(65) Prior Publication Data
US 2017/0008889 A1 Jan. 12, 2017

(30) Foreign Application Priority Data

Feb. 25, 2014 (CN) .......................... 2014 1 0065195

(51) Int. Cl.
| C07D 401/12 | (2006.01) |
| C07D 471/04 | (2006.01) |
| A61K 31/506 | (2006.01) |
| A61K 31/53 | (2006.01) |
| A61K 31/5377 | (2006.01) |
| A61K 31/5386 | (2006.01) |
| A61K 31/553 | (2006.01) |
| A61K 45/06 | (2006.01) |
| C07D 239/48 | (2006.01) |
| C07D 401/04 | (2006.01) |
| C07D 401/14 | (2006.01) |
| C07D 491/08 | (2006.01) |

(52) U.S. Cl.
CPC .......... *C07D 471/04* (2013.01); *A61K 31/506* (2013.01); *A61K 31/53* (2013.01); *A61K 31/5377* (2013.01); *A61K 31/5386* (2013.01); *A61K 31/553* (2013.01); *A61K 45/06* (2013.01); *C07D 239/48* (2013.01); *C07D 401/04* (2013.01); *C07D 401/12* (2013.01); *C07D 401/14* (2013.01); *C07D 491/08* (2013.01)

(58) Field of Classification Search
CPC .................................................. C07D 401/12
See application file for complete search history.

(56) References Cited

U.S. PATENT DOCUMENTS

| 2009/0318405 A1 | 12/2009 | Li et al. |
| 2010/0029610 A1 | 2/2010 | Singh et al. |
| 2010/0249092 A1 | 9/2010 | Singh et al. |
| 2012/0316135 A1 | 12/2012 | Dalgarno et al. |

FOREIGN PATENT DOCUMENTS

| CN | 101910152 A | 12/2010 |
| CN | 102083800 A | 1/2011 |
| CN | 102740847 A | 10/2012 |
| CN | 103501612 A | 1/2014 |
| CN | 104788427 A | 7/2015 |
| CN | 104860941 A | 8/2015 |

(Continued)

OTHER PUBLICATIONS

Han, H. "Targeted Prodrug Design to Optimize Drug Delivery." AAPS Pharmsci. (2000), vol. 2 (1) article 6, pp. 1-11.* Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Komposch, K., et al. "EGFR Signaling in Liver Diseases." International Journal of Molecular Sciences. (Dec. 29, 2015). (Year: 2015).*
Vallath, S., et al. "Targeting EGFR signaling in lung disease: therapeutic challenges and opportunities." Eur. Respir. J. (Aug. 2014), vol. 44, Issue 2, pp. 513-522. (Year: 2014).*
International Search Report dated May 6, 2015 corresponding to International Patent Application No. PCT/CN2015/073044, filed on Aug. 29, 2005, 3 pages.

(Continued)

Primary Examiner — Andrew D Kosar
Assistant Examiner — John S Kenyon
(74) Attorney, Agent, or Firm — Mintz Levin Cohn Ferris Glovsky and Popeo PC

(57) ABSTRACT

The present invention provides a class of 2,4-substituted phenylene-1,5-diamine derivatives, having an inhibiting effect on EGFR tyrosine kinases, and pharmaceutically acceptable salt, stereoisomer, solvate or prodrug of said derivatives. See the description for the definition of each group in the formula. In addition, the present invention also (Continued)

discloses pharmaceutical compositions, pharmaceutically acceptable compositions and applications thereof.

9 Claims, No Drawings

(56) References Cited

FOREIGN PATENT DOCUMENTS

WO     WO-2013014448 A1 *   1/2013  ........... C07D 401/02
WO        2006/021458 A2     3/2016

OTHER PUBLICATIONS

Ward, Richard A. et al., "Structure- and Reactivity-Based Development of Covalent Inhibitors of the Activating and Gatekeeper Mutant Forms of the Epidermal Growth Factor Receptor (EGFR)," *J. Med. Chem* (Aug. 9, 2013); 56:7025-7048.

* cited by examiner

2,4-DISUBSTITUTED PHENYLENE-1,5-DIAMINE DERIVATIVES AND APPLICATIONS THEREOF, AND PHARMACEUTICAL COMPOSITIONS AND PHARMACEUTICALLY ACCEPTABLE COMPOSITIONS PREPARED THEREFROM

TECHNICAL FIELD

The present invention relates to the field of medical technology, particularly to a 2,4-disubstituted benzene-1,5-diamine derivatives and uses thereof as EGFR tyrosine kinase inhibitors, and pharmaceutical compositions and medicinal compositions prepared therefrom.

BACKGROUND

Lung cancer is of the highest incidence in the world. In China, the incidence of lung cancer ranks first among all cancers, and the incidence and mortality rates of the cancer are also the highest in China. In the lung cancer patients in China, 30% of patients have EGFR mutations, over 90% of which are L858R and exon 19 deletion mutation, and these patients are more sensitive to EGFR inhibitors. The marketed first-generation of EGFR inhibitors, such as erlotinib, gefitinib have good effect for these patients, and the tumor in more than 60% of patients will shrink, significantly prolonging the progression-free survival of patients. However, most of patients acquire resistance in 6-12 months, the first generation of EGFR inhibitors will no longer take effect, and currently no drugs are available for these patients. EGFR T790M mutation is clinically detected in 50% of patients who are resistant to the first-generation of EGFR inhibitors. In T790M mutant cell line H1975, the activity of the first-generation of EGFR inhibitors, such as gefitinib and erlotinib, was greater than 3 uM, which means almost no activity.

The therapeutic effect of the second generation of irreversible pan-EGFR inhibitors (Afatinib (BIBW2992)) currently launched was significantly better than that of the first-generation of EGFR inhibitors for lung cancer patients with EGFR mutations. However, the second-generation of inhibitors also have strong inhibitory activity for wild-type EGFR, and the inhibitory activity for wild-type EGFR was significantly higher than that for resistant T790M mutation, and side effects, such as skin rashes, were severe in patients, and the effect of the second-generation of inhibitors on drug resistant patients was poor, only a small part of patients who are resistant to the first generation of EGFR inhibitors response to these drugs.

For improving the inhibitory activity for resistant T790M mutation while reducing the inhibitory activity for wild-type EGFR, it is of great significance to develop the third generation of selective inhibitors for EGFR mutants with higher activity, better selectivity, and lower toxicity.

SUMMARY OF INVENTION

The object of the present invention is to provide a 2,4-disubstituted benzene-1,5-diamine derivatives or a pharmaceutical acceptable salt, stereoisomer, solvate, or prodrug thereof; and a pharmaceutical composition including the above-mentioned derivative.

The second object of the present invention is to provide the use of the above-mentioned derivative or composition for the manufacture of a medicament for adjusting EGFR tyrosine kinase activity or treating EGFR-relevant diseases.

In the first aspect of the present invention, a compound of formula (I), or a pharmaceutically acceptable salt, stereoisomer, solvate or a prodrug thereof is provided:

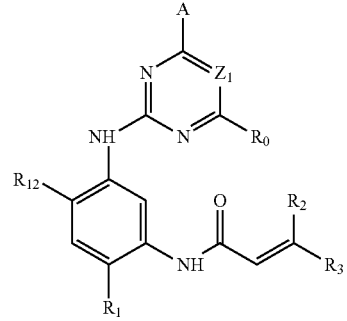

wherein A is any one selected from:

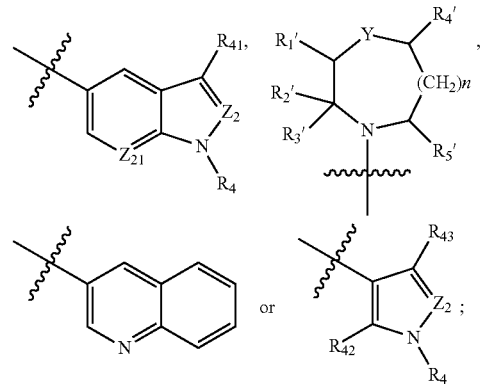

wherein, $Z_2$ is $CR_5$ or N; $R_5$ is a hydrogen, halogen, trifluoromethyl or $C_{1-10}$ alkoxy; $Z_{21}$ is N or CH; each of $R_4$, $R_{42}$, $R_{43}$ is independently a hydrogen or $C_{1-10}$ alkyl, $C_{3-10}$ cycloalkyl, $C_{3-10}$ heterocycloalkyl (e.g., piperidinyl), or $C_{1-10}$ haloalkyl; $R_{41}$ is a hydrogen, halogen, trifluoromethyl, $C_{1-10}$ alkyl or $C_{1-10}$ alkoxy; (preferably, each of $R_4$, $R_{42}$, $R_{43}$ is independently a hydrogen, methyl or ethyl; $R_{41}$ is a hydrogen, chloro, fluoro, trifluoromethyl, methyl or methoxy); each of $R_1'$, $R_2'$ and $R_5'$ is independently a hydrogen, $C_{1-10}$ alkyl; (preferably, each of $R_1'$, $R_2'$ and $R_5'$ is independently a hydrogen, methyl or ethyl); each of $R_3'$, $R_4'$ is independently a hydrogen, $C_{1-10}$ alkyl, or $R_3'$ and $R_4'$ are connected to form a bridged ring structure; (preferably, each of $R_3'$, $R_4'$ is independently a hydrogen, methyl or ethyl; or $R_3'$ and $R_4'$ are connected to be —$CH_2$—); Y is O, $CH_2$, $NR_a'$; wherein $R_a'$ is a hydrogen, methyl, tert-butoxycarbonyl, acetyl, methylsulfonyl; and n is 0 or 1;

$R_0$ is a hydrogen, halogen, $C_{1-10}$ alkyl, —$NR_aR_b$ or —CO—$NR_aR_b$, wherein, each of $R_a$, $R_b$ is independently a $C_{1-10}$ alkyl;

Z1 is $CR_6$ or N; wherein, $R_6$ is a hydrogen, halo, trifluoromethyl, methoxy or —$CO_2C_{1-10}$ alkyl;

$R_1$ is a hydrogen, or any one selected from a group consisting of:

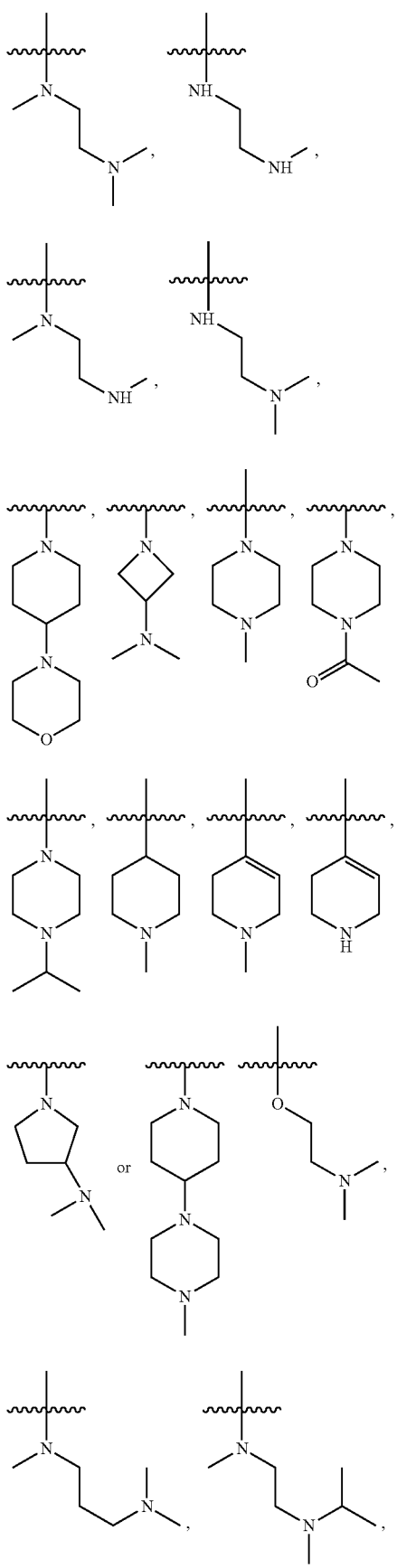

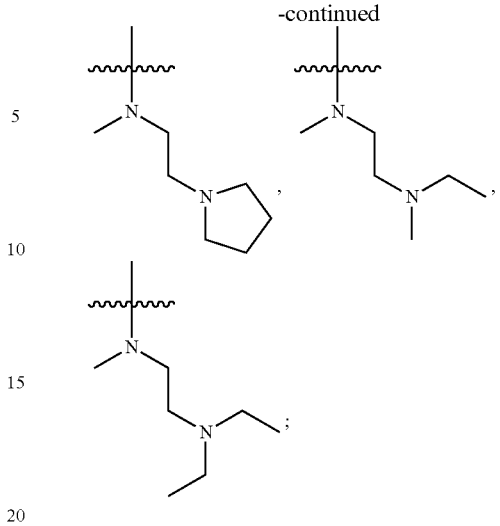

each of $R_2$ and $R_3$ is independently a hydrogen or —$CH_2NR_7R_8$; wherein, (1) each of $R_7$, $R_8$ is independently a hydrogen or methyl; or (2) $R_7$ and $R_8$, together with the nitrogen atom to which they are attached, form a 5-6 membered nitrogen-containing saturated heterocyclic ring;

$R_{12}$ is a hydrogen, halogen, $C_{1-10}$ alkyl or $C_{1-10}$ alkoxy (preferably methoxy).

In another preferred embodiment, A of formula (I) is any one selected from a group consisting of:

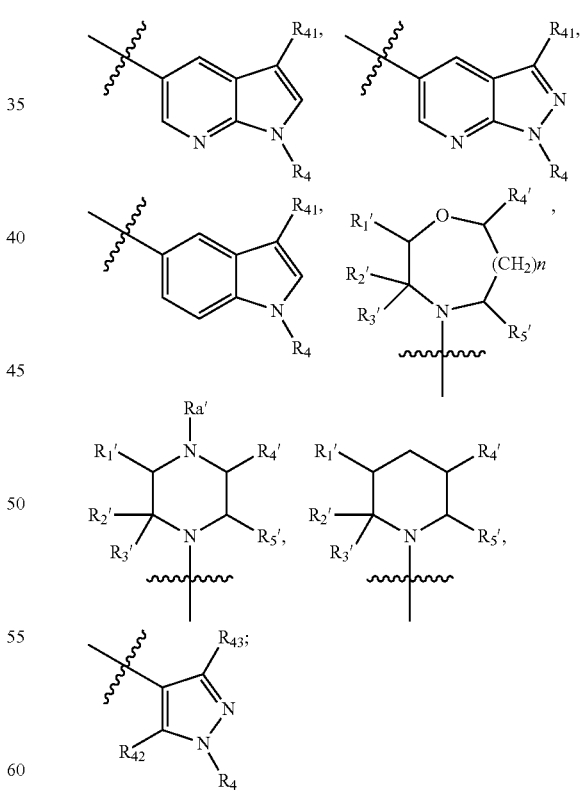

Wherein, n, $R_4$, $R_{41}$, $R_{42}$, $R_{43}$, $R_1'$, $R_2'$, $R_3'$, $R_4'$, $R_5'$, $R_a'$ are defined as in formula (I).

In another preferred embodiment, $R_4$ of formula (I) is a hydrogen, methyl, ethyl, isopropyl, cyclopropyl, difluoromethyl or piperidinyl; $R_{41}$ is a hydrogen, chloro, fluoro, trifluoromethyl, methyl or methoxy; $R_{42}$ is a hydrogen, methyl or ethyl; $R_{43}$ is a hydrogen, methyl or ethyl.

In another preferred embodiment, each of $R_2$ and $R_3$ of formula (I) is independently a hydrogen; and $R_{12}$ is a methoxy.

In another preferred embodiment, $Z_1$ of formula (I) is $CR_6$ or N; wherein, $R_6$ is a hydrogen, fluoro, chloro, trifluoromethyl, methoxy or —$CO_2C_{1-10}$ alkyl; In another preferred embodiment, $Z_1$ of formula (I) is $CR_6$, wherein, $R_6$ is a hydrogen, fluoro, chloro, trifluoromethyl, methoxy or —$CO_2CH_3$.

In another preferred embodiment, $R_0$ of formula (I) is a hydrogen.

In another preferred embodiment, A of formula (I) is any one selected from a group consisting of:

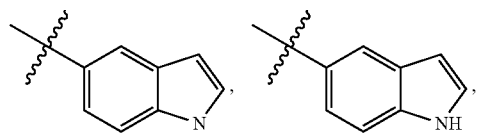

herein, can be and respectively.

In another preferred embodiment, each of $R_2$ and $R_3$ of formula (I) is independently a hydrogen.

In another preferred embodiment, each of $R_2$ and $R_3$ of formula (I) is independently a hydrogen or —$CH_2NR_7R_8$, and each of $R_7$ and $R_8$ is independently a hydrogen or methyl.

In another preferred embodiment, each of $R_2$ and $R_3$ of formula (I) is independently a hydrogen or —$CH_2NR_7R_8$, and $R_7$ and $R_8$, together with the nitrogen atom to which they are attached, form a 5-6 membered saturated nitrogen-containing heterocyclic ring.

In another preferred embodiment, each of $R_2$ and $R_3$ of formula (I) is independently a hydrogen or —$CH_2NR_7R_8$, and $R_7$ and $R_8$, together with the adjacent nitrogen atom, form a 5-6 membered nitrogen-containing saturated heterocyclic ring, and the structure of the 5-6 membered nitrogen-containing saturated heterocyclic ring is shown as formula (III):

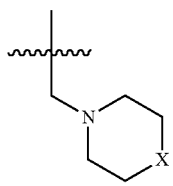

(III)

wherein, X is O, S, $NR_9$ or $CR_{10}R_{11}$; wherein, each of $R_9$, $R_{10}$, $R_{11}$ is independently a hydrogen, $C_{1-10}$ alkoxy or —CO—$C_{1-10}$ alkyl.

In another preferred embodiment, the compound of formula (I) is a compound of formula (IV-1):

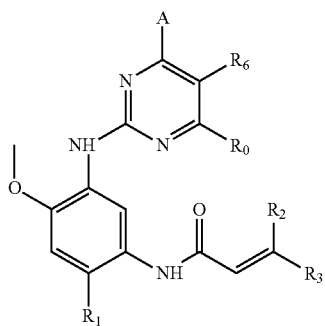

(IV-1)

wherein, A, $R_0$, $R_1$, $R_2$, $R_3$ and $R_6$ are defined as in formula (I).

In another preferred embodiment, the compound of formula (I) is a compound of formula (IV-2):

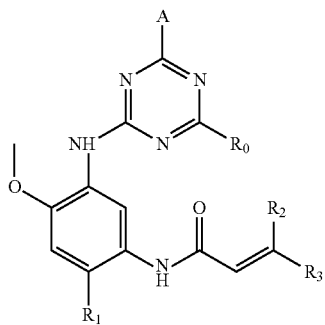

(IV-2)

wherein, A, $R_0$, $R_1$, $R_2$ and $R_3$ are defined as in formula (I).

In another preferred embodiment, the compound of formula (I) is a compound of formula (V-1):

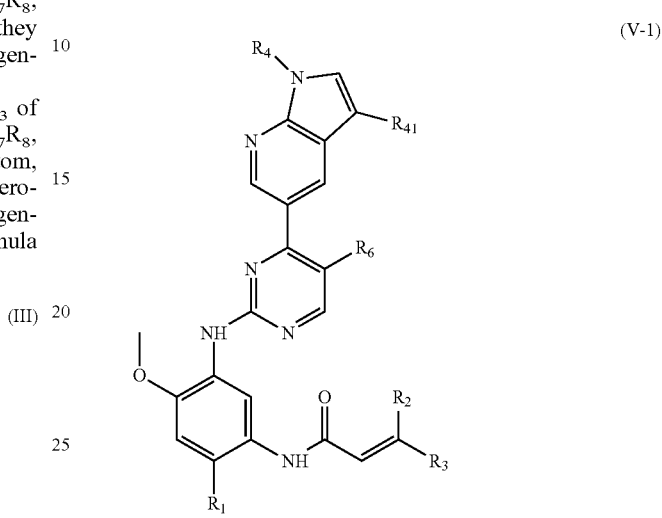

(V-1)

wherein, $R_1$, $R_2$, $R_3$, $R_4$, $R_{41}$ and $R_6$ are defined as in formula (I).

In another preferred embodiment, the compound of formula (I) is a compound of formula (V-2):

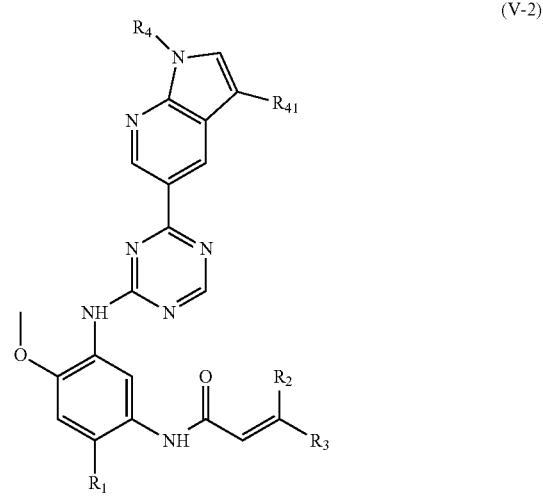

(V-2)

wherein, $R_1$, $R_2$, $R_3$, $R_4$ and $R_{41}$ are defined as in formula (I).

In another preferred embodiment, the compound of formula (I) is shown as formula (VI-1):

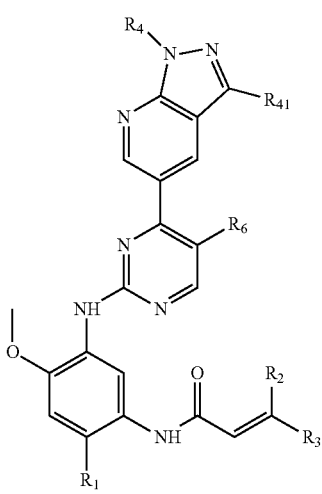

(VI-1)

wherein, $R_1$, $R_2$, $R_3$, $R_4$, $R_{41}$ and $R_6$ are defined as in formula (I).

In another preferred embodiment, the compound of formula (I) is shown as formula (VI-2):

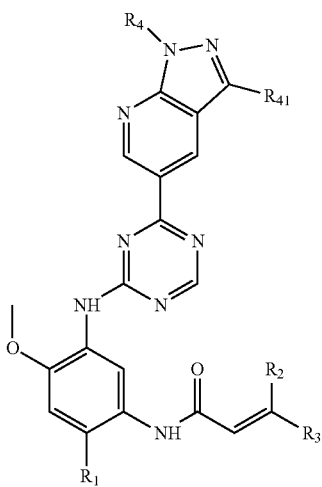

(VI-2)

wherein, $R_1$, $R_2$, $R_3$, $R_4$ and $R_{41}$ are defined as in formula (I).

In another preferred embodiment, the compound of formula (I) is shown as formula (VII-1):

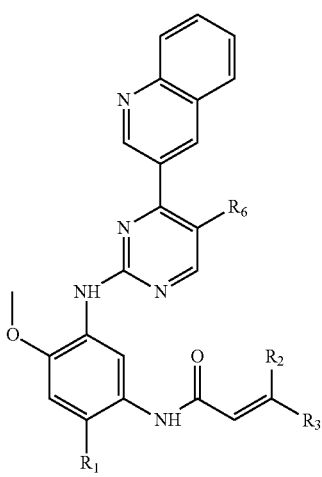

(VII-1)

wherein, $R_1$, $R_2$, $R_3$ and $R_6$ are defined as in formula (I).

In another preferred embodiment, the compound of formula (I) is shown as formula (VII-2):

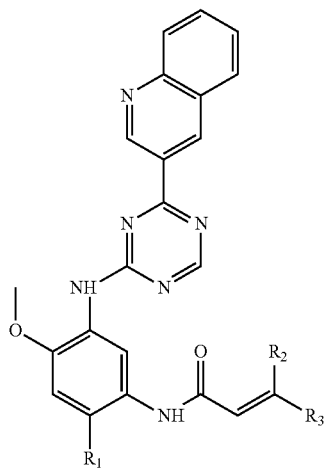

(VII-2)

wherein, $R_1$, $R_2$ and $R_3$ are defined as in formula (I).

In another preferred embodiment, the compound of formula (I) is a compound represented by formula (VIII-1):

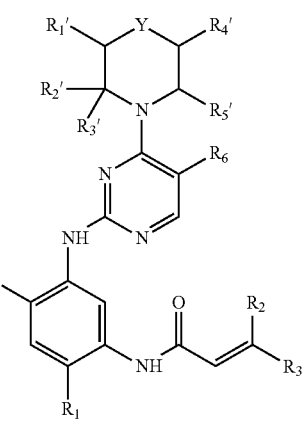

(VIII-1)

wherein, $R_1'$, $R_2'$, $R_3'$, $R_4'$, $R_5'$, $R_1$, $R_2$, $R_3$, $R_6$ and Y are defined as in formula (I).

In another preferred embodiment, the compound of formula (I) is a compound represented by formula (VIII-2):

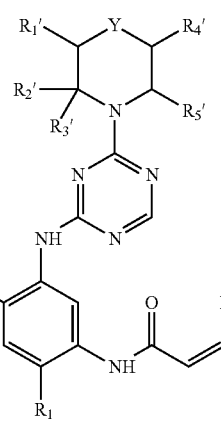

(VIII-2)

wherein, $R_1'$, $R_2'$, $R_3'$, $R_4'$, $R_5'$, $R_1$, $R_2$, $R_3$ and Y are defined as in formula (I).

In another preferred embodiment, the compound of formula (I) is shown as formula (IX-1):

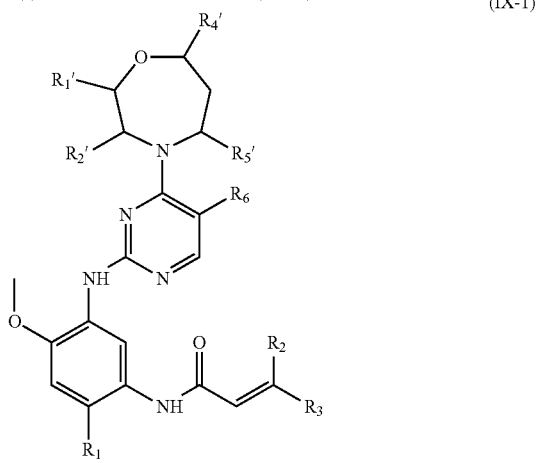

(IX-1)

wherein, $R_1'$, $R_2'$, $R_4'$, $R_5'$, $R_1$, $R_2$, $R_3$ and $R_6$ are defined as in formula (I).

In another preferred embodiment, the compound of formula (I) is shown as formula (IX-2):

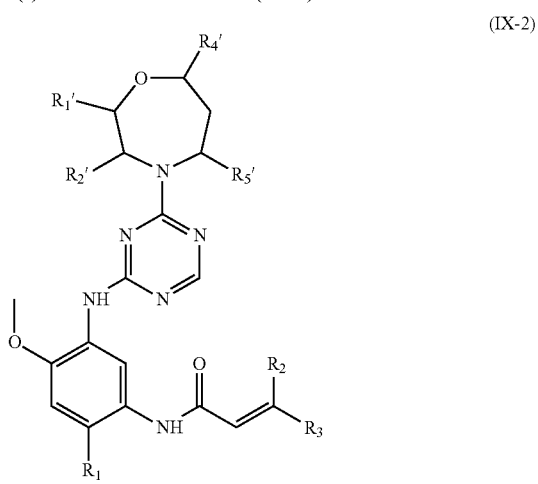

(IX-2)

wherein, $R_1'$, $R_2'$, $R_4'$, $R_5'$, $R_1$, $R_2$ and $R_3$ are defined as in formula (I).

In another preferred embodiment, the compound of formula (I) is a compound of formula (X-1):

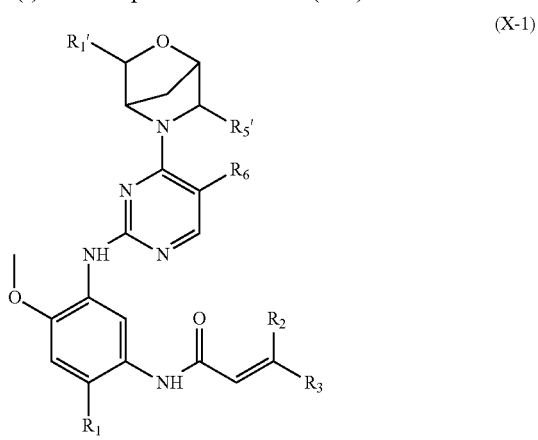

(X-1)

wherein, $R_1'$, $R_5'$, $R_1$, $R_2$, $R_3$ and $R_6$ are defined as in formula (I).

In another preferred embodiment, the compound of formula (I) is a compound of formula (X-2):

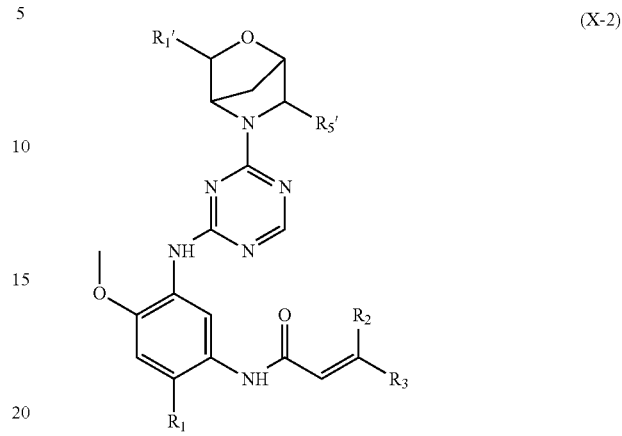

(X-2)

wherein, $R_1'$, $R_5'$, $R_1$, $R_2$ and $R_3$ are defined as in formula (I).

In another preferred embodiment, the compound of formula (I) is a compound of formula (XI-1):

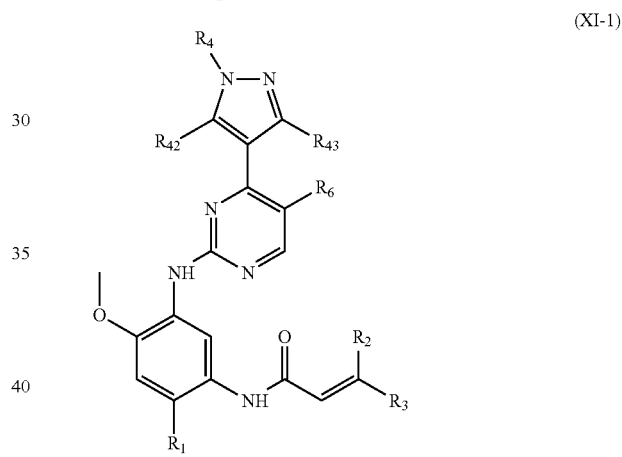

(XI-1)

wherein, $R_1$, $R_2$, $R_3$, $R_4$, $R_{42}$, $R_{43}$ and $R_6$ are defined as in formula (I).

In another preferred embodiment, the compound of formula (I) is a compound of formula (XI-2):

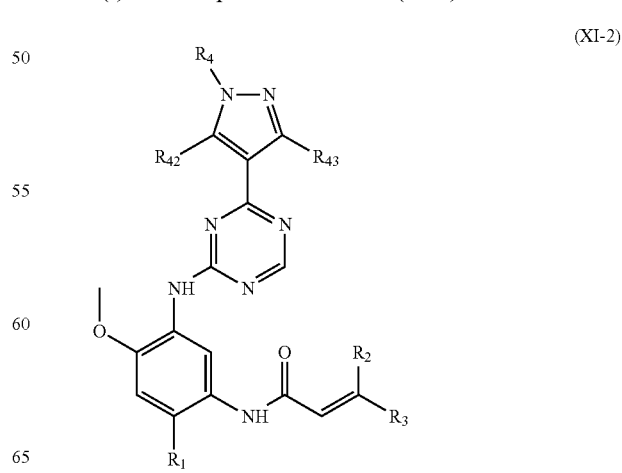

(XI-2)

wherein, $R_1$, $R_2$, $R_3$, $R_4$, $R_{42}$ and $R_{43}$ are defined as in formula (I).

In another preferred embodiment, the compound of formula (I) is a compound of formula (XII-1):

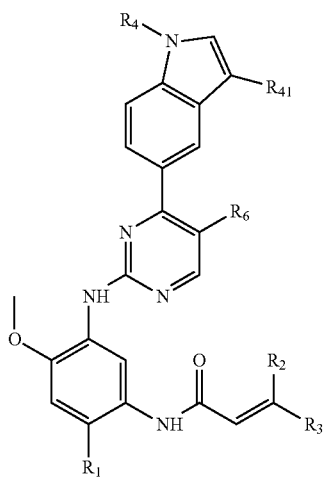

(XII-1)

wherein, $R_1$, $R_2$, $R_3$, $R_4$, $R_{41}$ and $R_6$ are defined as in formula (I).

In another preferred embodiment, the compound of formula (I) is a compound of formula (XII-2):

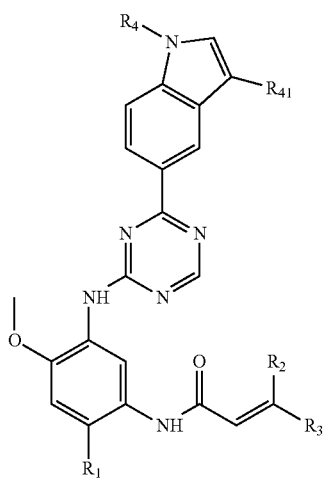

(XII-2)

wherein, $R_1$, $R_2$, $R_3$, $R_4$ and $R_{41}$ are defined as in formula (I).

In another preferred embodiment, in the compound of formula (XI-1), $R_6$ is a hydrogen, fluoro, chloro, or trifluoromethyl.

In another preferred embodiment, in the compound of formula (XI-1) or formula (XI-2), each of $R_2$ and $R_3$ is independently a hydrogen.

In another preferred embodiment, in the compound of formula (XI-1) or formula (XI-2), $R_1$ is selected from:

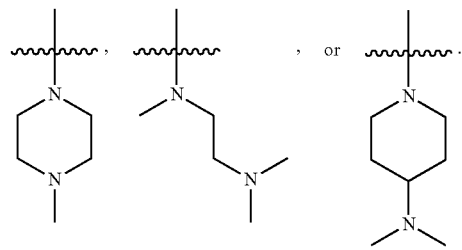

In another preferred embodiment, in the compound of formula (XI-1) or formula (XI-2), each of $R_4$, $R_{42}$, $R_{43}$ is independently a hydrogen, $C_{1-10}$ alkyl, $C_{1-10}$ haloalkyl or piperidinyl;

In another preferred embodiment, in the compound of formula (XI-1) or formula (XI-2), each of $R_4$, $R_{42}$ and $R_{43}$ is independently a hydrogen, methyl, ethyl, difluoromethyl or piperidinyl.

In another preferred embodiment, in the compound of formula (XI-1) or formula (XI-2), $R_4$ is a hydrogen, methyl, difluoromethyl or piperidinyl, and each of $R_{42}$, $R_{43}$ is independently a hydrogen or methyl.

In another preferred embodiment, in the compound of formula (V-1), formula (V-2), formula (VI-1), formula (VI-2), formula (XII-1) or formula (XII-2), $R_4$ is a hydrogen, $C_{1-10}$ alkyl, $C_{3-10}$ cycloalkyl or $C_{1-10}$ haloalkyl.

In another preferred embodiment, in the compound of formula (V-1), formula (V-2), formula (VI-1), formula (VI-2), formula (XII-1) or formula (XII-2), $R_4$ is a hydrogen, methyl, ethyl, isopropyl, cyclopropyl or difluoromethyl.

In another preferred embodiment, in the compound of formula (V-1), formula (V-2), formula (VI-1), formula (VI-2), formula (XII-1) or formula (XII-2), $R_{41}$ is a hydrogen, chloro, fluoro, trifluoromethyl, methyl or methoxy.

In another preferred embodiment, in the compound of formula (V-1), formula (V-2), formula (VI-1), formula (VI-2), formula (XII-1) or formula (XII-2), each of $R_2$ and $R_3$ is independently a hydrogen.

In another preferred embodiment, in the compound of formula (V-1), formula (VI-1) or formula (XII-1), $R_6$ is a hydrogen, fluoro, chloro, trifluoromethyl, methoxy or —$CO_2CH_3$.

In another preferred embodiment, in the compound of formula (V-1), formula (V-2), formula (VI-1), formula (VI-2), formula (XII-1) or formula (XII-2), $R_1$ is selected from:

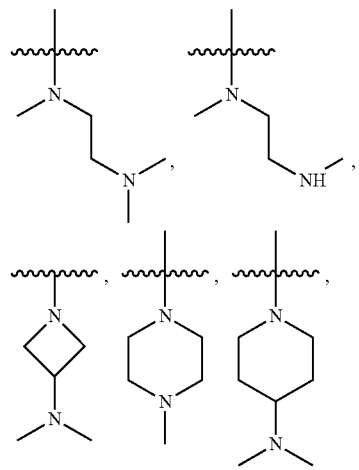

-continued
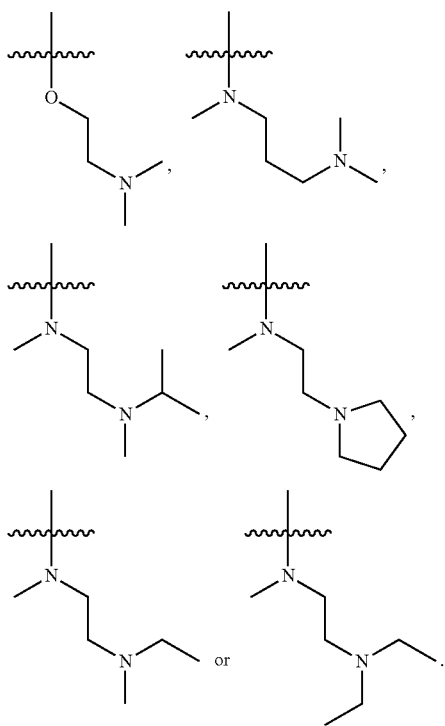
In another preferred embodiment, the compound is selected from:
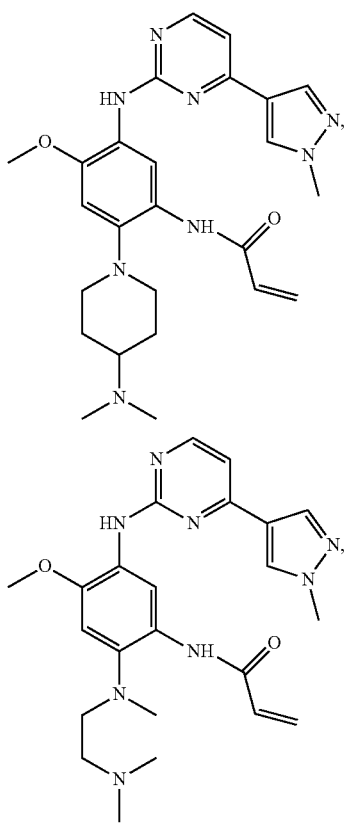
-continued
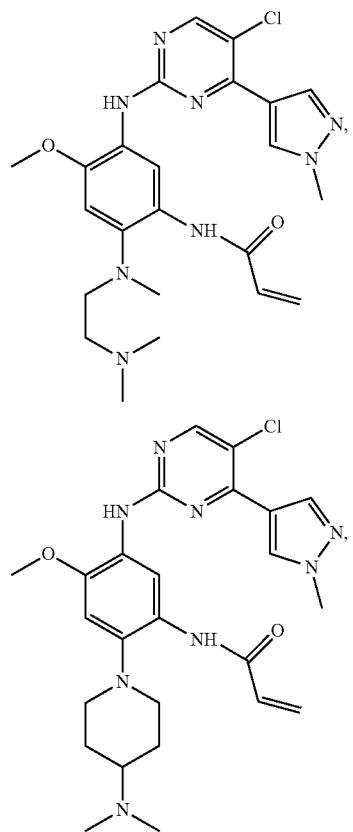
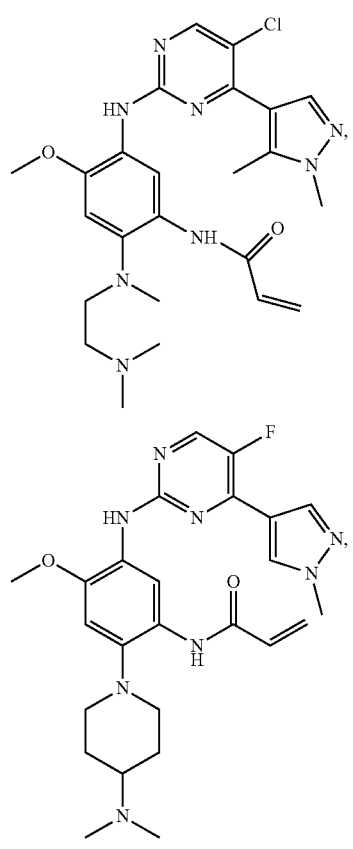

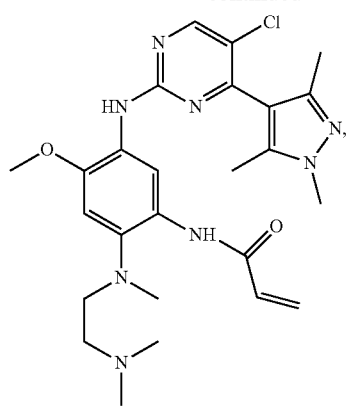
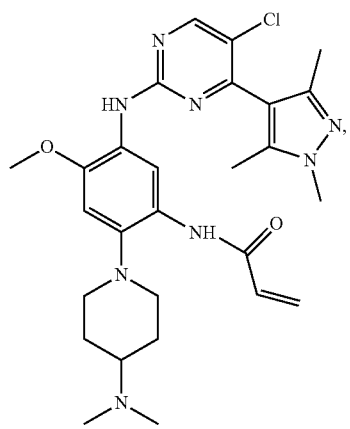
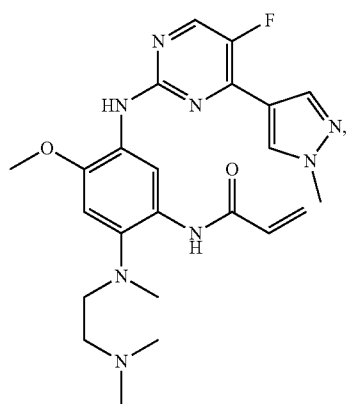
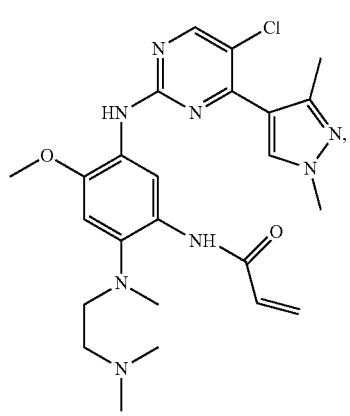
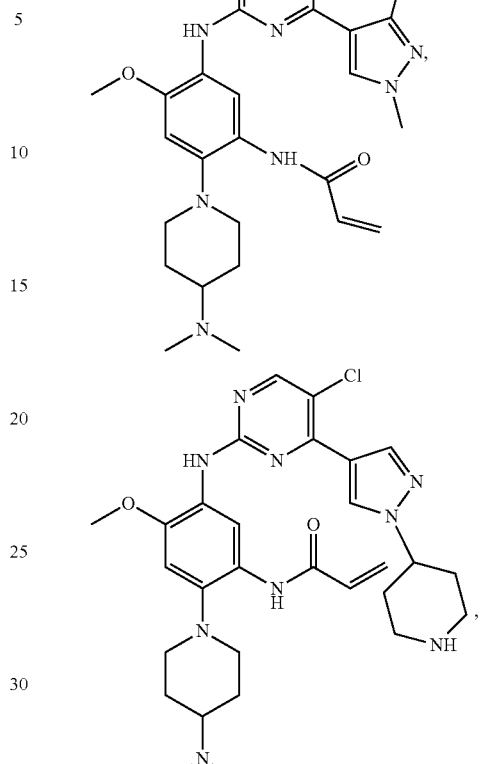
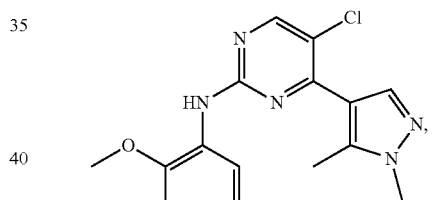
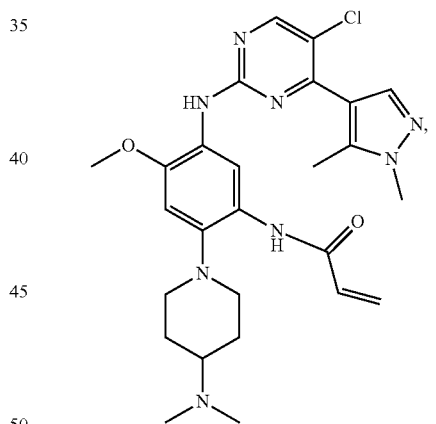
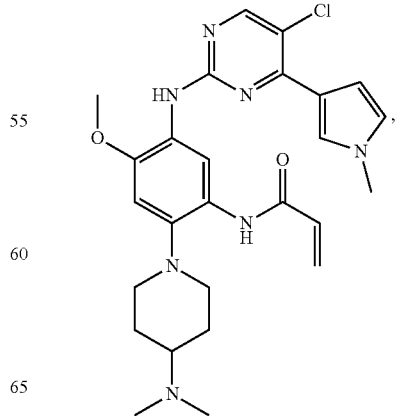

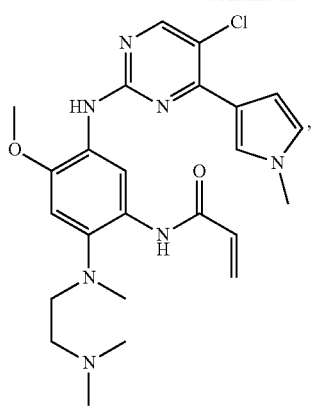
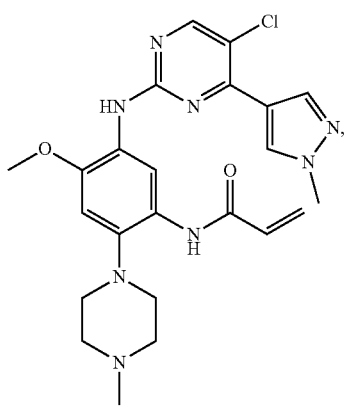
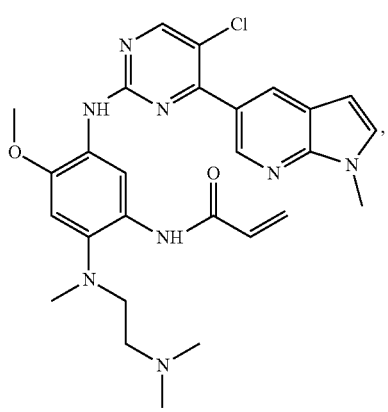
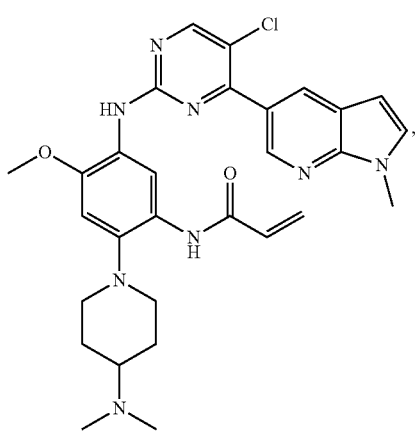
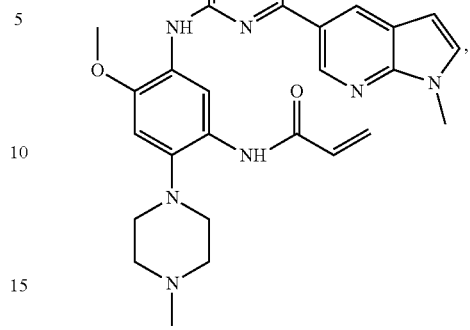
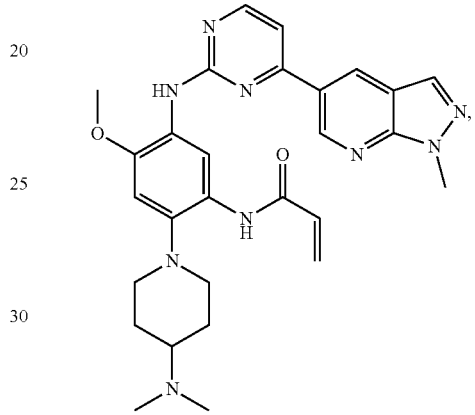
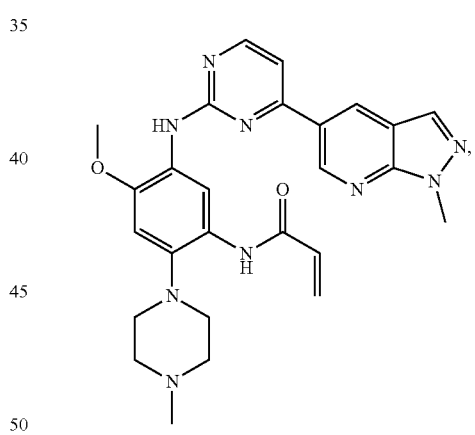
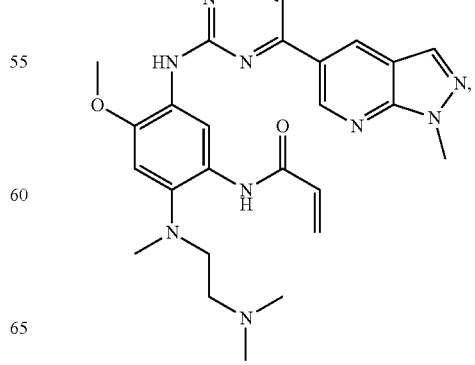

21
-continued
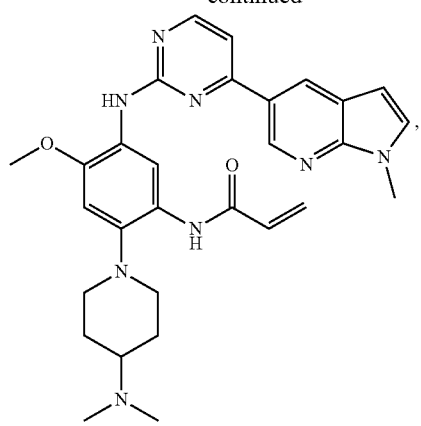
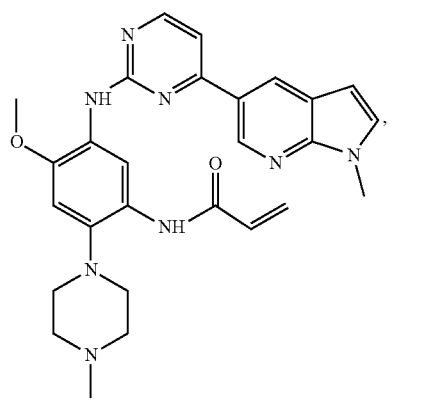
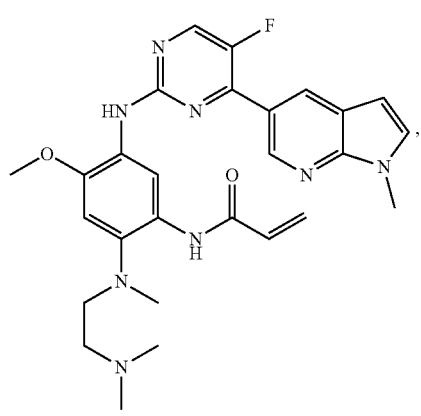
22
-continued
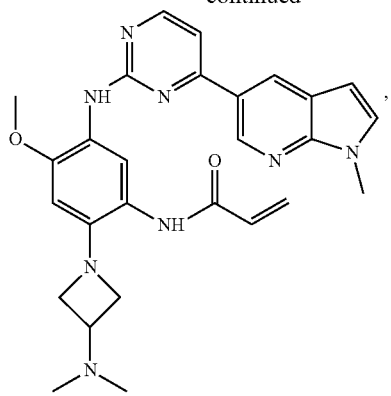
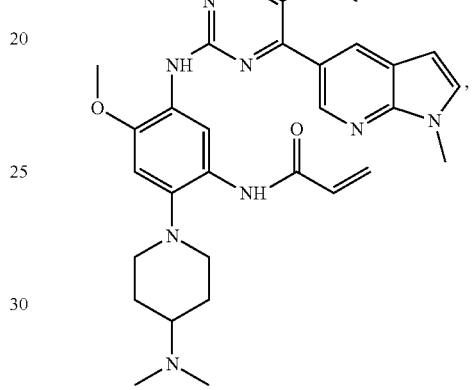
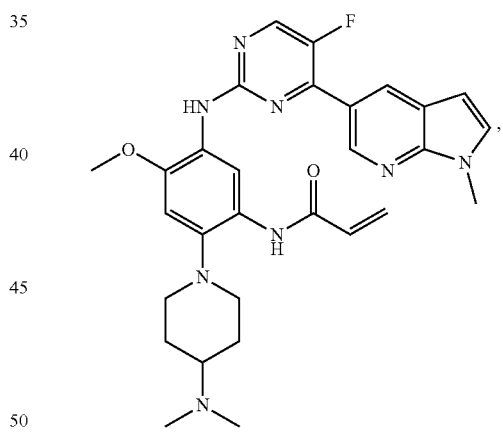
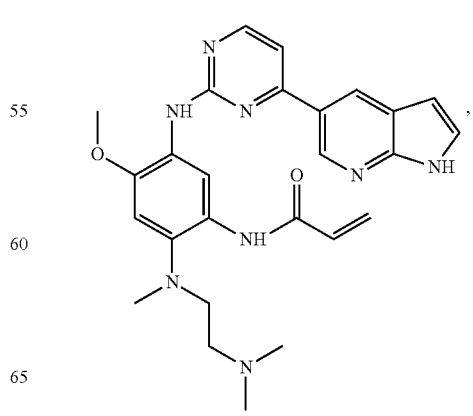

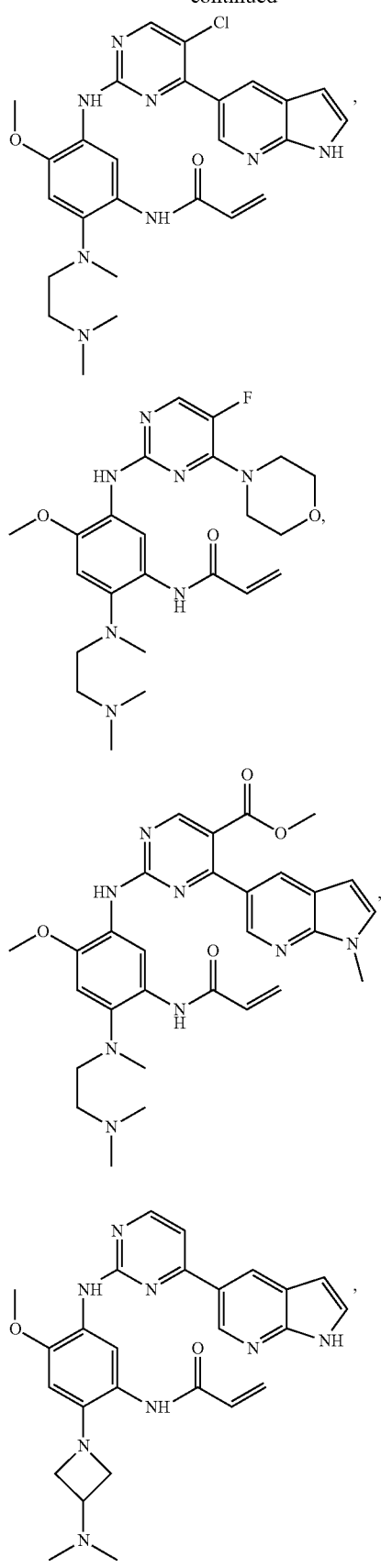
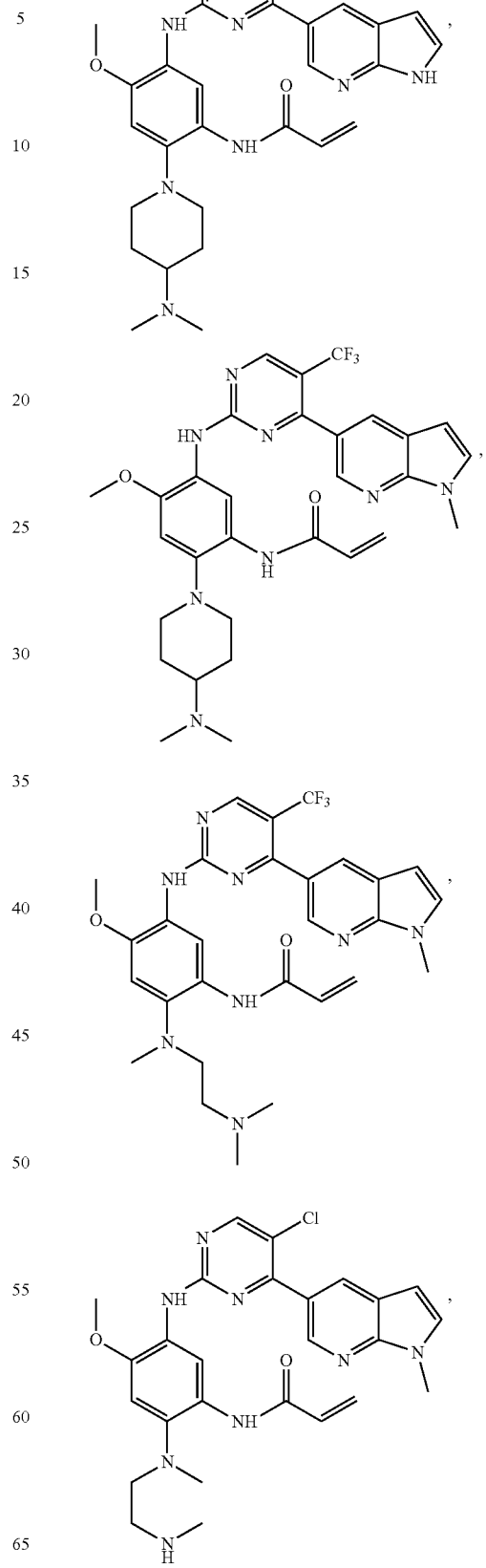

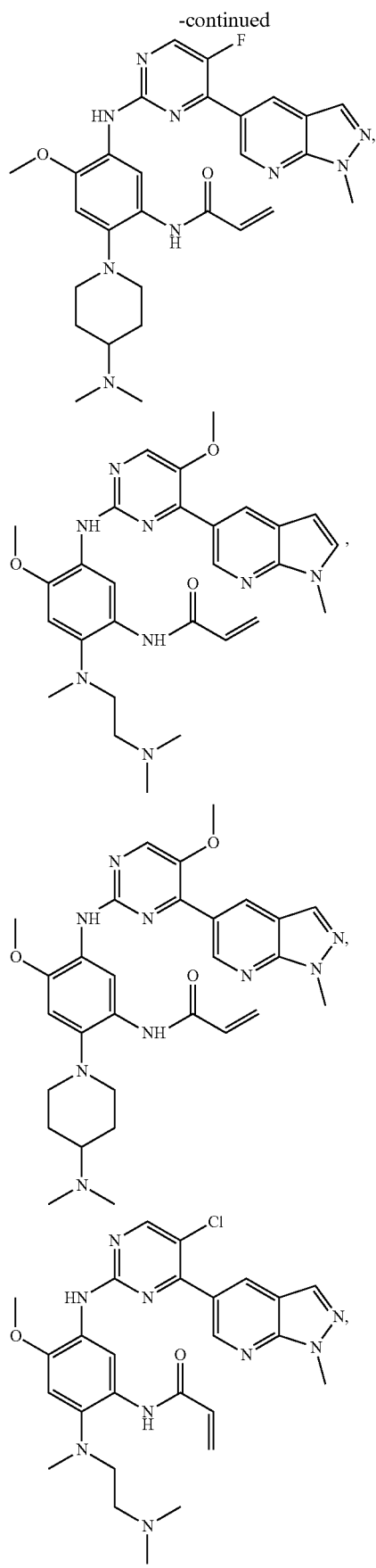
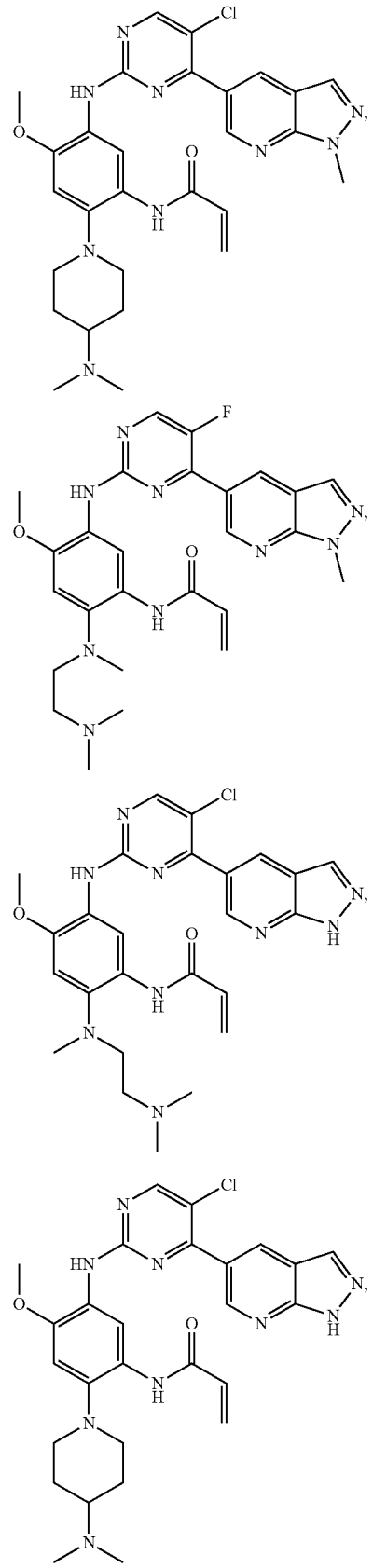

27
-continued
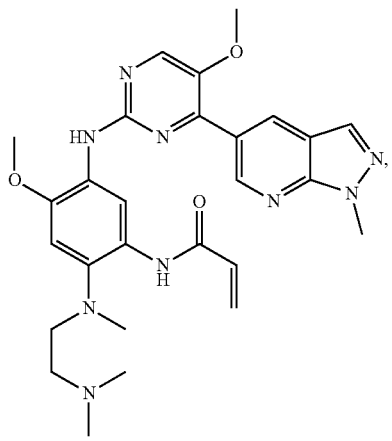
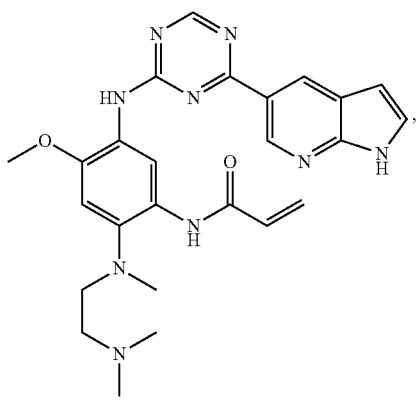
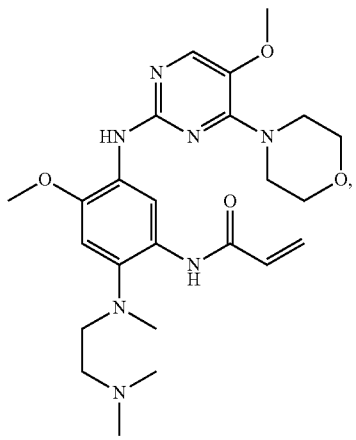
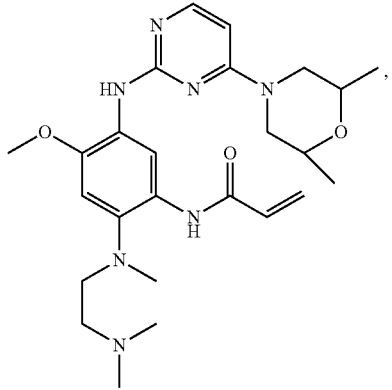
28
-continued
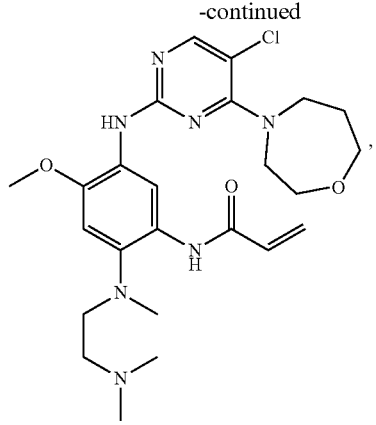
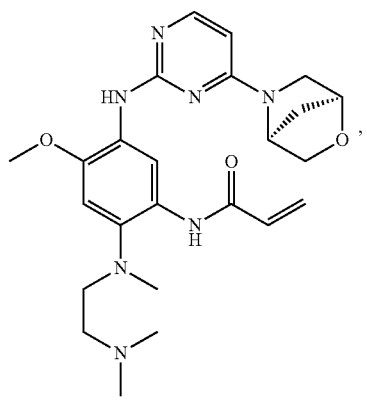
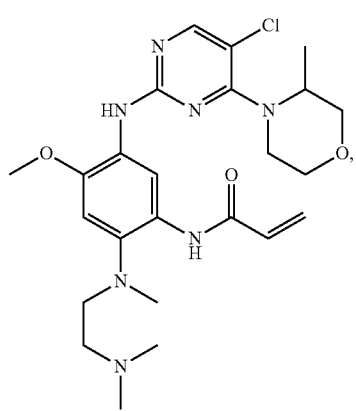
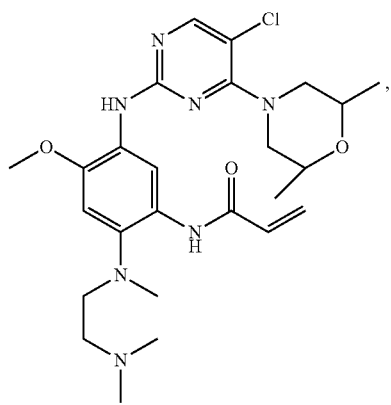

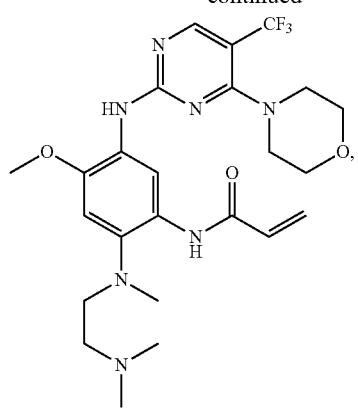
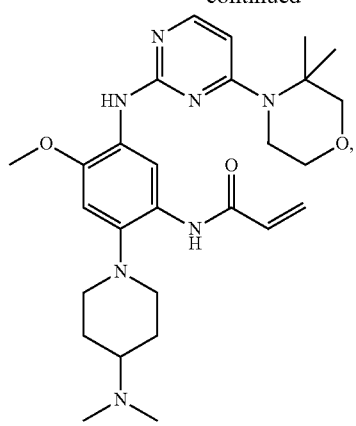
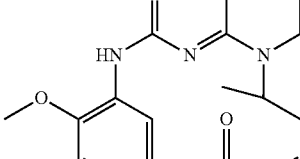

31
-continued
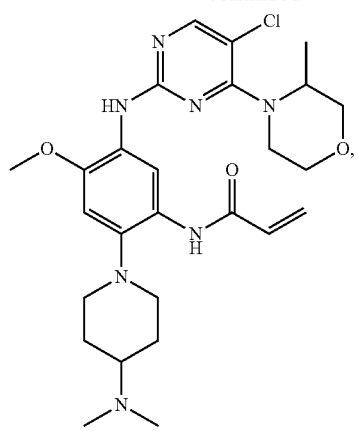
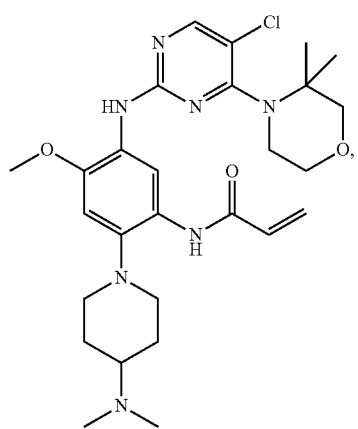
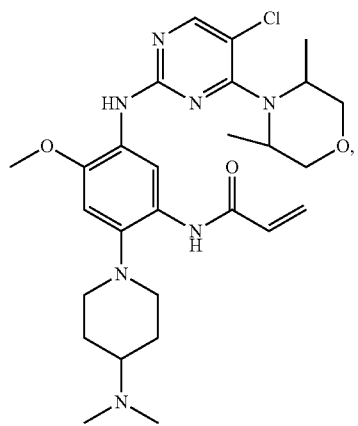
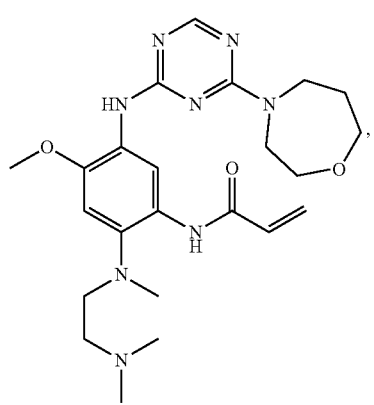
32
-continued
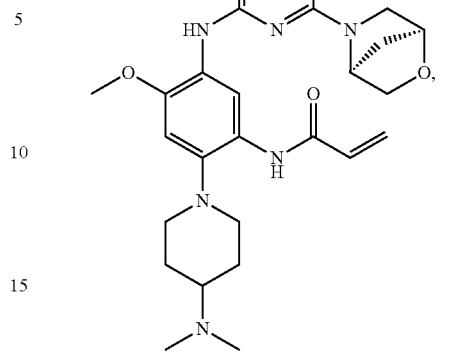
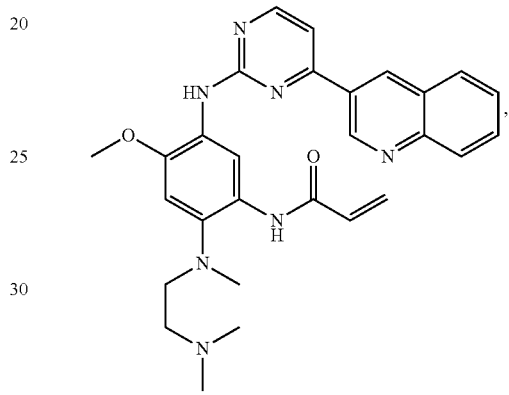
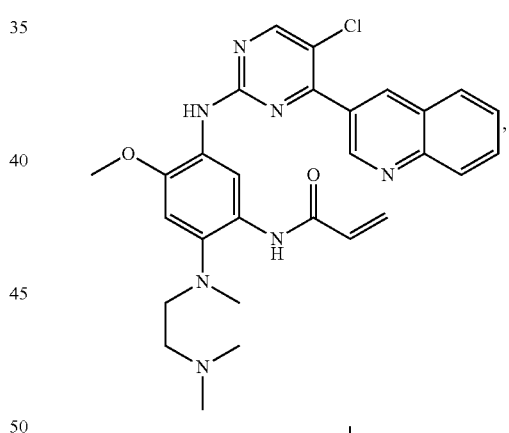
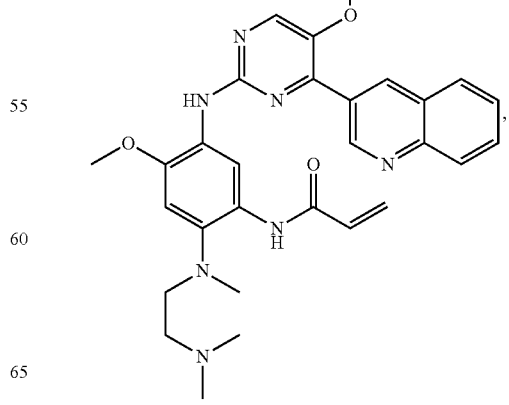

-continued
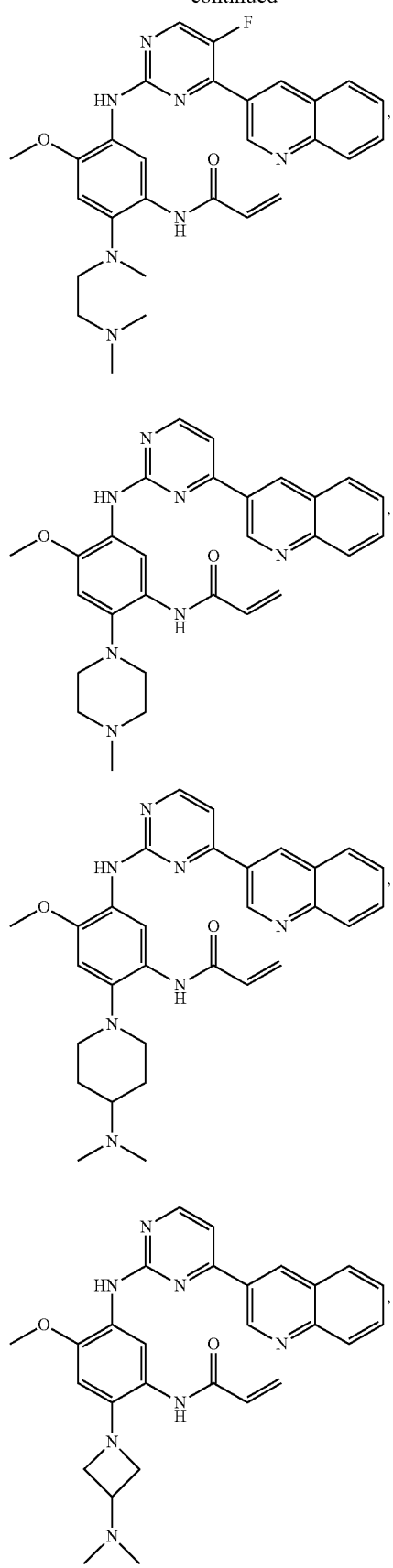
-continued
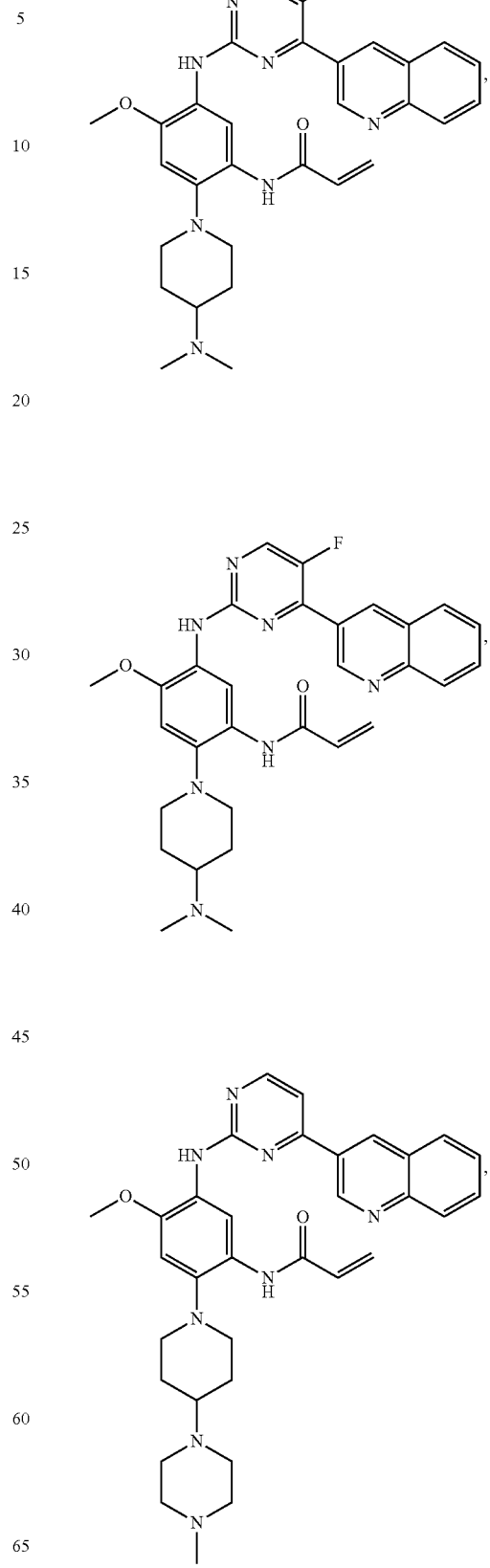

35
-continued
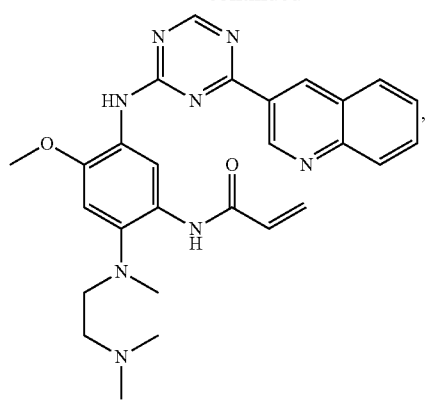
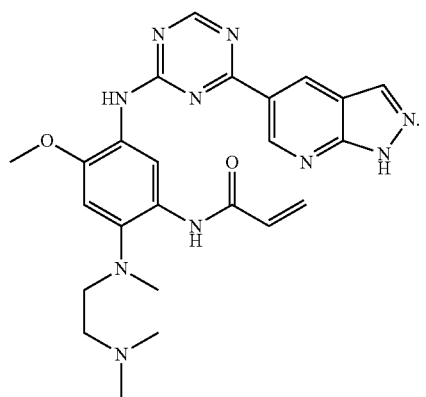
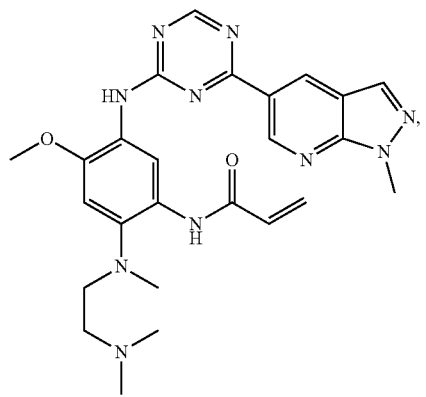
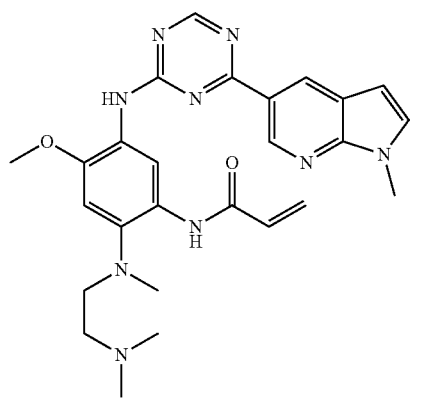
or
36
-continued
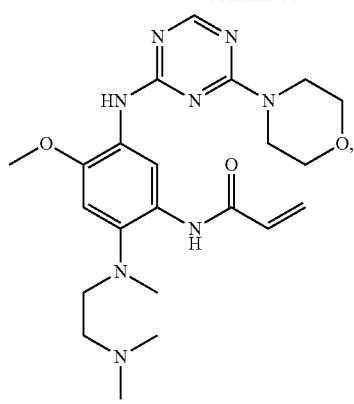
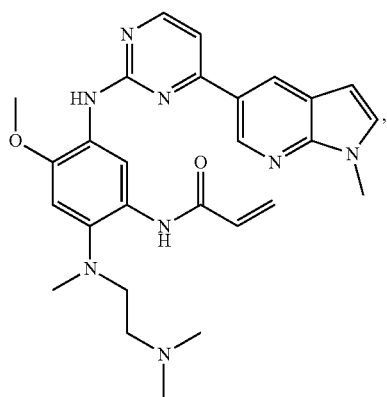
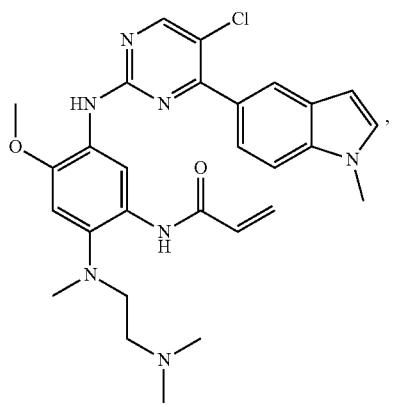
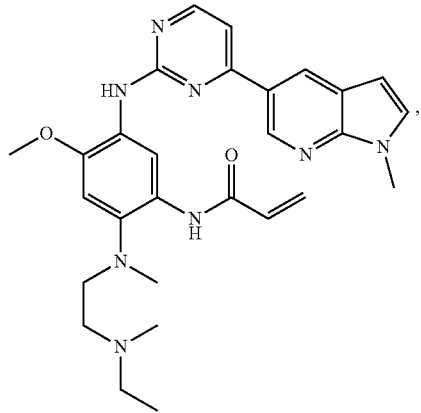

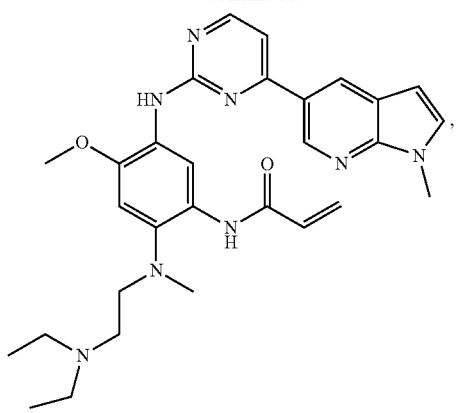
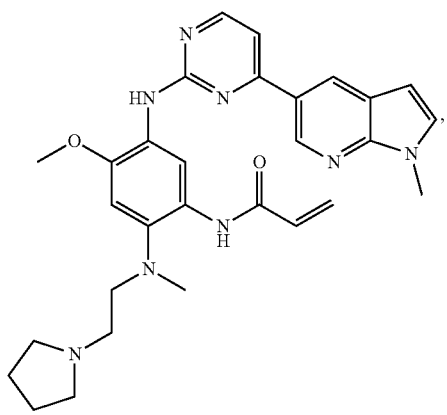
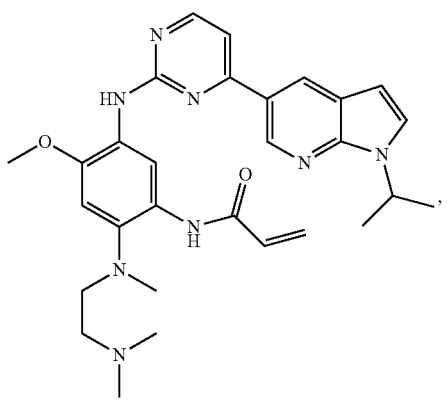
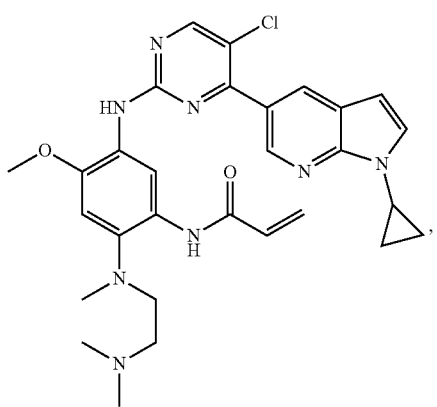

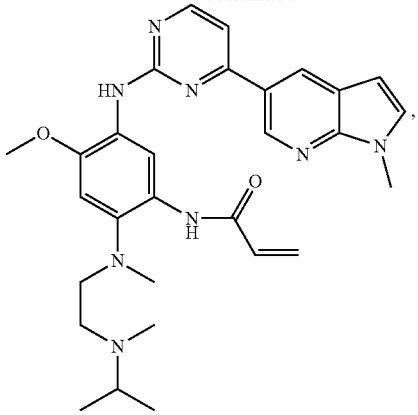
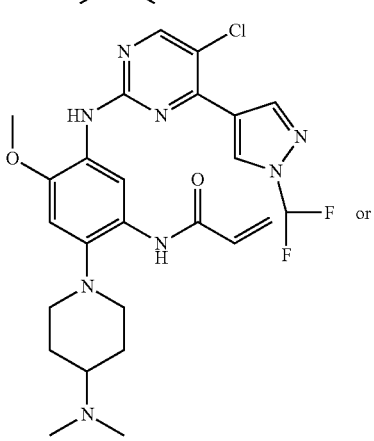
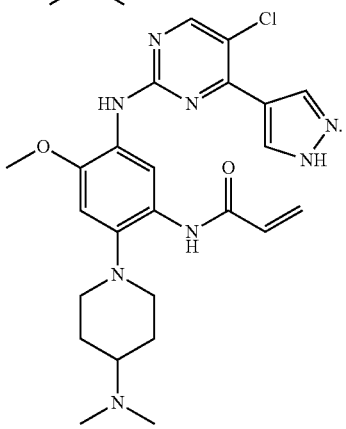

In the second aspect of the present invention, a pharmaceutical composition is provided, including a compound of the first aspect of the present invention, or a pharmaceutically acceptable salt, stereoisomer, solvate or prodrug thereof, and a pharmaceutically acceptable carrier.

In another preferred embodiment, the pharmaceutical composition includes a therapeutically effective amount of the compound of the first aspect of the present invention, such as a compound of formula (I), a compound of formula (IV-1), a compound of formula (IV-2), a compound of formula (V-1), a compound of formula (V-2), a compound of formula (VI-1), a compound of formula (VI-2), a compound of formula (VII-1), a compound of formula (VII-2), a compound of formula (VIII-1) a compound of formula (VIII-2), a compound of formula (IX-1), a compound of formula (IX-2), a compound of formula (X-1), a compound of formula (X-2), a compound of formula (XI-1), a compound of formula (XI-2), or the above examplary compounds, or a pharmaceutically acceptable salt, stereoisomer, solvate or prodrug thereof, and a pharmaceutically acceptable carrier.

Generally, the compound of the present invention or a pharmaceutically acceptable salt thereof may form a suitable dosage form for administration with one or more pharmaceutically acceptable carriers. These dosage forms are suitable for oral, rectal, topical, intraoral administration, and other parenteral administration (e.g., subcutaneous, intramuscular, intravenous administration, etc.). For example, dosage forms suitable for oral administration include capsules, tablets, granules and syrups. Compounds of the present invention contained in these formulations may be solid powders or granules; aqueous or non-aqueous liquid solutions or suspensions; water-in-oil or oil-in-water emulsions. Such dosage forms may be prepared with active compounds and one or more carriers or excipients through the conventional pharmacy methods. The above-mentioned carriers should be compatible with active compounds or other excipients. For solid formulations, conventional non-toxic carriers include, but not limited to mannitol, lactose, starch, magnesium stearate, cellulose, glucose, sucrose and the like. Carriers used for liquid preparations include water, saline, aqueous dextrose, ethylene glycol and polyethylene glycol. The active compounds may form a solution or suspension with the above-mentioned carriers.

The compositions of the present invention are formulated, quantified and administrated in a manner consistent with the practice of medicine. The "effective amount" of the administrated compound depends on the factors such as the specific disease to be treated, the individual being treated, the cause of diseases, the drug targets and the mode of administration, etc.

In the third aspect of the present invention, the use of a compound of the first aspect of the present invention, or a pharmaceutically acceptable salt, stereoisomer, solvate or prodrug thereof for the manufacture of a medicament for adjusting EGFR tyrosine kinase activity or treating EGFR-related diseases is provided.

Preferably, the EGFR-related disease is cancer, diabetes, immune system diseases, neurodegenerative diseases or cardiovascular diseases.

Preferably, the cancer is non-small cell lung cancer, head and neck cancer, breast cancer, renal cancer, pancreatic cancer, cervical cancer, esophageal cancer, pancreatic cancer, prostate cancer, bladder cancer, colorectal cancer, ovarian cancer, stomach cancer, brain malignancies including glioblastoma, etc., or any combination thereof.

Preferably, the non-small cell lung cancer is caused by EGFR mutations, including sensitive mutations (such as L858R mutation or exon 19 deletions) and resistance mutations (such as EGFR T790M mutation).

Preferably, the compound, or a pharmaceutically acceptable salt, stereoisomer, solvate or prodrug thereof can also be used to manufacture a medicament for treating a disease with EGFR abnormal expression, or a disease that has acquired resistance during the treatment using EGFR modulators.

Preferably, the acquired resistance is the resistance caused by the T790 mutations encoded by EGFR exon 20, or by comprising the T790 mutations encoded by EGFR exon 20, such as T790M.

In the present invention, the EGFR modulator refers to a small molecule tyrosine kinase inhibitor which targets EGFR, such as gefitinib, erlotinib, Icotinib, lapatinib or afatinib.

In the fourth aspect of the present invention, a pharmaceutical composition is provided, including a therapeutically effective amount of the compound of the first aspect of the present invention, or a pharmaceutically acceptable salt, stereoisomer, solvate or prodrug thereof, as well as one or more other drugs selected from a group consisting of gefitinib, erlotinib, icotinib, lapatinib, XL647, NVP-AEE-788, ARRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, Zemab, Her2 vaccine PX 1041, HSP90 inhibitors, CNF2024, tanespimycin, alvespimycin, IPI-504, SNX-5422, NVP-AUY922, or combinations thereof.

In addition to the compound of the present invention, or a pharmaceutically acceptable salt, stereoisomer, solvate or prodrug thereof, the other drugs in the pharmaceutical composition described above are the antitumor drugs well known to those skilled in the art.

As used herein, "therapeutically effective amount" refers to the amount that yields a function or activity to humans and/or animals and may be tolerated by humans and/or animals.

The therapeutically effective amount of the compound of the present invention, or a pharmaceutically acceptable salt, stereoisomer, solvate or prodrug thereof contained in the pharmaceutical composition or medicinal composition of the present invention is preferably 0.1 mg-5 g/kg (weight).

The pharmaceutical compositions of the present invention are useful for treating EGFR-related diseases such as cancer, diabetes, immune system disorders, neurodegenerative diseases or cardiovascular diseases, or treating a disease with acquired resistance during the treatment of EGFR modulator.

The disease with the acquired resistance is caused by the T790 mutations encoded by EGFR exon 20, or by comprising the T790 mutations encoded by EGFR exon 20.

In another preferred embodiment, the T790 encoded by EGFR exon 20 is T790M.

For certain diseases, the compounds of the present invention may be used in combination with other drugs in order to achieve the desired therapeutic effect. An example of the combination is for treating advanced NSCLC. For example, a therapeutically effective amount of the compound of formula I of the present invention is used in combination with mTOR inhibitors (e.g., rapamycin); or Met inhibitors (include Met antibody MetMAb and small molecule Met inhibitors PF02341066) MS; or IGF1R inhibitors (e.g., OSI-906); or heat shock protein inhibitors and the like.

It should be understood that each of the above technical features of the invention and each technical feature specifically described below (such as in Examples) can be combined with each other within the scope of the present invention so as to constitute new or preferred technical solutions.

DETAIL DESCRIPTION OF INVENTION

Inventors unexpectedly discovered a class of selective inhibitors of EGFR mutations after a long and intensive study. Assays in vitro showed that the selective inhibitors can inhibit the EGFR T790M/L858R double mutant enzyme and the proliferation of H1975 cell line at nanomolar concentrations, and also exhibit a high intensity of inhibition against EGFR sensitive mutant cell line HCC827 (exon 19 deletion) but have a relatively weak inhibition against wild-type EGFR enzyme and A431 cell line. Thus, the compounds with such structures can be used not only for the treatment of EGFR sensitive mutant cancer but also for the treatment of secondary resistance cases generated during the current EGFR-TKI therapy; meanwhile, the side effects generated by the inhibition of wild-type EGFR are greatly reduced due to the mutation selectivity of the compounds. In addition, these compounds exhibit low cytotoxicity in normal cells (such as 3T3 cells), thereby greatly reducing the non-specific side effects, and are the ideal substitutes of the second-generation of EGFR-TKI.

Definition of Terms

As used herein, "$C_{1-10}$ alkyl" refers to a straight or branched saturated aliphatic hydrocarbon group having 1 to 10 carbon atoms, for example, methyl, ethyl, propyl, isopropyl, butyl, isobutyl, sec-butyl, tert-butyl, pentyl, hexyl, heptyl, octyl, nonyl, decyl and the like.

As used herein, "$C_{1-10}$ alkoxy" refers to $C_{1-10}$ alkyl —O—, for example, methoxy, ethoxy, propoxy, isopropoxy, butoxy, isobutoxy, sec-butoxy, t-butoxy and the like.

As used herein, "halogen" refers to fluoro, chloro, bromo or iodo.

As used herein, "$C_{3-10}$ cycloalkyl" refers to a saturated or partially unsaturated monocyclic or polycyclic cyclic hydrocarbon substituent having 3 to 10 carbon atoms, preferably a cycloalkyl including 3 to 8 carbon atoms ($C_{3-8}$ cycloalkyl), most preferably a cycloalkyl including 3 to 6 carbon atoms ($C_{3-6}$ cycloalkyl). Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, and cyclooctyl, preferably cyclopropyl, cyclopentyl, cyclohexenyl. Polycyclic cycloalkyl include spiro ring, fused ring and bridged ring.

As used herein, "$C_{3-10}$ heterocycloalkyl" refers to a saturated or partially unsaturated monocyclic or polycyclic cyclic hydrocarbon substituent including 3 to 10 ring atoms, wherein one or more ring atoms are heteroatoms selected from nitrogen, oxygen or S(O)t (wherein t is an integer from 0 to 2) and other ring atoms are carbon, but $C_{3-10}$ heterocycloalkyl does not include the ring moiety such as —O—O—, —O—S— or —S—S—. Preferably a heterocycloalkyl includes 3 to 8 ring atoms, wherein 1 to 3 ring atoms are heteroatoms, preferably, a heterocycloalkyl including 3 to 6 ring atoms, and more preferably a heterocycloalkyl including 5 to 6 ring atoms. Non-limiting examples of monocyclic heterocyclic group include pyrrolidinyl, piperidinyl, piperazinyl, morpholinyl, thiomorpholinyl, homopiperazinyl, pyranyl, tetrahydrofuranyl and the like. Polycyclic heterocycloalkyl includes spiro ring, fused ring and bridged ring.

As used herein, "$C_{1-10}$ haloalkyl" refers to an alkyl substituted with 1, 2, 3, 4 or 5 halogens, wherein alkyl is defined as above, preferably $C_{1-10}$ haloalkyl, more preferably $C_{1-6}$ haloalkyl, and most preferably $C_{1-3}$ haloalkyl, including (but not limited to) chloroethyl, dichloromethyl, 1,2-dichloroethyl, bromoethyl, fluoroethyl, fluoromethyl, difluoromethyl, trifluoromethyl and the like.

Active Ingredients

The term "the active material of the invention" or "the active compound of the invention" refers to the compound of formula (I) of the invention, or a pharmaceutically acceptable salt thereof, or a solvate thereof, or a stereoisomer thereof, or a prodrug thereof having significant inhibitory activity against resistance to EGFR T790M mutation (especially EGFR T790M/L858R double mutation).

As used herein, "pharmaceutically acceptable salt(s)" includes pharmaceutically acceptable acid addition salt(s) and base addition salt(s). "Pharmaceutically acceptable acid addition salts" refers to salts that are able to retain the biological effectiveness of the free base without other side effects and are formed with inorganic or organic acids. Inorganic acid salts include, but not limited to, hydrochloride, hydrobromide, sulfate, phosphate and the like; organic acid salts include, but not limited to, formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art. "Pharmaceutically acceptable base addition salts" include, but not limited to the salts of inorganic bases such as sodium, potassium, calcium and magnesium salts, or include but not limited to the salts of organic bases, such as ammonium salt, triethylamine salt, lysine salt, arginine salt and the like. These salts can be prepared by the methods known in the art.

As used herein, the compounds of formula (I) may exit in one or more crystalline forms, the active compounds of the present invention include various polymorphs and mixtures thereof.

The "solvate" mentioned in the present invention refers to a complex formed with the compound of the present invention and a solvent. The solvate can be formed either through a reaction in a solvent or precipitated or crystallized from the solvent. For example, a complex formed with water is referred to as "hydrate." The solvates of the compounds of formula (I) are within the scope of the present invention.

The compounds of formula (I) of the invention may contain one or more chiral centers, and may exist in different optically active forms. When the compound contains a chiral center, the compound includes enantiomers. The present invention includes both of two isomers and a mixture thereof, such as racemic mixtures. Enantiomers can be resolved using methods known in the art, such as crystallization and chiral chromatography and the like. When the compound of formula (I) contain more than one chiral centers, the compounds may include diastereomers. The present invention includes specific isomers resolved into optically pure isomers as well as the mixtures of diastereomeric isomers. Diastereomeric isomers can be resolved using methods known in the art, such as crystallization and preparative chromatography.

The present invention includes prodrugs of the above-mentioned compounds. Prodrugs include known amino protecting groups and carboxyl protecting groups which are hydrolyzed under physiologic conditions or released by enzyme reaction to obtain the parent compounds. Specific preparation methods of prodrugs can refer to (Saulnier, M G; Frennesson, D B; Deshpande, M S; Hansel, S B and Vysa, D M Bioorg. Med. Chem Lett. 1994, 4, 1985-1990; and Greenwald, R B; Choe, Y H; Conover, C D; Shum, K.; Wu, D.; Royzen, M. J. Med. Chem. 2000, 43, 475).

Preparation Method

The present invention provides the preparation method of compounds of formula (I), the compounds of the present invention can be easily prepared by a variety of synthetic operations, and these operations are familiar to those skilled in the art. An exemplary preparation of these compounds may include (but not limited to) the processes described below.

Preferably, the compounds of formula (I) can be prepared through the following schemes and exemplary methods described in embodiment, as well as the related publications available for those skilled in the art.

The procedures of method can be extended or combined as desired in practice.

Scheme 1:

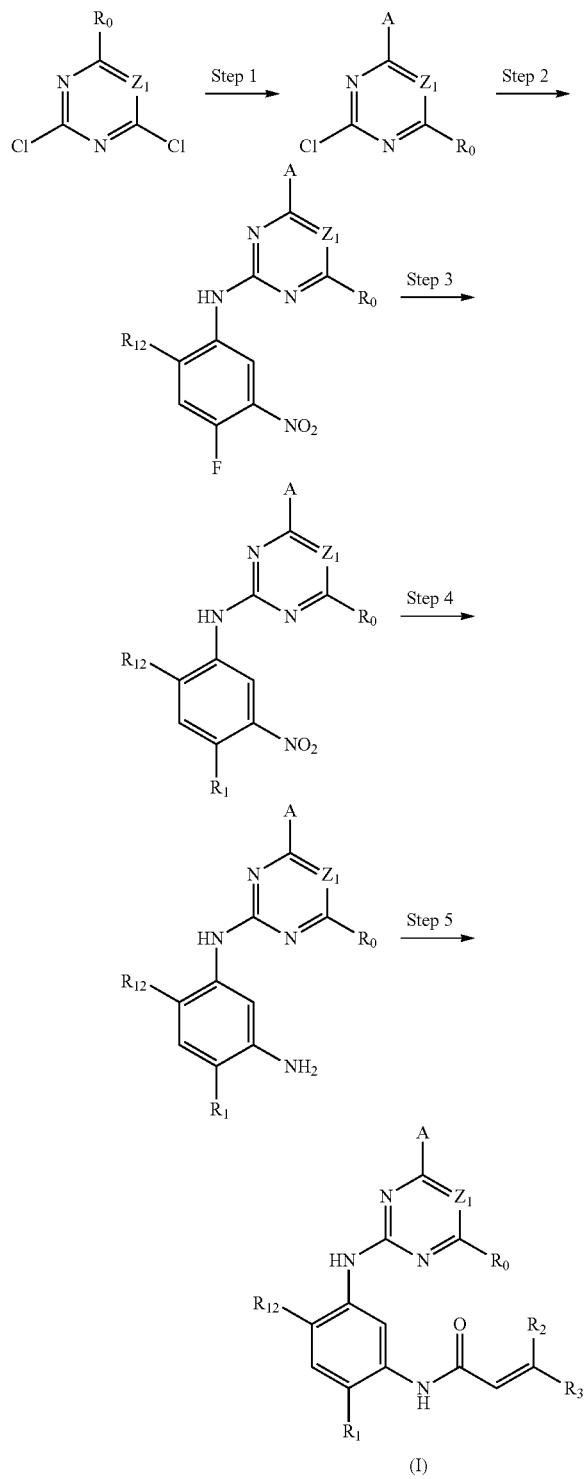

Step 1: The reaction of 4-chloro on pyrimidine with a borate or a boric acid, or with an appropriate amine can be carried out in the presence of a suitable catalyst and a suitable solvent at a certain temperature. The palladium catalyst used in the Suzuki reaction may be, but not limited to, $PdCl_2$ (dppf), and the used base may be, but not limited to, sodium carbonate.

Step 2: The substitution of 2-chloro on pyrimidine by amine can take place in the presence of a suitable catalyst and a suitable solvent at a certain temperature. Acid can be used as a catalyst which may be, but not limited to, TFA or p-toluenesulfonate. Buchwald-Hartwig amination can be used, the used palladium catalyst may be, but not limited to $Pd_2(dba)_3$, the used ligand may be, but not limited to XantPhos (4,5-bis(diphenylphosphino)-9,9-dimethyl xanthene), the used base may be, but not limited to cesium carbonate.

Step 3: The substitution of 4-fluoro on benzene by amine can take place in the presence of a suitable base and a suitable solvent at a certain temperature. The used base may be, but not limited to potassium carbonate.

Step 4: The nitro compound can be converted to the corresponding amino compound under acidic conditions by using a metal (may be, but not limited to, iron powder, zinc powder) or stannous chloride through reduction; or by hydrogenation reduction in the presence of catalyst of palladium carbon.

Step 5: The amine compound can be condensed with the corresponding acyl chloride to get the amide under basic conditions, or condensed with the corresponding carboxylic acid to get the amide in the presence of a condensation agent.

The reactions in each of those steps are conventional reactions known to those skilled in the art.

Compounds of formula (I), preparation methods thereof, pharmaceutical compositions and treatment strategy disclosed in the present invention can be achieved by the person skilled in the art through the reference to this article and the appropriate improvements of process parameters.

It should be particularly noted that all such alterations and changes are obvious to the skilled artisan, and they are deemed to be included in the present invention. Preferred embodiments of products, methods and applications of the present invention have been described, and relevant personnel can obviously alter or change and combine the methods and uses of the present invention without departing from the content, spirit and scope of the present invention for implementation and application of the present technology.

Compared with the prior art, the main advantages of the present invention are that:

(1) The compounds of the present invention show a high inhibitory activity to EGFR T790M mutant (especially EGFR T790M/L858R double mutant) enzymes and cells, but a low inhibitory activity to EGFR wild type (EGFR WT) enzyme and cells, and therefore possess a high selective inhibition.

(2) The compounds of the present invention not only exhibit a high selective inhibition to EGFR double mutant enzyme and cells, but also exhibit a low non-specific cytotoxicity.

(3) The compounds of the present invention also exhibit advantageous physical properties (for example, a high aqueous solubility), favorable toxicity profiles (for example, a low hERG blocking liability), and advantageous metabolic profiles (for example, better pharmacokinetic characteristics such as bioavailability) in comparison with other known EGFR-mutant inhibitors.

In order to make those skilled in the art to better understand the technical solution of the invention, the present invention will be further described in detail combined with the following specific embodiments.

Reagents and Instruments

The structure and purity of the compounds are identified by nuclear magnetic resonance ($^1$HNMR) and/or LC-MS mass spectrometry (LC-MS) in the present invention. $^1$HNMR: Bruker AVANCE-400 NMR machine, the internal standard was tetramethylsilane (TMS). LC-MS: Agilent 1200 HPLC System/6140 MS liquid-mass spectrometer (available from Agilent), column WatersX-Bridge, 150×4.6 mm, 3.5 μm. Preparative high performance liquid chromatography (pre-HPLC): Waters PHW007, column XBridge C18, 4.6*150 mm, 3.5 um.

ISCO Combiflash-Rf75 or Rf200 automatic eluting column instrument, Agela 4 g, 12 g, 20 g, 40 g, 80 g, 120 g disposable silica gel column.

Thin-layer silica gel plate was Yantai Huanghai HSGF254 or Qingdao GF254 silica gel plates, thin layer chromatography (TLC), silica gel plates used for detection of reaction are 0.15 mm-0.2 mm, silica gel plates using for TLC purification of products are 0.4 mm-0.5 mm. Yantai Huanghai 200-300 mesh silica gel is generally used as a carrier. FCP200-300 mesh alkaline aluminum oxide is commonly used as a carrier in alkaline aluminum oxide column.

The known starting materials of the invention may be synthesized by using the methods known in the art, or may be purchased from ABCR GmbH & Co. KG, Acros Organics, Aldrich Chemical Company, Accela ChemBio Inc and Darui Chemical Company etc.

All examples were performed under nitrogen or argon atmosphere and the solution refers to the aqueous solution if without special explanation.

As used herein, DMF refers to dimethylformamide, DMSO refers to dimethylsulfoxide, THF refers to tetrahydrofuran, DIEA refers to N,N-diisopropylethylamine, EA refers to ethyl acetate, PE refers to petroleum ether. BINAP refers to (2R,3S)-2,2'-bis diphenylphosphino-1,1'-binaphthyl, NBS refers to N-bromosuccinimide, NCS refers to N-chlorosuccinimide, Pd$_2$(dba)$_3$ refers to tris(dibenzylideneacetone)dipalladium, Pd(dppf)Cl$_2$ refers to [1,1'-bis(diphenylphosphino) ferrocene]palladium dichloride.

As used herein, room temperature refers to be about 25° C.

Preparation of Compound 1a:

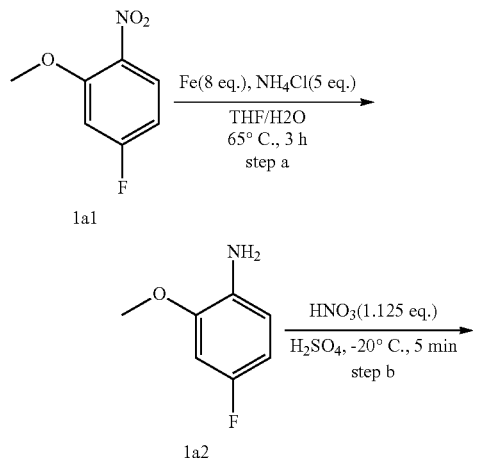

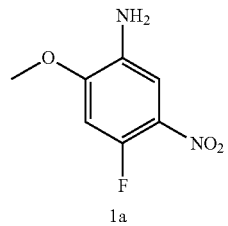

Step a: Compound 1a1 (10.6 g, 58 mmol) was added into a 500 ml reaction flask, and THF/water (100 ml/60 ml) mixed solution was added to dissolve the compound. Ammonium chloride (15.5 g, 292 mmol) and reduced iron powder (26 g, 467 mmol) were sequentially added with stirring at room temperature, and then the reaction system was heated to 65° C. and stirred continually for 3 h. The reaction progress was monitored by TLC.

After completion of the reaction, the excess iron powder was removed by filtration, and the filter cake was washed for three times with EA. Filtrate was extracted with EA/water system for three times, and the organic layer was separated, washed with water, saturated brine, dried over anhydrous Na$_2$SO$_4$, and concentrated under reduced pressure to give compound 1a2 (8.0 g) which was used directly in the next reaction. Yield: 93%; purity: 90%; MS m/z (ESI): 142.0 [M+H]+.

Step b: Compound 1a2 (8.0 g, 43 mmol) was added into a 500 ml reaction flask, and concentrated sulfuric acid (100 ml) was added to dissolve the substrate under constant agitation. At −20° C., concentrated nitric acid (6.15 ml, 48 mmol) was slowly added dropwise with stirring, and the reaction mixture was stirred for 5 mins at this temperature. The reaction progress was monitored by TLC. After completion of the reaction, the mixture was poured into ice water. Sodium hydroxide/water solution (150 ml/300 ml) were added slowly to the reaction system at −20° C. in an ice-water bath, and the mixture was adjusted to pH 8-9. The reaction solution was extracted with EA/water system for three times, the organic layer was separated, washed with water, saturated brine, dried over anhydrous Na$_2$SO$_4$, and concentrated under reduced pressure to give compound 1a (8.7 g) which was used directly in the next reaction. Yield: 80%; purity: 100%; MS m/z (ESI): 187.0 [M+H]+; 1H NMR (400 MHz, DMSO-d6): δ 7.34 (d, J=7.8 Hz, 1H), 7.04 (d, J=13.4 Hz, 1H), 5.25 (brs, 2H), 3.90 (s, 3H).

Preparation of Intermediate 2a

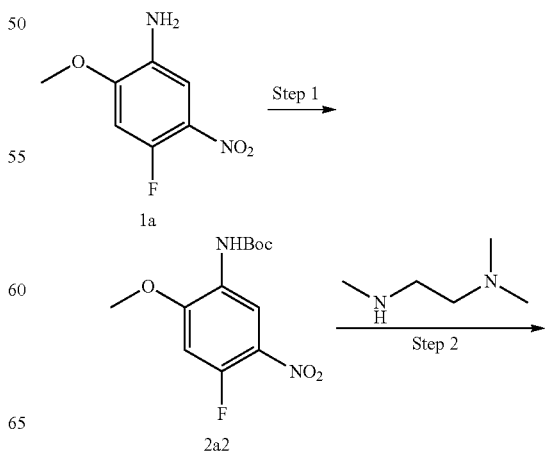

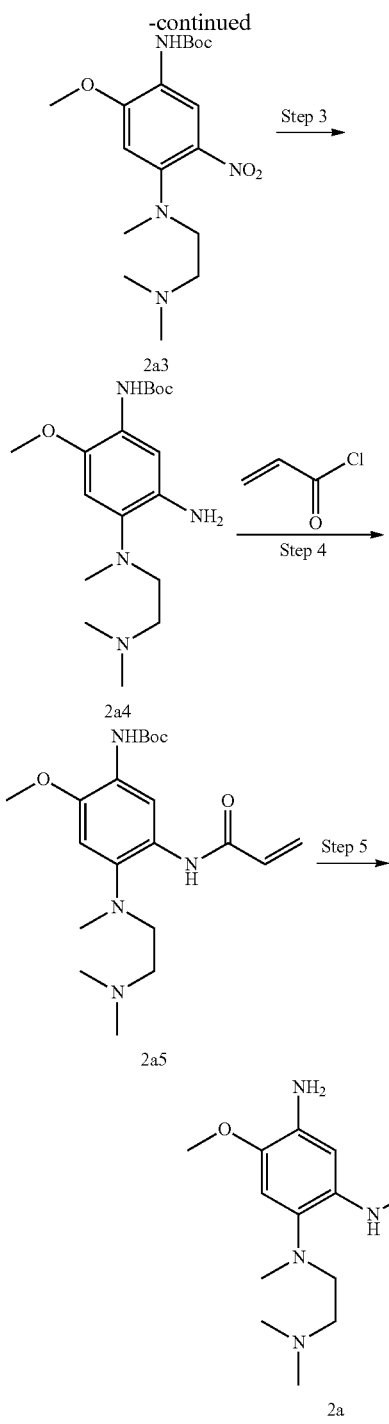

ethylenediamine (4.90 g, 48 mmol), N,N-diisopropylethylamine (7.74 g, 60 mmol) were added and heated to 90° C. and stirred for 6 h. The reaction progress was monitored by TLC. After completion of the reaction, the reaction solution was cooled to room temperature, poured into ice water, extracted with ethyl acetate, washed with water and saturated brine, dried over anhydrous $Na_2SO_4$, and concentrated under reduced pressure to give the title product compound 2a3 (12.51 g, 85%). It was used directly in the next reaction. MS m/z (ESI): 369 [M+H]+.

Step 3: Compound 2a3 (12 g, 32.6 mmol) was dissolved in 200 ml of methanol, and 1.0 g 10% Pd/C was added. After the replacement of air with hydrogen, the reaction solution was stirred for 1 h under hydrogen filled in the balloon at room temperature. The reaction progress was monitored by TLC. After completion of the reaction, the reaction system was filtered by buchuer funnel, the filter cake was washed with small amount of methanol, and the filtrate was concentrated to give the title product compound 2a4 (10.70 g, 97%). It was used directly in the next reaction. MS m/z (ESI): 339 [M+H]+.

Step 4: Compound 2a4 (10.1 g, 30 mmol) and triethylamine (6.12 g, 60 mmol) were dissolved in 200 ml of dichloromethane, and cooled to 0° C. Acryloyl chloride (3.24 g, 36 mmol) was added and stirred under nitrogen at room temperature for 3 h. The reaction progress was monitored by TLC. After completion of the reaction, the reaction solution was washed successively with saturated aqueous sodium bicarbonate solution and saturated brine, dried over anhydrous $Na_2SO_4$, filtered, and concentrated under reduced pressure to give the title product compound 2a5 (9.64 g, 82%). It was used directly in the next reaction. MS m/z (ESI): 393 [M+H]+.

Step 5: Compound 2a5 (9.41 g, 24 mmol) was dissolved in 100 ml of dichloromethane, cooled to 0° C., 20 ml of trifluoroacetic acid was added, and the reaction was stirred under nitrogen at room temperature for 18 h. The reaction progress was monitored by TLC. After completion of the reaction, the reaction solution was concentrated under reduced pressure. The residue was dissolved in 300 ml of dichloromethane, washed with saturated aqueous sodium bicarbonate solution, and saturated brine successively, dried over anhydrous $Na_2SO_4$, filtered, and concentrated under reduced pressure to give the crude product, which was purified by column chromatography [DCM:MeOH=10:1] to give the title product Compound 2a (3.26 g, 46.5%). MS m/z (ESI): 293 [M+H]+.

Preparation of Intermediate 3a

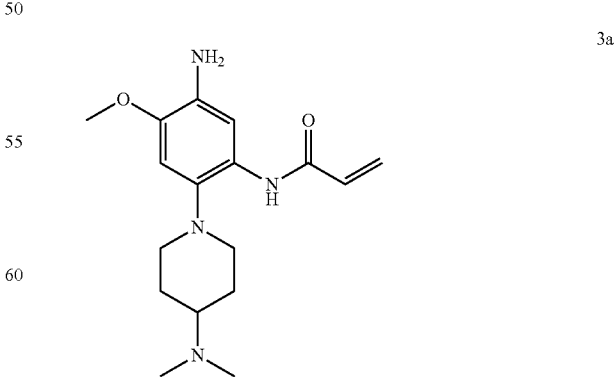

3a

Step 1: Compound 1a (11.16 g, 60 mmol) was dissolved in 150 ml of dichloromethane, di-tert-butyl dicarbonate (15.60 g, 72 mmol), triethylamine (12.24 g, 120 mmol) and 4-dimethylaminopyridine (0.74 g of, 6 mmol) were added and stirred at room temperature for 18 h. The reaction progress was monitored by TLC. After completion of the reaction, the reaction solution was concentrated under reduced pressure, isolated and purified by column chromatography [PE:EA=80:20] to give the title compound 2a2 (12.56 g, 73%). MS m/z (ESI): 285 [M−H]+.

Step 2: Compound 2a2 (11.46 g, 40 mmol) was dissolved in 60 ml N,N-dimethylacetamide, and N,N,N'-trimethyl- The preparation method was similar to that of compound 2a, except that N,N,N'-trimethyl ethylenediamine in step 2 of preparation method of compound 2a was replaced by 4-dimethylamino piperidine. MS m/z (ESI): 319.2 [M+H]+.

Preparation of Intermediate 4a

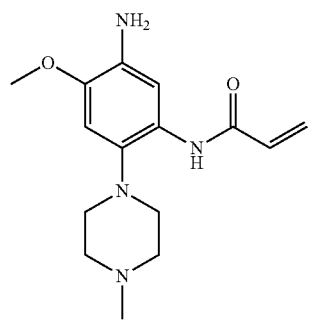

The preparation method was similar to that of compound 2a, except that N,N,N'-trimethyl ethylenediamine in step 2 of preparation method of compound 2a was replaced by methylpiperazine. MS m/z (ESI): 291 [M+H]+.

Example 1: N-(5-(5-chloro-4-(1-methyl-1H-pyrrolo[2,3-b]pyridin-5-yl)pyrimidin-2-amino)-2-((2-(dimethylamino)ethyl)methylamino)-4-methoxyphenyl)acrylamide (Compound Z-1)

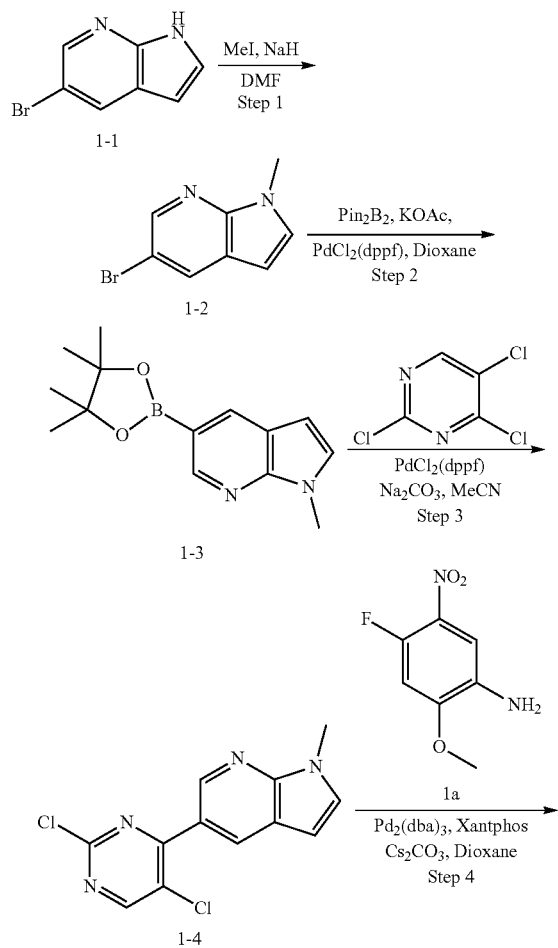

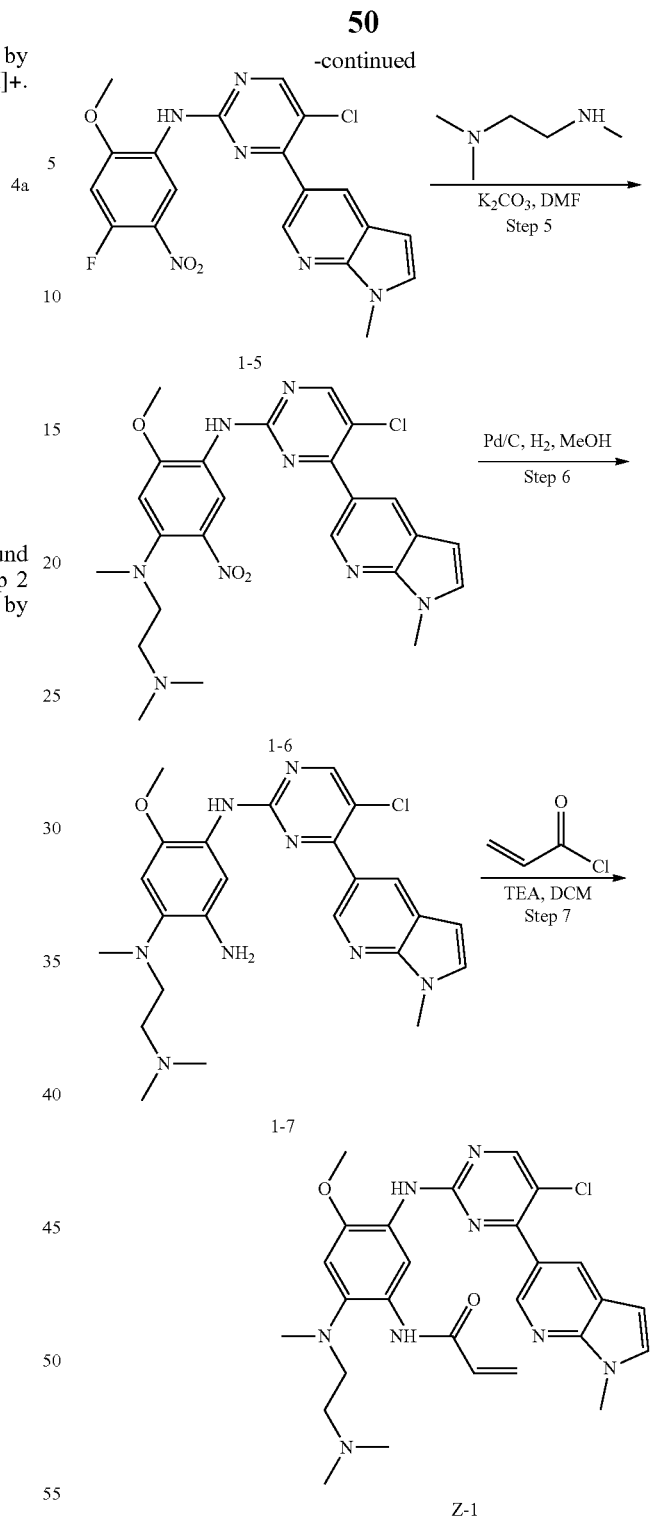

Step 1: 5-bromo-1-methyl-1H-pyrrolo[2,3-b]pyridine (Compound 1-2)

At 0° C., a solution of compound 5-bromo-1H-pyrrolo[2,3-b]pyridine (5 g, 25.4 mmol, commercially available) in DMF was added to a solution of sodium hydride (4.32 g, 30.5 mmol) in 40 ml of DMF, and vigorously stirred at 0° C. for 0.5 h, and then methyl iodide (1.22 g, 30.5 mmol) was added, and stirred vigorously at room temperature for 3 h.

The reaction progress was monitored by TLC. After completion of the reaction, the reaction solution was poured into ice water. After the solids were completely precipitated, the solids were filtered and dissolved in dichloromethane and methanol (10:1), washed with water three times, and dried. The organic layer was separated, and concentrated under reduced pressure to give compound 1-2 (5.4 g, 99%). The product was used directly in the next step. MS m/z (ESI): 211.0 [M+H]+.

Step 2: 1-methyl-5-(4,4,5,5-tetramethyl-1,3,2-dioxaborolan-2-yl)-1H-pyrrolo[2,3-b]pyridine (Compound 1-3)

Bis(pinacolato) borate (11.26 g, 43.6 mmol), PdCl$_2$ (dppf) (814 mg, 1.11 mmol) and potassium acetate (6.53 g, 32.7 mmol) were added to a solution of compound 1-2 (4.6 g, 21.8 mmol) in 50 ml of 1,4-dioxane, and vigorously stirred under N$_2$ atmosphere at 90° C. for 8 h. After completion of the reaction, the mixture was filtered, and the filtrate was concentrated to give the crude product compound 1-3 (13.9 g) which was used directly in the next step. MS m/z (ESI): 259.1 [M+H]+.

Step 3: 5-(2,5-dichloropyrimidin-4-yl)-1-methyl-1H-pyrrolo[2,3-b]pyridine (Compound 1-4)

2,4,5-trichloropyrimidine (4.93 g, 26.2 mmol), PdCl$_2$ (dppf) (1.66 g, 2.26 mmol, commercially available) and 23 ml of 2.0 mol/l sodium carbonate solution were added to a solution of compound 1-3 (13.9 g, 21.8 mmol) in 50 ml of acetonitrile, and vigorously stirred under N$_2$ atmosphere at 85° C. for 4 h. After completion of the reaction, the reaction solution was diluted with water, extracted with EA/water system, washed with water for 3 times, and dried, and the organic layer was concentrated under reduced pressure to give the crude product which was purified by Combi-flash column chromatography [PE:EA=100:0-20:80] to give compound 1-4 (2.16 g, 36%). MS m/z (ESI): 279.0[M+H]+.

Step 4: 5-chloro-N-(4-fluoro-2-methoxy-5-nitrophenyl)-4-(1-methyl-1H-pyrrolo[2,3-b]pyridin-5-yl)pyrimidin-2-amine (Compound 1-5)

Compound 4-fluoro-2-methoxy-5-nitroaniline (1.13 g, 6.09 mmol), Pd$_2$(dba)$_3$ (558 mg, 0.61 mmol), Xantphos (705 mg, 1.22 mmol) and cesium carbonate (3.97 g, 12.2 mmol) were added to a solution of compound 1-4 (1.70 g, 6.09 mmol) in 20 ml of 1,4-dioxane, and vigorously stirred under N$_2$ atmosphere at 120° C. for 5 h. After completion of the reaction, filtered, and the filtrate was concentrated under reduced pressure to give the crude product, purified by Combi-flash column chromatography [PE:EA=100:0-0:100] to give compound 1-5 (420 mg, 16%). MS m/z (ESI): 429.0[M+H]+.

Step 5: N$^1$-(5-chloro-4-(1-methyl-1H-pyrrolo[2,3-b]pyridin-5-yl)pyrimidin-2-yl)-N$^4$-(2-(dimethylamino)ethyl)-2-methoxy-N$^4$-methyl-5-nitrobenzene-1,4-diamine (Compound 1-6)

N,N,N'-trimethylethylenediamine (72 mg, 0.70 mmol) and potassium carbonate (193 mg, 1.40 mmol) were added to a solution of compound 1-5 (200 mg, 0.47 mmol) in 4 ml of DMF, and vigorously stirred at 100° C. for 2 h. The reaction progress was monitored by TLC. After completion of the reaction, 10 ml of water was added, and extracted with EA/water system for three times. The organic layer was separated, and concentrated under reduced pressure to give compound 1-6 (240 mg, 90%). MS m/z (ESI): 511.3[M+H]+.

Step 6: N$^4$-(5-chloro-4-(1-methyl-1H-pyrrolo[2,3-b]pyridin-5-yl)pyrimidin-2-yl)-N$^1$-(2-(dimethylamino)ethyl)-5-methoxy-N$^1$-methylbenzene-1,2,4-triamine (Compound 1-7)

Pd/C (20 mg) was added to a solution of compound 1-6 (100 mg, 0.20 mmol) in 20 ml of methanol, and vigorously stirred under H$_2$ atmosphere at room temperature for 4 h. After completion of the reaction, the reaction solution was filtered, and the filtrate was concentrated to give compound 1-7 (80 mg, 83%) which was used directly in the next step. MS m/z (ESI): 481.2 [M+H]+.

Step 7: N-(5-(5-chloro-4-(1-methyl-1H-pyrrolo[2,3-b]pyridin-5-yl)pyrimidin-2-amino)-2-((2-(dimethylamino)ethyl)methylamino)-4-methoxyphenyl)acrylamide (Compound Z-1)

Acryloyl chloride (17 mg, 0.17 mmol) and triethylamine (28 mg, 0.25 mmol) were added to a solution of compound 1-7 (80 mg, 0.17 mmol) in 2 ml of dichloromethane at 0° C., and vigorously stirred at 0° C. for 2 h. After completion of the reaction, the mixture was diluted with water and extracted with dichloromethane/water system for three times, and the organic layer was concentrated under reduced pressure to give the crude product, which was separated and purified by preparative liquid chromatography to give compound Z-1 (2.39 mg, 6%). MS m/z (ESI): 534.9 [M+H]+; 1H NMR (400 MHz, DMSO-d6) δ 10.11 (s, 1H), 8.87-8.75 (m, 2H), 8.57 (d, J=17.2 Hz, 3H), 7.62 (d, J=3.5 Hz, 1H), 7.00 (s, 1H), 6.57 (d, J=3.4 Hz, 1H), 6.44-6.35 (m, 1H), 6.29 (d, J=16.7 Hz, 1H), 5.77 (d, J=12.0 Hz, 1H), 3.87 (s, 3H), 3.82 (s, 3H), 2.85 (s, 2H), 2.70 (s, 3H), 2.29 (d, J=5.7 Hz, 2H), 2.19 (s, 6H).

Example 2: N-(5-(5-chloro-4-(1-methyl-1H-pyrrolo[2,3-b]pyridin-5-yl)pyrimidin-2-amino)-2-(4-(dimethylamino)piperidin-1-yl)-4-methoxyphenyl)acrylamide (Compound Z-2)

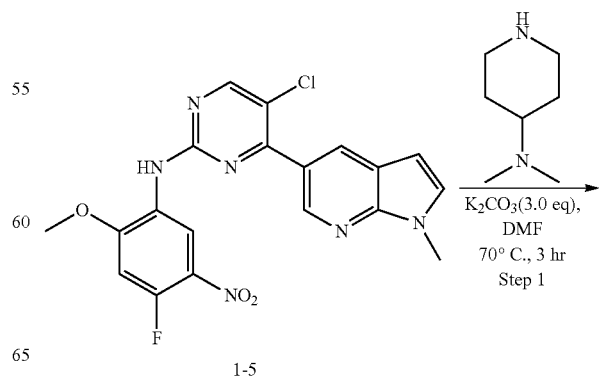

1-5

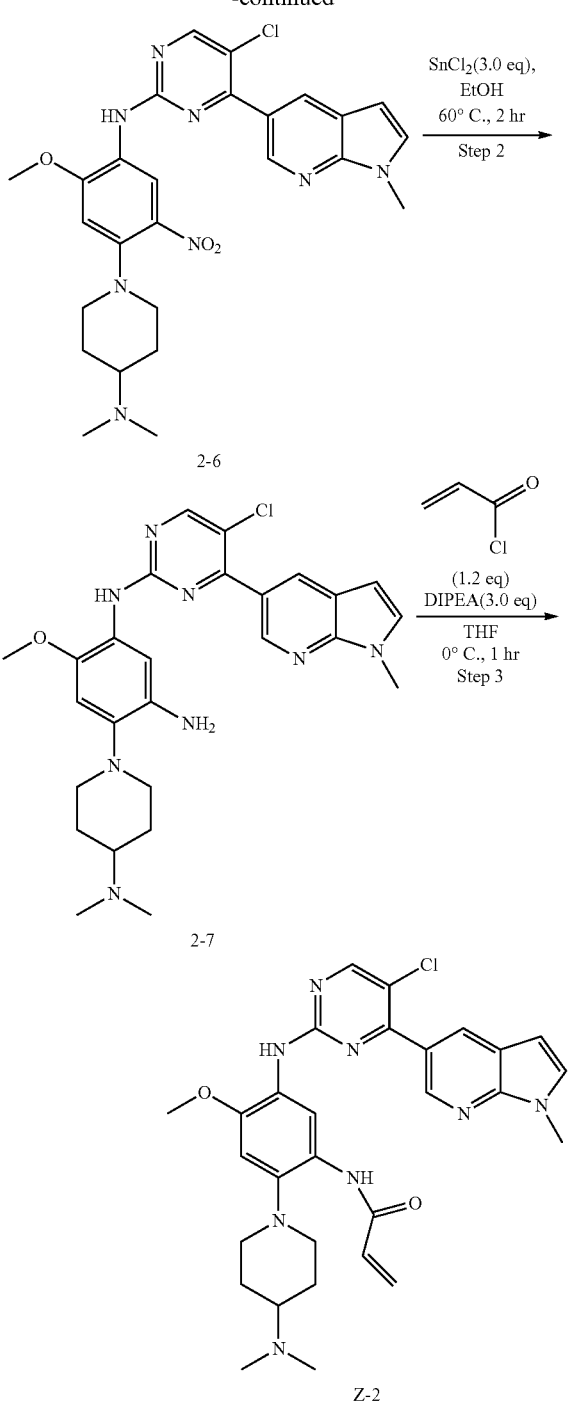

monitored by TLC. After completion of the reaction, the reaction solution was extracted with EA/water system for three times, and the organic layer was separated, washed with water, saturated brine, dried over anhydrous $Na_2SO_4$, and concentrated under reduced pressure to give the crude compound 2-6, 220 mg, yield 68%. MS M/Z (ESI) 537.2 [M+H]+.

Step 2: $N^1$-(5-chloro-4-(1-methyl-1H-pyrrolo[2,3-b]pyridin-5-yl)pyrimidin-2-yl)-4-(4-(dimethylamino)piperidin-1-yl)-6-methoxybenzene-1,3-diamine (Compound 2-7)

The reaction substrate 2-6 (110 mg, 0.205 mmol) was added into a 25 ml reaction flask, and ethanol (6 mL) was added. Stannous chloride (138 mg, 0.615 mmol) was added into the reaction flask with stirring at room temperature, and the reaction system was maintained at 60° C. for 2 h. The reaction progress was monitored by TLC. After completion of the reaction, the reaction solution was concentrated by evaporation, and extracted with EA/water system for three times, and the organic layer was separated, and washed with water, saturated brine, and dried over anhydrous $Na_2SO_4$. The filtrate was concentrated under reduced pressure to give the crude product 2-7 (80 mg, 76.9%) which was used directly in the next reaction.

Step 3: N-(5-(5-chloro-4-(1-methyl-1H-pyrrolo[2,3-b]pyridin-5-yl)pyrimidin-2-amino)-2-(4-(dimethylamino)piperidin-1-yl)-4-methoxyphenyl)acrylamide (Compound Z-2)

Acryloyl chloride (17 mg, 0.188 mmol) and DIEA (60.8 mg, 0.471 mmol) were added to a solution of compound 2-7 (80 mg, 0.157 mmol) in 3 ml of THF at 0° C., and vigorously stirred at 0° C. for 2 h. After completion of the reaction, the reaction solution was diluted with water and extracted with dichloromethane/water system for three times, and the organic layer was concentrated under reduced pressure to give the crude product, which was separated and purified by preparative liquid chromatography to give compound Z-2 (9.0 mg, 10%). MS m/z (ESI): 560.8 [M+H]+; $^1$HNMR (400 MHz, DMSO-d6) δ 8.98 (s, 1H), 8.75-8.74 (d, J=4.0 Hz, 1H), 8.48-8.53 (m, 4H), 7.62-7.61 (d, J=4.0 Hz, 1H), 6.84 (s, 1H), 6.71-6.57 (m, 2H), 6.29-6.25 (d, J=16.0 Hz, 1H), 5.77-5.74 (d, J=12.0 Hz, 1H), 3.87 (s, 3H), 3.82 (s, 3H), 3.05-3.02 (d, J=12.0 Hz, 2H), 2.69-2.63 (m, 2H), 2.30-2.19 (m, 7H), 1.91-1.83 (m, 2H), 1.70-1.68 (m, 2H).

Example 3: N-(5-(5-chloro-4-(1-methyl-1H-pyrrolo[2,3-b]pyridin-5-yl)pyrimidin-2-amino)-4-methoxy-2-(4-methylpiperazin-1-yl)phenyl)acrylamide (Compound Z-3)

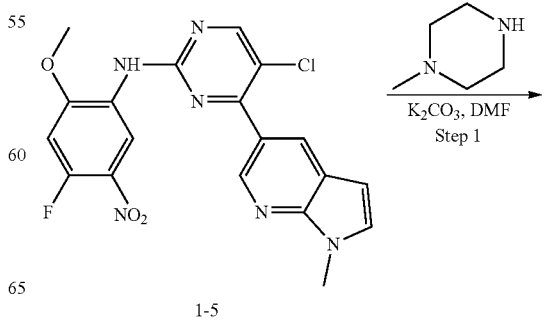

Step 1: 5-chloro-N-(4-(4-(dimethylamino)piperidin-1-yl)-2-methoxy-5-nitrophenyl)-4-(1-methyl-1H-pyrrolo[2,3-b]pyridin-5-yl)pyrimidin-2-amine (Compound 2-6)

Compound 1-5 (260 mg, 0.607 mmol) and potassium carbonate (251 mg, 1.822 mmol) were added into a 25 ml reaction flask, DMF (10 mL) was added to partially dissolve the substrate, and then N,N-dimethylamino piperidine (85.4 mg, 0.667 mmol) was added, and the reaction system was maintained at 70° C. for 3 h. The reaction progress was

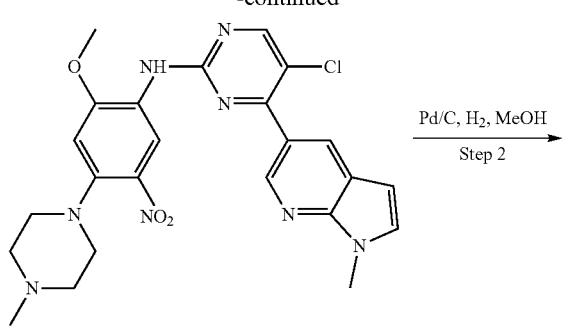

3-6

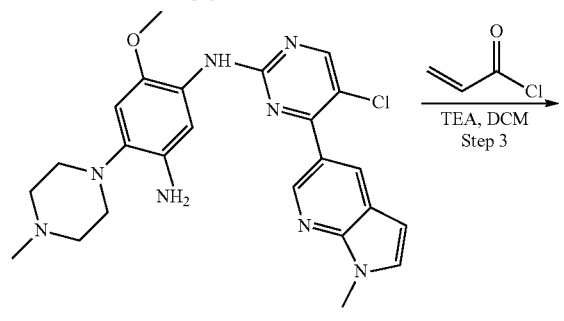

3-7

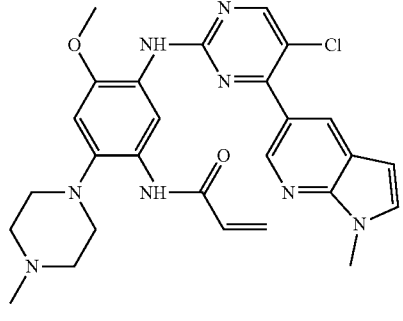

Z-3

Step 1: 5-chloro-N-(2-methoxy-4-(4-methylpiper-azin-1-yl)-5-nitrophenyl)-4-(1-methyl-1H-pyrrolo[2,3-b]pyridin-5-yl)pyrimidin-2-amine (Compound 3-6)

N-methylpiperazine (126 mg, 1.26 mmol) and potassium carbonate (261 mg, 1.89 mmol) were added to a solution of compound 1-5 (200 mg, 0.47 mmol) in 4 ml of DMF, and vigorously stirred at 100° C. for 2 h. The reaction progress was monitored by TLC. After completion of the reaction, 10 ml of water was added, extracted with EA/water system for three times, and the organic layer was separated, and concentrated under reduced pressure to give compound 3-6 (200 mg, 84%). MS m/z (ESI): 509.2[M+H]+.

Step 2: $N^1$-(5-chloro-4-(1-methyl-1H-pyrrolo[2,3-b]pyridin-5-yl)pyrimidin-2-yl)-6-methoxy-4-(4-methylpiperazin-1-yl)benzene-1,3-diamine (Compound 3-7)

By using compound 3-6 (200 mg, 0.39 mmol) as the starting material, compound 3-7 (140 mg, 75%) was synthesized with reference to step 6 of Example 1, and used directly in the next step. MS m/z (ESI): 479.1 [M+H]+.

Step 3: N-(5-(5-chloro-4-(1-methyl-1H-pyrrolo[2,3-b]pyridin-5-yl)pyrimidin-2-amino)-4-methoxy-2-(4-methylpiperazin-1-yl)phenyl)acrylamide (Compound Z-3)

By using compound 3-7 (140 mg, 0.29 mmol) as the starting material, compound Z-3 (1.60 mg, 1%) was synthesized with reference to step 7 of Example 1. MS m/z (ESI): 533.2 [M+H]+; $^1$HNMR (400 MHz, DMSO-d6) δ 8.98 (s, 1H), 8.76 (s, 1H), 8.51 (d, J=32.1 Hz, 3H), 7.63 (s, 1H), 6.86 (s, 1H), 6.63 (d, J=28.9 Hz, 2H), 6.27 (d, J=16.2 Hz, 1H), 5.76 (d, J=9.1 Hz, 1H), 5.33 (s, 1H), 3.88 (s, 3H), 3.84 (s, 3H), 2.86 (s, 4H), 2.55 (s, 2H), 2.26 (s, 3H), 1.99 (s, 2H).

Example 4: N-(2-(4-(dimethylamino)piperidin-1-yl)-4-methoxy-5-(4-(1-methyl-1H-pyrazolo[3,4-b]pyridin-5-yl)pyrimidin-2-ylamino)phenyl)acrylamide (Compound Z-4)

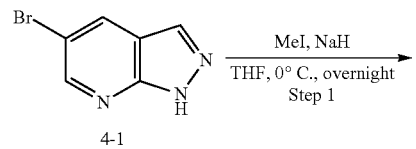

4-1

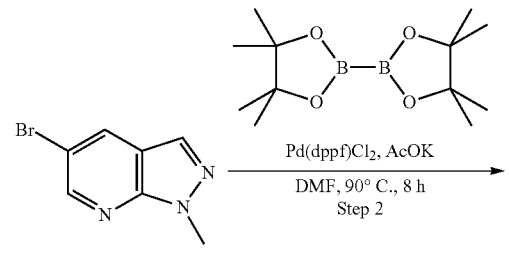

4-2

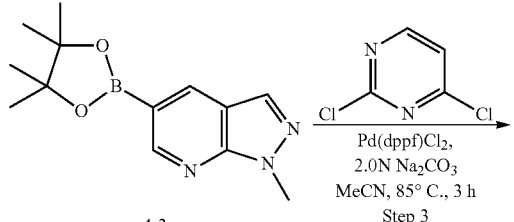

4-3

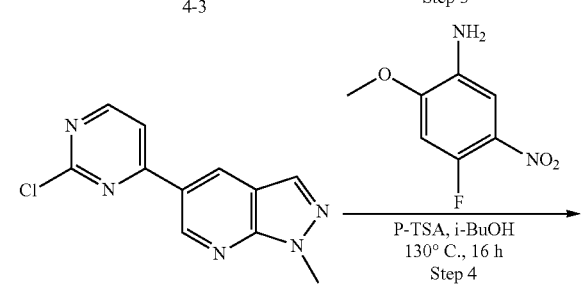

4-4

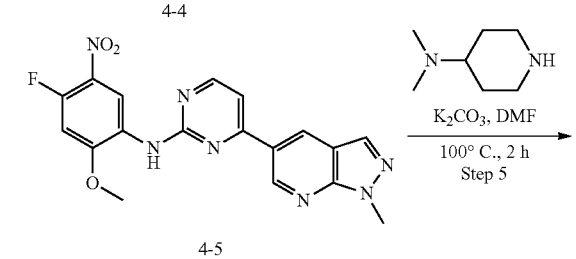

4-5

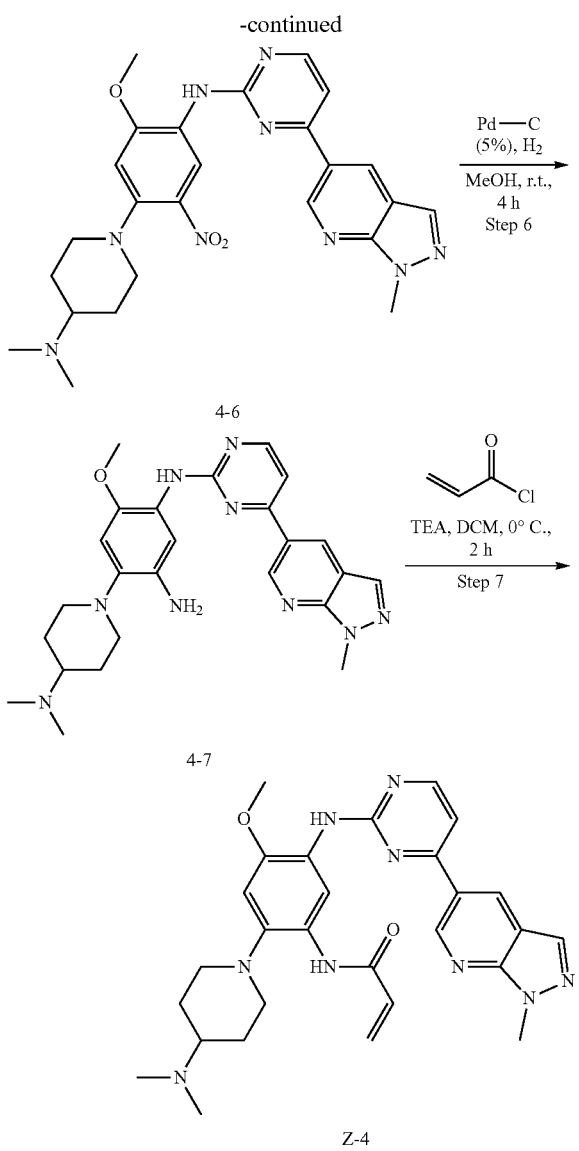

Step 1: 5-bromo-1-methyl-1H-pyrazolo[3,4-b]pyridine (Compound 4-2)

Sodium hydride (720 mg, 30 mmol) was added into a 100 ml reaction flask, and anhydrous THF (40 mL) was added to the reaction flask. After stirring at 0° C. for 5 min, the reaction substrate 5-bromo-1H-pyrazolo[3,4-b]pyridine (4.0 g, 20 mmol, commercially available) was dissolved in THF (20 ml), and the resulting solution was slowly added dropwise to the reaction flask through the constant pressure funnel, and stirred for 30 min. Afterwards, iodomethane (1.6 ml, 26 mmol) was added dropwise to the reaction system. After completion of the addition, the reaction solution was slowly warmed to room temperature and stirred overnight. The reaction progress was monitored by TLC. After completion of the reaction, 10 ml of ice water was added to the reaction system to quench the reaction, THF was removed by concentration under reduced pressure, and the residue was extracted with dichloromethane (60 ml) and water (20 ml×3). The organic layer was dried over anhydrous $Na_2SO_4$, and concentrated under reduced pressure to give 4.1 g brown solid, which was separated and purified by Combi-flash chromatography [PE:EA=10:90-40:60] to give the title compound 4-2 (3.1 g, 73%). MS m/z (ESI): 211.9 [M+H]+.

Step 2: 1-methyl-5-(4,4,5,5-tetramethyl-1,3,2-dioxaborolan-2-yl)-1H-pyrazolo[3,4-b]pyridine (Compound 4-3)

Compound 4-2 (3.1 g, 14.6 mmol) and bis(pinacolato)borate (11.1 g, 43.8 mmol) were added into a 250 ml reaction flask, and DMF (150 ml) and potassium acetate (4.3 g, 43.8 mmol) was added. After the air of reaction system was replaced by argon for three times, $Pd(dppf)Cl_2$ (0.55 g, 0.73 mmol) was added, and then the air was replaced with nitrogen for another three times. The reaction system was heated to 90° C., and stirred for 8 h. The reaction progress was monitored by LC-MS. After completion of the reaction, the reaction solution was filtered, the filter cake was washed with EA (30 ml×3), and the filtrate was concentrated under reduced pressure to remove DMF and give compound 4-3 (13.5 g) as brown solid which was used directly in next reaction. MS m/z (ESI): 260.2 [M+H]+.

Step 3: 5-(2-chloropyrimidin-4-yl)-1-methyl-1H-pyrazolo[3,4-b]pyridine (Compound 4-4)

The reaction substrate 4-3 (3.8 g, 14.6 mmol) and 2,4-dichloropyrimidine (2.6 g, 17.5 mmol) were added into a 250 ml reaction flask, and acetonitrile (130 ml) and sodium carbonate solution (22 mL, 2M) were added. After the air of reaction system was replaced by argon for three times, $Pd(dppf)Cl_2$ (0.55 g, 0.73 mmol) was added, and then the air was replaced with nitrogen for another three times. The reaction system was heated to 85° C., and stirred continuously for 3 h. The reaction progress was monitored by LC-MS. After completion of the reaction, the reaction mixture was cooled to room temperature and large amount of solids precipitated, and filtered, the filter cake was washed with EA (10 ml×3) and dried to constant weight to give 2.2 g yellow solid, and the filtrate was extracted with EA and water, dried, concentrated, and then purified by Combi-flash chromatography [PE:EA=10:90-70:30] to get 0.6 g yellow solids. The solids were combined to give the title compound 4-4 (2.8 g, 78%). MS m/z (ESI): 246.1 [M+H]+

Step 4: N-(4-fluoro-2-methoxy-5-nitrophenyl)-4-(1-methyl-1H-pyrazolo[3,4-b]pyridin-5-yl)pyrimidin-2-amine (Compound 4-5)

The reaction substrate 4-4 (420 mg, 1.7 mmol) and 4-fluoro-2-methoxy-5-nitroaniline (316 mg, 1.7 mmol) were placed in 100 mL sealed tube, and iso-butanol (40 mL) was added to partially solve the substrate. Then p-toluenesulfonic acid (807 mg, 4.25 mmol) was added, and the reaction system was sealed and heated at 130° C. for 16 h. After completion of the reaction, the reaction mixture was cooled to room temperature and large amount of solids precipitated from the solution. The solids were filtered with Buchner filtration to obtain a filter cake, which was beat in ethanol at reflux, to give the title compound 4-5 (524 mg, 78%), which was used directly in the next reaction. Purity: 47%. MS m/z (ESI): 396.2 [M+H]+

Step 5

N-(4-(4-(dimethylamino)piperidin-1-yl)-2-methoxy-5-nitrophenyl)-4-(1-methyl-1H-pyrazolo[3,4-b]pyridin-5-yl)pyrimidin-2-amine (Compound 4-6)

The reaction substrate 4-5 (146 mg, 0.25 mmol) and potassium carbonate (104 mg, 0.75 mmol) were added into a 25 ml reaction flask, DMF (10 mL) was added to completely dissolve the substrate. Afterwards, 4-dimethylamino piperidine (42 mg, 0.325 mmol) was added, and the reaction system was heated at 100° C. for 2 h. The reaction progress was monitored by TLC. After completion of the reaction, the reaction solution was extracted with EA/water system for three times, the organic layer was separated, washed with water, saturated brine, dried over anhydrous Na$_2$SO$_4$, and concentrated under reduced pressure to give the title compound 4-6 (120 mg, 98%). MS m/z (ESI): 504.2 [M+H]+.

Step 6: 4-(4-(dimethylamino)piperidin-1-yl)-6-methoxy-N$^1$-(4-(1-methyl-1H-pyrazolo[3,4-b]pyridin-5-yl)pyrimidin-2-yl)benzene-1,3-diamine (Compound 4-7)

By using compound 4-6 (120 mg, 0.24 mmol) as the starting material, compound 4-7 (113 mg) was synthesized with reference to step 6 of Example 1, and used directly in the next step. MS m/z (ESI): 474.3 [M+H]+.

Step 7: N-(2-(4-(dimethylamino)piperidin-1-yl)-4-methoxy-5-(4-(1-methyl-1H-pyrazolo[3,4-b]pyridin-5-yl)pyrimidin-2-ylamino)phenyl)acrylamide (Compound Z-4)

By using compound 4-7 (113 mg, 0.24 mmol) as the starting material, the crude product was synthesized with reference to step 7 of Example 1, and purified by prep-TLC chromatography [DCM:MeOH:NH4OH=9:1:0.1] to give the title compound Z-4 (6 mg, 5%). MS m/z (ESI): 528.3 [M+H]+; $^1$HNMR (400 MHz, DMSO-d6) δ 9.33 (s, 1H), 9.22 (s, 1H), 9.04 (s, 1H), 8.80 (s, 1H), 8.51-8.50 (d, J=5.6 Hz, 2H), 8.13 (s, 1H), 7.53-7.51 (d, J=5.6 Hz, 1H), 6.86 (s, 1H), 6.74-6.67 (m, 1H), 6.32-6.28 (d, J=17.0 Hz, 2H), 5.79-5.67 (d, J=13.4 Hz, 1H), 4.24 (s, 3H), 3.86 (s, 3H), 3.33 (s, 1H), 3.05-3.03 (d, J=10.7 Hz, 2H), 2.70-2.64 (t, J=11.7 Hz, 3H), 2.22 (s, 6H), 1.85-1.82 (d, J=11.3 Hz, 2H), 1.70-1.67 (d, J=12.1 Hz, 2H).

Example 5: N-(4-methoxy-5-(4-(1-methyl-1H-pyrazolo[3,4-b]pyridin-5-yl)pyrimidin-2-ylamino)-2-(4-methylpiperazin-1-yl)phenyl)acrylamide (Compound Z-5)

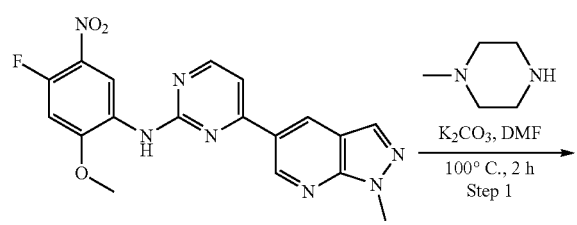

4-5

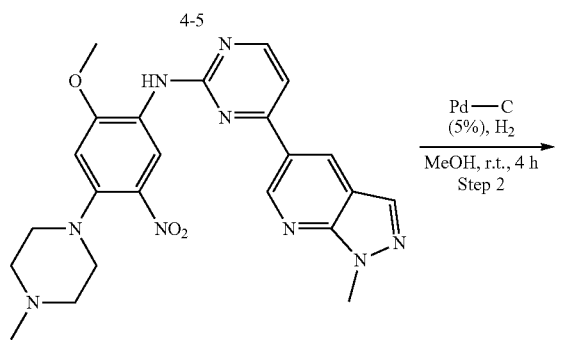

5-6

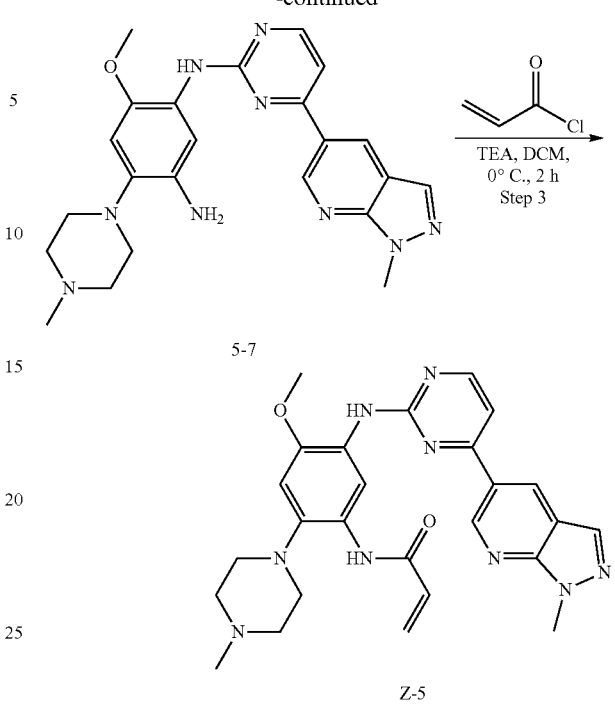

Step 1: N-(2-methoxy-4-(4-methylpiperazin-1-yl)-5-nitrophenyl)-4-(1-methyl-1H-pyrazolo[3,4-b]pyridin-5-yl)pyrimidin-2-amine (Compound 5-6)

Compound 4-5 (146 mg, 0.25 mmol) and potassium carbonate (104 mg, 0.75 mmol) were added into a 25 ml reaction flask, and DMF (10 mL) was added to completely dissolve the substrate. N-methylpiperazine (32 mg, 0.325 mmol) was then added, and the reaction system maintained at 100° C. for 2 h. The reaction progress was monitored by TLC. After completion of the reaction, the reaction solution was extracted with EA/water system for three times, and the organic layer was separated, washed with water, saturated brine, dried over anhydrous Na$_2$SO$_4$, and concentrated under reduced pressure to give the title compound 5-6 which was used directly in the next step. Purity: 88%. MS m/z (ESI): 476.2 [M+H]+.

Step 2: 6-methoxy-N$^1$-(4-(1-methyl-1H-pyrazolo[3,4-b]pyridin-5-yl)pyrimidin-2-yl)-4-(4-methylpiperazin-1-yl)benzene-1,3-diamine (Compound 5-7)

By using compound 5-6 (119 mg, 0.25 mmol) as the starting material, compound 5-7 was synthesized with reference to step 6 of Example 1, and used directly in the next reaction. Purity: 59%. MS m/z (ESI): 446.2 [M+H]+.

Step 3: N-(4-methoxy-5-(4-(1-methyl-1H-pyrazolo[3,4-b]pyridin-5-yl)pyrimidin-2-ylamino)-2-(4-methylpiperazin-1-yl)phenyl)acrylamide (Compound Z-5)

By using compound 5-7 (111 mg, 0.25 mmol) as the starting material, the crude product was synthesized with reference to step 7 of Example 1, and purified by prep-TLC chromatography [DCM:MeOH:NH4OH=9:1:0.1] to give the title compound Z-5 (8 mg, 6%). Purity: 96.5%. MS m/z (ESI): 500.2 [M+H]+; $^1$HNMR (400 MHz, DMSO-d6) δ 9.33 (s, 1H), 9.21 (s, 1H), 9.03 (s, 1H), 8.79 (s, 1H), 8.51-8.50 (d, J=5.2 Hz, 2H), 8.12 (s, 1H), 7.52-7.51 (d, J=5.2 Hz, 1H), 6.88 (s, 1H), 6.68-6.61 (m, 1H), 6.31-6.27 (d, J=16.9 Hz, 2H), 5.78-5.76 (d, J=9.9 Hz, 1H), 4.24 (s, 3H), 3.87 (s, 3H), 2.86 (s, 4H), 2.53-2.49 (d, J=13.6 Hz, 4H), 2.25 (s, 3H).

Example 6: N-(2-((2-(dimethylamino)ethyl)(methyl)amino)-4-methoxy-5-(4-(1-methyl-1H-pyrazolo[3,4-b]pyridin-5-yl)pyrimidin-2-ylamino)phenyl)acrylamide (Compound Z-6)

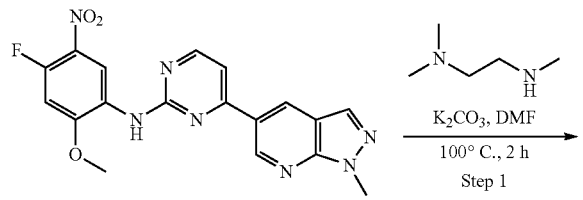

Step 1: $N^1$-(2-(dimethylamino)ethyl)-5-methoxy-$N^1$-methyl-$N^4$-(4-(1-methyl-1H-pyrazolo[3,4-b]pyridin-5-yl)pyrimidin-2-yl)-2-nitrobenzene-1,4-diamine (Compound 6-6)

Compound 4-5 (146 mg, 0.25 mmol) and potassium carbonate (104 mg, 0.75 mmol) were added into a 25 ml reaction flask, and DMF (10 mL) was added to completely dissolve the substrate. N,N,N-trimethyl ethylenediamine (34 mg, 0.325 mmol) was then added, and the reaction system maintained at 100° C. for 2 h. The reaction progress was monitored by TLC. After completion of the reaction, the reaction solution was extracted with EA/water system for three times, and the organic layer was separated, washed with water, saturated brine, dried over anhydrous Na$_2$SO$_4$, and concentrated under reduced pressure to give the title compound 6-6 which was used directly in the next step. Purity: 94%. MS m/z (ESI): 478.2 [M+H]+.

Step 2: $N^1$-(2-(dimethylamino)ethyl)-5-methoxy-$N^1$-methyl-$N^4$-(4-(1-methyl-1H-pyrazolo[3,4-b]pyridin-5-yl)pyrimidin-2-yl)benzene-1,2,4-triamine (Compound 6-7)

By using compound 6-6 (119 mg, 0.25 mmol) as the starting material, compound 6-7 was synthesized with reference to step 6 of Example 1, and used directly in the next reaction. Purity: 83%. MS m/z (ESI): 448.2 [M+H]+.

Step 3: N-(2-((2-(dimethylamino)ethyl)(methyl)amino)-4-methoxy-5-(4-(1-methyl-1H-pyrazolo[3,4-b]pyridin-5-yl)pyrimidin-2-ylamino)phenyl)acrylamide (Compound Z-6)

By using compound 6-7 (111 mg, 0.25 mmol) as the starting material, the crude product was synthesized with reference to step 7 of Example 1, and purified by prep-HPLC to give the title compound Z-6 (1 mg, 1%). Purity: 96.5%. MS m/z (ESI): 502.2 [M+H]+; $^1$HNMR (400 MHz, DMSO-d6) δ 10.13 (s, 1H), 9.35 (s, 1H), 9.27 (s, 1H), 9.12 (s, 1H), 8.52-8.51 (d, J=5.3 Hz, 1H), 8.50 (s, 2H), 8.20 (s, 1H), 8.14 (s, 1H), 7.54-7.53 (d, J=5.2 Hz, 1H), 7.03 (s, 1H), 6.50-6.44 (d, J=10.0 Hz, 1H), 6.34-6.29 (d, J=17.3 Hz, 1H), 5.80-5.78 (d, J=10.6 Hz, 1H), 4.24 (s, 3H), 3.87 (s, 3H), 2.92-2.90 (d, J=5.4 Hz, 2H), 2.69 (s, 3H), 2.39-2.36 (t, J=5.4 Hz, 2H), 2.25 (s, 6H).

Example 7: N-(5-(5-chloro-4-morpholinopyrimidin-2-ylamino)-2-(4-(dimethylamino)piperidin-1-yl)-4-methoxyphenyl)acrylamide (Compound Z-7) formate

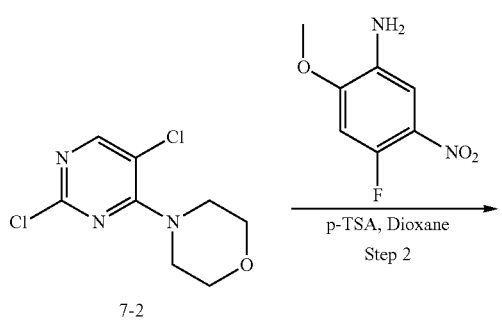

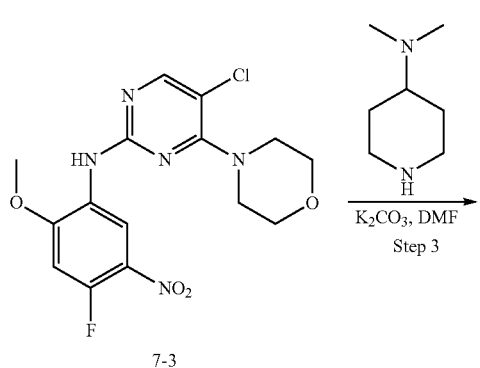

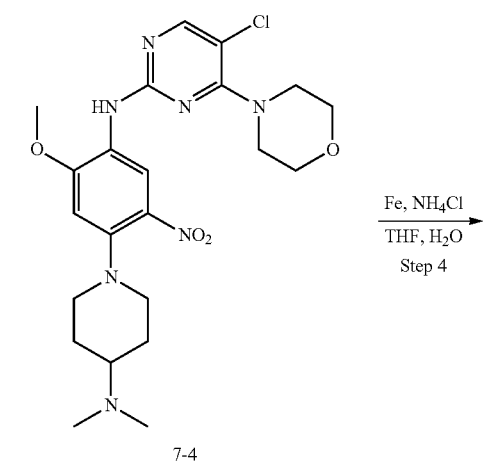

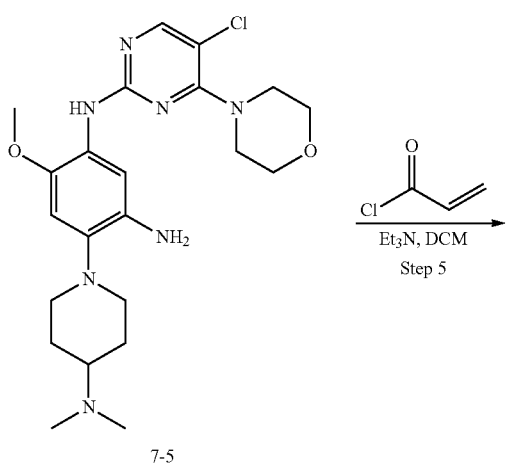

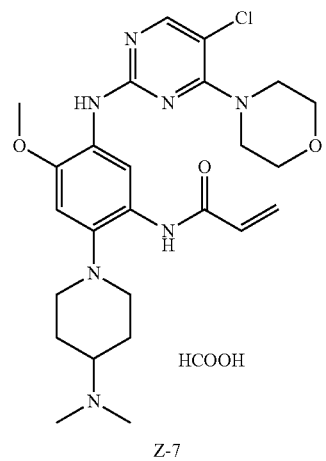 [SMILES: C=CC(=O)Nc1cc(Nc2ncc(Cl)c(N3CCOCC3)n2)c(OC)cc1N1CCC(N(C)C)CC1 ; "HCOOH"]

Step 1: 4-(2,5-dichloro-4-yl) morpholine (Compound 7-2)

At 25° C., Compound 2,4,5-trichloropyrimidine (5 g, 27.0 mmol) was added to 25 ml of THF, triethylamine (5.5 g, 54.0 mmol) was added, and morpholine (2.37 g, 27.0 mmol) was added dropwise to the reaction mixture, and stirred at room temperature for 1 h. The reaction progress was monitored by TLC. After completion of the reaction, water and EA were added, and the organic layer was separated, washed with saturated aqueous sodium chloride, dried, and concentrated under reduced pressure to give compound 7-2 (5.2 g) which was used directly in the next step. MS m/z (ESI): 234.0 [M+H]+.

Step 2: 5-chloro-N-(4-fluoro-2-methoxy-5-nitrophenyl)-4-morpholinopyrimidin-2-amine (Compound 7-3)

Compound 7-2 (1.0 g, 4.2 mmol), 4-fluoro-2-methoxy-5-nitroaniline (0.83 g, 4.4 mmol) and p-toluenesulfonic acid (2.57 g, 15.0 mmol) were added to 10 ml of 1,4-dioxane, and vigorously stirred under $N_2$ atmosphere at 110° C. for 8 h. After completion of the reaction, the reaction solution was filtered, and the filter cake was washed with EA, and dried at 50° C. to give the crude product compound 7-3 (1.16 g) which was used directly in the next step. MS m/z (ESI): 284.1 [M+H]+.

Step 3: 5-chloro-N-(4-(4-(dimethylamino)piperidin-1-yl)-2-methoxy-5-nitrophenyl)-4-morpholinopyrimidin-2-amine (Compound 7-4)

Compound 7-3 (0.1 g, 0.26 mmol), 4-dimethylamino piperidine (0.033 g, 0.26 mmol) and potassium carbonate (0.072 g, 0.52 mmol) were added to DMF, and vigorously stirred under $N_2$ atmosphere at 100° C. for 2 h. After completion of the reaction, the reaction mixture was diluted with water and extracted with EA/water system for three times, and dried, and the organic layer was concentrated under reduced pressure to give the crude product compound 7-4 (0.21 g) which was used directly in the next step. MS m/z (ESI): 492.2[M+H]+.

Step 4: N-(5-chloro-4-morpholinopyrimidin-2-yl)-4-(4-(dimethylamino)piperidin-1-yl)-6-methoxybenzene-1,3-diamine (Compound 7-5)

Compound 7-4 (0.2 g, 0.41 mmol), iron powder (0.51 g, 8.1 mmol) and ammonium chloride (0.11 g, 2.0 mmol) were added to 16 ml of mixed solution of water and THF, and vigorously stirred under N₂ atmosphere at 65° C. for 3 h. After completion of the reaction, the reaction mixture was filtered, and the filtrate was extracted with EA, washed with water, dried, and concentrated under reduced pressure to give compound 7-5 (0.19 g) which was used directly in the next step. MS m/z (ESI): 462.2[M+H]+.

Step 5: N-(5-(5-chloro-4-morpholinopyrimidin-2-yl)amino)-2-(4-(dimethylamino)piperidin-1-yl)-4-methoxyphenyl)acrylamide (Compound Z-7) formate At 0° C., acryloyl chloride (40 mg, 0.43 mmol) and triethylamine (50 mg, 0.49 mmol) were added to a solution of compound 7-5 (190 mg, 0.41 mmol) in 5 ml of dichloromethane, and vigorously stirred at 0° C. for 2 h. After completion of the reaction, the reaction mixture was diluted with water and extracted with dichloromethane/water system for three times, and the organic layer was concentrated under reduced pressure to give the crude product which was purified by preparative liquid chromatography to give the formate of compound Z-7 (4.27 mg, 3.1% yield of five steps). MS m/z (ESI): 562.2 [M+H]+; ¹HNMR (400 MHz, DMSO-d6) δ 8.98 (s, 1H), 8.57 (s, 1H), 8.28 (s, 1H), 8.06 (s, 1H), 7.83 (s, 1H), 6.80 (s, 1H), 6.65 (dd, J=17.0, 10.1 Hz, 1H), 6.21 (d, J=17.0 Hz, 1H), 5.72 (d, J=10.3 Hz, 1H), 3.84 (s, 3H), 3.65 (d, J=7.6 Hz, 8H), 3.02 (d, J=11.0 Hz, 2H), 2.64 (t, J=11.0 Hz, 2H), 2.27 (overlap, 7H), 1.84 (d, J=10.7 Hz, 2H), 1.68 (d, J=9.6 Hz, 2H).

Example 8: N-(5-(5-chloro-4-morpholinopyrimidin-2-ylamino)-4-methoxy-2-(4-methylpiperazin-1-yl)phenyl)acrylamide (Compound Z-8)

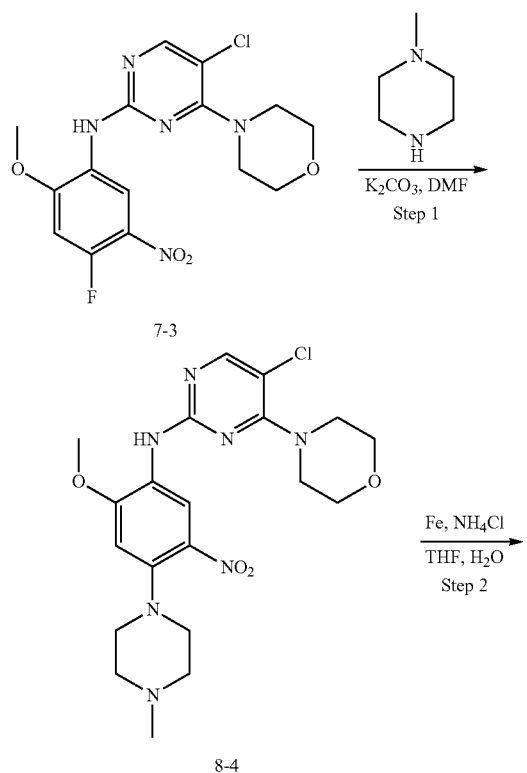

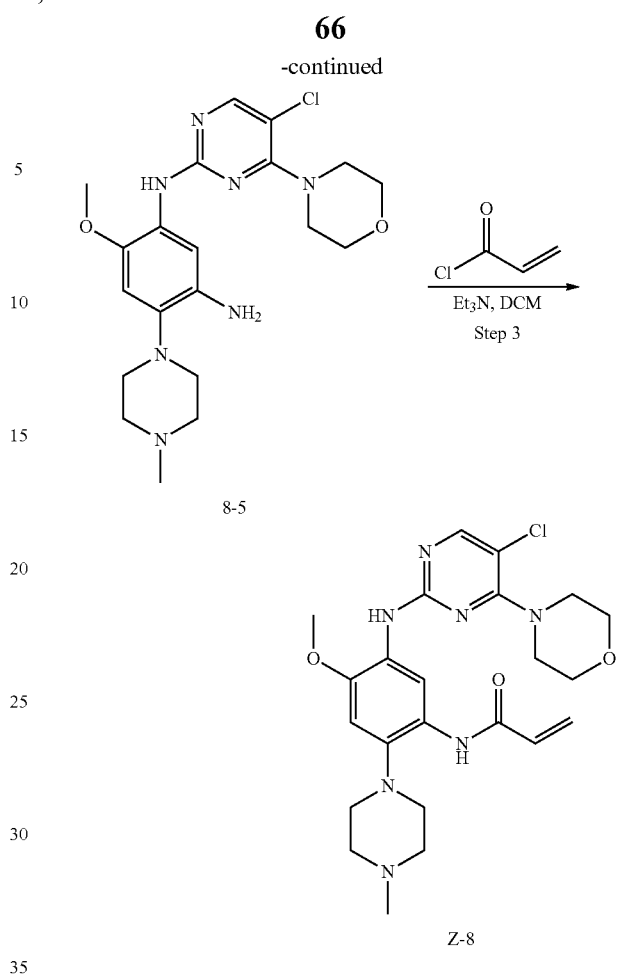

Step 1: 5-chloro-N-(2-methoxy-4-(4-methylpiperazin-1-yl)-5-nitrophenyl)-4-morpholinopyrimidin-2-amine (Compound 8-4)

Compound 7-3 (0.5 g, 1.3 mmol), N-methylpiperazine (0.13 g, 1.3 mmol) and potassium carbonate (0.36 g, 2.6 mmol) were added to DMF, and stirred under N₂ atmosphere at 100° C. for 2 h. After completion of the reaction, the reaction mixture was diluted with water and extracted with EA/water system, washed with water for three times, and dried, and the organic layer was concentrated under reduced pressure to give the crude product compound 8-4 (0.6 g) which was used directly in the next step. MS m/z (ESI): 464.1 [M+H]+.

Step 2: N-(5-chloro-4-morpholinopyrimidin-2-yl)-6-methoxy-4-(4-methylpiperazin-1-yl)benzene-1,3-diamine (Compound 8-5)

By using compound 8-4 (0.6 g, 1.3 mmol) as the starting material, compound 8-5 (0.56 g) was synthesized with reference to step 4 of Example 7, and was used directly in the next step. MS m/z (ESI): 434.2[M+H]+.

Step 3: N-(5-(5-chloro-4-morpholinopyrimidin-2-ylamino)-4-methoxy-2-(4-methylpiperazin-1-yl)phenyl)acrylamide (Compound Z-8)

By using compound 8-5 (0.56 g, 1.3 mmol) as the starting material, the crude product was synthesized with reference to step 7 of Example 1, and purified by preparative liquid chromatography to give compound Z-8 (44.51 mg, yield of three steps 7.0%). MS m/z (ESI): 488.2 [M+H]+; ¹HNMR (400 MHz, CDCl₃) δ 9.26 (s, 1H), 8.46 (s, 1H), 7.94 (s, 1H), 7.43 (s, 1H), 6.69 (s, 1H), 6.29 (d, J=16.8 Hz, 1H), 6.18 (dd, J=16.8, 10.0 Hz, 1H), 5.66 (dd, J=10.0, 1.3 Hz, 1H), 3.78 (s, 3H), 3.76 (s, 8H), 2.82 (d, J=4.2 Hz, 4H), 2.55 (d, J=13.4 Hz, 4H), 2.32 (s, 3H).

Example 9: N-(5-(5-chloro-4-morpholinopyrimidin-2-ylamino)-2-((2-(dimethylamino)ethyl)methyl amino)-4-methoxyphenyl)acrylamide (Compound Z-9)

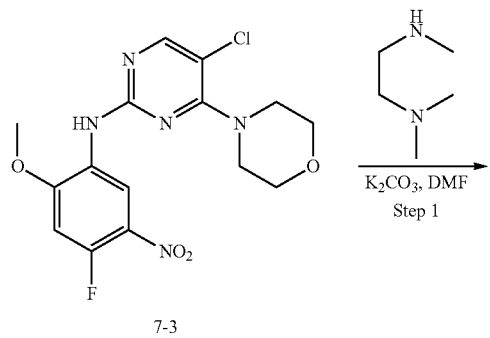

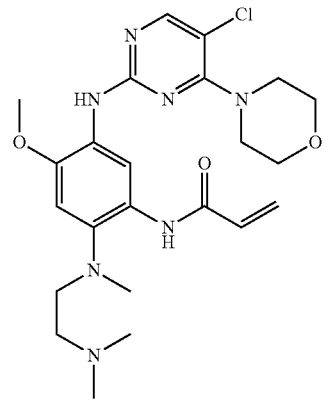

Step 1: N-(5-chloro-4-morpholinopyrimidin-2-yl)-N-(2-(dimethylamino)ethyl)-2-methoxy-N-methyl-5-nitrobenzene-1,4-diamine (Compound 9-4)

Compound 7-3 (0.5 g, 1.3 mmol), N,N,N'-trimethyl ethylenediamine (0.26 g, 2.6 mmol) and potassium carbonate (0.36 g, 2.6 mmol) were added to DMF, and stirred under N₂ atmosphere at 100° C. for 2 h. After completion of the reaction, the reaction mixture was diluted with water and extracted with EA/water system, washed with water for three times, and dried, and the organic layer was concentrated under reduced pressure to give the crude product compound 9-4 (0.6 g) which was used directly in the next step. MS m/z (ESI): 466.1[M+H]+.

Step 2: N-(5-chloro-4-morpholinopyrimidin-2-yl)-N-(2-(dimethylamino)ethyl)-5-methoxy-N-methyl-benzene-1,2,4-triamine (Compound 9-5)

By using compound 9-4 (0.6 g, 1.3 mmol) as the starting material, compound 9-5 (0.56 g) was synthesized with reference to step 4 of Example 7, and was used directly in the next step. MS m/z (ESI): 436.2[M+H]+.

Step 3: N-(5-((5-chloro-4-morpholinopyrimidin-2-yl)amino)-2-((2-(dimethylamino)ethyl)methyl-amino)-4-methoxyphenyl)acrylamide (Compound Z-9)

By using compound 9-5 (0.50 g, 1.2 mmol) as the starting material, the crude product was synthesized with reference to step 7 of Example 1, and purified by preparative liquid chromatography to give compound Z-9 (77.19 mg, yield of three steps 12.1%). MS m/z (ESI): 490.2 [M+H]+; ¹HNMR (400 MHz, CDCl₃) δ 10.00 (s, 1H), 9.29 (s, 1H), 7.94 (s, 1H), 7.44 (s, 1H), 6.69 (s, 1H), 6.31 (dd, J=16.9, 1.8 Hz, 1H), 6.21 (d, J=9.6 Hz, 1H), 5.59 (dd, J=10.0, 1.8 Hz, 1H), 3.78 (d, J=7.3 Hz, 9H), 2.79 (s, 2H), 2.62 (s, 3H), 2.18 (s, 6H), 1.53 (s, 4H).

Example 10: N-(2-(3-(dimethylamino)azetidin-1-yl)-4-methoxy-5-((4-(quinolin-3-yl)pyrimidin-2-yl)amino)phenyl)acrylamide (Compound Z-10)

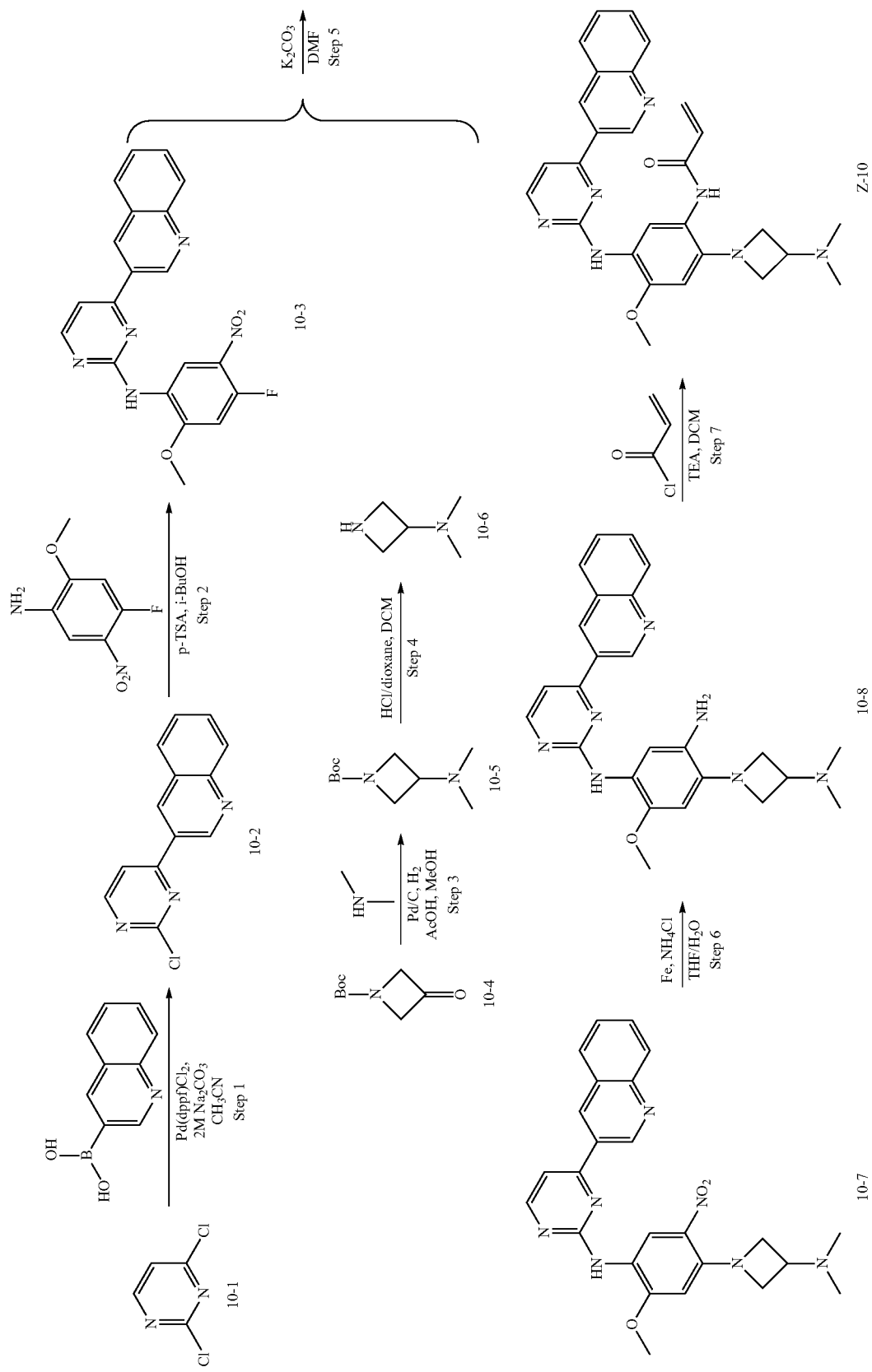

Step 1: 3-(2-chloropyrimidin-4-yl)quinoline (Compound 10-2)

Compound 2,4-dichloropyrimidine (5.0 g, 34 mmol, commercially available) and quinoline-3-boronic acid (5.8 g, 34 mmol, commercially available) were added to a solution of acetonitrile (120 ml) and sodium carbonate (50 ml, 2M). After the air of reaction system was replaced by argon for three times, Pd(dppf)Cl$_2$ (494 mg, 0.68 mmol) was added, and then the air was replaced with nitrogen for another three times. The reaction system was heated to 80° C., and stirred continuously for 6 h. The reaction progress was monitored by TLC. After completion of the reaction, the reaction mixture was diluted with water, the precipitated gray solids were filtered by Buchner, and the filter cake was washed with water, and dried to constant weight to give compound 10-2 (4.6 g, 57%) which was used directly in the next step. MS m/z (ESI): 242.7 [M+H]+.

Step 2: N-(4-fluoro-2-methoxy-5-nitrophenyl)-4-(quinolin-3-yl)pyrimidin-2-amine (Compound 10-3)

4-fluoro-2-methoxy-5-nitroaniline (2.2 g, 12 mmol) and compound 10-2 (2.9 g, 12 mmol) were added to a solution of p-toluenesulfonic acid (p-TSA) (2.1 g, 12 mmol) in 40 ml of n-butanol, and the reaction mixture was heated at 130° C. for 6 h in the sealed tube. After completion of the reaction, the reaction mixture was cooled to room temperature and large amount of solids precipitated from the solution. The solids were filtered by Buchner to obtain a filter cake which was beat in ethanol at reflux to give compound 10-3 (4.3 g, 64%), which was used directly in the next reaction. MS m/z (ESI): 392.0[M+H]+.

Step 3: tert-butyl 3-(dimethylamino)azetidine-1-carboxylate (Compound 10-5)

Compound tert-butyl 3-oxo-azetidine-1-carboxylate (2.0 g, 11.7 mmol, commercially available) and dimethylamine hydrochloride (1.3 g, 17 mmol) were added to a 100 ml solution of acetic acid (1 ml) in methanol, and palladium on carbon (1.4 g) was added. After the air was replaced by hydrogen for three times, the reaction mixture was stirred under hydrogen atmosphere for 5 h. After completion of the reaction, the remaining palladium-carbon was filtered off, and the filtrate was concentrated under reduced pressure to give compound 10-5 (2.2 g, 80%) which was used directly in the next reaction. MS m/z (ESI): 200.1 [M+H]+

Step 4: 3-(dimethylamino) azetidine (compound 10-6) hydrochloride

A solution of hydrochloric acid in 1,4-dioxane (10 ml) was added to 15 ml of compound 10-5 (2.2 g, 11 mmol), and stirred at room temperature for 3 h. After completion of the reaction, the reaction mixture was concentrated under reduced pressure to give compound 10-6 (1.3 g, 90%) which was used directly in the next reaction. MS m/z (ESI): 100.1 [M+H]+.

Step 5: N-(4-(3-(dimethylamino)azetidin-1-yl)-2-methoxy-5-nitrophenyl)-4-(quinolin-3-yl)pyrimidin-2-amine (compound 10-7)

Compound 10-6 (160 mg, 1.16 mmol) and potassium carbonate (350 mg, 2.3 mmol) were added to a solution of compound 10-3 (300 mg, 0.58 mmol) in 4 ml of DMF, stirred at 100° C. for 2 h. The reaction progress was monitored by TLC. After completion of the reaction, 10 ml of water was added, the reaction mixture was extracted with EA/water system for three times, and the organic layer was separated, and concentrated under reduced pressure to give compound 10-7 (130 mg, 50%) which was used directly in the next reaction. MS m/z (ESI): 472.2[M+H]+.

Step 6: 4-(3-(dimethylamino)azetidin-1-yl)-6-methoxy-N$^1$-(4-(quinolin-3-yl)pyrimidin-2-yl)phenyl-1,3-diamine (Compound 10-8)

By using compound 10-7 (130 mg, 0.27 mmol) as the starting material, compound 10-8 (80 mg. 70%) was synthesized with reference to step 4 of Example 7, and was used directly in the next step. MS m/z (ESI): 441.2 [M+H]+.

Step 7: N-(2-(3-(dimethylamino)azetidin-1-yl)-4-methoxy-5-((4-(quinolin-3-yl)pyrimidin-2-yl)amino)phenyl)acrylamide (Compound Z-10)

By using compound 10-8 (80 mg, 0.17 mmol) as the starting material, the crude product was synthesized with reference to step 7 of Example 1, and purified by preparative liquid chromatography to give compound Z-10 (30.69 mg, 30%). MS m/z (ESI): 496.2 [M+H]+, $^1$HNMR (400 MHz, CDCl$_3$) δ 9.40 (d, J=2.0 Hz, 1H), 9.32 (s, 1H), 9.16 (s, 1H), 8.45 (d, J=5.1 Hz, 1H), 8.25 (s, 1H), 8.06 (d, J=8.5 Hz, 1H), 7.68 (dd, J=18.2, 10.0 Hz, 2H), 7.54-7.43 (m, 2H), 7.22 (d, J=5.2 Hz, 1H), 6.49-6.37 (m, 2H), 6.33 (d, J=10.1 Hz, 1H), 5.73 (d, J=10.2 Hz, 1H), 3.92-3.78 (m, 5H), 3.58 (t, J=6.5 Hz, 2H), 3.07 (d, J=6.3 Hz, 1H), 2.13 (d, J=17.8 Hz, 6H).

Example 11: (R)-N-(2-(3-(dimethylamino)pyrrolidin-1-yl)-4-methoxy-5-((4-(quinolin-3-yl)pyrimidine-2-yl)amino) phenyl) acrylamide (Compound Z-11)

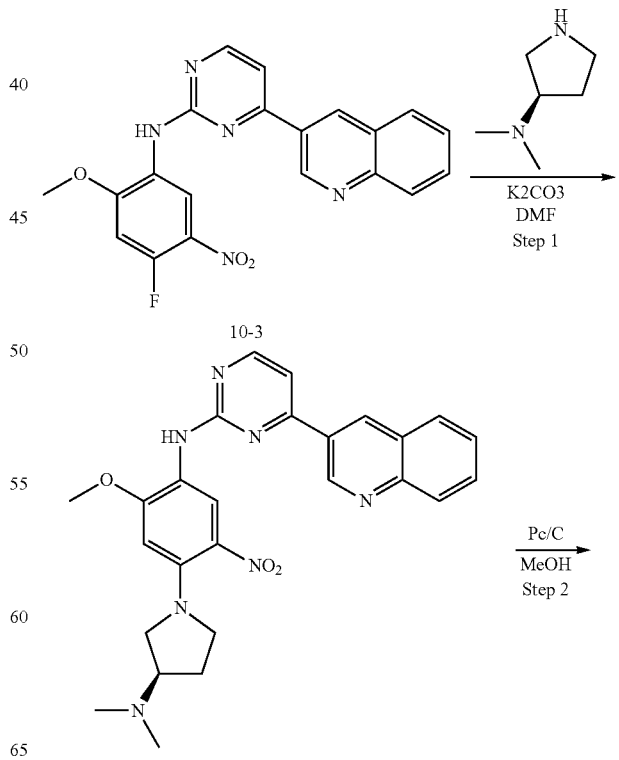

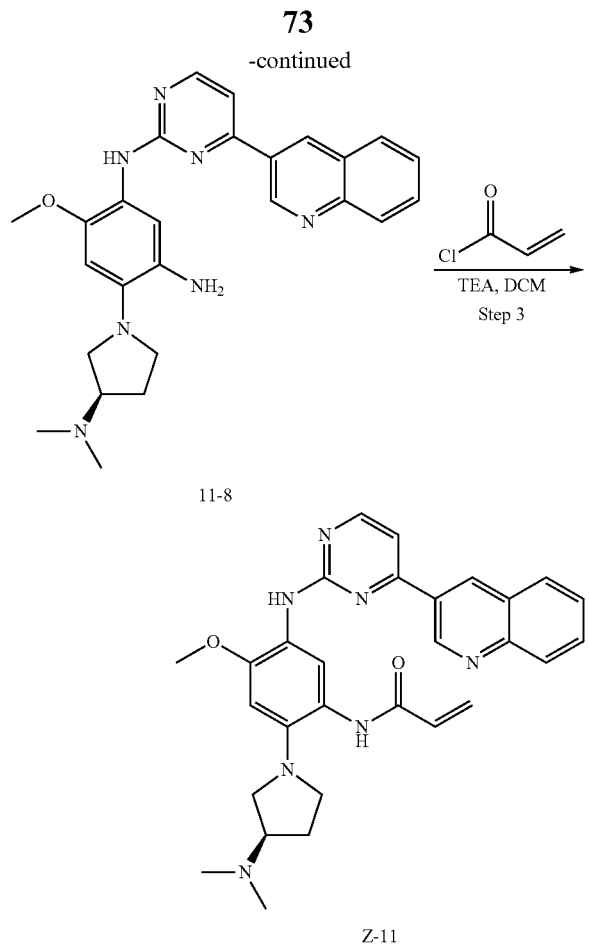

reference to step 7 of Example 1, and purified by preparative liquid chromatography to give compound Z-11 (23.58 mg, 9.87%). MS m/z (ESI): 509.9 [M+H]+; ¹HNMR (400 MHz, DMSO-d6): δ 9.67 (1s, 1H), 9.40 (1s, 1H), 8.59 (d, J=4 Hz, 1H), 8.39 (s, 1H), 8.31 (s, 1H), 8.07 (d, J=8 Hz, 1H), 7.70 (m, 2H), 7.50 (m, 1H), 7.27 (m, 1H), 6.74 (s, 1H), 6.35 (m, 2H), 5.73 (d, J=8 Hz, 1H), 3.83 (s, 3H), 3.05 (m, 4H), 1.16 (m, 1H), 2.24 (s, 6H), 2.05 (m, 2H).

Example 12: N-(4-methoxy-2-(1-methyl-1,2,3,6-tetrahydropyridin-4-yl)-5-((4-(quinolin-3-yl)pyrimidin-2-yl)amino)phenyl)acrylamide (Compound Z-12)

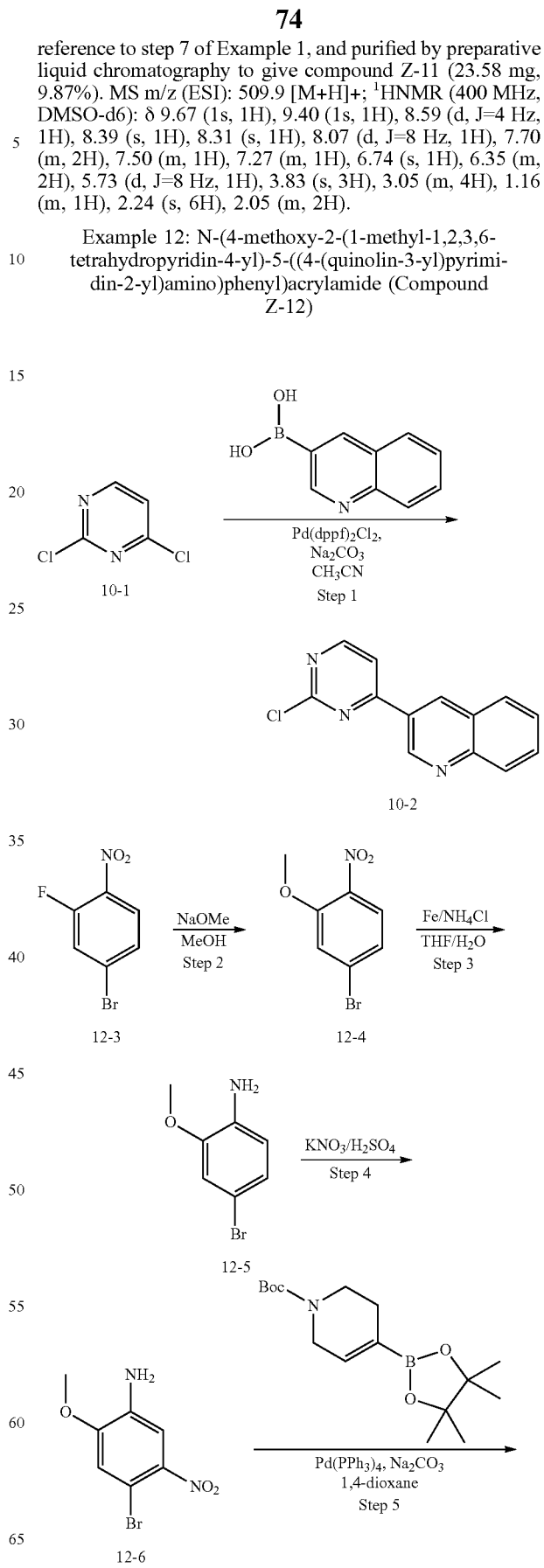

Step 1: (R)-N-(4-(3-(dimethylamino)pyrrolidin-1-yl)-2-methoxy-5-nitrophenyl)-4-(quinolin-3-yl)pyrimidin-2-amine (Compound 11-7)

(R)-N,N-dimethylpyrrolidin-3-amine (80 mg, 0.70 mmol, commercially available) and potassium carbonate (193 mg, 1.40 mmol) were added to a solution of compound 10-3 (200 mg, 0.47 mmol) in 4 ml of DMF, and vigorously stirred at 100° C. for 2 h. The reaction progress was monitored by TLC. After completion of the reaction, 10 ml of water was added, extracted with EA/water system for three times, and the organic layer was separated, and concentrated under reduced pressure to give compound 11-7 (180 mg, 79%). MS m/z (ESI): 486.2 [M+H]+.

Step 2: (R)-4-(3-(dimethylamino)pyrrolidin-1-yl)-6-methoxy-N¹-(4-(quinolin-3-yl) pyrimidin-2-yl) benzene-1,3-diamine (Compound 11-8)

By using compound 11-7 (180 mg, 0.37 mmol) as the starting material, compound 11-8 (150 mg, 89%) was synthesized with reference to step 6 of Example 1, which was used directly in the next step. MS m/z (ESI): 456.2 [M+H]+.

Step 3: (R)-N-(2-(3-(dimethylamino)pyrrolidin-1-yl)-4-methoxy-5-((4-(quinolin-3-yl) pyrimidine-2-yl)amino)phenyl)acrylamide (Compound Z-11)

By using compound 11-8 (150 mg, 0.3 mmol) as the starting material, the crude product was synthesized with

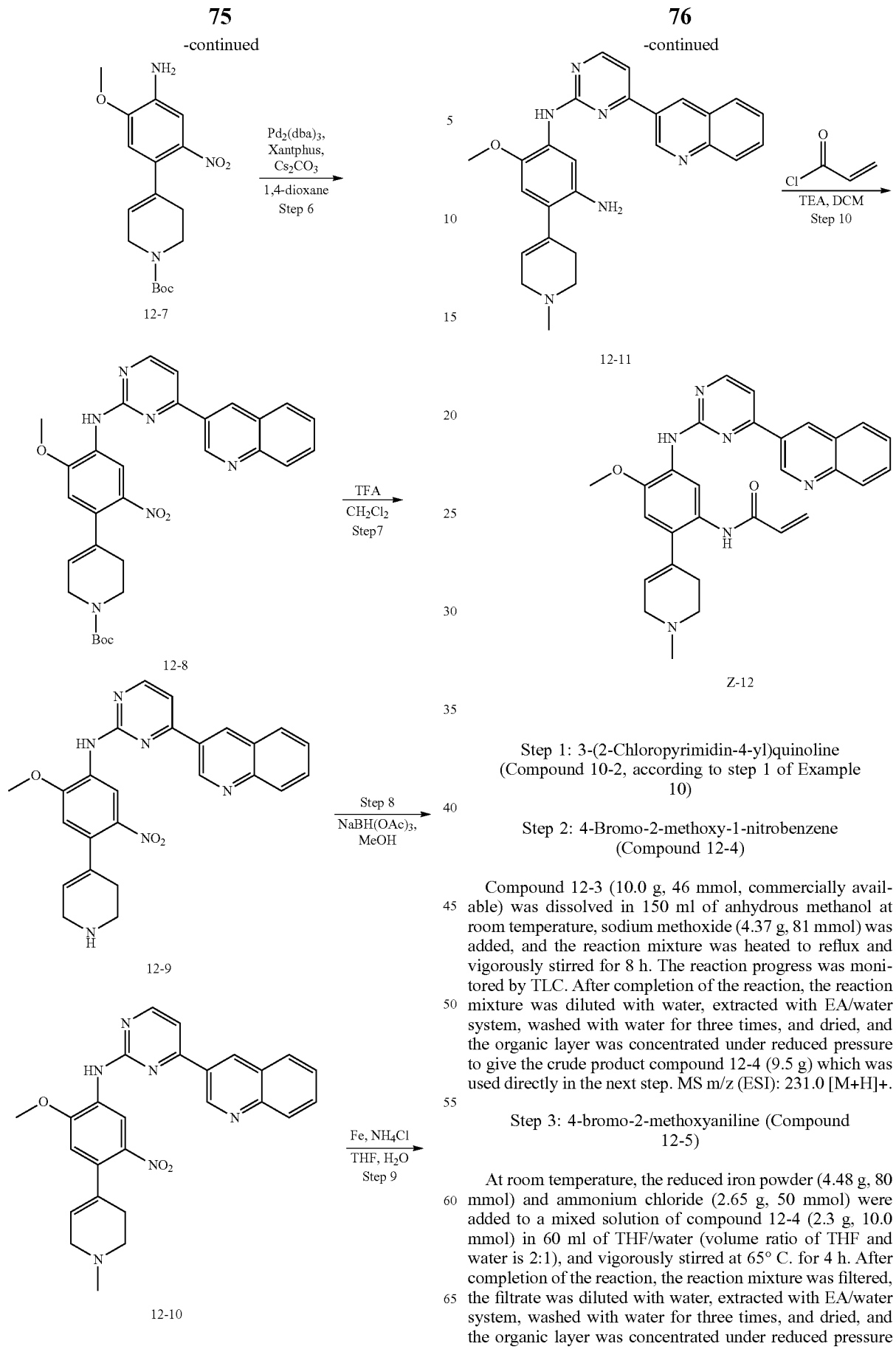

Step 1: 3-(2-Chloropyrimidin-4-yl)quinoline (Compound 10-2, according to step 1 of Example 10)

Step 2: 4-Bromo-2-methoxy-1-nitrobenzene (Compound 12-4)

Compound 12-3 (10.0 g, 46 mmol, commercially available) was dissolved in 150 ml of anhydrous methanol at room temperature, sodium methoxide (4.37 g, 81 mmol) was added, and the reaction mixture was heated to reflux and vigorously stirred for 8 h. The reaction progress was monitored by TLC. After completion of the reaction, the reaction mixture was diluted with water, extracted with EA/water system, washed with water for three times, and dried, and the organic layer was concentrated under reduced pressure to give the crude product compound 12-4 (9.5 g) which was used directly in the next step. MS m/z (ESI): 231.0 [M+H]+.

Step 3: 4-bromo-2-methoxyaniline (Compound 12-5)

At room temperature, the reduced iron powder (4.48 g, 80 mmol) and ammonium chloride (2.65 g, 50 mmol) were added to a mixed solution of compound 12-4 (2.3 g, 10.0 mmol) in 60 ml of THF/water (volume ratio of THF and water is 2:1), and vigorously stirred at 65° C. for 4 h. After completion of the reaction, the reaction mixture was filtered, the filtrate was diluted with water, extracted with EA/water system, washed with water for three times, and dried, and the organic layer was concentrated under reduced pressure to give the crude product compound 12-5 (2.0 g) which was used directly in the next step. MS m/z (ESI): 201.9 [M+H]+.

Step 4: 4-bromo-2-methoxy-5-nitroaniline (Compound 12-6)

Potassium nitrate (217 mg, 2.25 mmol) was added to a solution of compound 12-5 (400 mg, 2.0 mmol) in 3.5 ml of concentrated sulfuric acid at −20° C., and vigorously stirred at −20° C. for 5 min. After completion of the reaction, the reaction mixture was diluted with water, extracted with EA/water system, washed with water for three times, and dried, and the organic layer was concentrated under reduced pressure to give the crude product compound 12-6 (300 mg) which was used directly in the next step. MS m/z (ESI): 246.9 [M+H]+.

Step 5: tert-butyl 4-(4-amino-5-methoxy-2-nitrophenyl)-5,6-dihydropyridine-1 (2H)-carboxylate (Compound 12-7)

Compound 12-6 (100 mg, 0.40 mmol), Pd (PPh3) 4 (24 mg, 0.02 mmol) and 0.5 ml of 2.0 mol/L sodium carbonate solution were added to a solution of compound tert butyl 4-(4,4,5,5-tetramethyl-1,3,2-dioxaborolan-2-yl)-5,6-dihydropyridin-1(2H)-carboxylate (125 mg, 0.40 mmol) in 5 ml of 1,4-dioxane, and vigorously stirred under $N_2$ atmosphere at 100° C. for 4 h. After completion of the reaction, the reaction mixture was filtered, and the filtrate was concentrated under reduced pressure to give the crude product which was purified by Combi-flash column chromatography [PE:EA=100:0-0:100] to give compound 12-7 (50 mg, 35%). MS m/z (ESI): 350.1 [M+H]+.

Step 6: tert-butyl 4-(5-methoxy-2-nitro-4-((4-(quinolin-3-yl)pyrimidin-2-yl)amino)phenyl)-5,6-dihydropyridine-1(2H)-carboxylate (Compound 12-8)

Compound 12-7 (500 mg, 1.43 mmol), $Pd_2(dba)_3$ (131 mg, 0.143 mmol), Xantphos (165 mg, 0.286 mmol) and cesium carbonate (925 mg, 2.86 mmol) were added to a solution of compound 10-2 (345 mg, 1.43 mmol) in 30 ml of 1,4-dioxane, and vigorously stirred under $N_2$ atmosphere at 100° C. for 5 h. After completion of the reaction, the reaction mixture was filtered, and the filtrate was concentrated under reduced pressure to give the crude product which was purified by Combi-flash column chromatography [DCM:MeOH=100:0-0:100] to give compound 12-8 (600 mg, 76%). MS m/z (ESI): 545.0[M+H]+.

Step 7: N-(2-methoxy-5-nitro-4-(1,2,3,6-tetrahydropyridin-4-yl)phenyl)-4-(quinolin-3-yl)pyrimidin-2-amine (Compound 12-9)

1 ml of trifluoroacetic acid was added dropwise to a solution of compound 12-8 (150 mg, 0.27 mmol) in dichloromethane (10 ml) at room temperature, and stirred at room temperature for 3 h after addition. The reaction solution was neutralized with saturated aqueous sodium bicarbonate and the organic phase was separated, the aqueous phase was extracted with dichloromethane (2*10 ml), the combined organic phases were washed with saturated brine (10 ml), dried over anhydrous $Na_2SO_4$, filtered, and concentrated under reduced pressure to give compound 12-9 (115 mg, 93%) which was used directly in the next reaction. MS m/z (ESI): 455.2[M+H]+.

Step 8: N-(2-methoxy-4-(1-methyl-1,2,3,6-tetrahydropyridin-4-yl)-5-nitrophenyl)-4-(quinolin-3-yl)pyrimidin-2-amine (Compound 12-10)

Paraformaldehyde (45 mg, 0.5 mmol) and sodium triacetoxyborohydride (106 mg, 0.5 mmol) were added to a solution of compound 12-9 (115 mg, 0.25 mmol) in methanol (5 ml) at room temperature, and after stirring at room temperature for 3 h, 20 ml of dichloromethane was added. The organic phase was washed successively with water (10 ml), saturated brine (10 ml), dried over anhydrous $Na_2SO_4$, filtered, and concentrated to give compound 12-10 (95 mg, 81%) which was used directly in the next reaction. MS m/z (ESI): 469.2[M+H]+.

Step 9: 6-methoxy-4-(1-methyl-1,2,3,6-tetrahydropyridin-4-yl)-$N^1$-(4-(quinolin-3-yl)pyrimidin-2-yl)benzene-1,3-diamine (Compound 12-11)

By using compound 12-10 (95 mg, 0.2 mmol) as the starting material, compound 12-11 (74 mg, 84%) was synthesized with reference to step 4 of Example 7, and was used directly in the next step. MS m/z (ESI): 439.2[M+H]+.

Step 10: N-(4-methoxy-2-(1-methyl-1,2,3,6-tetrahydropyridin-4-yl)-5-((4-(quinolin-3-yl)pyrimidin-2-yl)amino)phenyl)acrylamide (Compound Z-12)

By using compound 12-11 (74 mg, 0.17 mmol) as the starting material, the crude product was synthesized with reference to step 7 of Example 1, and purified by preparative liquid chromatography to give compound Z-12 (14 mg, 17%). MS m/z (ESI): 493.2[M+H]+.

Example 13: N-(2-((2-(dimethylamino)ethyl)(methyl)amino)-4-methoxy-5-(5-methoxy-4-(quinolin-3-yl)pyrimidin-2-ylamino)phenyl)acrylamide (Z-13)

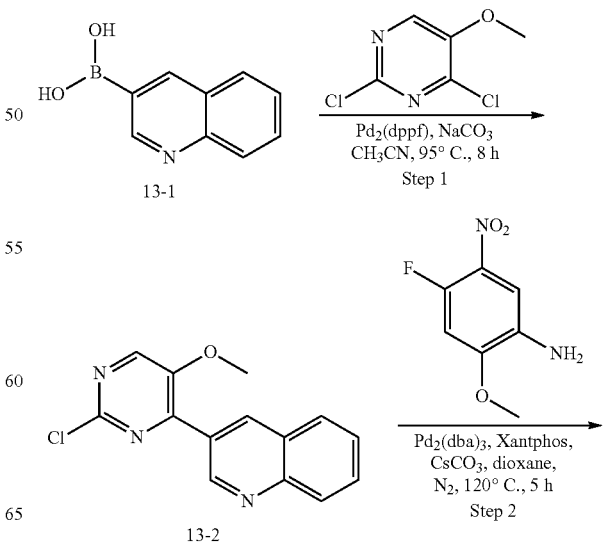

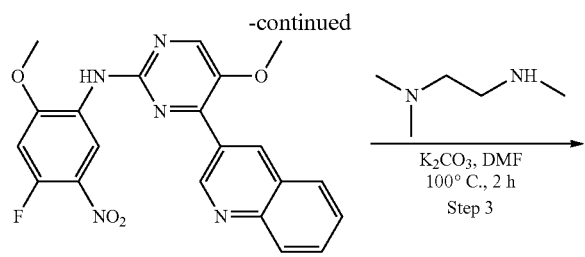

13-3

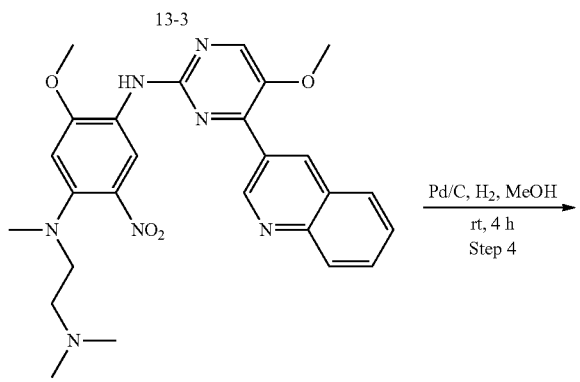

13-4

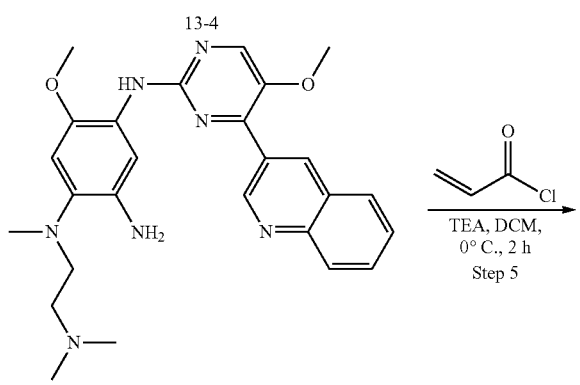

13-5

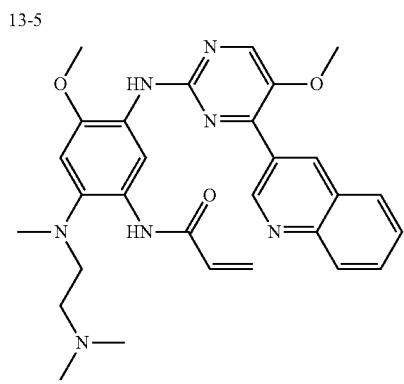

Z-13

Step 1: 3-(2-chloro-5-methoxypyrimidin-4-yl)quinoline (Compound 13-2)

Quinoline-3-boronic acid (2.93 g, 16.9 mmol), PdCl$_2$(dppf) (250 mg, 0.34 mmol) and 50 ml of 2.0 mol/L sodium carbonate solution were added to a solution of compound 13-1 (3 g, 16.9 mmol, commercially available) in 80 ml of acetonitrile, and vigorously stirred under N$_2$ atmosphere at 95° C. for 8 h. After completion of the reaction, the reaction mixture was poured into a large amount of cold water until the solids completely precipitated, which were filtered, thoroughly washed with water, and dried to give compound 13-2 (4 g, 100%). MS m/z (ESI): 272.7[M+H]+.

Step 2: N-(4-fluoro-2-methoxy-5-nitrophenyl)-5-methoxy-4-(quinolin-3-yl)pyrimidin-2-amine (Compound 13-3)

Compound 4-nitro-2-methoxy-5-nitroaniline (343 mg, 1.85 mmol), Pd$_2$(dba)$_3$ (169 mg, 0.18 mmol), Xantphos (214 mg, 0.37 mmol) and cesium carbonate (1.2 g, 3.69 mmol) were added to a solution of compound 13-2 (500 mg, 1.85 mmol) in 9 ml of 1,4-dioxane, and vigorously stirred under N$_2$ atmosphere at 120° C. for 5 h. After completion of the reaction, the reaction mixture was filtered, and the filtrate was concentrated under reduced pressure to give the crude product which was purified by Combi-flash column chromatography [PE:EA=100:0-0:100] to give compound 13-3 (180 mg, 65%). MS m/z (ESI): 422.1[M+H]+.

Step 3: N$^1$-(2-(dimethylamino)ethyl)-5-methoxy-N$^4$-(5-methoxy-4-(quinolin-3-yl)pyrimidin-2-yl)-N$^1$-methyl-2-nitrobenzene-1,4-diamine (Compound 13-4)

N,N,N'-trimethylethylenediamine (65 mg, 0.64 mmol) and potassium carbonate (193 mg, 1.29 mmol) were added to a solution of compound 13-3 (180 mg, 0.43 mmol) in 3 ml of DMF, and vigorously stirred at 100° C. for 2 h. The reaction progress was monitored by TLC.

After completion of the reaction, 10 ml of water was added, the resulting mixture was extracted with EA/water system for three times, and the organic layer was separated, and concentrated under reduced pressure to give compound 13-4 (200 mg, 91%). MS m/z (ESI): 504.3 [M+H]+.

Step 4: N$^1$-(2-(dimethylamino)ethyl)-5-methoxy-N$^4$-(5-methoxy-4-(quinolin-3-yl)pyrimidin-2-yl)-N$^1$-methylbenzene-1,2,4-triamine (Compound 13-5)

By using compound 13-4 (200 mg, 0.40 mmol) as the starting material, compound 13-5 (100 mg, 92%) was synthesized with reference to step 6 of Example 1, and was used directly in the next step. MS m/z (ESI): 474.1 [M+H]+.

Step 5: N-(2-((2-(dimethylamino)ethyl)(methyl)amino)-4-methoxy-5-(5-methoxy-4-(quinolin-3-yl)pyrimidin-2-ylamino)phenyl)acrylamide (Compound Z-13)

By using compound 13-5 (100 mg, 0.21 mmol) as the starting material, the crude product was synthesized with reference to step 7 of Example 1, and purified by preparative liquid chromatography to give compound Z-13 (4.55 mg, 4%). MS m/z (ESI): 527.8 [M+H]+; $^1$HNMR (400 MHz, DMSO-d6) δ9.57 (s, 1H), 9.21 (d, J=16.7 Hz, 2H), 8.57 (s, 1H), 8.28-8.19 (m, 2H), 8.07 (d, J=8.2 Hz, 1H), 7.96 (s, 1H), 7.85 (t, J=7.4 Hz, 1H), 7.65 (t, J=7.3 Hz, 1H), 7.02 (s, 1H), 6.61-6.47 (m, 1H), 6.32 (d, J=17.1 Hz, 1H), 5.80 (d, J=10.8 Hz, 1H), 3.97 (s, 3H), 3.88 (s, 3H), 2.94 (s, 2H), 2.68 (s, 3H), 2.45 (s, 2H), 2.30 (s, 6H).

Example 14: N-(2-((2-(dimethylamino)ethyl)(methyl)amino)-4-methoxy-5-(4-(quinolin-3-yl)-1,3,5-triazin-2-ylamino)phenyl)acrylamide (Z-14)

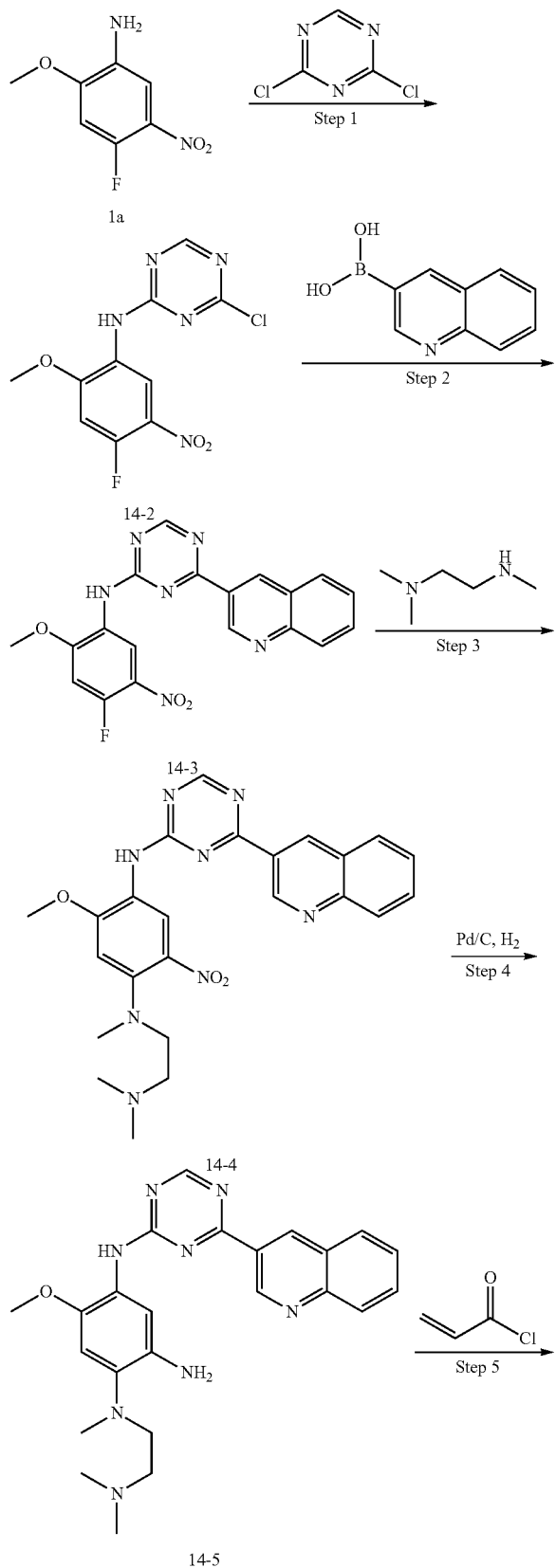

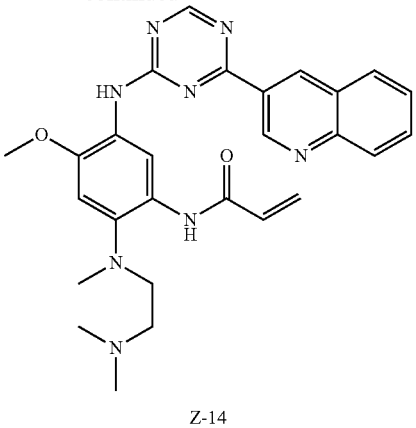 [SMILES: C=CC(=O)Nc1cc(Nc2ncnc(-c3cnc4ccccc4c3)n2)c(OC)cc1N(C)CCN(C)C]

Step 1: 4-chloro-N-(4-fluoro-2-methoxy-5-nitrophenyl)-1,3,5-triazin-2-amine (Compound 14-2)

Compound 1a (200 mg, 1.1 mmol, commercially available) was added into a 250 ml reaction flask, and THF (10 ml) was added to dissolve the substrate. A solution of 4-fluoro-2-methoxy-5-nitroaniline (200 mg, 1.1 mmol) in THF (30 ml) was then added dropwise in 50 min to the reaction flask with mixing at 80° C. After the addition was completed, the reaction was continued for 10 min. The reaction progress was monitored by TLC. After completion of the reaction, the reaction solution was concentrated under reduced pressure to give the crude product which was purified by Combi-Flash column to give the title product compound 14-2 (110 mg, 34%). MS m/z (ESI): 300.0 [M+H]+.

Step 2

N-(4-fluoro-2-methoxy-5-nitrophenyl)-4-(quinolin-3-yl)-1,3,5-triazin-2-amine (Compound 14-3)

The reaction substrate compound 14-2 (1.2 g, 4 mmol), 3-quinolinylboronic acid (5.8 g, 34 mmol), potassium carbonate (1.11 g, 8 mmol) were added into a 250 ml reaction flask, and ethylene glycol dimethyl ether (20 ml) and water (5 ml) were added. After the air of reaction system was replaced by argon for three times, Pd(dppf)Cl$_2$ (300 mg, 0.4 mmol) was added, and then the air was replaced with nitrogen for another three times. The reaction system was heated to 100° C., and stirred continuously for 4 h. The reaction progress was monitored by TLC. After completion of the reaction, the reaction solution was concentrated under reduced pressure to give the crude product which was purified by Combi-Flash column to give the title product compound 14-3 (700 mg, 45%). MS m/z (ESI): 393.1 [M+H]+.

Step 3: N$^1$-(2-(dimethylamino)ethyl)-5-methoxy-N$^1$-methyl-2-nitro-N$^4$-(4-(quinolin-3-yl)-1,3,5-triazin-2-yl)benzene-1,4-diamine (Compound 14-4)

The reaction substrate compound 14-3 (400 mg, 1 mmol), N,N,N'-trimethylethylenediamine (156 mg, 1.5 mmol) and cesium carbonate (670 mg, 2 mmol) were added into a 50 ml reaction flask, and dimethylamino formamide (6 ml) was added. After the air of reaction system was replaced by nitrogen for three times, the reaction system was heated to 80° C., and stirred continuously for 4 h. The reaction progress was monitored by TLC. After completion of the reaction, the reaction solution was diluted with water and filtered to give a crude product which was purified by Combi-Flash column chromatography to give the title product compound 14-4 (200 mg, 42%). MS m/z (ESI): 475.2 [M+H]+.

Step 4: $N^1$-(2-(dimethylamino)ethyl)-5-methoxy-N-methyl-$N^4$-(4-(quinolin-3-yl)-1,3,5-triazin-2-yl) benzene-1,2,4-triamine (Compound 14-5)

By using compound 14-4 (190 mg, 0.4 mmol) as the starting material, compound 14-5 (180 mg) was synthesized with reference to step 6 of Example 1, and was used directly in the next step. MS m/z (ESI): 445.2 [M+H]+.

Step 5: N-(dimethylamino)ethyl)(methyl)amino)-4-methoxy-5-(4-(quinolin-3-yl)-1,3,5-triazin-2-ylamino)phenyl)acrylamide (Compound Z-14)

By using compound 14-5 (180 mg, 0.41 mmol) as the starting material, the crude product was synthesized with reference to step 7 of Example 1, and purified by Prep-TLC to give the title compound Z-14 (2.01 mg, 1%). Purity: 94.99%. MS m/z (ESI): 499.3 [M+H]+.

Example 15: N-(2-(4-(dimethylamino)piperidin-1-yl)-4-methoxy-5-(4-(quinolin-3-yl)-1,3,5-triazin-2-ylamino)phenyl)acrylamide (Z-15)

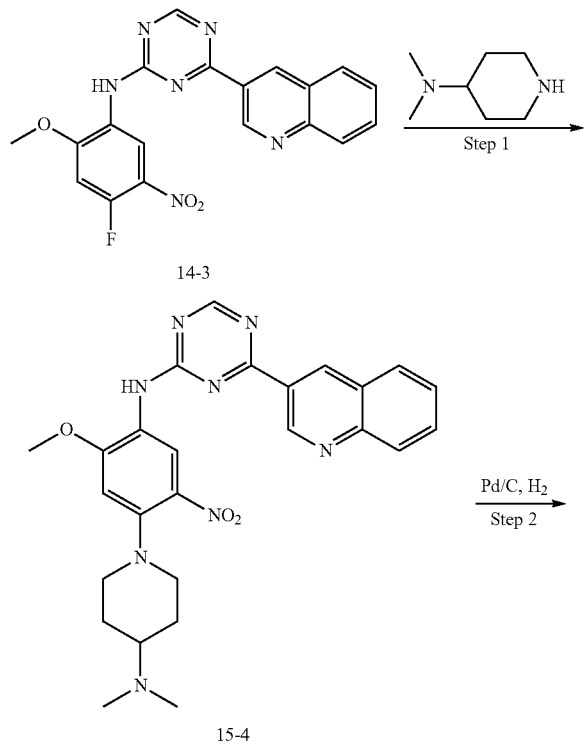

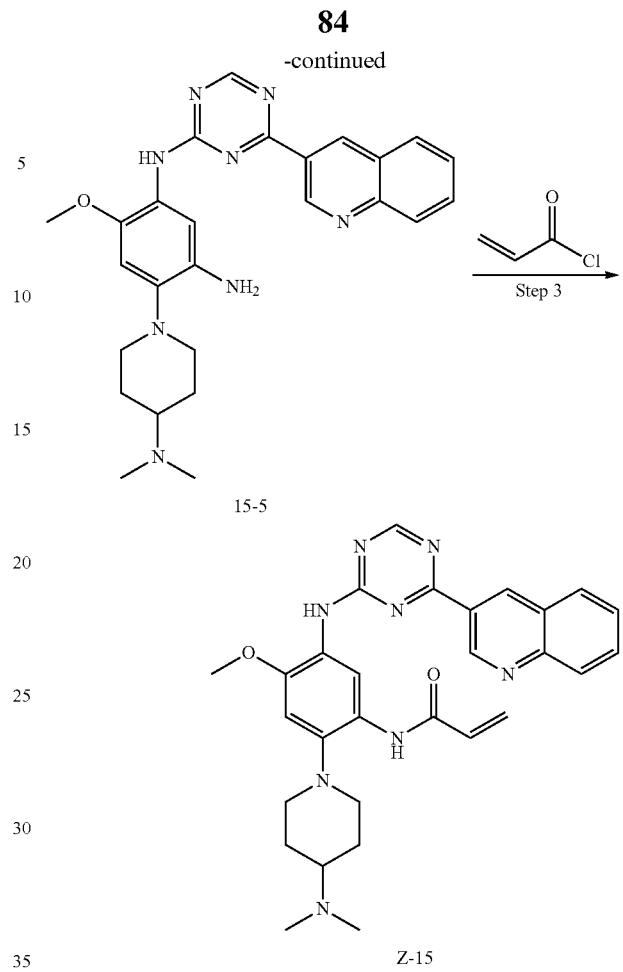

Step 1: N-(4-(4-(dimethylamino)piperidin-1-yl)-2-methoxy-5-nitrophenyl)-4-(quinolin-3-yl)-1,3,5-triazin-2-amine (Compound 15-4)

Compound 14-3 (100 mg, 0.25 mmol), 4-dimethylamino piperidine (66 mg, 0.51 mmol) and potassium carbonate (140 mg, 1.02 mmol) were added into a 20 ml reaction flask, and dimethylformamide (4 ml) was added. After the air of reaction system was replaced by nitrogen for three times, the reaction system was heated to 100° C., and stirred continuously for 4 h. The reaction progress was monitored by TLC. After completion of the reaction, the reaction solution was extracted with EA/water system for three times, the organic layer was separated, washed with water, saturated brine, dried over anhydrous $Na_2SO_4$, and concentrated under reduced pressure to give the crude product which was purified by Combi-Flash column to give the title product compound 15-4 (110 mg, 43%). MS m/z (ESI): 501.2 [M+H]+.

Step 2: 4-(4-(dimethylamino)piperidin-1-yl)-6-methoxy-$N^1$-(4-(quinolin-3-yl)-1,3,5-triazin-2-yl) benzene-1,3-diamine (Compound 15-5)

By using compound 15-4 (100 mg, 0.2 mmol) as the starting material, compound 15-5 (90 mg) was synthesized with reference to step 6 of Example 1, and was used directly in the next reaction. MS m/z (ESI): 471.3 [M+H]+

Step 3: N-(2-(4-(dimethylamino)piperidin-1-yl)-4-methoxy-5-(4-(quinolin-3-yl)-1,3,5-triazin-2-ylamino)phenyl)acrylamide (Compound Z-15)

By using compound 15-5 (90 mg, 0.2 mmol) as the starting material, the crude product was synthesized with reference to step 7 of Example 1, and purified by Prep-HPLC to give the title compound Z-15 (2.09 mg, 2%, FA salt). Purity: 100.0%. MS m/z (ESI): 525.3 [M+H]+.

Example 16: N-(2-((2-(dimethylamino)ethyl)(methyl)amino)-4-methoxy-5-((4-(1-methyl-1H-pyrrolo[2,3-b]pyridin-5-yl)pyrimidin-2-yl)amino)phenyl)acrylamide (Compound Z-16)

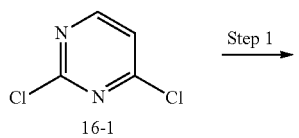

16-1

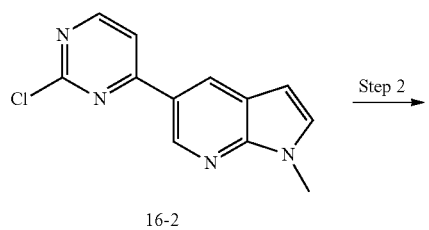

16-2

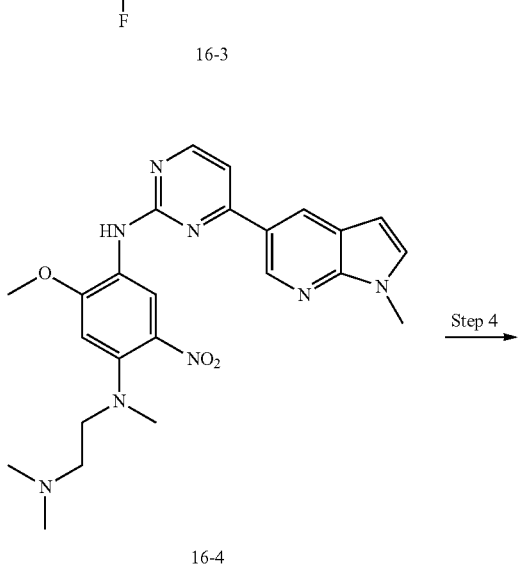

16-3

16-4

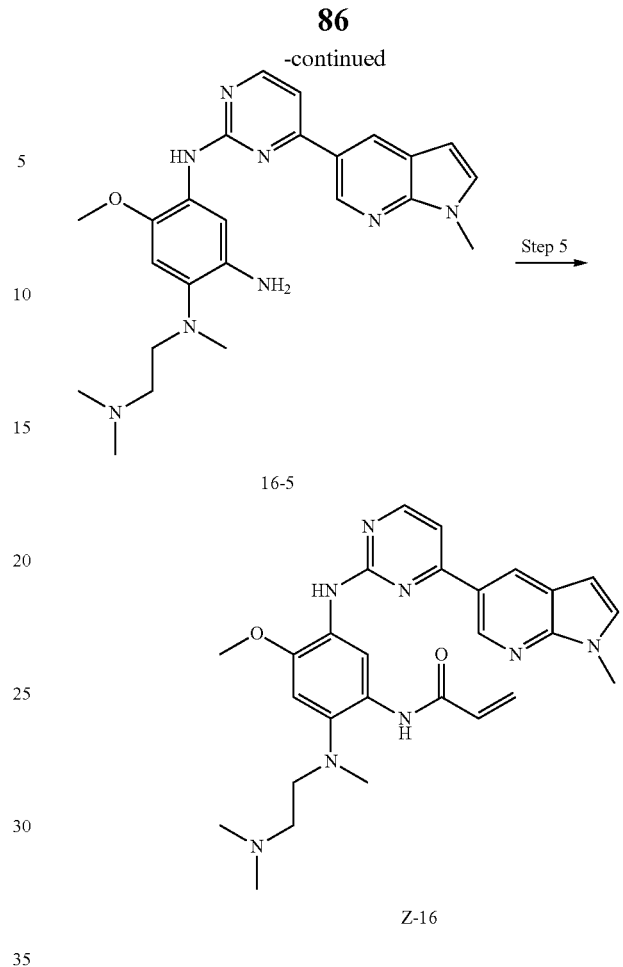

16-5

Z-16

Step 1: 5-(2-chloropyrimidin-4-yl)-1-methyl-1H-pyrrolo[2,3-b]pyridine (Compound 16-2)

Compound 16-1 (2.0 g, 13.5 mmol), PdCl$_2$ (dppf) (1.04 g, 1.35 mmol) and 13.5 ml of 2.0 mol/L sodium carbonate solution were added to a solution of compound 1-methyl-5-(4,4,5,5-tetramethyl-1,3,2-dioxaborolan-2-yl) 1H-pyrrolo[2,3-b]pyridine (8.6 g, 13.5 mmol) in 50 ml of acetonitrile, and vigorously stirred under N$_2$ atmosphere at 80° C. for 4 h. After completion of the reaction, the reaction mixture was diluted with water and extracted with EA/water system, washed with water for three times, and dried, and the organic layer was concentrated under reduced pressure to give the crude product which was purified by Combi-flash column chromatography [PE:EA=100:0-20:80] to give compound 16-2 (2.1 g, 36%). MS m/z (ESI): 245.0[M+H]+.

Step 2: N-(4-fluoro-2-methoxy-5-nitrophenyl)-4-(1-methyl-1H-pyrrolo[2,3-b]pyridin-5-yl)pyrimidin-2-amine (Compound 16-3)

4-fluoro-2-methoxy-5-nitroaniline (1.6 g, 8.6 mmol) and compound 16-2 (2.1 g, 8.6 mmol) were added to a solution of p-toluenesulfonic acid (3.7 g, 21.5 mmol) in 20 ml of isobutanol, and the reaction mixture was heated at 130° C. for 6 h in the sealed tube. After completion of the reaction, the reaction mixture was cooled to room temperature and large amount of solids precipitated from the solution. The solids were filtered by Buchner to obtain a filter cake which was beat in ethanol at reflux to give compound 16-3 (1.2 g, 44%), which was used directly in the next reaction. MS m/z (ESI): 429.0[M+H]+.

Step 3: $N^1$-(2-(dimethylamino)ethyl)-5-methoxy-N-methyl-$N^4$-(4-(1-methyl-1H-pyrrolo[2,3-b]pyridin-5-yl)pyrimidin-2-yl)-2-nitrobenzene-1,4-diamine (Compound 16-4)

By using compound 16-3 (370 mg, 0.62 mmol) as the starting material, compound 16-4 (300 mg, 90%) was synthesized with reference to step 5 of Example 1. MS m/z (ESI): 477.2 [M+H]+.

Step 4: $N^1$-(2-(dimethylamino)ethyl)-5-methoxy-N-methyl-$N^4$-(4-(1-methyl-1H-pyrrolo[2,3-b]pyridin-5-yl)pyrimidin-2-yl)benzene-1,2,4-triamine (Compound 16-5)

By using compound 16-4 (300 mg, 0.6 mmol) as the starting material, compound 16-5 (200 mg) was synthesized with reference to step 4 of Example 7, which was used directly in the next step. MS m/z (ESI): 447.2[M+H]+.

Step 5: N-(2-((2-(dimethylamino)ethyl)(methyl)amino)-4-methoxy-5-((4-(1-methyl-1H-pyrrolo[2,3-b]pyridin-5-yl)pyrimidin-2-yl)amino)phenyl)acrylamide (Compound Z-16)

By using compound 16-5 (200 mg, 0.44 mmol) as the starting material, the crude product was synthesized with reference to step 7 of Example 1, and purified by preparative liquid chromatography to give compound Z-16 (23 mg, 10%). MS m/z (ESI): 501.3 [M+H]+; $^1$HNMR (400 MHz, CDCl$_3$) δ 10.04 (s, 1H), 9.78 (s, 1H), 9.20 (s, 1H), 8.90 (d, J=2.0 Hz, 1H), 8.41 (d, J=5.2 Hz, 1H), 7.70 (s, 1H), 7.15 (dd, J=6.9, 4.4 Hz, 2H), 6.73 (s, 1H), 6.59 (d, J=3.4 Hz, 1H), 6.49-6.42 (m, 1H), 6.30 (d, J=10.1 Hz, 1H), 5.65 (d, J=10.1 Hz, 1H), 3.84 (d, J=13.7 Hz, 6H), 2.86-2.77 (m, 2H), 2.64 (s, 3H), 2.22 (d, J=5.8 Hz, 2H), 2.19 (s, 6H).

Example 17: N-(2-(4-(dimethylamino)piperidin-1-yl)-4-methoxy-5-((4-(1-methyl-1H-pyrazol-4-yl)pyrimidin-2-yl)amino)phenyl)acrylamide (Z-17)

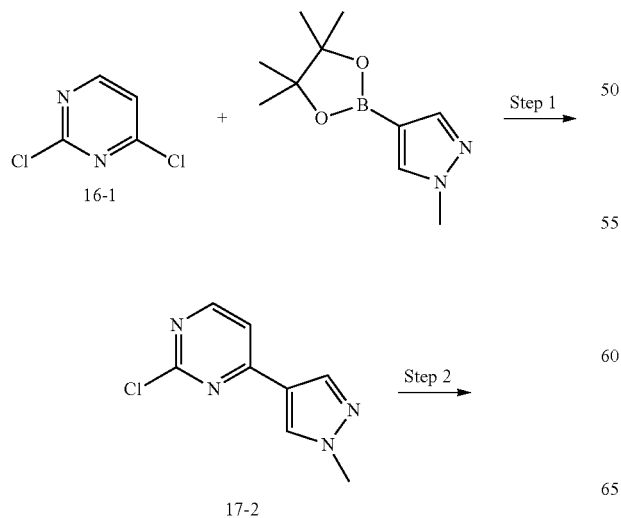

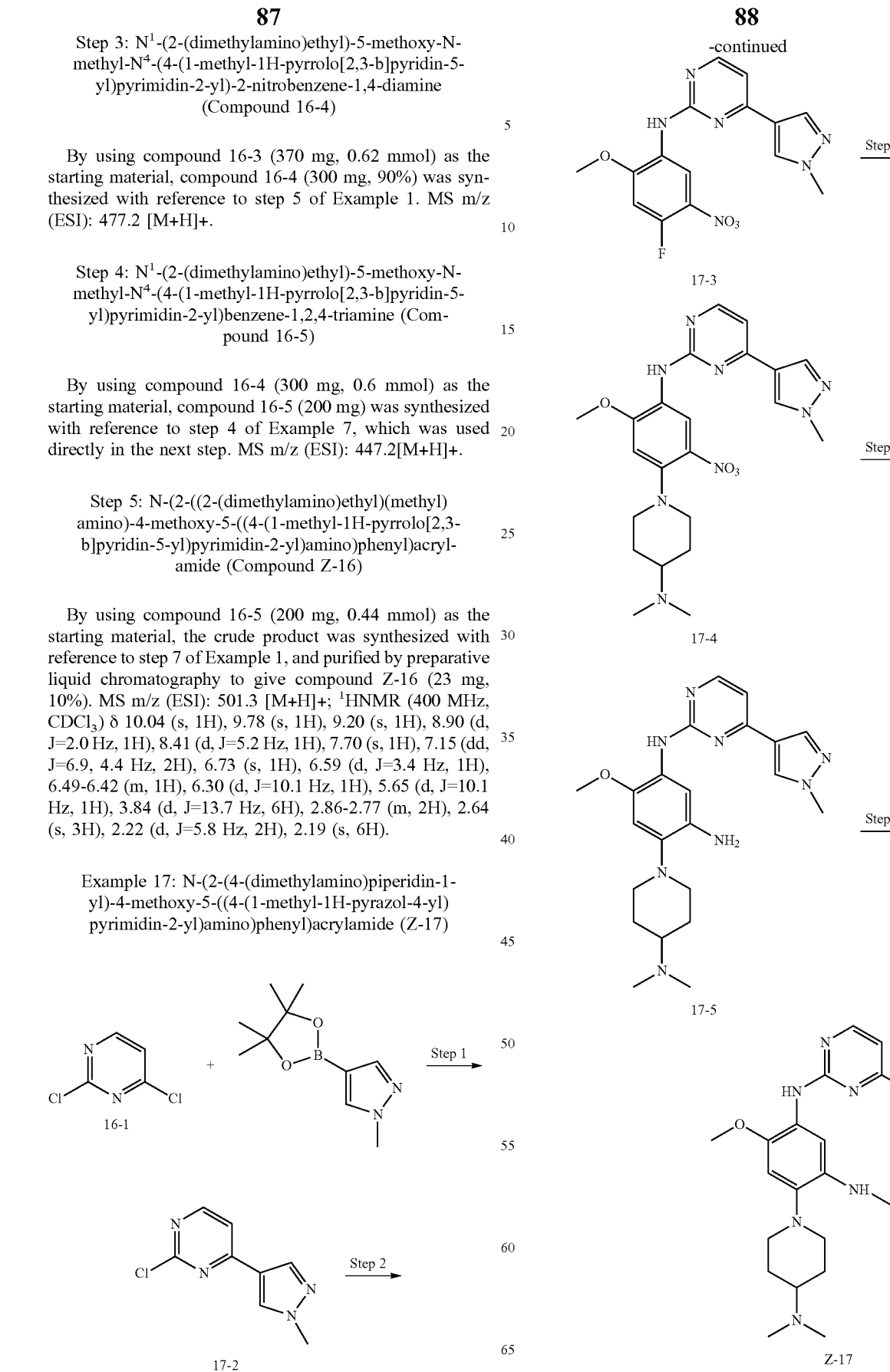

Step 1: 2-chloro-4-(1-methyl-1H-pyrazol-4-yl)pyrimidine (Compound 17-2)

Compound 16-1 (745 mg, 5 mmol) and methyl-4-pyrazoleboronic acid pinacol ester (1.092 g, 5.25 mmol, commercially available) were added into a 100 ml reaction flask, and acetonitrile (30 ml) and sodium carbonate solution (5 ml, 2M) were added. After the air of reaction system was replaced by nitrogen for three times, Pd(dppf)Cl$_2$ (109.7 mg, 0.15 mmol) was added, and then the air was replaced with nitrogen for another three times. The reaction system was heated to 110° C., and stirred continuously for 6 h. The reaction progress was monitored by TLC. After completion of the reaction, the reaction solution was diluted with water, extracted with EA/water system for three times, and the organic layer was separated, washed with water, saturated brine, dried over anhydrous Na$_2$SO$_4$, and concentrated under reduced pressure to give 1.1 g of crude product which was purified by Combi-Flash column chromatography [EA:PE=1:5–1:2] to give the title product compound 17-2 (600 mg, 93%). MS m/z (ESI): 195.1 [M+H]+.

Step 2: N-(4-fluoro-2-methoxy-5-nitrophenyl)-4-(1-methyl-1H-pyrazol-4-yl)pyrimidin-2-amine (Compound 17-3)

Compound 17-2 (500 mg, 2.577 mmol) and 4-fluoro-2-methoxy-5-nitroaniline (479 g, 2.577 mmol) were added into a 50 ml sealed tube, and n-butanol (12 ml) was added to partially dissolve the substrate. p-toluenesulfonic acid (1.108 g, 6.44 mmol) was then added, and the reaction system was heated at 130° C. for 6 h in the sealed tube. After completion of the reaction, the reaction mixture was cooled to room temperature and large amount of solids precipitated from the solution. The solids were filtered by Buchner to obtain a filter cake which was beat in ethanol at reflux to give the title compound 17-3 (600 mg, 67.8%), which was used directly in the next reaction.

Step 3: N-(4-(4-(dimethylamino)piperidin-1-yl)-2-methoxy-5-nitrophenyl)-4-(1-methyl-1H-pyrazol-4-yl)pyrimidin-2-amine (Compound 17-4)

Compound 17-3 (70 mg, 0.203 mmol) and potassium carbonate (84 mg, 0.609 mmol) were added into a 25 ml reaction flask, and DMF (5 ml) was added to partially dissolve the substrate. N,N-dimethylamino piperidine (31.2 mg, 0.244 mmol) was then added, and the reaction system was maintained at 70° C. for 2 h. The reaction progress was monitored by TLC. After completion of the reaction, the reaction solution was extracted with EA/water system for three times, and the organic layer was separated, washed with water, saturated brine, dried over anhydrous Na$_2$SO$_4$, and concentrated under reduced pressure to give compound 17-4 (70 mg, 76%). MS m/z (ESI): 453.2 [M+H]+.

Step 4: 4-(4-(dimethylamino)piperidin-1-yl)-6-methoxy-N$^1$-(4-(1-methyl-1H-pyrazol-4-yl)pyrimidin-2-yl)benzene-1,3-diamine (Compound 17-5)

By using compound 17-4 (70 mg, 0.155 mmol) as the starting material, the crude product compound 17-5 (60 mg, 92%) was synthesized with reference to step 6 of Example 1, and was used directly in the next step.

Step 5: N-(2-(4-(dimethylamino)piperidin-1-yl)-4-methoxy-5-((4-(1-methyl-1H-pyrazol-4-yl)pyrimidin-2-yl)amino)phenyl)acrylamide (Z-17)

By using compound 17-5 (50 mg, 0.118 mmol) as the starting material, the crude product was synthesized with reference to step 7 of Example 1, and purified by preparative plate [DCM:MeOH=10:1] to give compound Z-17 (30 mg, 44%). MS m/z (ESI): 477.2 [M+H]+; $^1$HNMR (400 MHz, DMSO-d6): δ 9.14 (s, 1H), 9.05 (s, 1H), 8.81 (s, 1H), 8.36-8.35 (d, J=4.0 Hz, 1H), 8.21 (s, 1H), 7.76 (s, 1H), 7.10-7.09 (d, J=4.0 Hz, 1H), 6.86 (s, 1H), 6.76-6.69 (m, 1H), 6.33-6.29 (d, J=16.0 Hz, 1H), 5.80-5.77 (d, J=12.0 Hz, 1H), 3.92 (s, 3H), 3.88 (s, 3H), 3.03-3.00 (m, 2H), 2.69-2.64 (m, 2H), 2.27-2.15 (m, 7H), 1.85-1.82 (m, 2H), 1.73-1.68 (m, 2H).

Example 18: N-(2-((2-(dimethylamino)ethyl)(methyl)amino)-4-methoxy-5-((4-(1-methyl-1H-pyrazol-4-yl)pyrimidin-2-yl)amino)phenyl)acrylamide (Z-18)

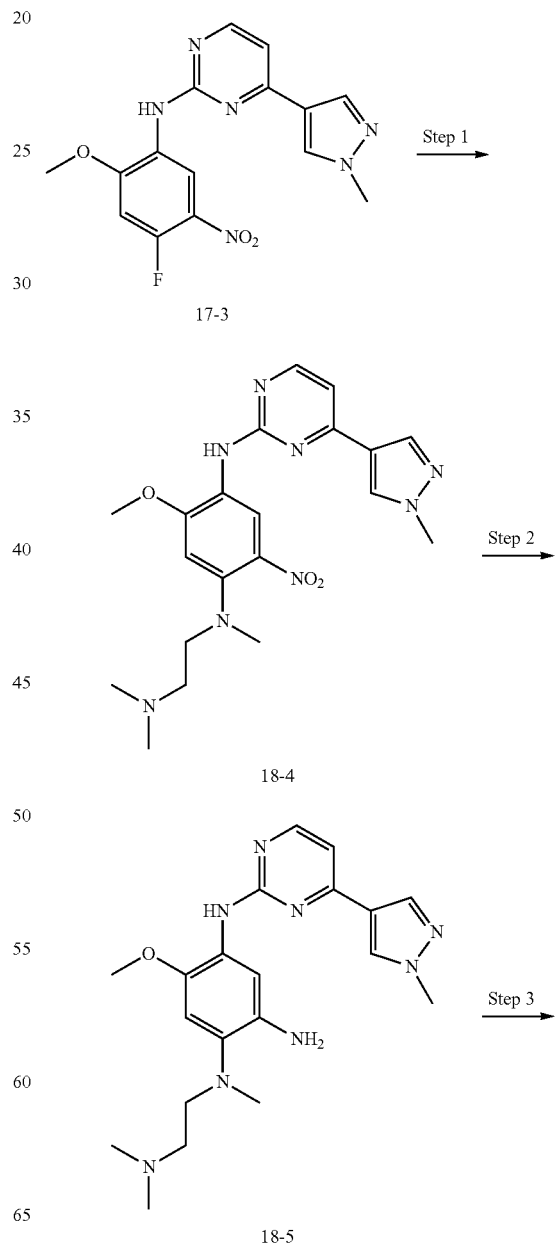

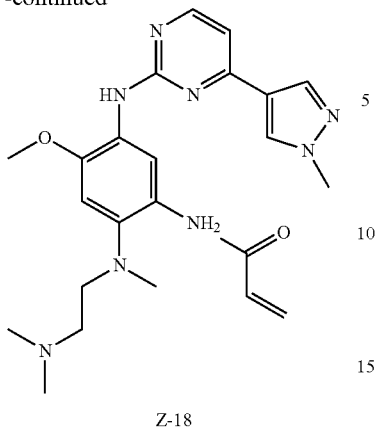

Z-18

Step 1: $N^1$-(2-(dimethylamino)ethyl)-5-methoxy-N-methyl-$N^4$-(4-(1-methyl-1H-pyrazol-4-yl)pyrimidin-2-yl)-2-nitrobenzene-1,4-diamine (Compound 18-4)

Compound 17-3 (130 mg, 0.378 mmol, prepared with reference to step 2 of Example 17), and potassium carbonate (156 mg, 1.133 mmol) were added into a 50 ml reaction flask, and DMF (5 ml) was added to partially dissolve the substrate. N,N,N'-trimethyl ethylenediamine (57.8 mg, 0.567 mmol) was then added, and the reaction system was maintained at 70° C. for 3 h. The reaction progress was monitored by TLC. After completion of the reaction, the reaction solution was extracted with EA/water system for three times, the organic layer was separated, washed with water, saturated brine, dried over anhydrous $Na_2SO_4$, and concentrated under reduced pressure to give the crude product compound 18-4 (110 mg, 68%). MS m/z (ESI): 427.2[M+H]+.

Step 2: $N^1$-(2-(dimethylamino)ethyl)-5-methoxy-N-methyl-$N^4$-(4-(1-methyl-1H-pyrazol-4-yl)pyrimidin-2-yl)benzene-1,2,4-triamine (Compound 18-5)

By using compound 18-4 (110 mg, 0.258 mmol) as the starting material, the crude product compound 18-5 (110 mg, 100%) was synthesized with reference to step 6 of Example 1, and was used directly in the next step.

Step 3: N-(2-((2-(dimethylamino)ethyl)(methyl)amino)-4-methoxy-5-((4-(1-methyl-1H-pyrazol-4-yl)pyrimidin-2-yl)amino)phenyl)acrylamide (Compound Z-18)

By using compound 18-5 (110 mg, 0.278 mmol) as the starting material, the crude product was synthesized with reference to step 7 of Example 1, and purified by preparative plate [DCM:MeOH=10:1] to give the title product compound Z-18 (10.0 mg, 8.2%). MS m/z (ESI): 451.1 [M+H]+; $^1$HNMR (400 MHz, DMSO-d6): δ 10.18 (s, 1H), 9.42 (s, 1H), 8.90 (s, 1H), 8.38-8.37 (d, J=4.0 Hz, 1H), 8.23 (s, 1H), 7.79 (s, 1H), 7.12-7.11 (d, J=4.0 Hz, 1H), 7.03 (s, 1H), 6.46-6.32 (m, 2H), 5.82-5.76 (m, 1H), 3.93 (s, 3H), 3.86 (s, 3H), 2.97-2.93 (m, 2H), 2.68 (s, 3H), 2.08-2.47 (m, 8H).

Example 19: N-(5-((5-chloro-4-(1-methyl-1H-pyrazol-4-yl)pyrimidin-2-yl)amino)-2-((2-(dimethylamino)ethyl)(methyl)amino)-4-methoxyphenyl)acrylamide (Z-19)

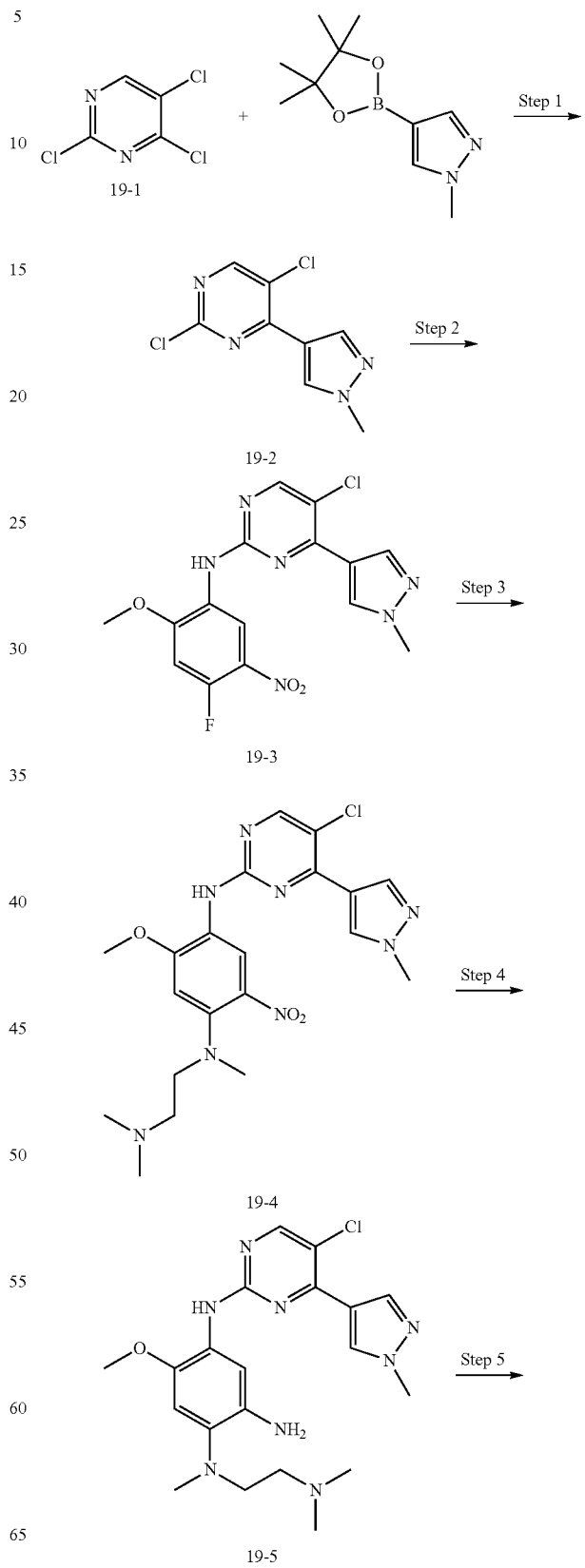

93

-continued

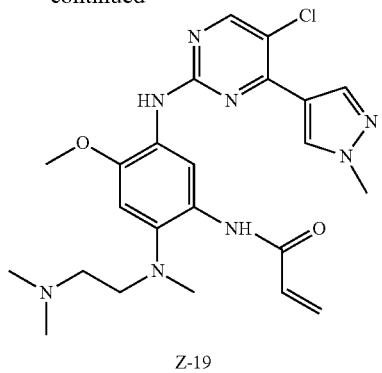

Z-19

Step 1: 2,5-dichloro-4-(1-methyl-1H-pyrazol-4-yl)pyrimidine (Compound 19-2)

By using 2,4,5-trichloropyrimidine (1.32 g, 7.21 mmol) and methyl-4-pyrazole boronic acid pinacol ester (1.5 g, 7.21 mmol) as the starting materials, the crude product was synthesized with reference to step 1 of Example 17, and purified by Combi-Flash column chromatography (EA:PE=1:5) to give compound 19-2 (1.4 g, 84.8%). MS m/z (ESI): 229.3 [M+H]+.

Step 2: 5-chloro-N-(4-fluoro-2-methoxy-5-nitrophenyl)-4-(1-methyl-1H-pyrazol-4-yl)pyrimidin-2-amine (Compound 19-3)

Compound 19-2 (1.1 g, 4.8 mmol), Pd$_2$(dba)$_3$ (439 mg, 0.48 mmol), Xantphos (277 mg, 0.48 mmol) and cesium carbonate (4.68 g, 14.4 mmol) were added to a solution of 4-fluoro-2-methoxy-5-nitroaniline (892 mg, 4.8 mmol) in 30 ml of 1,4-dioxane, and vigorously stirred under N$_2$ atmosphere at 100° C. for 5 h. After completion of the reaction, the reaction mixture was filtered, and the filtrate was concentrated under reduced pressure to give the crude product which was purified by Combi-flash column chromatography [PE:EA=100:0-0:100] to give compound 19-3 (600 mg, 33.1%). MS m/z (ESI): 379.3[M+H]+.

Step 3: N$^1$-(5-chloro-4-(1-methyl-1H-pyrazol-4-yl)pyrimidin-2-yl)-N$^4$-(2-(dimethylamino)ethyl)-2-methoxy-N$^4$-methyl-5-nitrobenzene-1,4-diamine (Compound 19-4)

By using compound 19-3 (600 mg, 1.587 mmol) as the starting material, the crude product compound 19-4 (400 mg, 57.7%) was synthesized with reference to step 5 of Example 1, and was used directly in the next step. MS m/z (ESI): 461.1[M+H]+.

Step 4: N$^4$-(5-chloro-4-(1-methyl-1H-pyrazol-4-yl)pyrimidin-2-yl)-N$^1$-(2-(dimethylamino)ethyl)-5-methoxy-N-methylbenzene-1,2,4-triamine (Compound 19-5)

By using compound 19-4 (200 mg, 0.435 mmol) as the starting material, the crude product compound 19-5 (200 mg) was synthesized with reference to step 2 of Example 2, and was used directly in the next step. MS m/z (ESI): 431.3[M+H]+.

94

Step 5: N-(5-((5-chloro-4-(1-methyl-1H-pyrazol-4-yl)pyrimidin-2-yl)amino)-2-((2-(dimethylamino)ethyl)(methyl)amino)-4-methoxyphenyl)acrylamide (Compound Z-19)

By using compound 19-5 (200 mg, 0.465 mmol) as the starting material, the crude product was synthesized with reference to step 7 of Example 1, and purified by Prep-HPLC to give compound Z-19 (23 mg, 10%). MS m/z (ESI): 485.2 $^1$HNMR (400 MHz, DMSO-d6) δ 10.21 (s, 1H), 9.11 (s, 1H), 8.99 (s, 1H), 8.46 (s, 1H), 8.37 (s, 1H), 8.07 (s, 1H), 7.04 (s, 1H), 6.29-6.47 (m, 2H), 5.79-5.81 (m, 1H), 3.97 (s, 3H), 3.87 (s, 3H), 2.89 (m, 2H), 2.70 (s, 3H), 2.15-2.39 (m, 8H).

Example 20: N-(2-((2-(dimethylamino)ethyl)(methyl)amino)-5-((5-fluoro-4-(1-methyl-1H-pyrrolo[2,3-b]pyridin-5-yl)pyrimidin-2-yl)amino)-4-methoxyphenyl)acrylamide (Z-20)

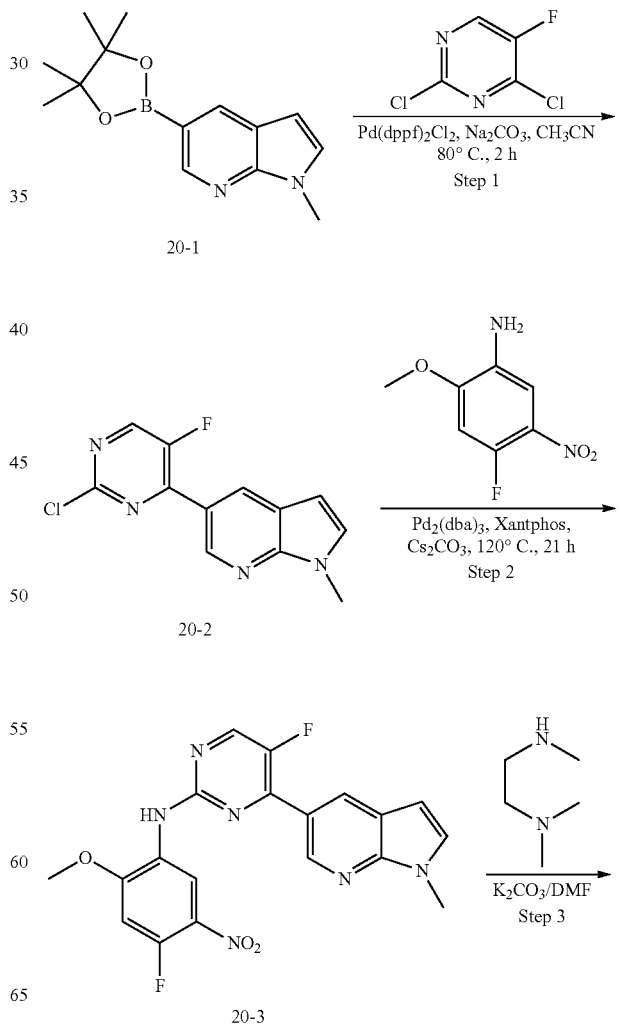

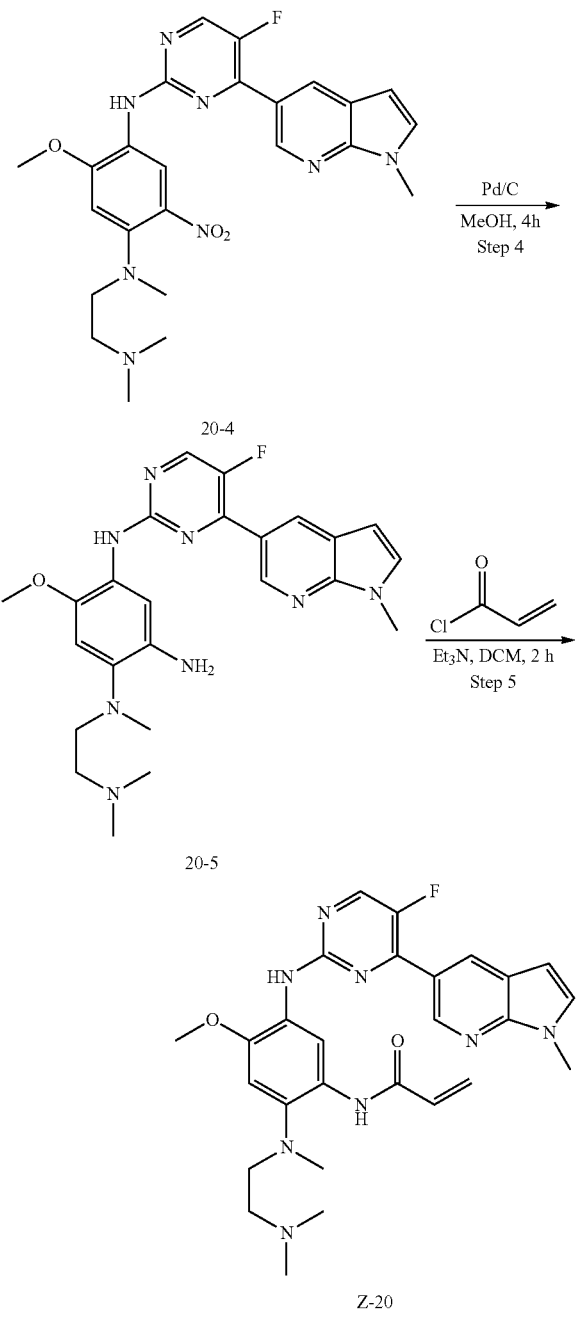

Combi-flash column chromatography [PE:EA=100:0-60:40] to give compound 20-2 (1.12 g, 55%). MS m/z (ESI): 263.1[M+H]+.

Step 2: 5-fluoro-N-(4-fluoro-2-methoxy-5-nitrophenyl)-4-(1-methyl-1H-pyrrolo[2,3-b]pyridin-5-yl)pyrimidin-2-amine (Compound 20-3)

By using compound 20-2 (1.5 g, 5.46 mmol) as the starting material, the crude product was synthesized with reference to step 2 of Example 19, and purified by Combi-flash column chromatography (PE:EA=50:50) to give compound 20-3 (0.8 g, 45%), except that in step 2 of Example 20, the reaction mixture vigorously stirred under $N_2$ atmosphere at 120° C. for 21 h. MS m/z (ESI): 413.1[M+H]+.

Step 3: $N^1$-(2-(dimethylamino)ethyl)-$N^4$-(5-fluoro-4-(1-methyl-1H-pyrrolo[2,3-b]pyridin-5-yl)pyrimidin-2-yl)-5-methoxy-N-methyl-2-nitrobenzene-1,4-diamine (Compound 20-4)

By using compound 20-3 (300 mg, 1.18 mmol) as the starting material, compound 20-4 (330 mg, 92%) was synthesized with reference to step 5 of Example 1, and was used directly in the next step. MS m/z (ESI): 495.2[M+H]+.

Step 4: $N^1$-(2-(dimethylamino)ethyl)-$N^4$-(5-fluoro-4-(1-methyl-1H-pyrrolo[2,3-b]pyridin-5-yl)pyrimidin-2-yl)-5-methoxy-$N^1$-methylbenzene-1,2,4-triamine (Compound 20-5)

By using compound 20-4 (330 mg, 0.67 mmol) as the starting material, compound 20-5 (317 mg, 100%) was synthesized with reference to step 6 of Example 1, and was used directly in the next step. MS m/z (ESI): 465.2[M+H]+.

Step 5: N-(2-((2-(dimethylamino)ethyl)(methyl)amino)-5-((5-fluoro-4-(1-methyl-1H-pyrrolo[2,3-b]pyridin-5-yl)pyrimidin-2-yl)amino)-4-methoxyphenyl)acrylamide (Compound Z-20)

By using compound 20-5 (317 mg, 0.68 mmol) as the starting material, the crude product was synthesized with reference to step 7 of Example 1, and purified by preparative plate [DCM:MeOH:NH4OH=90:10:1] to give compound Z-20 (11.9 mg, 3.4%). MS m/z (ESI): 519.2[M+H]+; $^1$HNMR (400 MHz, $CDCl_3$)=9.92 (br. s., 1H), 9.64 (s, 1H), 9.07 (d, J=9.2 Hz, 2H), 8.31 (d, J=2.8 Hz, 1H), 7.66 (s, 1H), 7.14 (d, J=1.6 Hz, 1H), 6.70 (s, 1H), 6.59 (d, J=1.6 Hz, 1H), 6.42 (br. s., 2H), 5.66-5.63 (m, 1H), 3.86 (s, 3H), 3.81 (s, 3H), 2.87 (br. s., 2H), 2.63 (s, 3H), 2.25 (br. s., 8H).

Example 21: N-(2-((2-(dimethylamino)ethyl)(methyl)amino)-4-methoxy-5-((5-methoxy-4-(1-methyl-1H-pyrrolo[2,3-b]pyridin-5-yl)pyrimidin-2-yl)amino)phenyl)acrylamide (Compound Z-21)

Step 1: 5-(2-chloro-5-fluoropyrimidin-4-yl)-1-methyl-1H-pyrrolo[2,3-b]pyridine (Compound 20-2)

2,4-dichloro-5-fluoropyrimidine (2.0 g, 7.8 mmol), $PdCl_2$ (dppf)$_2$ (0.57 g, 0.78 mmol) and sodium carbonate (1.64 g, 15.6 mmol) were added to a mixed solution of compound 1-methyl-5-(4,4,5,5-tetramethyl-1,3,2-dioxaborolan-2-yl)-1H-pyrrolo[2,3-b]pyridine (2.0 g, 7.8 mmol commercially available) in 20 ml of acetonitrile and 4 ml of water, and vigorously stirred under $N_2$ atmosphere at 80° C. for 2 h. After completion of the reaction, the reaction mixture was filtered, and the filtrate was concentrated under reduced pressure to give the crude product which was purified by

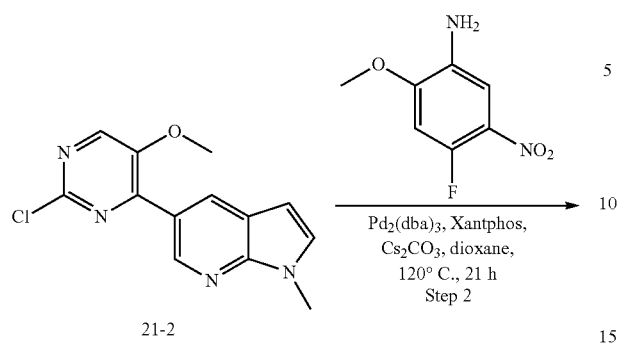

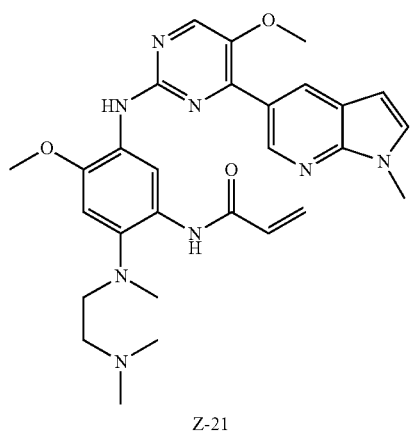 [SMILES: C=CC(=O)Nc1cc(Nc2ncc(OC)c(-c3cnc4c(ccn4C)c3)n2)c(OC)cc1N(C)CCN(C)C]

21-2

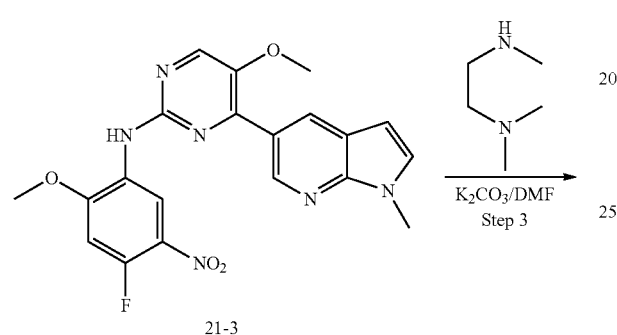

21-3

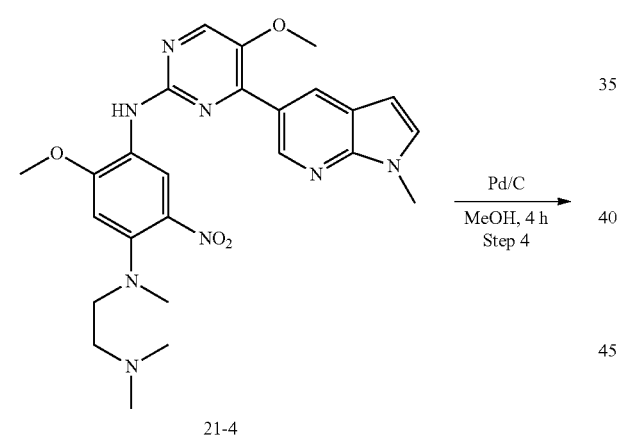

21-4

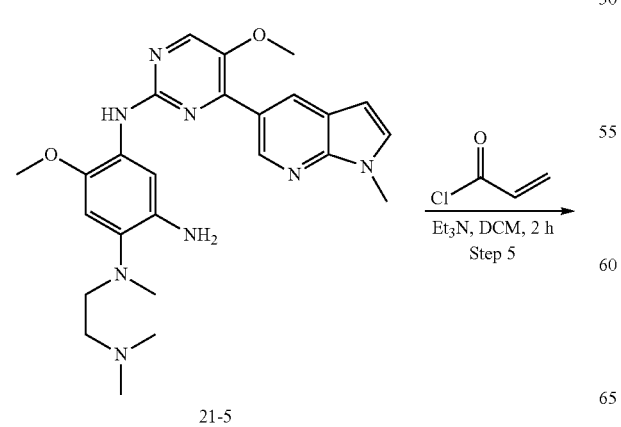

21-5

Z-21

Step 1: 5-(2-chloro-5-methoxypyrimidin-4-yl)-1-methyl-1H-pyrrolo[2,3-b]pyridine (Compound 21-2)

2,4-dichloro-5-methoxypyrimidine (1.25 g, 7.0 mmol), $PdCl_2$ $(dppf)_2$ (0.5 g, 0.7 mmol) and sodium carbonate (1.5 g, 14.0 mmol) were added to a mixed solution of compound 1-methyl-5-(4,4,5,5-tetramethyl-1,3,2-dioxaborolan-2-yl)-1H-pyrrolo[2,3-b]pyridine (1.8 g, 7.0 mmol commercially available) in 20 ml of acetonitrile and 4 ml of water, and vigorously stirred under $N_2$ atmosphere at 80° C. for 2 h. After completion of the reaction, the reaction mixture was filtered, and the filtrate was concentrated under reduced pressure to give the crude product which was purified by Combi-flash column chromatography [PE:EA=100:0-60:40] to give compound 21-2 (1.54 g, 80%). MS m/z (ESI): 275.1[M+H]+.

Step 2: N-(4-fluoro-2-methoxy-5-nitrophenyl)-5-methoxy-4-(1-methyl-1H-pyrrolo[2,3-b]pyridin-5-yl)pyrimidin-2-amine (Compound 21-3)

By using compound 21-2 (1.5 g, 5.46 mmol) as the starting material, the crude product was synthesized with reference to step 2 of Example 19, and purified by Combi-flash column chromatography [PE:EA=50:50] to give compound 21-3 (1.2 g, 52%), except that in step 2 of Example 21, the reaction mixture vigorously stirred under $N_2$ atmosphere at 120° C. for 21 h. MS m/z (ESI): 425.2[M+H]+.

Step 3: $N^1$-(2-(dimethylamino)ethyl)-5-methoxy-$N^4$-(5-methoxy-4-(1-methyl-1H-pyrrolo[2,3-b]pyridin-5-yl)pyrimidin-2-yl)-$N^1$-methyl-2-nitrobenzene-1,4-diamine (Compound 21-4)

By using compound 21-3 (500 mg, 1.18 mmol) as the starting material, compound 21-4 (620 mg, 100%) was synthesized with reference to step 5 of Example 1, and was used directly in the next step. MS m/z (ESI): 507.3[M+H]+.

Step 4: $N^1$-(2-(dimethylamino)ethyl)-5-methoxy-$N^4$-(5-methoxy-4-(1-methyl-1H-pyrrolo[2,3-b]pyridin-5-yl)pyrimidin-2-yl)-$N^1$-methylbenzene-1,2,4-triamine (Compound 21-5)

By using compound 21-4 (500 mg, 0.99 mmol) as the starting material, compound 21-5 (332 mg, 70.3%) was synthesized with reference to step 6 of Example 1, and was used directly in the next step. MS m/z (ESI): 477.2[M+H]+.

Step 5: N-(2-((2-(dimethylamino)ethyl)(methyl)amino)-4-methoxy-5-((5-methoxy-4-(1-methyl-1H-pyrrolo[2,3-b]pyridin-5-yl)pyrimidin-2-yl)amino)phenyl)acrylamide (Compound Z-21)

By using compound 21-5 (332 mg, 0.7 mmol) as the starting material, the crude product was synthesized with reference to step 7 of Example 1, and purified by preparative plate [DCM:MeOH:NH4OH=90:10:1] to give compound Z-21 (59 mg, 15.6%). MS m/z (ESI): 531.2[M+H]+; $^1$HNMR (400 MHz, CDCl$_3$): 9.83 (br. s., 1H), 9.63 (s, 1H), 9.13 (d, J=1.6 Hz, 1H), 8.93 (s, 1H), 8.23 (s, 1H), 7.52 (s, 1H), 7.11 (d, J=3.6 Hz, 1H), 6.67 (s, 1H), 6.53 (d, J=3.2 Hz, 1H), 6.48-6.34 (m, 2H), 5.63 (d, J=11.6 Hz, 1H), 3.84 (s, 3H), 3.81 (s, 3H), 3.80 (s, 3H), 2.87 (br. s., 2H), 2.61 (s, 3H), 2.37 (br. s., 2H), 2.28 (br. s., 6H).

Example 22: N-(2-((2-(dimethylamino)ethyl)(methyl)amino)-4-methoxy-5-((4-(1-methyl-1H-pyrrolo[2,3-b]pyridin-5-yl)-5-(trifluoromethyl)pyrimidin-2-yl)amino)phenyl)acrylamide (Compound Z-22)

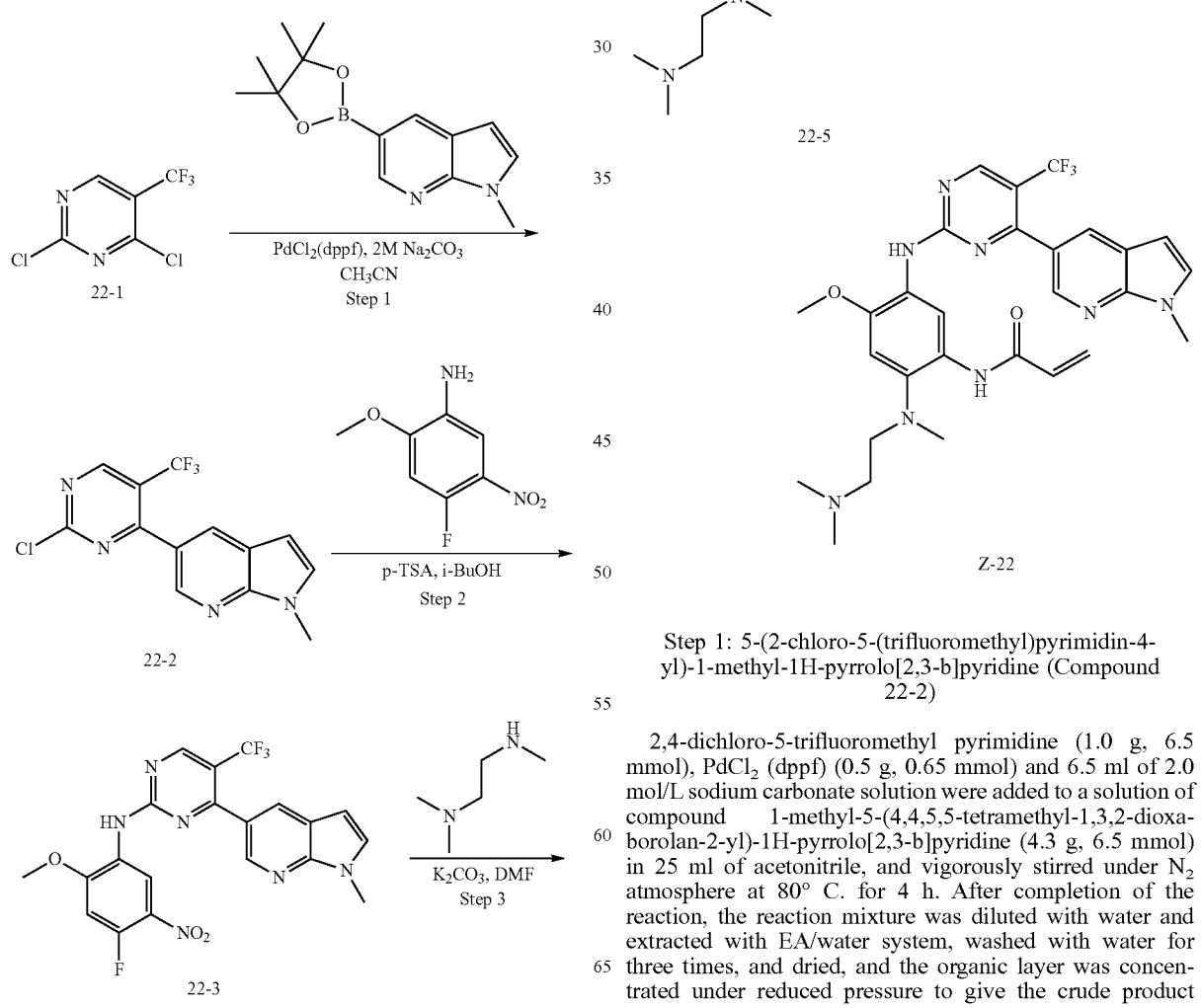

Step 1: 5-(2-chloro-5-(trifluoromethyl)pyrimidin-4-yl)-1-methyl-1H-pyrrolo[2,3-b]pyridine (Compound 22-2)

2,4-dichloro-5-trifluoromethyl pyrimidine (1.0 g, 6.5 mmol), PdCl$_2$ (dppf) (0.5 g, 0.65 mmol) and 6.5 ml of 2.0 mol/L sodium carbonate solution were added to a solution of compound 1-methyl-5-(4,4,5,5-tetramethyl-1,3,2-dioxaborolan-2-yl)-1H-pyrrolo[2,3-b]pyridine (4.3 g, 6.5 mmol) in 25 ml of acetonitrile, and vigorously stirred under N$_2$ atmosphere at 80° C. for 4 h. After completion of the reaction, the reaction mixture was diluted with water and extracted with EA/water system, washed with water for three times, and dried, and the organic layer was concentrated under reduced pressure to give the crude product which was purified by Combi-flash column chromatography

[PE:EA=100:0-20:80] to give compound 22-2 (0.6 g, 36%). MS m/z (ESI): 313.0[M+H]+.

Step 2: N-(4-fluoro-2-methoxy-5-nitrophenyl)-4-(1-methyl-1H-pyrrolo[2,3-b]pyridin-5-yl)-5-(trifluoromethyl)pyrimidin-2-amine (Compound 22-3)

4-fluoro-2-methoxy-5-nitroaniline (760 mg, 4.1 mmol) and compound 22-2 (1.0 g, 4.1 mmol) were added to a solution of p-toluenesulfonic acid (p-TSA)(1.7 g, 10.5 mmol) in 20 ml of isobutanol, and the reaction mixture was heated at 130° C. for 6 h in the sealed tube. After completion of the reaction, the reaction mixture was cooled to room temperature and large amount of solids precipitated from the solution. The solids were filtered by Buchner to obtain a filter cake which was beat in ethanol at reflux to give compound 22-3 (740 mg, 44%) which was used directly in the next reaction. MS m/z (ESI): 463.1 [M+H]+.

Step 3: $N^1$-(2-(dimethylamino)ethyl)-5-methoxy-N-methyl-$N^4$-(4-(1-methyl-1H-pyrrolo[2,3-b]pyridin-5-yl)-5-(trifluoromethyl)pyrimidin-2-yl)-2-nitrobenzene-1,4-diamine (Compound 22-4)

By using compound 22-3 (370 mg, 0.62 mmol) as the starting material, compound 22-4 (300 mg, 90%) was synthesized with reference to step 5 of Example 1. MS m/z (ESI): 544.2[M+H]+.

Step 4: $N^1$-(2-(dimethylamino)ethyl)-5-methoxy-N-methyl-$N^4$-(4-(1-methyl-1H-pyrrolo[2,3-b]pyridin-5-yl)-5-(trifluoromethyl)pyrimidin-2-yl)benzene-1,2,4-triamine (Compound 22-5)

By using compound 22-4 (300 mg, 0.6 mmol) as the starting material, compound 22-5 (200 mg) was synthesized with reference to step 4 of Example 7, and was used directly in the next step. MS m/z (ESI): 514.2[M+H]+.

Step 5: N-(2-((2-(dimethylamino)ethyl)(methyl)amino)-4-methoxy-5-((4-(1-methyl-1H-pyrrolo[2,3-b]pyridin-5-yl)-5-(trifluoromethyl)pyrimidin-2-yl)amino)phenyl)acrylamide (Compound Z-22)

By using compound 22-5 (200 mg, 0.44 mmol) as the starting material, the crude product was synthesized with reference to step 7 of Example 1, and purified by preparative liquid chromatography to give compound Z-22 (44.9 mg, 20%). MS m/z (ESI): 568.8 [M+H]+; $^1$HNMR (400 MHz, CDCl$_3$) δ 10.03 (s, 1H), 9.60 (s, 1H), 8.76 (s, 1H), 8.56 (s, 1H), 7.85 (s, 1H), 7.16 (s, 2H), 6.72 (s, 1H), 6.52 (s, 1H), 6.42 (d, J=16.8 Hz, 1H), 6.24 (dd, J=17.0, 10.1 Hz, 1H), 5.64 (d, J=10.2 Hz, 1H), 3.83 (d, J=24.8 Hz, 6H), 2.79 (s, 2H), 2.63 (s, 3H), 2.20 (d, J=12.4 Hz, 8H).

Example 23: N-(5-((5-chloro-4-(1,4-oxazepan-4-yl)pyrimidin-2-yl)amino)-2-((2-(dimethylamino)ethyl)(methyl)amino)-4-methoxyphenyl)acrylamide (Z-23)

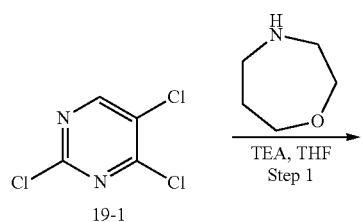

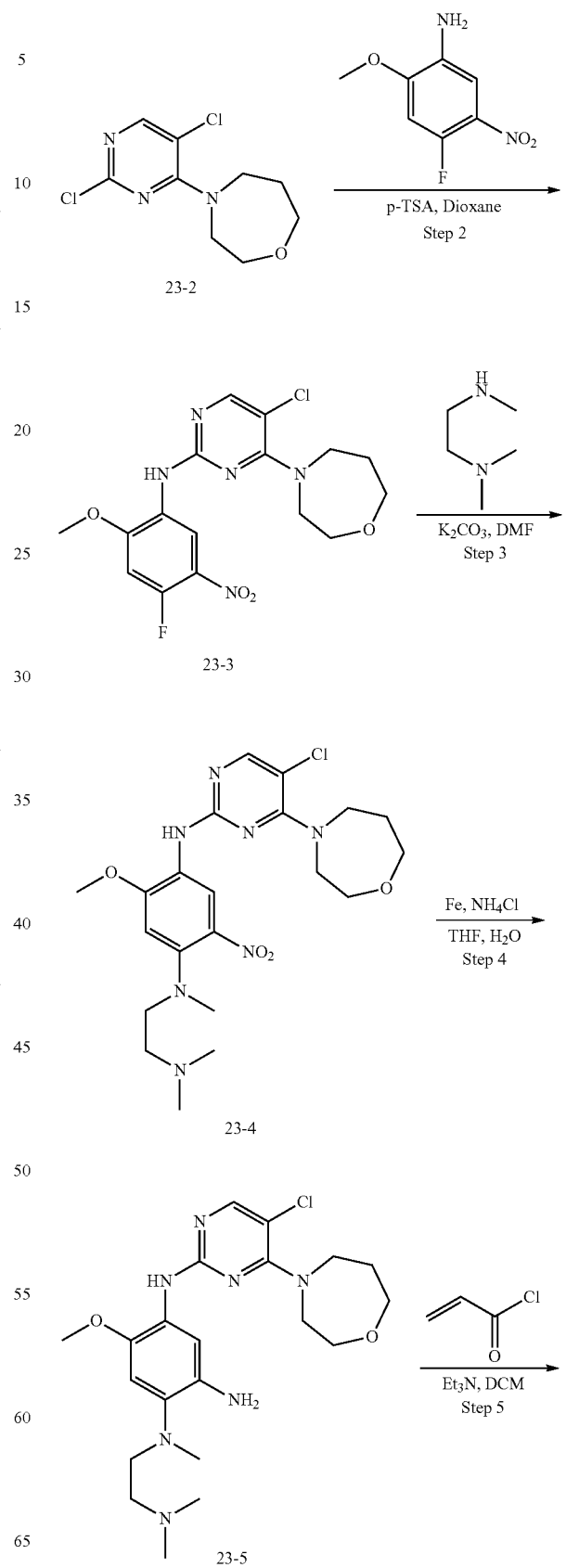

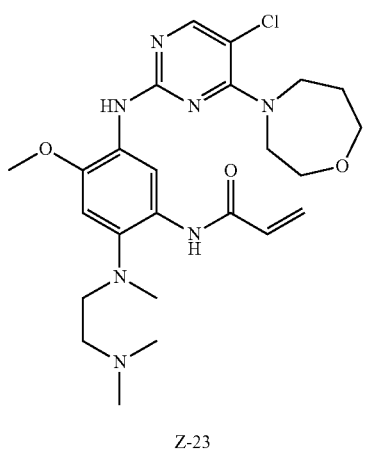 [SMILES: C=CC(=O)Nc1cc(Nc2ncc(Cl)c(N3CCCOCC3)n2)c(OC)cc1N(C)CCN(C)C]

Z-23

Step 1: 4-(2,5-dichloropyrimidin-4-yl)-1,4-oxazepane (Compound 23-2)

Compound 2,4,5-trichloropyrimidine (0.3 g, 1.65 mmol) was added to 10 ml of THF at 0° C., and triethylamine (0.49 g, 4.9 mmol), homomorpholine (0.22 g, 1.65 mmol, commercially available) were added to the reaction solution, and stirred at room temperature for 1 h. The reaction progress was monitored by TLC. After completion of the reaction, water and EA were added, and the organic layer was separated, washed with saturated aqueous sodium chloride, dried, and concentrated under reduced pressure to give compound 23-2 (0.5 g) which was used directly in the next step. MS m/z (ESI): 248.0 [M+H]+.

Step 2: 5-chloro-N-(4-fluoro-2-methoxy-5-nitrophenyl)-4-(1,4-oxazepan-4-yl)pyrimidin-2-amine (Compound 23-3)

Compound 23-2 (0.5 g, 2.0 mmol), 4-fluoro-2-methoxy-5-nitroaniline (0.37 g, 2.0 mmol) and p-toluenesulfonic acid (0.87 g, 5.0 mmol) were added to 10 ml of 1,4-dioxane, and stirred under $N_2$ at 110° C. for 8 h. After completion of the reaction, the reaction mixture was filtered, and the filter cake was washed with EA, dried at 50° C. to give the crude product compound 23-3 (0.45 g) which was used directly in the next step. MS m/z (ESI): 398.1 [M+H]+.

Step 3: $N^1$-(5-chloro-4-(1,4-oxazepan-4-yl)pyrimidin-2-yl)-$N^4$-(2-(dimethylamino)ethyl)-2-methoxy-$N^4$-methyl-5-nitrobenzene-1,4-diamine (Compound 23-4)

By using compound 23-3 (0.45 g, 1.1 mmol) as the starting material, compound 23-4 (0.4 g) was synthesized with reference to step 5 of Example 1, and was used directly in the next step. MS m/z (ESI): 480.2[M+H]+.

Step 4: $N^4$-(5-chloro-4-(1,4-oxazepan-4-yl)pyrimidin-2-yl)-$N^1$-(2-(dimethylamino)ethyl)-5-methoxy-N-methylbenzene-1,2,4-triamine (Compound 23-5)

By using compound 23-4 (0.4 g, 0.83 mmol) as the starting material, compound 23-5 (0.25 g) was synthesized with reference to step 4 of Example 7, and was used directly in the next step. MS m/z (ESI): 450.2[M+H]+.

Step 5: N-(5-((5-chloro-4-(1,4-oxazepan-4-yl)pyrimidin-2-yl)amino)-2-((2-(dimethylamino)ethyl)(methyl)amino)-4-methoxyphenyl)acrylamide (Z-23)

By using compound 23-5 (0.25 g, 0.55 mmol) as the starting material, the crude product was synthesized with reference to step 7 of Example 1, and purified by preparative liquid chromatography to give compound Z-23 (69.8 mg, 8.4%). MS m/z (ESI): 504.2 [M+H]+; $^1$HNMR (400 MHz, CDCl$_3$) δ 9.99 (s, 1H), 9.18 (s, 1H), 7.89 (s, 1H), 7.32 (s, 1H), 6.68 (s, 1H), 6.30 (dd, J=17.0, 1.9 Hz, 1H), 6.20 (d, J=9.9 Hz, 1H), 5.58 (dd, J=10.0, 1.9 Hz, 1H), 4.03-3.98 (m, 2H), 3.96 (t, J=6.2 Hz, 2H), 3.83-3.79 (m, 2H), 3.78 (s, 3H), 3.72-3.66 (m, 2H), 2.84-2.75 (m, 2H), 2.61 (s, 3H), 2.19 (s, 2H), 2.17 (s, 6H), 1.98 (dd, J=11.9, 5.9 Hz, 2H).

Example 24: N-(5-((4-((1S,4S)-2-oxa-5α-azabicyclo[2.2.1]heptan-5-yl)-5-chloropyrimidin-2-yl)amino)-2-((2-(dimethylamino)ethyl)(methyl)amino)-4-methoxyphenyl)acrylamide (Z-24)

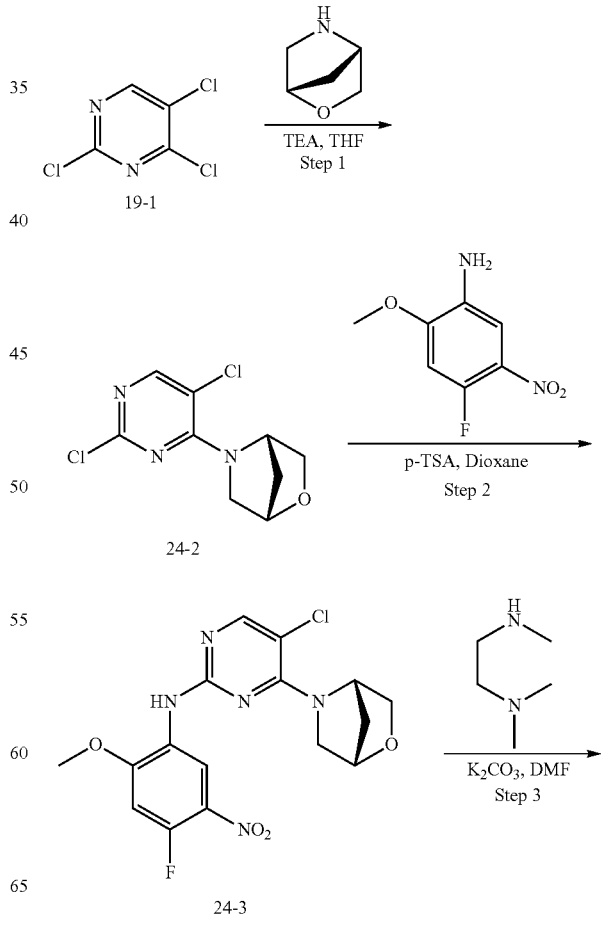

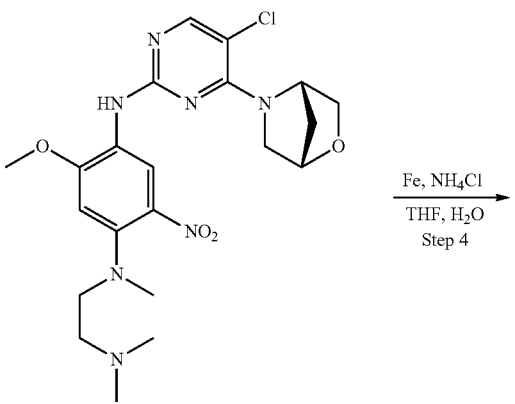

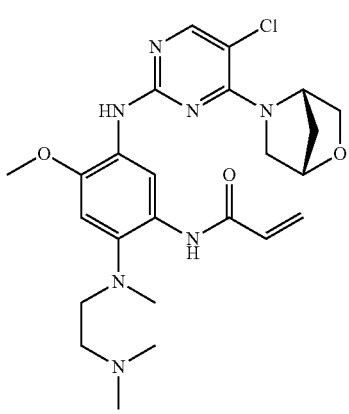

sodium chloride, dried, and concentrated under reduced pressure to give compound 24-2 (0.36 g) which was used directly in the next step. MS m/z (ESI): 246.0 [M+H]+.

Step 2

4-((1S,4S)-2-oxa-5-azabicyclo[2.2.1]hept-5-yl)-5-chloro-N-(4-fluoro-2-methoxy-5-nitrophenyl)pyrimidin-2-amine (Compound 24-3)

By using compound 24-2 (0.36 g, 1.4 mmol) as the starting material, compound 24-3 (0.32 g) was synthesized with reference to step 2 of Example 23, and was used directly in the next step. MS m/z (ESI): 396.1 [M+H]+.

Step 3: $N^1$-(4-((1S,4S)-2-oxa-5-azabicyclo[2.2.1]hept-5-yl)-5-chloropyrimidin-2-yl)-$N^4$-2-(dimethyl amino)ethyl)yl-2-methoxy-$N^4$-methyl-5-nitrophenyl-1,4-diamine (Compound 24-4)

By using compound 24-3 (0.32 g, 0.81 mmol) as the starting material, compound 24-4 (0.31 g) was synthesized with reference to step 5 of Example 1, and was used directly in the next step. MS m/z (ESI): 478.1[M+H]+.

Step 4: $N^4$-(4-((1S,4S)-2-oxa-5-azabicyclo[2.2.1]hept-5-yl)-5-chloro-pyrimidin-2-yl)-$N^1$-(2-(dimeth ylamino)ethyl)yl-5-methoxy-$N^1$-methylphenyl-1,2,4-triamine (Compound 24-5)

By using compound 24-4 (0.31, 0.65 mmol) as the starting material, compound 24-5 (0.22 g) was synthesized with reference to step 4 of Example 7, and was used directly in the next step. MS m/z (ESI): 448.2[M+H]+.

Step 5: N-(5-(4-((1S,4S)-2-oxa-5α-azabicyclo[2.2.1]heptan-5-yl)-5-chloropyrimidin-2-yl)amino)-2-((2-(dimethylamino)ethyl)(methyl)amino)-4-methoxyphenyl)acrylamide (Z-24)

By using compound 24-5 (0.2 g, 0.44 mmol) as the starting material, the crude product was synthesized with reference to step 7 of Example 1, and purified by preparative liquid chromatography to give compound Z-24 (60.1 mg, 7.3%). MS m/z (ESI): 502.2 [M+H]+; $^1$HNMR (400 MHz, DMSO-d6) δ 10.09 (s, 1H), 8.85 (s, 1H), 7.96 (s, 1H), 7.67 (s, 1H), 6.96 (s, 1H), 6.37 (dd, J=16.9, 10.0 Hz, 1H), 6.22 (dd, J=16.9, 2.1 Hz, 1H), 5.73 (dd, J=10.0, 2.1 Hz, 1H), 5.32 (s, 1H), 4.61 (s, 1H), 3.88 (d, J=10.5 Hz, 1H), 3.85 (s, 3H), 3.81 (d, J=7.6 Hz, 1H), 3.73 (d, J=7.5 Hz, 1H), 3.59 (d, J=10.5 Hz, 1H), 2.85 (t, J=5.2 Hz, 2H), 2.68 (s, 3H), 2.25 (t, J=5.9 Hz, 2H), 2.18 (s, 6H), 1.90 (d, J=9.9 Hz, 1H), 1.78 (d, J=9.7 Hz, 1H).

Example 25-78, 87, 88

Step 1: (1S,4S)-5-(2,5-dichloro-pyrimidin-4-yl)-2-oxa-5-azabicyclo[2.2.1]heptane (Compound 24-2)

Compound 2,4,5-trichloropyrimidine (0.3 g, 1.65 mmol) was added to 10 ml of THF at 0° C., triethylamine (0.5 g, 4.9 mmol), (1S,4S)-2-oxa-5-aza-bicyclo[2.2.1]heptane (0.22 g, 1.65 mmol, commercially available) were added to the reaction solution, and stirred at room temperature for 1 h. The reaction progress was monitored by TLC. After completion of the reaction, water and EA were added, and the organic layer was separated, washed with saturated aqueous

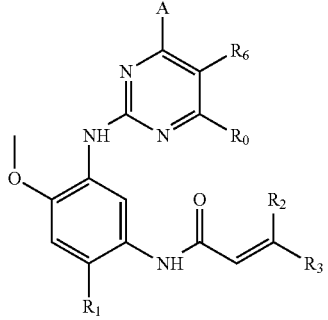

(IV-1)

The title compounds of Example 25-78, 87 and 88 are shown as formula (IV-1), wherein substituents $R_0$, $R_2$ and $R_3$ are hydrogen, and the other substituents A, $R_1$, $R_6$ are shown as the following table.

General Procedure: The preparation methods of compounds Z-25 to Z-56, Z-87, Z-88 were similar to Example 1, by using boronate ester or boronic acid substituted with different substituents and using 5-substituted 2,4-dichloropyrimidine as the starting materials.

By using different amines and 5-substituted 2,4-dichloropyrimidine as the starting materials, compounds Z-57 to Z-78 were prepared with reference to the method similar to Example 7.

| Example No. | Compound | A | $R_1$ | $R_6$ | MS [M + H]+ |
|---|---|---|---|---|---|
| 25 | Z-25 | 5-(1-methyl-1H-pyrrolo[2,3-b]pyridin-5-yl) | 4-(dimethylamino)piperidin-1-yl | H | 527.3 |
| 26 | Z-26 | 5-(1-methyl-1H-pyrrolo[2,3-b]pyridin-5-yl) | 4-methylpiperazin-1-yl | H | 499.2 |
| 27 | Z-27 | 5-(1-methyl-1H-pyrrolo[2,3-b]pyridin-5-yl) | 3-(dimethylamino)azetidin-1-yl | H | 499.2 |
| 28 | Z-28 | 5-(1-methyl-1H-pyrrolo[2,3-b]pyridin-5-yl) | 4-(dimethylamino)piperidin-1-yl | $OCH_3$ | 557.3 |
| 29 | Z-29 | 5-(1-methyl-1H-pyrrolo[2,3-b]pyridin-5-yl) | 4-(dimethylamino)piperidin-1-yl | F | 545.2 |
| 30 | Z-30 | 5-(1H-pyrrolo[2,3-b]pyridin-5-yl) | N,N,N'-trimethylethylenediamine | H | 486.9 |
| 31 | Z-31 | 5-(1H-pyrrolo[2,3-b]pyridin-5-yl) | N,N,N'-trimethylethylenediamine | Cl | 521.3 |
| 32 | Z-32 | 5-(1-methyl-1H-pyrrolo[2,3-b]pyridin-5-yl) | N,N,N'-trimethylethylenediamine | $CO_2CH_3$ | 559.2 |

-continued

| Example No. | Compound | A | R₁ | R₆ | MS [M + H]+ |
|---|---|---|---|---|---|
| 33 | Z-33 | 5-(1H-pyrrolo[2,3-b]pyridin-5-yl) | 3-(dimethylamino)azetidin-1-yl | H | 485.2 |
| 34 | Z-34 | 5-(1H-pyrrolo[2,3-b]pyridin-5-yl) | 4-(dimethylamino)piperidin-1-yl | H | 513.3 |
| 35 | Z-35 | 5-(1-methyl-1H-pyrrolo[2,3-b]pyridin-5-yl) | 4-(dimethylamino)piperidin-1-yl | CF₃ | 595.3 |
| 36 | Z-36 | 5-(1-methyl-1H-pyrrolo[2,3-b]pyridin-5-yl) | N-methyl-N'-methyl-ethylenediamine | Cl | 521.2 |
| 37 | Z-37 | 5-(1-methyl-1H-pyrazolo[3,4-b]pyridin-5-yl) | 4-(dimethylamino)piperidin-1-yl | F | 546.7 |
| 38 | Z-38 | 5-(1-methyl-1H-pyrazolo[3,4-b]pyridin-5-yl) | 4-(dimethylamino)piperidin-1-yl | OCH₃ | 558.3 |
| 39 | Z-39 | 5-(1-methyl-1H-pyrazolo[3,4-b]pyridin-5-yl) | N,N,N'-trimethyl-ethylenediamine | Cl | 536.7 |
| 40 | Z-40 | 5-(1-methyl-1H-pyrazolo[3,4-b]pyridin-5-yl) | 4-(dimethylamino)piperidin-1-yl | Cl | 562.7 |
| 41 | Z-41 | 5-(1-methyl-1H-pyrazolo[3,4-b]pyridin-5-yl) | N,N,N',N'-tetramethyl-ethylenediamine | F | 520.7 |

-continued
| Example No. | Compound | A | R₁ | R₆ | MS [M + H]+ |
|---|---|---|---|---|---|
| 42 | Z-42 | 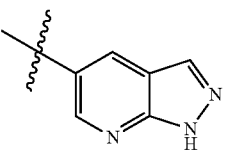 [SMILES: *c1cnc2[nH]ncc2c1] | 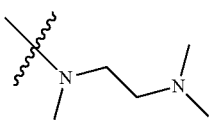 [SMILES: *N(C)CCN(C)C] | Cl | 522.2 |
| 43 | Z-43 | 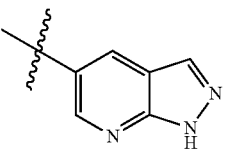 | 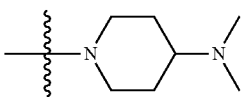 [SMILES: *N1CCC(N(C)C)CC1] | Cl | 548.2 |
| 44 | Z-44 | 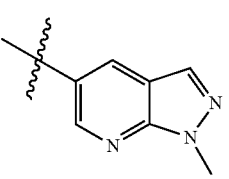 [SMILES: *c1cnc2c(cnn2C)c1] | 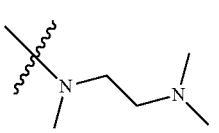 [SMILES: *N(C)CCN(C)C] | OCH₃ | 532.3 |
| 45 | Z-45 | 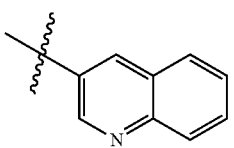 [SMILES: *c1cnc2ccccc2c1] | 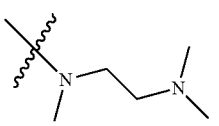 [SMILES: *N(C)CCN(C)C] | H | 498.7 |
| 46 | Z-46 | 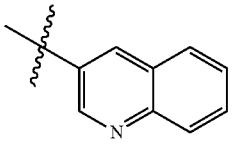 [SMILES: *c1cnc2ccccc2c1] | 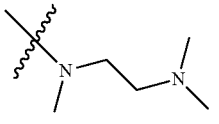 [SMILES: *N(C)CCN(C)C] | Cl | 532.7 |
| 47 | Z-47 | 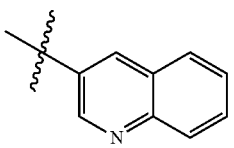 [SMILES: *c1cnc2ccccc2c1] | 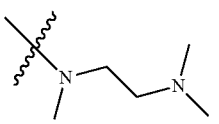 [SMILES: *N(C)CCN(C)C] | F | 516.2 |
| 48 | Z-48 | 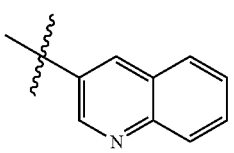 [SMILES: *c1cnc2ccccc2c1] | 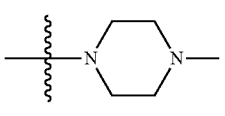 | H | 496.2 |
| 49 | Z-49 | 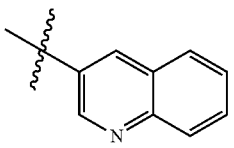 [SMILES: *c1cnc2ccccc2c1] | 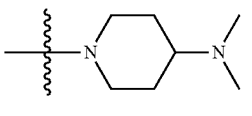 [SMILES: *N1CCC(N(C)C)CC1] | H | 524.7 |
| 50 | Z-50 | 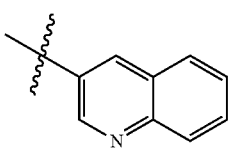 [SMILES: *c1cnc2ccccc2c1] | 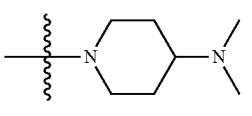 | OCH₃ | 554.3 |

-continued
| Example No. | Compound | A | R₁ | R₆ | MS [M + H]+ |
|---|---|---|---|---|---|
| 51 | Z-51 | 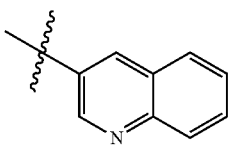 [SMILES: *c1cnc2ccccc2c1] | 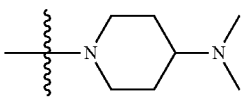 | F | 542.3 |
| 52 | Z-52 | 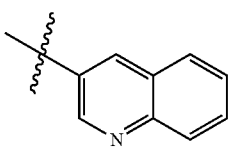 [SMILES: *c1cnc2ccccc2c1] | 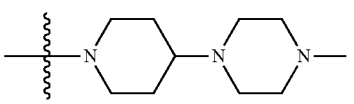 | H | 579.4 |
| 53 | Z-53 | 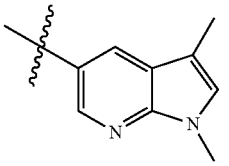 [SMILES: *c1cnc2c(c1)c(C)cn2C] | 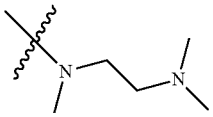 [SMILES: *N(C)CCN(C)C] | Cl | 549.2 |
| 54 | Z-54 | 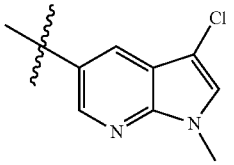 [SMILES: *c1cnc2c(c1)c(Cl)cn2C] | 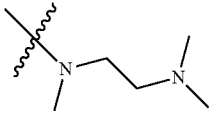 [SMILES: *N(C)CCN(C)C] | H | 535.2 |
| 55 | Z-55 | 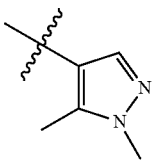 [SMILES: *c1cnn(C)c1C] | 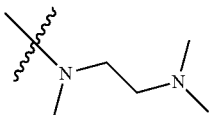 [SMILES: *N(C)CCN(C)C] | Cl | 499.2 |
| 56 | Z-56 | 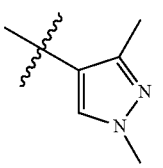 [SMILES: *c1cn(C)nc1C] | 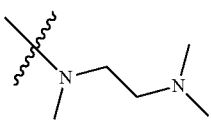 [SMILES: *N(C)CCN(C)C] | H | 465.3 |
| 57 | Z-57 | 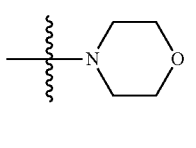 [SMILES: *N1CCOCC1] |  | F | 474.1 |
| 58 | Z-58 | 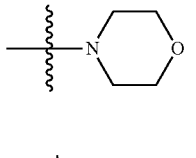 | 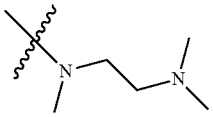 [SMILES: *N(C)CCN(C)C] | OCH₃ | 486.3 |
| 59 | Z-59 | 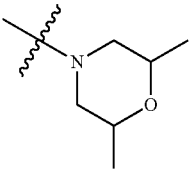 [SMILES: *N1CC(C)OC(C)C1] | 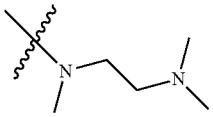 [SMILES: *N(C)CCN(C)C] | H | 483.9 |

-continued

| Example No. | Compound | A | R₁ | R₆ | MS [M + H]+ |
|---|---|---|---|---|---|
| 60 | Z-60 | (1,4-oxazepan-4-yl) | N,N,N'-trimethylethylenediamine | H | 470.3 |
| 61 | Z-61 | (8-oxa-3-azabicyclo[3.2.1]octan-3-yl) | N,N,N'-trimethylethylenediamine | H | 468.3 |
| 62 | Z-62 | 3-methylmorpholin-4-yl | N,N,N'-trimethylethylenediamine | Cl | 504.2 |
| 63 | Z-63 | 2,6-dimethylmorpholin-4-yl | N,N,N'-trimethylethylenediamine | Cl | 518.3 |
| 64 | Z-64 | morpholin-4-yl | N,N,N'-trimethylethylenediamine | CF₃ | 524.3 |
| 65 | Z-65 | 3,3-dimethylmorpholin-4-yl | 4-(dimethylamino)piperidin-1-yl | H | 510.3 |
| 66 | Z-66 | 3,5-dimethylmorpholin-4-yl | 4-(dimethylamino)piperidin-1-yl | H | 510.3 |
| 67 | Z-67 | 1,4-oxazepan-4-yl | 4-(dimethylamino)piperidin-1-yl | H | 496.3 |
| 68 | Z-68 | 3-methylmorpholin-4-yl | 4-(dimethylamino)piperidin-1-yl | Cl | 530.3 |
| 69 | Z-69 | 3,3-dimethylmorpholin-4-yl | 4-(dimethylamino)piperidin-1-yl | Cl | 544.3 |

-continued

| Example No. | Compound | A | R₁ | R₆ | MS [M + H]+ |
|---|---|---|---|---|---|
| 70 | Z-70 | 4,4-dimethylmorpholine linked via N | 4-(dimethylamino)piperidine linked via N | Cl | 544.3 |
| 71 | Z-71 | 2-oxa-5-azabicyclo[2.2.1]heptane linked via N | 4-(dimethylamino)piperidine linked via N | Cl | 528.2 |
| 72 | Z-72 | 4-methylpiperazine linked via N | N,N,N'-trimethylethylenediamine linked via N | Cl | 503.2 |
| 73 | Z-73 | 4-Boc-piperazine linked via N | N,N,N'-trimethylethylenediamine linked via N | Cl | 589.3 |
| 74 | Z-74 | 4-(methylsulfonyl)piperazine linked via N | N,N,N'-trimethylethylenediamine linked via N | Cl | 567.0 |
| 75 | Z-75 | piperazine linked via N | N,N,N'-trimethylethylenediamine linked via N | Cl | 489.3 |
| 76 | Z-76 | piperidine linked via N | N,N,N'-trimethylethylenediamine linked via N | Cl | 488.2 |
| 77 | Z-77 | piperidine linked via N | 4-methylpiperazine linked via N | Cl | 486.2 |
| 78 | Z-78 | piperidine linked via N | 4-(dimethylamino)piperidine linked via N | Cl | 514.2 |

| Example No. | Compound | A | R₁ | R₆ | MS [M + H]+ |
|---|---|---|---|---|---|
| 87 | Z-87 | 5-(1-methylindolyl) | N,N,N'-trimethylethylenediamine | H | 500.7 |
| 88 | Z-88 | 5-(1-methylindolyl) | N,N,N'-trimethylethylenediamine | Cl | 534.7 |

| Compound | ¹HNMR |
|---|---|
| Z-25 | ¹HNMR (400 MHz, CDCl₃) δ 9.79 (s, 1H), 9.25 (s, 1H), 8.98 (d, J = 2.0 Hz, 1H), 8.64 (s, 1H), 8.47 (d, J = 5.2 Hz, 1H), 7.74 (s, 1H), 7.23 (d, J = 5.3 Hz, 1H), 7.21 (d, J = 3.5 Hz, 1H), 6.76 (s, 1H), 6.65 (d, J = 3.4 Hz, 1H), 6.47 (dd, J = 16.9, 1.3 Hz, 1H), 6.36-6.28 (m, 1H), 5.77 (dd, J = 10.8, 0.8 Hz, 1H), 3.91 (d, J = 13.4 Hz, 6H), 3.05 (d, J = 11.5 Hz, 2H), 2.74 (dt, J = 11.9, 5.9 Hz, 2H), 2.36 (s, 6H), 2.28-2.19 (m, 1H), 2.05 (d, J = 11.2 Hz, 2H), 1.72-1.64 (m, 2H). |
| Z-26 | ¹HNMR (400 MHz, DMSO) δ 9.06 (d, J = 6.5 Hz, 2H), 8.99 (s, 1H), 8.91 (s, 1H), 8.49 (d, J = 4.8 Hz, 1H), 8.29 (s, 1H), 8.06 (s, 1H), 7.61 (s, 1H), 7.52 (d, J = 4.9 Hz, 1H), 6.90 (s, 1H), 6.73-6.62 (m, 1H), 6.58 (s, 1H), 6.32 (d, J = 17.7 Hz, 1H), 5.79 (d, J = 9.9 Hz, 1H), 3.89 (d, J = 8.2 Hz, 6H), 2.87 (s, 7H), 2.27 (s, 4H). |
| Z-27 | ¹HNMR (400 MHz, CDCl₃) δ 9.09 (s, 1H), 8.99 (s, 1H), 8.97 (s, 1H), 8.43 (d, J = 5.2 Hz, 1H), 7.60 (s, 1H), 7.38 (s, 1H), 7.21 (d, J = 3.4 Hz, 1H), 7.17 (d, J = 5.2 Hz, 1H), 6.63 (d, J = 3.2 Hz, 1H), 6.49 (d, J = 17.3 Hz, 1H), 6.42 (s, 1H), 6.37-6.30 (m, 1H), 5.78 (d, J = 10.5 Hz, 1H), 3.92 (s, 6H), 3.89 (t, J = 6.5 Hz, 2H), 3.62 (t, J = 6.5 Hz, 2H), 3.16-3.08 (m, 1H), 2.20 (s, 6H). |
| Z-32 | ¹HNMR (CHLOROFORM-d6, 400 MHz): 89.96 (br. s., 1 H), 9.66 (s, 1 H), 8.93 (s, 1 H), 8.66 (br. s., 1 H), 8.39 (s, 1 H), 7.89 (s, 1 H), 7.11 (d, J = 2.8 Hz, 1 H), 6.70 (s, 1 H), 6.52 (br. s., 1 H), 6.41-6.50 (m, 1 H), 6.36 (br. s., 1 H), 5.65 (d, J = 10.8 Hz, 1 H), 3.83 (s, 3 H), 3.79 (s, 3 H), 3.68 (s, 3 H), 2.81 (br. s., 2 H), 2.61 (s, 3 H), 2.21 ppm (br. s., 8 H). |
| Z-37 | ¹HNMR (400 MHz, CDCl₃) δ 9.60 (s, 1H), 9.44 (s, 1H), 9.43 (s, 1H), 8.54 (s, 1H), 8.50 (s, 1H), 8.40-8.39 (d, J = 3.6 Hz, 1H), 8.12 (s, 1H), 7.74 (s, 1H), 6.73 (s, 1H), 6.40-6.38 (m, 2H), 5.81-5.78 (dd, J1 = 2.9 Hz, J2 = 8.2 Hz, 1H), 4.29 (s, 3H), 3.89 (s, 3H), 3.11-3.08 (d, J = 12.0 Hz, 2H), 2.79-2.74 (m, 3H), 2.59 (s, 6H), 2.16-2.13 (d, J = 12.3 Hz, 2H), 1.88-1.84 (dd, J1 = 3.3 Hz, J2 = 11.8 Hz, 2H). |
| Z-38 | ¹HNMR (400 MHz, DMSO) δ 9.27 (d, J = 2.4 Hz, 1H), 9.04 (d, J = 2.0 Hz, 1H), 9.00 (s, 1H), 8.80 (s, 1H), 8.52 (s, 1H), 8.47 (s, 1H), 7.88 (s, 1H), 6.85 (s, 1H), 6.69 (m, 1H), 6.30 (d, J = 17.6 Hz, 1H), 5.78 (d, J = 12.0 Hz, 1H), 4.24 (s, 3H), 3.93 (s, 3H), 3.87 (s, 3H), 3.04 (m, 2H), 2.70 (m, 2H), 2.34 (s, 7H), 1.86 (m, 2H), 1.72 (m, 2H). |
| Z-39 | ¹HNMR (400 MHz, CDCl₃) δ 10.14 (s, 1H), 9.62 (s, 1H), 9.30 (s, 1H), 9.12 (s, 1H), 8.50 (s, 1H), 8.09 (s, 1H), 7.74 (s, 1H), 6.78 (s, 1H), 6.45-6.41 (d, J = 16.9 Hz, 1H), 6.35-6.33 (d, J = 9.2 Hz, 1H), 5.72-5.69 (d, J = 10.0 Hz, 1H), 4.29 (s, 3H), 3.88 (s, 3H), 3.48 (s, 2H), 2.85 (s, 2H), 2.69 (s, 3H), 2.24 (s, 6H). |
| Z-40 | ¹HNMR (400 MHz, CDCl₃) δ 9.54 (s, 1H), 9.30 (s, 1H), 9.09 (s, 1H), 8.58 (s, 1H), 8.49 (s, 1H), 8.08 (s, 1H), 7.70 (s, 1H), 6.74 (s, 1H), 6.40-6.25 (m, 2H), 5.77-5.75 (d, J = 9.9 Hz, 1H), 4.29 (s, 3H), 3.87 (s, 3H), 3.03-3.00 (d, J = 11.4 Hz, 2H), 2.73-2.68 (t, J = 10.6 Hz, 2H), 2.34 (s, 6H), 2.24-2.19 (t, J = 10.6 Hz, 1H), 2.05-2.02 (d, J = 11.2 Hz, 1H), 1.65 (s, 2H). |
| Z-41 | ¹HNMR (400 MHz, CDCl₃) δ 10.17 (s, 1H), 9.68 (s, 1H), 9.51 (s, 1H), 9.44 (s, 1H), 8.41-8.40 (d, J = 3.6 Hz, 1H), 8.14 (s, 1H), 7.77 (s, 1H), 6.80 (s, 1H), 6.47-6.42 (dd, J1 = 2.2 Hz, J2 = 17.0 Hz, 1H), 6.39-6.33 (dd, J1 = 9.7 Hz, J2 = 17.2 Hz, 1H), 5.74-5.71 (dd, J1 = 2.3 Hz, J2 = 9.7 Hz, 1H), 4.29 (s, 3H), 3.89 (s, 3H), 2.89-2.87 (t, J = 6.5 Hz, 2H), 2.70 (s, 3H), 2.29-2.27 (d, J = 5.8 Hz, 2H), 2.25 (s, 6H). |
| Z-44 | ¹HNMR (400 MHz, CDCl₃) δ 10.06 (s, 1H), 9.67 (s, 1H), 9.36 (d, J = 1.6 Hz, 1H), 9.31 (s, 1H), 8.25 (s, 1H), 8.11 (s, 1H), 7.57 (s, 1H), 6.71 (s, 1H), 6.44 (d, J = 16.8 Hz, 1H), 6.30 (m, 1H), 5.67 (d, J = 10.4 Hz, 1H), 4.12 (s, 3H), 3.85 (s, 3H), 3.81 (s, 3H), 2.80 (s, 2H), 2.63 (s, 3H), 2.18 (s, 8H). |
| Z-54 | ¹HNMR (400 MHz, DMSO) δ 10.13 (s, 1H), 9.17 (d, J = 1.6 Hz, 1H), 8.97 (s, |

| Compound | ¹HNMR |
|---|---|
| | 1H), 8.74 (d, J = 2.0 Hz, 1H), 8.50 (d, J = 5.2 Hz, 1H), 8.27 (s, 1H), 7.83 (s, 1H), 7.56 (d, J = 5.2 Hz, 1H), 7.03 (s, 1H), 6.39 (dd, J = 17.2, 10.0 Hz, 1H), 6.24 (dd, J = 17.2, 2.0 Hz, 1H), 5.74 (dd, J = 10.0, 2.0 Hz, 1H), 3.86 (s, 3H), 3.85 (s, 3H), 2.88 (t, J = 5.2 Hz, 2H), 2.72 (s, 3H), 2.36-2.28 (m, 2H), 2.22 (s, 6H). |
| Z-55 | ¹HNMR (400 MHz, CDCl₃) 89.37 (br. s., 1H), 9.26 (s, 1H), 8.44 (br. s., 1H), 8.35 (s, 1H), 8.02 (s, 1H), 7.45 (s, 1H), 6.81 (dd, J = 10.4, 16.8 Hz, 1H), 6.60 (s, 1H), 6.36 (d, J = 16.8 Hz, 1H), 5.64 (d, J = 10.4 Hz, 1H), 3.80 (s, 3H), 3.76 (s, 3H), 3.12 (t, J = 5.6 Hz, 2H), 2.91 (t, J = 5.6 Hz, 2H), 2.61 (s, 6H), 2.58 (s, 3H), 2.45 (s, 3H). |
| Z-87 | ¹HNMR (400 MHz, CDCl₃) δ 9.80 (s, 1H), 9.69 (s, 1H), 8.64 (s, 1H), 8.60 (s, 1H), 8.46-8.44 (d, J = 5.3 Hz, 1H), 8.12-8.10 (d, J = 8.5 Hz, 1H), 7.72 (s, 1H), 7.41-7.38 (d, J = 8.5 Hz, 1H), 7.22-7.21 (d, J = 5.3 Hz, 1H), 7.08-7.07 (d, J = 3.0 Hz, 1H), 6.72 (s, 1H), 6.63-6.63 (d, J = 3.1 Hz, 1H), 6.55-6.50 (dd, J1 = 1.7 Hz, J2 = 16.9 Hz, 1H), 5.74-5.72 (d, J = 10.0 Hz, 1H), 3.88 (s, 3H), 3.83 (s, 3H), 2.70-2.68 (d, J = 5.6 Hz, 2H), 2.66 (s, 3H), 2.63-2.62 (d, J = 5.6 Hz, 2H), 2.48 (s, 6H). |
| Z-88 | ¹HNMR (400 MHz, CDCl₃) δ 9.88 (s, 1H), 9.61 (s, 1H), 8.49 (s, 1H), 8.37 (s, 1H), 7.93-7.91 (d, J = 8.4 Hz, 1H), 7.68 (s, 1H), 7.42-7.40 (d, J = 8.6 Hz, 1H), 7.09-7.08 (d, J = 3.1 Hz, 1H), 6.73 (s, 1H), 6.61-6.61 (d, J = 3.0 Hz, 1H), 6.50-6.49 (d, J = 4.0 Hz, 2H), 5.72-5.69 (dd, J1 = 4.5 Hz, J2 = 7.4 Hz, 1H), 3.86 (s, 3H), 3.83 (s, 3H), 2.97-2.94 (t, J = 5.4 Hz, 2H), 2.67 (s, 3H), 2.49-2.47 (d, J = 5.1 Hz, 2H), 2.36 (s, 6H), 2.01 (s, 3H). |

Examples 79-86

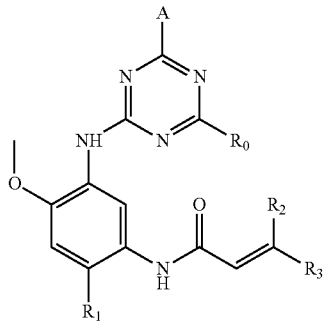

(IV-2)

The title compounds of Examples 79-86 are shown as formula (IV-2), wherein substituents $R_0$, $R_2$ and $R_3$ are hydrogen, the other substituents A, $R_1$ are shown as the following table.

General Procedure: The preparation methods of compounds Z-79 to Z-82 were similar to Example 23, by using different amines and 2,4-dichloro-1,3,5-triazine as the starting materials.

By using boronate ester or boronic acid substituted with different substituents and 2,4-dichloro-1,3,5-triazine as the starting materials, compounds Z-83 to Z-86 were prepared with reference to the method similar to Example 14.

| Example No. | Compound | A | $R_1$ | MS [M + H]+ |
|---|---|---|---|---|
| 79 | Z-79 | 3-methylmorpholinyl | N,N-dimethylethylenediaminyl | 471.3 |
| 80 | Z-80 | 2,6-dimethylmorpholinyl | N,N-dimethylethylenediaminyl | 485.2 |
| 81 | Z-81 | 1,4-oxazepanyl | N,N-dimethylethylenediaminyl | 471.3 |

-continued

| Example No. | Compound | A | R₁ | MS [M + H]+ |
|---|---|---|---|---|
| 82 | Z-82 | (morpholine) | (N,N,N'-trimethylethylenediamine) | 457.0 |
| 83 | Z-83 | (1H-pyrazolo[3,4-b]pyridin-5-yl) | (N,N,N'-trimethylethylenediamine) | 589.2 |
| 84 | Z-84 | (1-methyl-1H-pyrazolo[3,4-b]pyridin-5-yl) | (N,N,N'-trimethylethylenediamine) | 503.3 |
| 85 | Z-85 | (1H-pyrazolo[3,4-b]pyridin-5-yl) | (N,N,N'-trimethylethylenediamine) | 488.2 |
| 86 | Z-86 | (1-methyl-1H-pyrrolo[2,3-b]pyridin-5-yl) | (N,N,N'-trimethylethylenediamine) | 502.3 |

Example 89: Preparation of N-(5-(5-chloro-4-(1-methyl-1H-pyrazol-4-yl)pyrimidin-2-ylamino)-2-(4-(dimethylamino)piperidin-1-yl)-4-methoxyphenyl)acrylamide (Z-89)

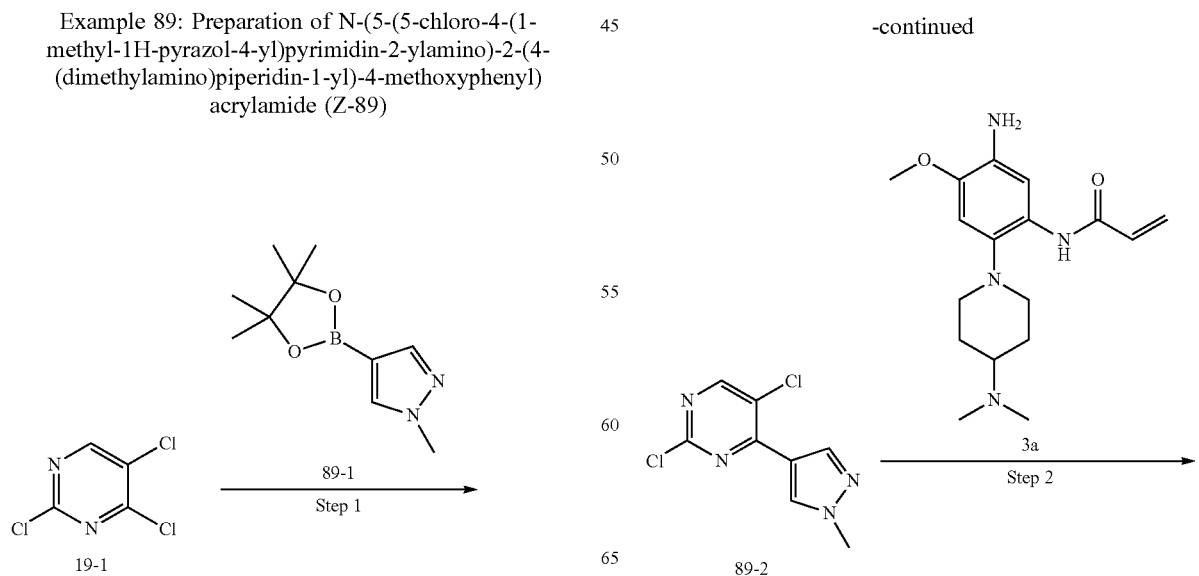

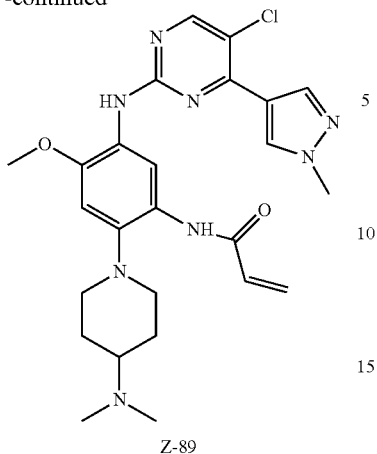

Z-89 step 1: The mixed solution of 1-methyl-4-(4,4,5,5-tetramethyl-1,3,2-dioxaborolan-2-yl)-1H-pyrazole (1.1 g, 5.25 mmol), compound 19-1 (745 mg, 4 mmol), Pd(dppf)Cl$_2$ (109.7 mg, 0.15 mmol) and sodium carbonate solution (5 ml, 2M) in acetonitrile (30 mL) was stirred under nitrogen atmosphere at 85° C. for 6 h. After completion of the reaction, the reaction was quenched with water, EA (150 ml) was added to the reaction mixture, the layers separated, the aqueous phase was extracted with EA (50 ml×2) twice, and the combined organic phase was dried over Na$_2$SO$_4$ and concentrated to give the crude product which was purified by Combi-flash column chromatography [PE:EA=5:1-2:1] to give 0.6 g title compound 89-2. MS m/z (ESI): 229[M+H]+.

Step 2: Cesium carbonate (487.5 mg, 0.5 mmol) was added to a solution of compound 3a (159 mg, 0.5 mmol), compound 89-2 (114 mg, 0.5 mmol), Pd$_2$(dba)$_3$ (45.75 mg, 0.05 mmol) and Xantphos (28.4 mg, 0.05 mmol) in 1,4-dioxane (4 ml), the reaction mixture was stirred at 100° C. for 3 h, EA (50 ml×2) and water (10 ml) were added to the reaction mixture, the organic phase was washed with water (10 ml×3), dried over Na$_2$SO$_4$, and concentrated to give the crude product, and the resulting crude product was separated and purified by preparative liquid chromatography to give the title compound Z-89 (19 mg, 4%), MS m/z (ESI): 511.2[M+H]+; $^1$HNMR (400 MHz, CDCl$_3$) δ 9.50 (s, 1H), 9.19 (s, 1H), 8.63 (s, 1H), 8.40 (s, 1H), 8.24 (s, 1H), 7.66 (s, 1H), 6.69 (s, 1H), 6.28 (ddd, J=26.8, 16.9, 5.7 Hz, 2H), 5.69 (dd, J=9.9, 1.6 Hz, 1H), 4.00 (s, 3H), 3.81 (s, 3H), 2.96 (d, J=12.1 Hz, 2H), 2.66 (t, J=10.9 Hz, 2H), 2.15 (dd, J=9.3, 5.5 Hz, 1H), 2.04-1.91 (m, 2H), 1.62 (s, 2H).

Example 90: Preparation of N-(2-(4-(dimethylamino)piperidin-1-yl)-5-(5-fluoro-4-(1-methyl-1H-pyrazol-4-yl)pyrimidin-2-ylamino)-4-methoxyphenyl)acrylamide (Z-90)

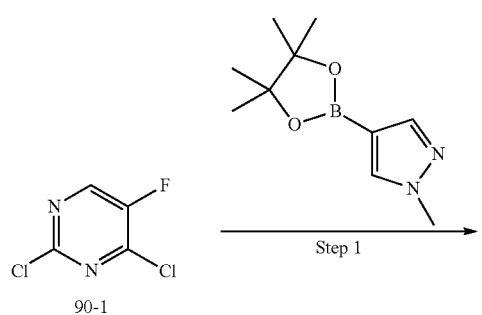

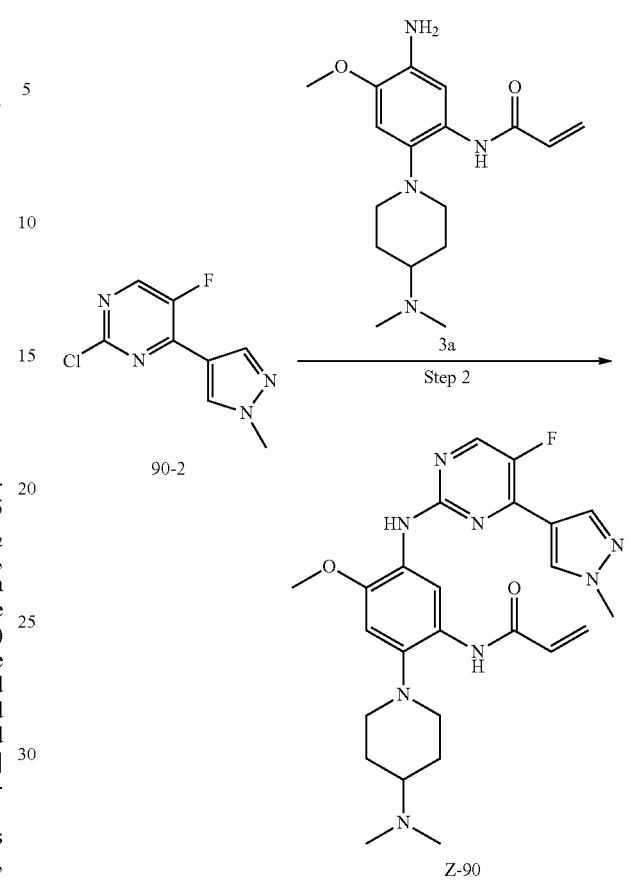

Z-90

The preparation method of the title compound Z-90 (42 mg, yield 9%) was similar to Example 89, except that compound 19-1 in step 1 of Example 89 was replaced with compound 90-1. MS m/z (ESI): 495.0 [M+H]+; $^1$HNMR (400 MHz, DMSO-d6) δ 9.05 (1s, 1H), 9.01 (1s, 1H), 8.80 (s, 1H), 8.48 (d, J=4 Hz, 1H), 8.18 (s, 1H), 7.89 (s, 1H), 6.87 (s, 1H), 6.73 (m, 1H), 6.32 (m, 1H), 5.78 (t, 1H), 3.97 (s, 3H), 3.88 (s, 3H), 3.01 (d, J=12 Hz, 2H), 2.66 (t, 2H), 2.19 (s, 6H), 2.16 (m, 1H), 1.84 (m, 2H), 1.71 (m, 2H).

Example 91: Preparation of N-(5-(5-chloro-4-(1,3,5-trimethyl-1H-pyrazol-4-yl)pyrimidin-2-ylamino)-2-((2-(dimethylamino)ethyl)(methyl)amino)-4-methoxyphenyl)acrylamide (Z-91)

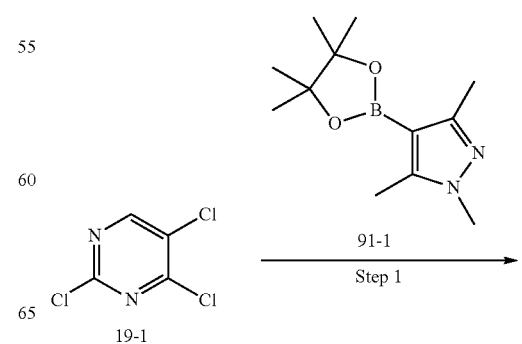

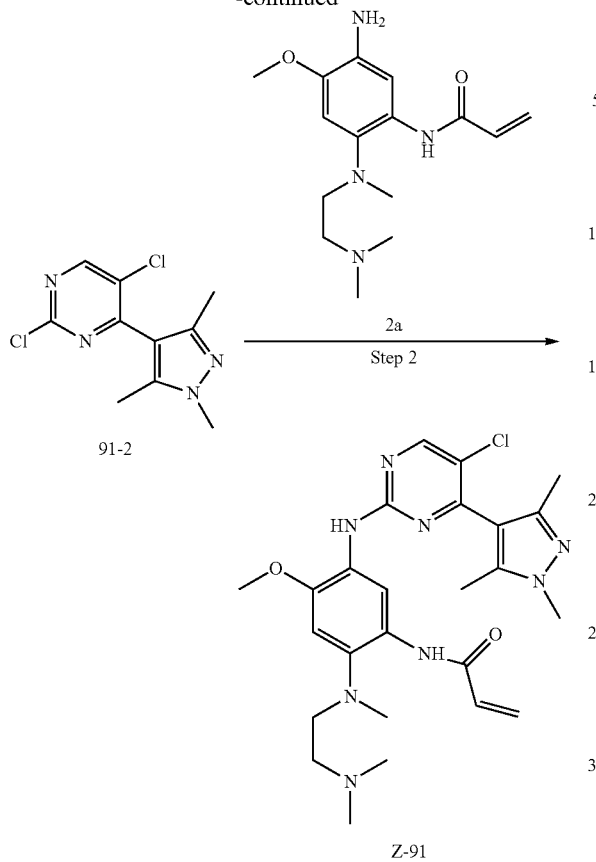

The preparation method of the title compound Z-91 (22 mg, yield 11%) was similar to Example 89, except that compound 89-1 in step 1 of Example 89 was replaced with compound 91-1 and compound 3a in step 2 was replaced with compound 2a. Compound Z-91 was a yellow solid. MS m/z (ESI): 513.2 [M+H]+; ¹HNMR (400 MHz, CDCl$_3$) δ9.32 (br. s., 1H), 8.43 (s, 1H), 7.54 (s, 1H), 6.66 (s, 1H), 6.35 (d, J=16.0 Hz, 1H), 5.62 (d, J=12.0 Hz, 1H), 3.78 (s, 3H), 3.70 (s, 3H), 2.92 (br. s., 2H), 2.63 (s, 3H), 2.34 (br. s., 6H), 2.21 (s, 3H), 2.19 (s, 3H), 1.60 (br. s., 2H).

Example 92: Preparation of N-(5-(5-chloro-4-(1,3,5-trimethyl-1H-pyrazol-4-yl)pyrimidin-2-ylamino)-2-(4-(dimethylamino)piperidin-1-yl)-4-methoxyphenyl)acrylamide (Z-92)

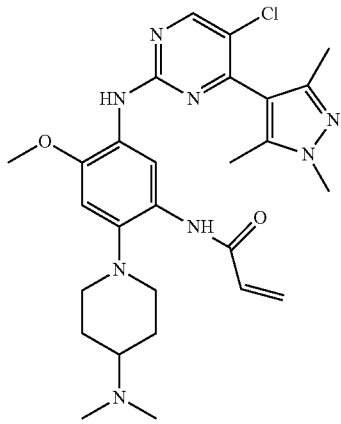

The preparation method of the title compound Z-92 (4.9 mg, yield 2.3%) was similar to Example 91, except that compound 2a in step 2 of Example 91 was replaced with compound 3a. Compound Z-92 was a white solid. MS m/z (ESI): 539.2 [M+H]+; ¹HNMR (400 MHz, CDCl$_3$) M2.78 (br. s., 1H), 9.28 (br. s., 1H), 8.42 (s, 1H), 7.59 (br. s., 1H), 6.62 (br. s., 1H), 6.20-6.40 (m, 2H), 5.70 (d, J=9.6 Hz, 1H), 3.80 (s, 3H), 3.71 (s, 3H), 3.08-3.17 (m, 2H), 2.77 (s, 3H), 2.76 (s, 3H), 2.71 (br. s., 2H), 2.28 (br. s, 2H), 2.13-2.25 (m, 7H), 1.95-2.11 (m, 2H).

Example 93: Preparation of N-(2-((2-(dimethylamino)ethyl)(methyl)amino)-5-(5-fluoro-4-(1-methyl-1H-pyrazol-4-yl)pyrimidin-2-ylamino)-4-methoxyphenyl)acrylamide (Z-93)

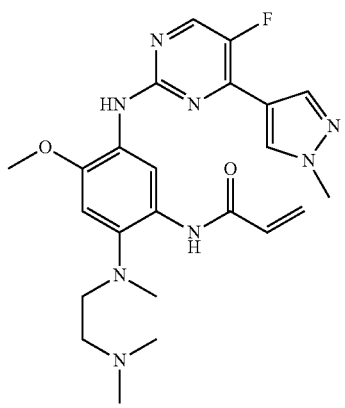

The preparation method of the title compound Z-93 (86 mg, yield 20%) was similar to Example 90, except that compound 3a in step 2 of Example 90 was replaced with compound 2a. Compound Z-93 was a yellow solid. MS m/z (ESI): 469.0 [M+H]+; ¹HNMR (400 MHz, DMSO-d6) δ 10.25 (s, 1H), 9.33 (s, 1H), 8.90 (s, 1H), 8.50 (s, 1H), 8.22 (d, J=4 Hz, 1H), 7.91 (s, 1H), 7.04 (s, 1H), 6.35 (m, 2H), 5.80 (m, 1H), 3.98 (s, 3H), 3.89 (s, 3H), 2.87 (t, 2H), 2.70 (s, 3H), 2.27 (m, 2H), 2.21 (s, 6H).

Example 94: Preparation of N-(5-(5-chloro-4-(1,3-dimethyl-1H-pyrazol-4-yl)pyrimidin-2-ylamino)-2-((2-(dimethylamino)ethyl)(methyl)amino)-4-methoxyphenyl)acrylamide (Z-94)

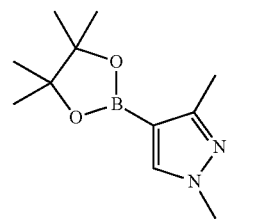

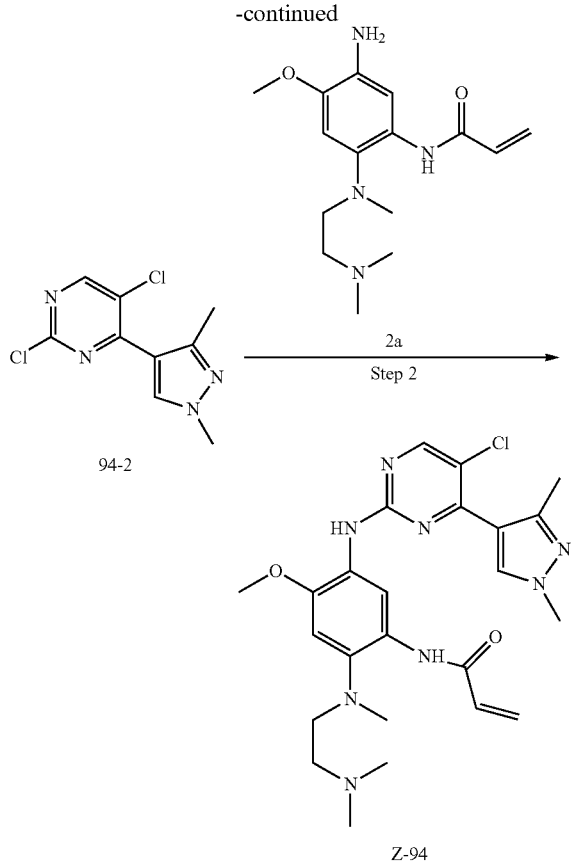

The preparation method of the title compound Z-94 (13 mg, 2.6%) was similar to Example 91, except that compound 91-1 in step 1 of Example 91 was replaced with compound 94-1. MS m/z (ESI): 499.2[M+H]+; ¹HNMR (400 MHz, DMSO-d6) δ 10.13 (s, 1H), 8.46 (d, J=3.1 Hz, 3H), 8.40 (s, 1H), 7.00 (s, 1H), 6.41 (dd, J=16.7, 10.0 Hz, 1H), 6.22 (dd, J=16.9, 2.0 Hz, 1H), 5.75 (dd, J=10.1, 1.9 Hz, 1H), 3.81 (d, J=17.7 Hz, 6H), 2.90 (s, 2H), 2.72 (s, 3H), 2.33 (s, 2H), 2.21 (d, J=24.6 Hz, 9H).

Example 95: Preparation of N-(5-(5-chloro-4-(1,3-dimethyl-1H-pyrazol-4-yl)pyrimidin-2-ylamino)-2-(4-(dimethylamino)piperidin-1-yl)-4-methoxyphenyl)acrylamide (Z-95)

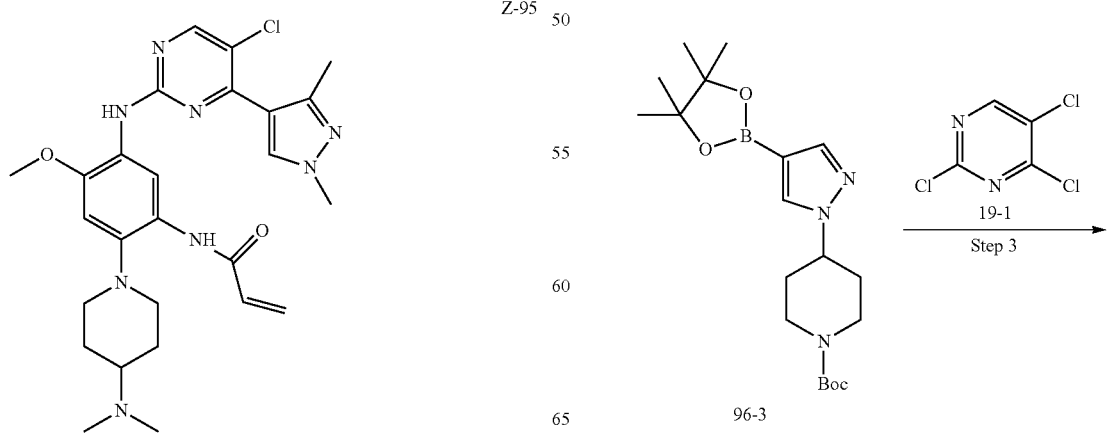

The preparation method of the title compound Z-95 (75 mg, yield 17.4%) was similar to Example 94, except that compound 2a in step 2 of Example 94 was replaced with compound 3a. Compound Z-95 was a yellow solid. MS m/z (ESI): 525.2[M+H]+; ¹HNMR (400 MHz, CDCl₃) δ=9.30 (br. s., 1H), 8.26-8.37 (m, 2H), 8.20 (s, 1H), 7.43 (s, 1H), 6.64 (s, 1H), 6.29-6.38 (m, 1H), 6.11-6.29 (m, 1H), 5.68 (d, J=10.3 Hz, 1H), 3.84 (s, 3H), 3.81 (s, 3H), 3.03 (d, J=12.0 Hz, 2H), 2.67 (t, J=11.2 Hz, 3H), 2.44-2.58 (m, 7H), 2.39 (s, 3H), 2.11 (d, J=11.5 Hz, 2H), 1.80 (d, J=9.8 Hz, 2H).

Example 96: Preparation of N-(5-(5-chloro-4-(1-(piperidin-4-yl)-1H-pyrazol-4-yl)pyrimidin-2-ylamino)-2-(4-(dimethylamino)piperidin-1-yl)-4-methoxyphenyl)acrylamide (Z-96)

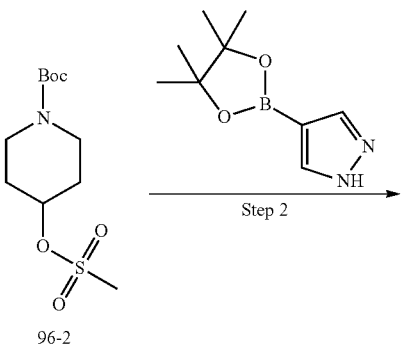

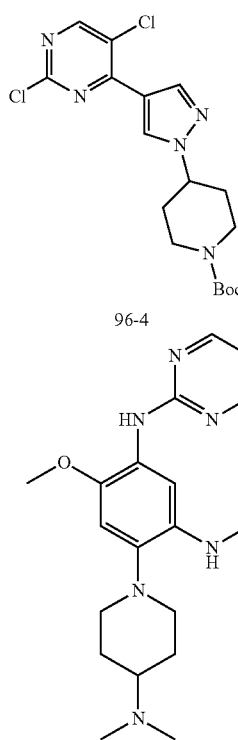

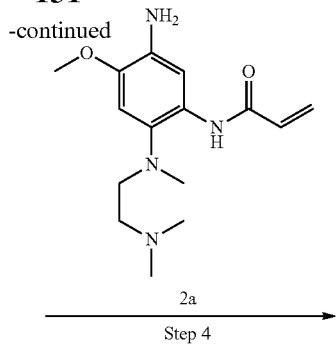

Step 2: Compound 96-2 (134 mg, 0.5 mmol) and cesium carbonate (245 mg, 0.75 mmol) was added to a solution of 4-(4,4,5,5-tetramethyl-1,3,2-dioxaborolan-2-yl)-1H-pyrazole (97 mg, 0.5 mmol) in DMF, the reaction mixture was stirred at 90° C. for 12-16 h, and the reaction solution was cooled to room temperature, diluted with water, extracted with EA, and the combined organic phase was washed with brine, dried over anhydrous $Na_2SO_4$ and concentrated to give the crude product which was purified by Combi-flash column chromatography [PE:EA=100:0-50:50] to give the title compound 96-3 (2 g, yield 44%), MS m/z (ESI): 378.2[M+1]+.

Step 3: By using compound 19-1 (549 mg, 3.0 mmol) and compound 96-3 (754 mg, 2.0 mmol) as the starting materials, the title compound 96-4 (580 mg, yield 73%) was prepared with reference to step 1 of Example 89. MS m/z (ESI): 398 [M+H]+.

Step 4: $Pd_2(dba)_3$ (46 mg, 0.05 mmol) was added to a solution of compound 96-4 (298 mg, 0.75 mmol), compound 2a (159 mg, 0.5 mmol), cesium carbonate (326 mg, 1.0 mmol) and Xantphos (58 mg, 0.1 mmol) in 1,4-dioxane (2 ml), the reaction solution was purged by nitrogen for three times. After microwave reaction was performed at 160° C. for 0.5 h, the reaction mixture was filtered and concentrated to give the crude product. The crude product was purified by Combi-flash column chromatography [PE:EA=100:0-0:100] to give the title compound 96-5 (250 mg) as a yellow solid. MS m/z (ESI): 680.3 [M+H]+.

Step 5: A mixed solution of hydrochloric acid/1,4-dioxane was added to a solution of compound 96-5 (240 mg, 0.35 mmol) in dichloromethane (10 ml), the reaction mixture was stirred at room temperature for 2 h, $Na_2CO_3$ was added to adjust pH to 9, and then dichloromethane was added. The organic phase was washed with hydrochloric acid, and concentrated to give the crude product. The resulting crude product was purified by preparative liquid chromatography to give 20 mg of the title compound Z-96 as a yellow solid. MS m/z (ESI): 580[M+H]+.

Example 97: Preparation of N-(5-(5-chloro-4-(1,5-dimethyl-1H-pyrazol-4-yl)pyrimidin-2-ylamino)-2-(4-(dimethylamino)piperidin-1-yl)-4-methoxyphenyl)acrylamide (Z-97)

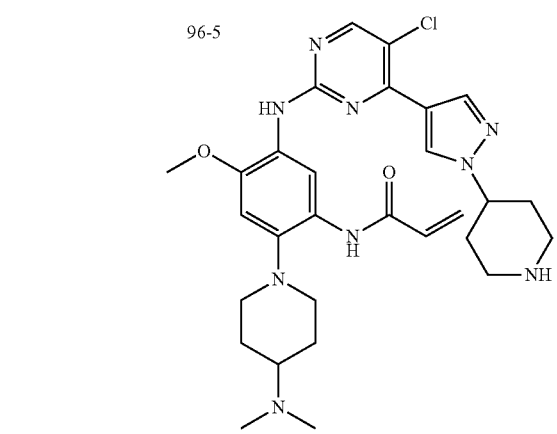

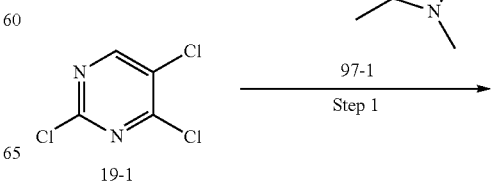

step 1: Triethylamine (2.0 g, 20 mmol) was added to a solution of tert butyl 4-hydroxypiperidine-1-carboxylate (2.0 g, 10 mmol) in dichloromethane (20 ml) at 0° C., and a solution of methanesulfonyl chloride (1.73 g, 15 mmol) in dichloromethane (5 ml) was then added dropwise. After stirred for 1 h, the reaction mixture was poured into ice-water, extracted with dichloromethane, and the organic phase was washed with brine, dried over anhydrous $Na_2SO_4$, and concentrated to give 2.5 g of crude product 96-2 which was used for the next step without purification; MS m/z (ESI): 223 [M-56]+.

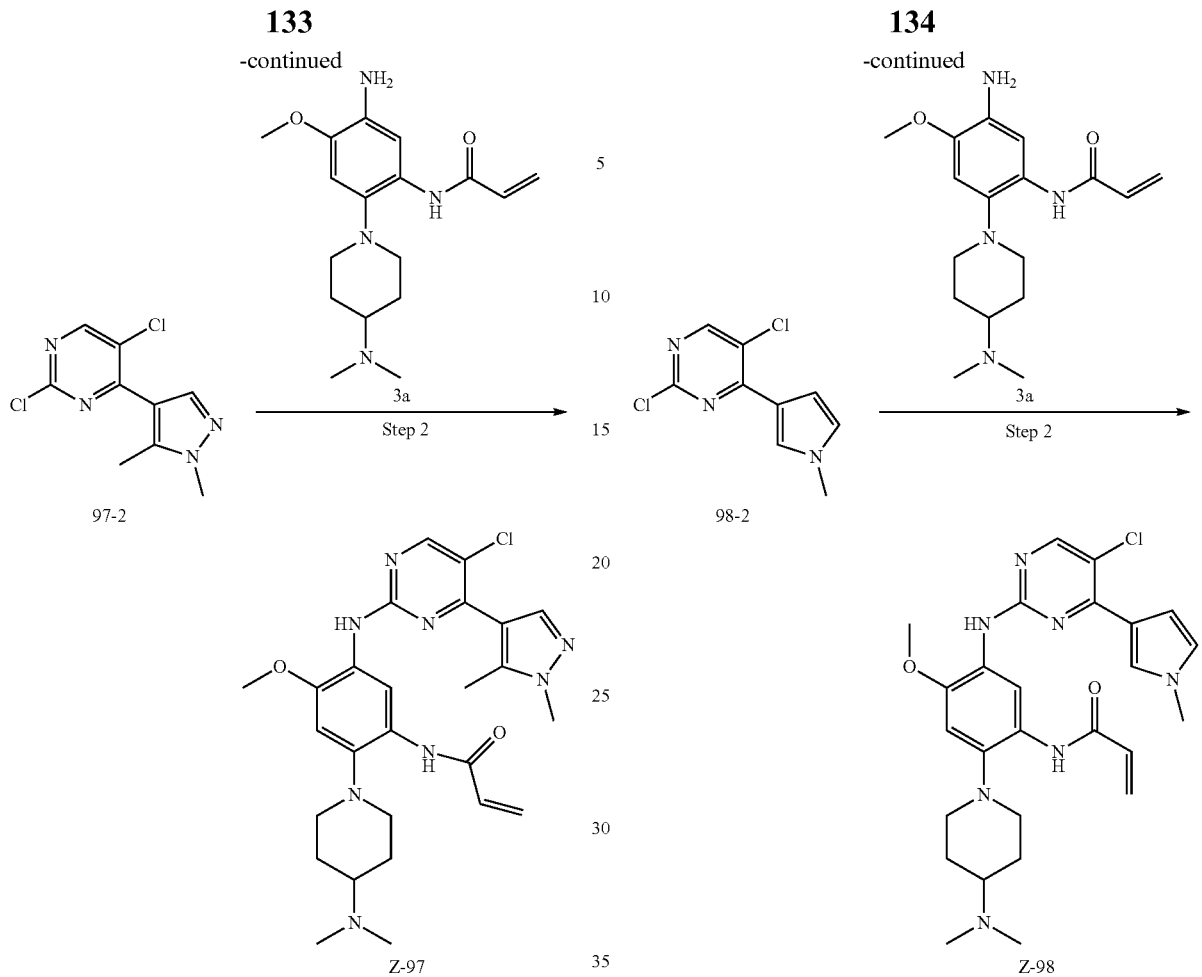

The preparation method of the title compound Z-97 (56.5 mg, yield 26%) was similar to Example 89, except that compound 89-1 in step 1 of Example 89 was replaced with compound 97-1. Compound Z-97 was a yellow solid. MS m/z (ESI): 525.2[M+H]+; ¹HNMR (400 MHz, DMSO-d6) δ 8.99 (s, 1H), 8.44 (s, 1H), 8.39 (s, 1H), 8.20 (s, 1.5H), 7.99 (s, 1H), 6.81 (s, 1H), 6.66 (dd, J=16.8, 10.0 Hz, 1H), 6.22 (dd, J=16.8 Hz, 2.0 Hz, 1H), 5.73 (d, J=10.4 Hz, 1H), 3.79 (s, 3H), 3.76 (s, 3H), 3.07 (d, J=11.0 Hz, 2H), 2.68 (t, J=11.0 Hz, 2H), 2.46 (br. s., 1H), 2.37 (s, 6H), 2.34 (s, 3H), 1.89 (d, J=10.5 Hz, 2H), 1.75 (t, J=11.0 Hz, 2H).

Example 98: Preparation of N-(5-(5-chloro-4-(1-methyl-1H-pyrrol-3-yl)pyrimidin-2-ylamino)-2-(4-(dimethylamino) piperidin-1-yl)-4-methoxyphenyl) acrylamide (Z-98)

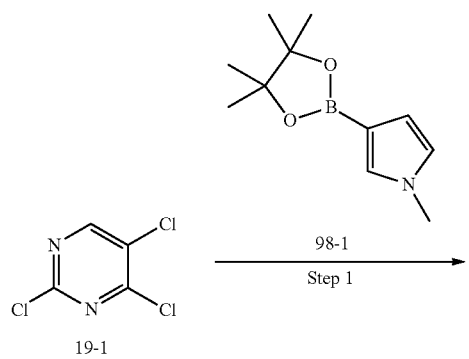

Step 1: By using compound 19-1 (400 mg, 2.2 mmol) and 1-methyl-3-(4,4,5,5-tetramethyl-1,3,2-dioxaborolan-2-yl)-1H-pyrrole (250 mg, 2.0 mmol) as the starting materials, the crude product was prepared with reference to step 1 of Example 89, and purified by Combi-flash column chromatography [PE:EA=3:1] to give the title compound 98-2 (80 mg, yield 17.6%). MS m/z (ESI): 228[M+H]+.

Step 2: compound 3a (140 mg, 0.4 mmol), Pd₂(dba)₃ (41 mg, 0.044 mmol), BINAP (55 mg, 0.088 mmol) and cesium carbonate (286 mg, 0.88 mmol) were added to a solution of compound 98-2 (100 mg, 0.44 mmol) in 1,4-dioxane (6 ml). The reaction mixture was reacted under microwave at 130° C. for 30 minutes. The reaction mixture was filtered to obtain the crude product which was purified by preparative liquid chromatography to give 94.47 mg of the title compound Z-98 as a yellow powder. MS m/z (ESI): 510.3 [M+H]+; ¹HNMR (400 MHz, DMSO-d6) δ 9.06 (s, 1H), 8.80 (s, 1H), 8.34 (s, 1H), 8.28 (s, 1H), 8.06 (s, 1H), 7.92 (s, 1H), 6.98 (s, 1H), 6.84 (dd, J=5.6, 3.2 Hz, 2H), 6.71 (dd, J=16.9, 10.2 Hz, 1H), 6.29 (dd, J=17.0, 1.6 Hz, 1H), 5.77 (d, J=11.5 Hz, 1H), 3.87 (s, 3H), 3.74 (s, 3H), 3.05 (d, J=11.4 Hz, 2H), 2.68 (t, J=11.0 Hz, 2H), 2.42 (t, J=11.1 Hz, 1H), 2.34 (s, 6H), 1.89 (d, J=10.6 Hz, 2H), 1.79-1.67 (m, 2H).

Example 99: Preparation of N-(5-(5-chloro-4-(1-methyl-1H-pyrrol-3-yl)pyrimidin-2-ylamino)-2-((2-(dimethylamino)ethyl)(methyl)amino)-4-methoxyphenyl)acrylamide (Z-99)

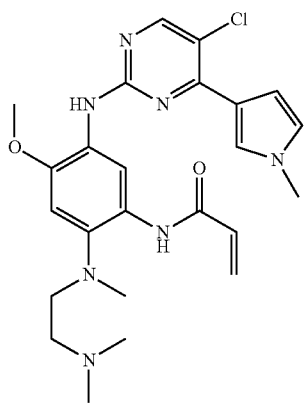

Z-99

The preparation method of the title compound Z-99 was similar to Example 98, except that compound 3a in step 2 of Example 98 was replaced with compound 2a. 103 mg of compound Z-99 was obtained as a yellow powder. MS m/z (ESI): 484.2 [M+H]+; $^1$HNMR (400 MHz, DMSO-d6) δ 10.16 (s, 1H), 9.06 (s, 1H), 8.35 (s, 1H), 8.26 (s, 1H), 8.14 (s, 1H), 7.93 (s, 1H), 7.05-6.98 (m, 2H), 6.84 (t, J=2.4 Hz, 1H), 6.48 (dd, J=16.9, 10.1 Hz, 1H), 6.29 (dd, J=16.9, 1.9 Hz, 1H), 5.78 (dd, J=10.1, 1.8 Hz, 1H), 3.87 (s, 3H), 3.74 (s, 3H), 2.92 (t, J=5.7 Hz, 2H), 2.69 (s, 3H), 2.38 (t, J=5.7 Hz, 2H), 2.26 (s, 6H).

Example 100: Preparation of N-(5-(5-chloro-4-(1-methyl-1H-pyrazol-4-yl)pyrimidin-2-ylamino)-4-methoxy-2-(4-methylpiperazin-1-yl)phenyl)acrylamide (Z-100)

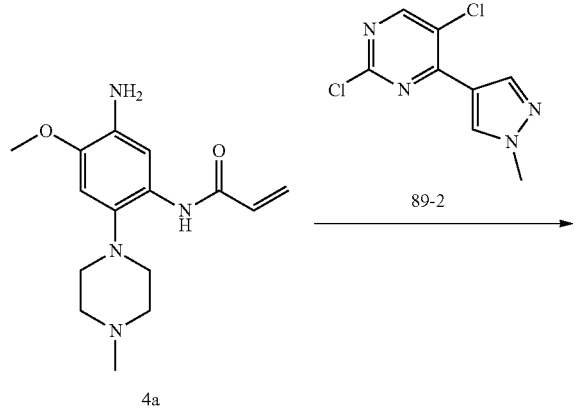

-continued

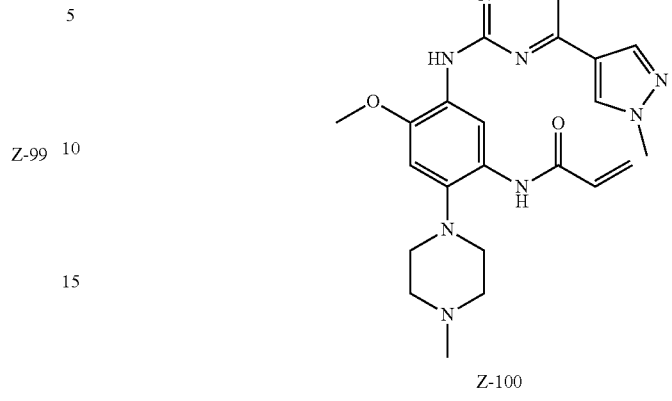

Z-100

By using compound 4a (100 mg, 0.34 mmol) and compound 89-2 (80 mg, 0.34 mmol) as the starting materials, the title compound Z-100 (200 mg, yield 70%) was synthesized with reference to step 2 of Example 89. MS m/z (ESI): 483[M+H]+; $^1$HNMR (400 MHz, CDCl$_3$) δ 9.51 (s, 1H), 9.10 (s, 1H), 8.41 (s, 2H), 8.26 (s, 1H), 8.20 (s, 1H), 7.70 (s, 1H), 6.73 (s, 1H), 6.43-6.32 (m, 1H), 6.26 (d, J=10.0 Hz, 1H), 5.82-5.65 (m, 1H), 3.99 (s, 3H), 3.83 (s, 3H), 3.03 (s, 8H), 2.62 (s, 4H).

Example 101: Preparation of N-(5-(5-chloro-4-(1-(difluoromethyl)-1H-pyrazol-4-yl)pyrimidin-2-ylamino)-2-(4-(dimethylamino)piperidin-1-yl)-4-methoxyphenyl)acrylamide (Z-101)

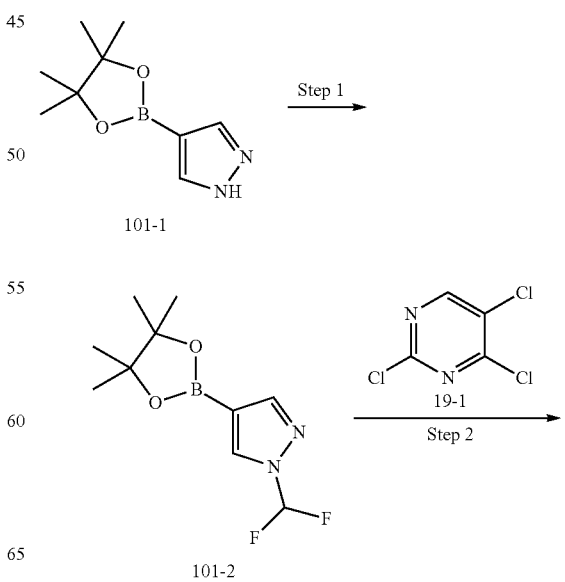

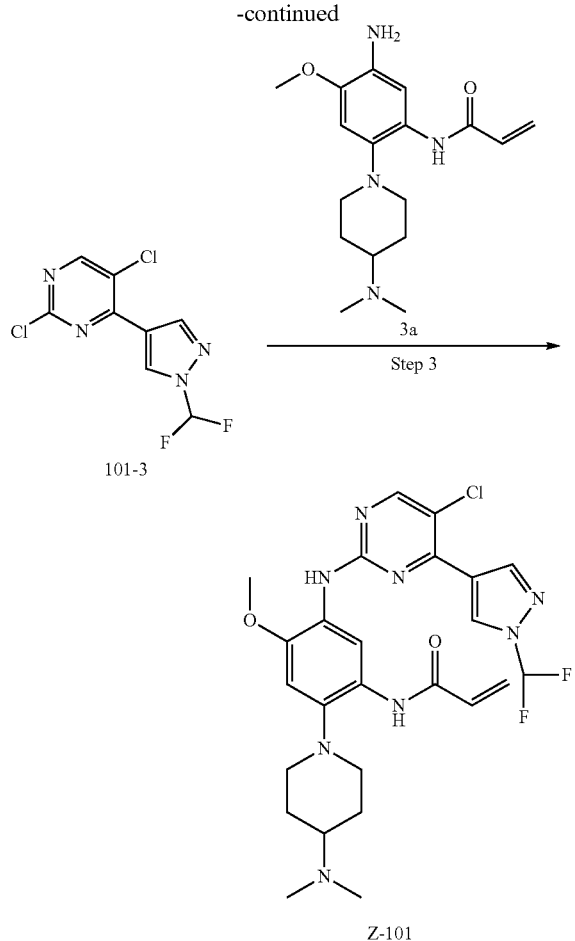

Step 1: To acetonitrile (100 ml) was added compound 4-(4,4,5,5-tetramethyl-1,3,2-dioxaborolan-2-yl)-1H-pyrazole 101-1 (4.0 g, 0.21 mol), sodium chlorodifluoroacetate (3.77 g 0.25 mol, 15-crown-5 (103.8 g, 0.65 mol), and the reaction mixture was heated to reflux under nitrogen and stirred for 24 h, cooled to room temperature, the reaction mixture was poured into water (50 ml) to quench the reaction, and extracted with EA (100 ml×3), washed with saturated brine (20 ml), dried over $Na_2SO_4$, and filtered, and the filtrate was evaporated to give compound 101-2 (4.1 g, yield 80%) as a white solid. MS m/z (ESI): 245.1 [M+H]+.

Step 2: To a reaction flask containing Tetrakis(triphenylphosphine)palladium(0.264 g, 2.58×10−4 mol) were added a solution of compound 101-2 (2.1 g, 8.9×10$^{-3}$ mol) in dimethoxyethane (20 ml), a solution of compound 19-1 (1.4 g, 8.0×10$^{-3}$ mol) in dimethoxyethane (20 ml) and a solution of sodium carbonate (1.8 g, 1.72×10$^{-2}$ mol) in water (11 ml), and the reaction mixture was heated to 100° C. under nitrogen and stirred overnight. The reaction solution was cooled to room temperature, and water (50 ml) was used to quench the reaction, and the resulting mixture was extracted with EA (3×100 ml), washed with saturated brine (30 ml), dried over $Na_2SO_4$, filtered and concentrated to give an oil which was purified by column chromatography (silica gel; 300-400 mesh), petroleum ether:EA=30:1, to give compound 101-3 (870 mg, yield 30%) as a white solid. MS m/z (ESI): 265.0 [M+H]+, purity=96.08% (UV214); $^1$HNMR (400 MHz, DMSO) δ:9.21 (s, 1H), 8.95 (s, 1H), 8.56 (s, 1H), 7.94 (t, J=58 Hz, 1H).

Step 3: By using compound 101-3 and compound 3a as the starting materials, the crude product was synthesized with reference to step 2 of Example 89, and purified by preparative liquid chromatography to give the title compound Z-101 as a yellow solid. MS m/z (ESI): 547[M+H]+; $^1$HNMR (400 MHz, DMSO-d6) δ 9.28 (s, 1H), 9.06 (s, 1H), 8.76 (s, 1H), 8.65 (s, 1H), 8.55 (s, 1H), 8.28 (d, J=3.6 Hz, 2H), 7.92 (t, J=58.6 Hz, 1H), 6.87 (s, 1H), 6.70 (dd, J=17.0, 10.2 Hz, 1H), 6.29 (dd, J=16.9, 1.7 Hz, 1H), 5.87-5.65 (m, 1H), 3.86 (s, 3H), 3.04 (d, J=11.6 Hz, 2H), 2.68 (t, J=10.9 Hz, 2H), 2.26 (s, 7H), 1.85 (d, J=10.5 Hz, 2H), 1.71 (d, J=8.9 Hz, 2H).

Example 102: Preparation of N-(5-(5-chloro-4-(1H-pyrazol-4-yl)pyrimidin-2-ylamino)-2-(4-(dimethylamino)piperidin-1-yl)-4-methoxyphenyl)acrylamide (Z-102)

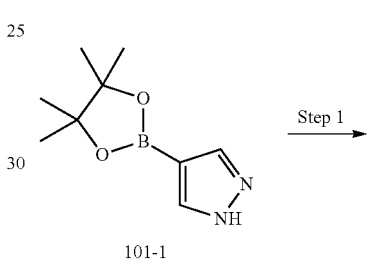

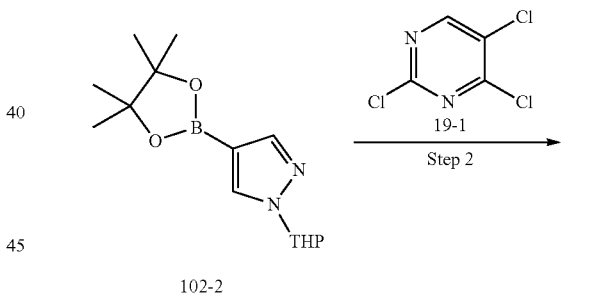

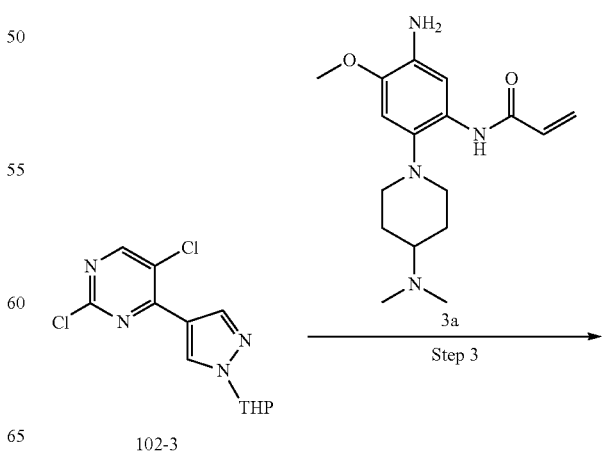

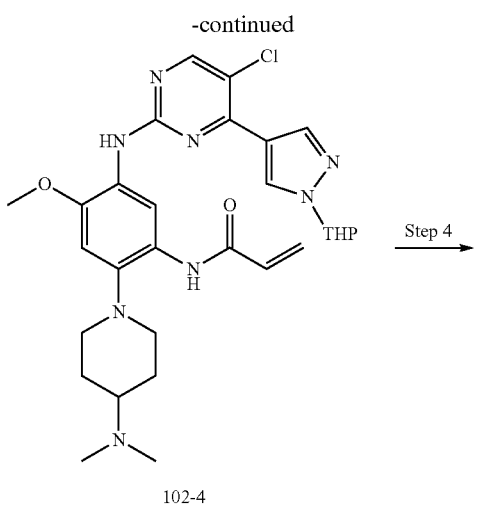

102-4

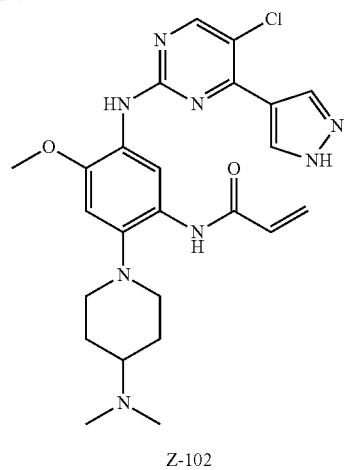 [SMILES: C=CC(=O)Nc1cc(Nc2ncc(Cl)c(-c3cn[nH]c3)n2)c(OC)cc1N1CCC(N(C)C)CC1]

Z-102 step 1: DTSA (463 mg, 2.6 mmol) was added to a solution of compound 101-1 (5.0 g, 25.8 mmol) and 2,3-dihydropyran (4.33 g, 51.5 mmol) in dichloromethane (100 ml) with stirring, and the reaction mixture was stirred at 40° C. for 2 h. After completion of the reaction, the reaction solution was washed with water, extracted with EA, and concentrated under reduced pressure to give the crude product 102-2 (7.0 g, 60%) which was used for the next step without purification, MS m/z (ESI): 279 [M+H]+.

Step 2: By using compound 19-1 (4.5 g, 25 mmol) and compound 102-2 (7.0 g, 25 mmol) as the starting materials, the crude product was synthesized with reference to step 1 of Example 89, and purified by Combi-flash column chromatography to give the title compound 102-3 (850 mg, yield 10%). MS m/z (ESI): 299 [M+H]+.

Step 3: By using compound 102-3 (300 mg, 1 mmol) and compound 3a (320 mg, 1 mmol) as the starting materials, the crude product 102-4 (60 mg, yield 70%) was prepared with reference to step 2 of Example 89, and was used directly in the next step. MS m/z (ESI): 581 [M+H]+.

Step 4: To a solution of compound 102-4 (700 mg, 1 mmol) in dichloromethane (5 ml) was added a solution of hydrochloric acid/1,4-dioxane (2 ml) with stirring, and the reaction mixture was stirred at room temperature for 4 h to give a crude product which was purified by preparative column chromatography to give the title compound Z-102 (80 mg, yield 60%) as a yellow solid. MS m/z (ESI): 497 [M+H]+; $^1$HNMR (400 MHz, CDCl$_3$) δ 9.55 (s, 1H), 8.92 (s, 2H), 8.70 (s, 1H), 8.35 (s, 1H), 7.72 (s, 1H), 6.76 (s, 1H), 6.32 (dt, J=17.0, 12.9 Hz, 2H), 5.76 (d, J=9.9 Hz, 1H), 3.89 (s, 3H), 3.04 (d, J=11.9 Hz, 2H), 2.73 (t, J=11.0 Hz, 2H), 2.36 (s, 6H), 2.24 (d, J=7.4 Hz, 1H), 2.05 (d, J=11.5 Hz, 2H), 1.70 (s, 2H).

Example 103-127

The title compounds of Examples 103 to 127 are shown as formula (IV-1), wherein substituents $R_0$, $R_2$ and $R_3$ are hydrogen, the other substituents A, $R_1$, $R_6$ are shown as the following table.

General Procedure: The preparation methods of compounds Z-103 to Z-127 were similar to Example 1, by using boronate ester or boronic acid substituted with different substituent groups and using 5-substituted 2,4-dichloropyrimidine as the starting materials.

| Example No. | Compound | A | $R_1$ | $R_6$ | MS [M + H]+ |
|---|---|---|---|---|---|
| 103 | Z-103 | 5-(1-methyl-1H-pyrazolo[3,4-b]pyridinyl) | N,N,N'-trimethylethylenediaminyl | CO$_2$Me | 560 |
| 104 | Z-104 | 5-(1-methyl-1H-pyrazolo[3,4-b]pyridinyl) | 4-(dimethylamino)piperidinyl | CO$_2$Me | 586 |
| 105 | Z-105 | 5-(1-methyl-1H-pyrrolo[2,3-b]pyridinyl) | N,N-dimethyl-N'-ethylethylenediaminyl | H | 515 |

-continued
| Example No. | Compound | A | R₁ | R₆ | MS [M + H]+ |
|---|---|---|---|---|---|
| 106 | Z-106 | 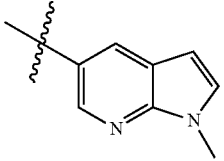 [SMILES: *c1cnc2c(ccn2C)c1] | 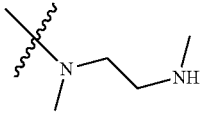 [SMILES: *N(C)CCNC] | H | 487 |
| 107 | Z-107 | 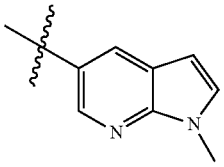 [SMILES: *c1cnc2c(ccn2C)c1] | 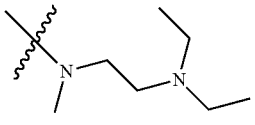 [SMILES: *N(C)CCN(CC)CC] | H | 529 |
| 108 | Z-108 | 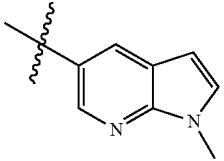 [SMILES: *c1cnc2c(ccn2C)c1] | 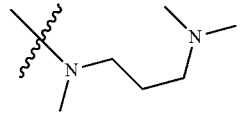 [SMILES: *N(C)CCCN(C)C] | H | 515 |
| 109 | Z-109 | 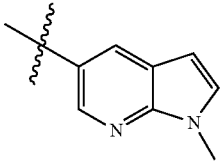 [SMILES: *c1cnc2c(ccn2C)c1] | 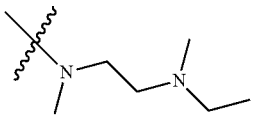 [SMILES: *N(C)CCN(C)CC] | Cl | 549 |
| 110 | Z-110 | 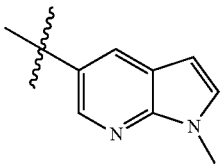 [SMILES: *c1cnc2c(ccn2C)c1] | 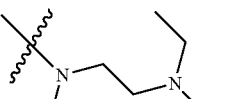 | Cl | 563 |
| 111 | Z-111 | 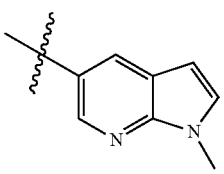 [SMILES: *c1cnc2c(ccn2C)c1] | 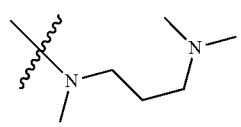 [SMILES: *N(C)CCCN(C)C] | Cl | 549 |
| 112 | Z-112 | 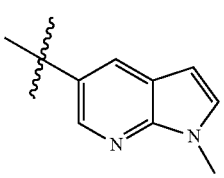 [SMILES: *c1cnc2c(ccn2C)c1] |  | H | 527 |
| 113 | Z-113 | 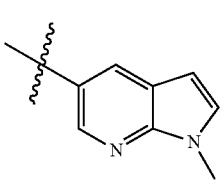 [SMILES: *c1cnc2c(ccn2C)c1] | 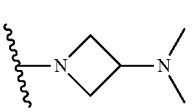 | Cl | 533 |

-continued

| Example No. | Compound | A | R₁ | R₆ | MS [M + H]+ |
|---|---|---|---|---|---|
| 114 | Z-114 | 5-(1-methyl-7-azaindol-5-yl) | -NH-CH₂CH₂CH₂-N(CH₃)₂ | Cl | 535 |
| 115 | Z-115 | 5-(1-methyl-7-azaindol-5-yl) | -N(CH₃)-CH₂CH₂-N(CH₃)(iPr) | H | 529 |
| 116 | Z-116 | 5-(1-methyl-7-azaindol-5-yl) | -N(CH₃)-CH₂CH₂-NH(CH₃) | Cl | 521 |
| 117 | Z-117 | 5-(1-methyl-7-azaindol-5-yl) | -O-CH₂CH₂-N(CH₃)₂ | H | 488 |
| 118 | Z-118 | 5-(1-methyl-7-azaindol-5-yl) | -O-CH₂CH₂-N(CH₃)₂ | F | 506 |
| 119 | Z-119 | 5-(1-methylindol-5-yl) | 4-dimethylamino-piperidin-1-yl | H | 526 |
| 120 | Z-120 | 5-(1-methylindol-5-yl) | 4-dimethylamino-piperidin-1-yl | Cl | 560 |
| 121 | Z-121 | 5-(3-chloro-1-methyl-7-azaindol-5-yl) | -N(CH₃)-CH₂CH₂-N(CH₃)₂ | Cl | 569 |

-continued

| Example No. | Compound | A | R₁ | R₆ | MS [M + H]+ |
|---|---|---|---|---|---|
| 122 | Z-122 | 5-(3-chloro-1-methyl-1H-pyrrolo[2,3-b]pyridin-5-yl) | 4-(dimethylamino)piperidin-1-yl | F | 579 |
| 123 | Z-123 | 5-(3-chloro-1-methyl-1H-pyrrolo[2,3-b]pyridin-5-yl) | N,N,N'-trimethylethane-1,2-diamine | F | 553 |
| 124 | Z-124 | 5-(1-isopropyl-1H-pyrrolo[2,3-b]pyridin-5-yl) | N,N,N'-trimethylethane-1,2-diamine | H | 529 |
| 125 | Z-125 | 5-(1-isopropyl-1H-pyrrolo[2,3-b]pyridin-5-yl) | N,N,N'-trimethylethane-1,2-diamine | Cl | 563 |
| 126 | Z-126 | 5-(1-cyclopropyl-1H-pyrrolo[2,3-b]pyridin-5-yl) | N,N,N'-trimethylethane-1,2-diamine | Cl | 561.2 |
| 127 | Z-127 | 5-(1-cyclopropyl-1H-pyrrolo[2,3-b]pyridin-5-yl) | 4-(dimethylamino)piperidin-1-yl | Cl | 587 |

| Compound | ¹HNMR |
|---|---|
| Z-105 | ¹HNMR (400 MHz, DMSO) δ 9.94 (s, 1H), 9.17 (s, 1H), 9.06 (d, J = 5.6 Hz, 2H), 8.49 (d, J = 5.1 Hz, 1H), 8.22 (s, 1H), 8.07 (s, 1H), 7.60 (d, J = 3.1 Hz, 1H), 7.52 (d, J = 5.2 Hz, 1H), 7.02 (s, 1H), 6.57 (d, J = 3.1 Hz, 2H), 6.55-6.47 (m, 1H), 6.36 (s, 1H), 5.81 (d, J = 10.1 Hz, 1H), 3.88 (d, J = 5.3 Hz, 6H), 2.93 (s, 2H), 2.69 (s, 2H), 2.26 (s, 2H), 2.09 (s, 6H), 1.02 (t, J = 6.9 Hz, 3H). |

-continued

| Compound | ¹HNMR |
| --- | --- |
| Z-106 | ¹HNMR (400 MHz, DMSO) δ 9.76 (s, 1H), 9.07 (d, J = 2.0 Hz, 2H), 9.00 (s, 1H), 8.49 (d, J = 5.3 Hz, 1H), 8.38 (s, 1H), 8.08 (s, 1H), 7.61 (d, J = 3.4 Hz, 1H), 7.52 (d, J = 5.3 Hz, 1H), 6.96 (s, 1H), 6.86-6.69 (m, 1H), 6.56 (d, J = 3.4 Hz, 1H), 6.35 (dd, J = 16.9, 1.9 Hz, 1H), 5.80 (d, J = 10.0 Hz, 1H), 3.88 (d, J = 8.5 Hz, 6H), 3.16-3.09 (m, 2H), 3.02-2.93 (m, 2H), 2.60 (s, 3H), 2.54 (s, 3H). |
| Z-107 | ¹HNMR (400 MHz, DMSO) δ 9.78 (s, 1H), 9.18 (s, 1H), 9.07 (d, J = 1.9 Hz, 1H), 9.05 (s, 1H), 8.49 (d, J = 5.2 Hz, 1H), 8.06 (s, 1H), 7.60 (d, J = 3.4 Hz, 1H), 7.52 (d, J = 5.3 Hz, 1H), 7.01 (s, 1H), 6.56 (d, J = 3.4 Hz, 1H), 6.54-6.47 (m, 1H), 6.37-6.30 (m, 1H), 5.81 (d, J = 10.0 Hz, 1H), 3.88 (d, J = 4.1 Hz, 6H), 2.87 (t, J = 5.9 Hz, 2H), 2.71 (s, 3H), 2.61-2.52 (m, 6H), 1.05-0.92 (m, 6H). |
| Z-108 | ¹HNMR (400 MHz, CDCl₃) δ 9.77 (s, 1H), 9.19 (s, 1H), 8.91 (d, J = 2.0 Hz, 1H), 8.75 (s, 1H), 8.41 (d, J = 5.3 Hz, 1H), 7.70 (s, 1H), 7.17-7.13 (m, 2H), 6.71 (s, 1H), 6.59 (d, J = 3.4 Hz, 1H), 6.42 (d, J = 15.6 Hz, 1H), 6.33-6.24 (m, 1H), 5.70 (d, J = 10.7 Hz, 1H), 3.86 (s, 3H), 3.83 (s, 3H), 2.82 (t, J = 7.2 Hz, 2H), 2.57 (s, 3H), 2.23 (t, J = 7.2 Hz, 2H), 2.12 (s, 6H), 1.18 (s, 2H). |
| Z-109 | ¹HNMR (400 MHz, CDCl₃) δ 9.74 (s, 1H), 9.57 (s, 1H), 8.92 (d, J = 1.6 Hz, 1H), 8.74 (s, 1H), 8.43 (s, 1H), 7.64 (s, 1H), 7.15 (d, J = 3.4 Hz, 1H), 6.71 (s, 1H), 6.55 (d, J = 3.4 Hz, 1H), 6.43 (d, J = 16.9 Hz, 1H), 6.27 (s, 1H), 5.64 (d, J = 11.1 Hz, 1H), 3.86 (s, 3H), 3.80 (s, 3H), 2.81 (s, 2H), 2.61 (s, 3H), 2.49-2.37 (m, 2H), 2.35-2.24 (m, 2H), 2.17 (s, 3H), 0.99 (t, J = 7.0 Hz, 3H). |
| Z-110 | ¹HNMR (400 MHz, DMSO) δ 9.71 (s, 1H), 8.75 (s, 2H), 8.57 (s, 1H), 8.53 (s, 2H), 7.61-7.60 (d, J = 3.3 Hz, 1H), 6.96 (s, 1H), 6.56-6.55 (d, J = 3.3 Hz, 1H), 6.50-6.43 (dd, J1 = 10.2 Hz, J2 = 17.0 Hz, 1H), 6.30-6.26 (d, J = 16.9 Hz, 1H), 5.78-5.75 (d, J = 10.3 Hz, 1H), 3.86 (s, 3H), 3.82 (s, 3H), 2.84-2.81 (t, J = 5.5 Hz, 2H), 2.68 (s, 3H), 2.50 (s, 4H), 2.45 (s, 2H), 0.95-0.91 (t, J = 7.0 Hz, 6H). |
| Z-112 | ¹HNMR (400 MHz, DMSO) δ 9.85 (s, 1H), 9.14 (s, 1H), 9.07 (d, J = 2.0 Hz, 2H), 9.04 (s, 1H), 8.49 (d, J = 5.2 Hz, 1H), 8.26 (s, 1H), 8.07 (s, 1H), 7.61 (d, J = 3.4 Hz, 1H), 7.53 (d, J = 5.3 Hz, 1H), 7.02 (s, 1H), 6.71-6.61 (m, 1H), 6.57 (d, J = 3.4 Hz, 1H), 6.37-6.29 (m, 1H), 5.80 (d, J = 10.0 Hz, 1H), 3.89 (s, 3H), 3.87 (s, 3H), 3.04 (t, J = 5.8 Hz, 2H), 2.69 (d, J = 10.1 Hz, 9H), 1.80 (s, 4H). |
| Z-113 | ¹HNMR (400 MHz, CDCl₃) δ 8.95 (s, 1H), 8.86 (s, 1H), 8.63 (s, 1H), 8.42 (s, 1H), 8.37 (s, 1H), 7.58 (s, 1H), 7.22 (d, J = 3.2 Hz, 1H), 6.59 (d, J = 3.2 Hz, 1H), 6.45 (d, J = 16.9 Hz, 1H), 6.37 (s, 1H), 6.34-6.25 (m, 1H), 5.76 (d, J = 9.9 Hz, 1H), 3.93 (s, 3H), 3.88 (d, J = 8.3 Hz, 5H), 3.61 (t, J = 6.4 Hz, 2H), 3.16-3.06 (m, 1H), 2.18 (s, 6H). |
| Z-114 | ¹HNMR (400 MHz, CDCl₃) δ 9.26 (s, 1H), 8.68 (s, 1H), 8.44-8.43 (d, J = 3.0 Hz, 1H), 8.42 (s, 2H), 7.61-7.60 (d, J = 3.4 Hz, 1H), 7.48 (s, 1H), 6.58-6.57 (d, J = 3.4 Hz, 1H), 6.49-6.42 (dd, J1 = 10.2 Hz, J2 = 17.0 Hz, 1H), 6.32 (s, 1H), 6.23-6.18 (dd, J1 = 2.0 Hz, J2 = 17.0 Hz, 1H), 5.72-5.69 (dd, J1 = 2.0 Hz, J2 = 10.2 Hz, 1H), 5.16-5.14 (t, J = 5.3 Hz, 1H), 3.86 (s, 3H), 3.79 (s, 3H), 3.15-3.11 (dd, J1 = 6.4 Hz, J2 = 12.2 Hz, 2H), 2.33-2.29 (t, J = 6.6 Hz, 2H), 2.12 (s, 6H), 1.73-1.68 (dd, J1 = 6.5 Hz, J2 = 13.2 Hz, 2H). |
| Z-115 | ¹HNMR (400 MHz, DMSO) δ 9.90 (s, 1H), 9.30 (s, 1H), 9.15 (d, J = 1.8 Hz, 2H), 8.56 (d, J = 5.2 Hz, 1H), 8.13 (s, 1H), 7.68 (d, J = 3.4 Hz, 1H), 7.60 (d, J = 5.3 Hz, 1H), 7.08 (s, 1H), 6.65 (d, J = 3.4 Hz, 1H), 6.56 (dd, J = 17.0, 10.0 Hz, 1H), 6.42 (dd, J = 16.9, 2.0 Hz, 1H), 5.93-5.86 (m, 1H), 3.96 (d, J = 3.0 Hz, 6H), 3.01-2.87 (m, 3H), 2.80 (s, 3H), 2.51 (t, J = 5.8 Hz, 2H), 2.28 (s, 3H), 1.06 (d, J = 6.6 Hz, 6H). |
| Z-117 | ¹HNMR (400 MHz, DMSO) δ 9.80 (s, 1H), 9.05 (d, J = 2.0 Hz, 1H), 8.97 (s, 1H), 8.92 (s, 1H), 8.47 (d, J = 5.2 Hz, 1H), 8.08 (s, 1H), 7.61 (d, J = 3.4 Hz, 1H), 7.49 (d, J = 5.3 Hz, 1H), 6.95 (s, 1H), 6.57 (d, J = 3.4 Hz, 1H), 6.54-6.46 (m, 1H), 6.31 (dd, J = 16.9, 1.9 Hz, 1H), 5.79 (dd, J = 10.1, 1.8 Hz, 1H), 4.19 (t, J = 5.6 Hz, 2H), 3.88 (d, J = 2.7 Hz, 6H), 2.58 (t, J = 5.6 Hz, 2H), 2.28 (s, 6H). |
| Z-118 | ¹HNMR (400 MHz, DMSO) δ 9.75 (s, 1H), 8.94 (s, 1H), 8.82 (s, 1H), 8.73 (s, 1H), 8.56 (d, J = 3.8 Hz, 1H), 8.26 (s, 1H), 7.63 (d, J = 3.4 Hz, 1H), 6.94 (s, 1H), 6.61 (d, J = 3.4 Hz, 1H), 6.49 (dd, J = 16.9, 10.1 Hz, 1H), 6.36-6.22 (m, 1H), 5.83-5.72 (m, 1H), 4.19 (t, J = 5.5 Hz, 2H), 3.88 (s, 3H), 3.86 (s, 3H), 2.60 (s, 2H), 2.29 (s, 6H). |
| Z-121 | ¹HNMR (400 MHz, DMSO) δ 10.00 (s, 1H), 8.84 (d, J = 1.9 Hz, 1H), 8.71 (s, 1H), 8.63 (s, 1H), 8.56 (s, 1H), 8.41 (d, J = 2.0 Hz, 1H), 8.16 (s, 0.3H), 7.86 (s, 1H), 7.01 (s, 1H), 6.41 (dd, J = 16.9, 10.2 Hz, 1H), 6.27-6.20 (m, 1H), 5.75 (d, J = 11.7 Hz, 1H), 3.87 (s, 3H), 3.83 (s, 3H), 2.92 (s, 2H), 2.70 (s, 3H), 2.43 (s, 2H), 2.28 (s, 6H). |
| Z-122 | ¹HNMR (400 MHz, DMSO) δ 9.01 (d, J = 13.8 Hz, 2H), 8.57 (d, J = 3.5 Hz, 2H), 8.51 (s, 1H), 8.43 (d, J = 1 Hz, 1H), 7.87 (s, 1H), 6.86 (s, 1H), 6.67 (dd, J = 17.0, 10.2 Hz, 1H), 6.23 (dd, J = 17.0, 1.8 Hz, 1H), 5.73 (d, J = 10.2 Hz, 1H), 3.85 (d, J = 12.6 Hz, 6H), 3.05 (d, J = 11.2 Hz, 2H), 2.67 (t, J = 10.8 Hz, 2H), 2.25 (s, 7H), 1.85 (d, J = 10.2 Hz, 2H), 1.79-1.63 (m, 2H). |
| Z-123 | ¹HNMR (400 MHz, DMSO) δ 10.07 (s, 1H), 9.04 (s, 1H), 8.83 (s, 1H), 8.63-8.56 (m, 2H), 8.43 (s, 1H), 8.26 (s, 1H), 7.86 (s, 1H), 7.02 (s, 1H), 6.44 (dd, J = 16.9, 10.1 Hz, 1H), 6.24 (dd, J = 16.9, 1.9 Hz, 1H), 5.78-5.69 (m, 1H), 3.92-3.79 (m, 6H), 2.92 (t, J = 5.6 Hz, 2H), 2.70 (s, 3H), 2.41 (t, J = 5.6 Hz, 2H), 2.27 (s, 6H). |
| Z-124 | ¹HNMR (400 MHz, DMSO) δ 10.15 (s, 1H), 9.24 (s, 1H), 9.05 (s, 1H), 8.49 (d, J = 5.2 Hz, 1H), 8.05 (s, 1H), 7.76 (d, J = 3.5 Hz, 1H), 7.52 (d, J = 5.2 Hz, 1H), 7.32 (s, 1H), 7.04 (s, 1H), 6.60 (d, J = 3.5 Hz, 1H), 6.54-6.40 (m, 1H), 6.35 (d, J = 17.1 Hz, 1H), 5.81 (d, J = 11.6 Hz, 1H), 5.19-5.09 (m, 1H), 3.89 (s, 3H), |

| Compound | $^1$HNMR |
|---|---|
| | 2.91 (s, 2H), 2.70 (s, 3H), 2.46-2.01 (m, 7H), 1.51 (d, J = 6.7 Hz, 6H). |
| Z-125 | $^1$HNMR (400 MHz, DMSO) δ 10.10 (s, 1H), 8.83 (s, 1H), 8.75-8.74 (d, J = 2.1 Hz, 1H), 8.58-8.57 (d, J = 1.9 Hz, 1H), 8.54 (s, 1H), 8.51 (s, 1H), 7.77-7.76 (d, J = 3.6 Hz, 1H), 7.00 (s, 1H), 6.59-6.58 (d, J = 3.6 Hz, 1H), 6.43-6.36 (dd, J1 = 10.2 Hz, J2 = 16.8 Hz, 1H), 6.31-6.26 (dd, J1 = 2.1 Hz, J2 = 16.8 Hz, 1H), 5.78-5.75 (dd, J1 = 2.1 Hz, J2 = 9.8 Hz, 1H), 5.15-5.09 (m, 1H), 3.82 (s, 3H), 3.30 (s, 1H), 2.86-2.83 (t, J = 5.5 Hz, 2H), 2.69 (s, 3H), 2.29-2.26 (t, J = 5.6 Hz, 2H), 2.18 (s, 6H), 1.50-1.48 (d, J = 6.8 Hz, 6H). |
| Z-126 | $^1$HNMR (400 MHz, DMSO) δ 10.11 (s, 1H), 8.83 (s, 1H), 8.78 (d, J = 2.0 Hz, 1H), 8.57 (m, 3H), 8.29 (s, 1H), 7.58 (d, J = 3.6 Hz, 1H), 7.01 (s, 1H), 6.54 (d, J = 3.6 Hz, 1H), 6.45 (dd, J = 16.4 Hz, 9.6 Hz, 1H), 6.32 (d, J = 16.8 Hz, 1H), 5.79 (d, J = 10.0 Hz, 1H), 3.83 (s, 3H), 3.68 (m, 1H), 2.88 (t, J = 5.2 Hz, 2H), 2.70 (s, 3H), 2.33 (m, 2H), 2.21 (s, 6H), 1.09 (m, 4H). |

Comparative Example

By using the corresponding boron ester and unsubstituted or 5-substituted 2,4-dichloropyrimidine as the starting materials, comparative compounds 2 and 3 were prepared with reference to Example 1.

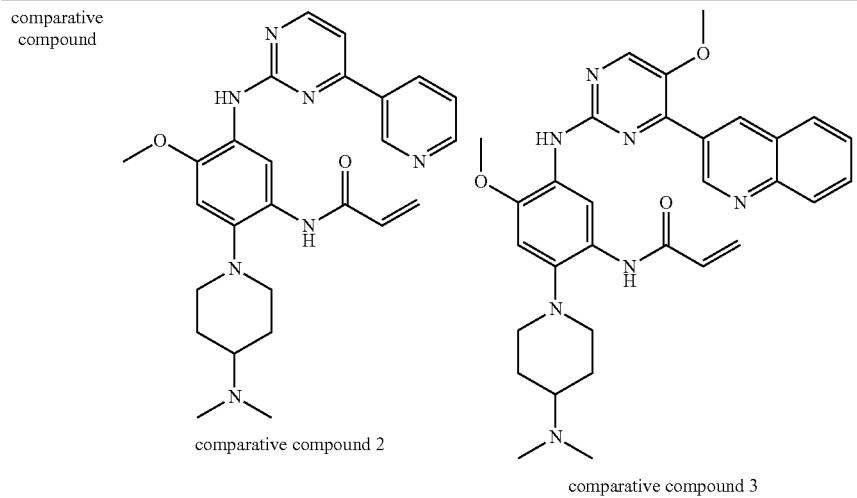

| comparative compound | comparative compound 2 | comparative compound 3 |
|---|---|---|
| MS [M + H]+ | 474 | 554 |

Assay 1: Wild Type EGFR and Mutant EGFR Kinase Inhibition Test

All the following reagents used in z-lyte test are commercially available from Invitrogen.

The inhibitory effects of compounds to be tested on double mutant EGFR kinase (EGFR T790M/L858R Kinase) (Invitrogen, PV4879) and wild-type EGFR kinase (EGFR WT) (Invitrogen, PV3872) were measured by z-lyte methods.

The working concentration of each component in 10 μl T790M/L858R kinase reaction system was: 25 μM ATP, 0.08 (or 0.1) ng/μl EGFR T790M/L858R kinase, 2 μM Tyr04 substrate (Invitrogen, PV3193, similarly hereinafter). After the compounds (i.e., test compounds) prepared by the above-mentioned examples described herein were added, the concentration of DMSO was 2%.

The working concentration of each component in 10 μl EGFR WT kinase reaction system was: 10 μM ATP, 0.8 ng/μl EGFR WT kinase, 2 μM Tyr04 substrate. After the test compounds were added, the concentration of DMSO was 2%.

Test Methods:

10 mM stock solutions of the test compounds dissolved at room temperature were gradiently diluted by 4% DMSO in water to final concentrations of 10-0.005 μM. To each well were added 2.5 μl of solution of the test compounds and 5 μl mixture of the EGFR T790M/L858R kinase (or EGFR WT kinase) and Tyr04 substrate diluted by reaction buffer, and then 2.5 μl of ATP was added to initiate the reaction. Reaction buffer instead of ATP were added to C1 wells, no drugs were added to C2 wells, and the phosphorylated substrates were added to C3 wells according to the instruction.

The reaction was performed on a shaking table at room temperature for 60 min. Afterwards, 5 μl of Development Reagent B (Invitrogen) was added, and reacted on a shaking table at room temperature for 60 min. The plates were read in a VictorX5 Microplate Reader (PerkinElmer), for measuring the absorbance at excitation wavelength of 405 nm, and emission wavelength of 450 nm and 520 nm. (For example, $C3_{520nm}$ represents the reading at 520 nm of C3 well).

Inhibition ratio was calculated as follows:

$$ER = \text{Coumarin Emission (450 nm)/Fluorescein Emission (520 nm)} \quad (1)$$

$$\text{Phosphorylation ratio} = (1-((ER \times C3_{520nm} - C3_{450nm})/((C1_{450nm} - C3_{450nm}) + ER \times (C3_{520nm} - C1_{520nm})))) \times 100\% \quad (2)$$

$$\text{Inhibition ratio } (IR) = (1 - \text{phosphorylation ratio of the test compound}/(\text{phosphorylation ratio of } C2)) \times 100\% \quad (3)$$

$IC_{50}$ was determined by fitting calculation with XLFIT 5.0 (IDBS company, UK). The results of inhibitory activity and selective inhibitory activity against enzyme were shown in Table 1 to Table 3.

TABLE 1

Inhibitory activity against enzyme

| Compound No. | T790M/L858R ($IC_{50}$/nM) | EGFR WT ($IC_{50}$/nM) |
|---|---|---|
| Z-1 | 3 | 25 |
| Z-2 | 17 | 272 |
| Z-4 | 14 | 45 |
| Z-5 | 43 | 105 |
| Z-6 | 4 | 10 |
| Z-16 | 1 | 4 |
| Z-20 | 2 | 4 |
| Z-21 | 4 | 9 |
| Z-22 | 9 | 57 |
| Z-25 | 12 | 61 |
| Z-26 | 27 | 114 |
| Z-27 | 4 | 19 |
| Z-29 | 38 | 118 |
| Z-32 | 2 | 4 |
| Z-37 | 5 | 89 |
| Z-38 | 16 | 35 |
| Z-39 | 4 | 33 |
| Z-40 | 13 | 233 |
| Z-41 | 9 | 20 |
| Z-44 | 8 | 30 |
| Z-54 | 0.5 | 2 |
| Z-87 | 3 | 8 |
| Z-88 | 3 | 11 |
| comparative compound 1 | 2 | 3 |

TABLE 2

Selective inhibitory activity against enzyme

| Compound No. | Selective inhibitory activity against enzyme [$IC_{50}$ (EGFR WT)/$IC_{50}$ (T790M/L858R)] |
|---|---|
| Z-1 | 8.33 |
| Z-2 | 16 |
| Z-3 | 7.27 |
| Z-4 | 3.2 |
| Z-5 | 2.4 |
| Z-6 | 2.5 |
| Z-16 | 4 |
| Z-20 | 2 |
| Z-21 | 2.25 |
| Z-22 | 6.3 |
| Z-25 | 5.1 |
| Z-26 | 4.2 |
| Z-27 | 4.8 |
| Z-29 | 3.1 |
| Z-32 | 2 |
| Z-37 | 17.8 |
| Z-38 | 2.2 |
| Z-39 | 8.25 |
| Z-40 | 17.9 |
| Z-41 | 2.2 |
| Z-44 | 3.8 |
| Z-54 | 4 |
| Z-87 | 2.7 |
| Z-88 | 3.7 |
| comparative compound 1 | 1.5 |

TABLE 3

Inhibitory activity and selective inhibitory activity against enzyme

| Compound | T790M/L858R ($IC_{50}$/nM) | EGFR WT ($IC_{50}$/nM) | selective inhibitory activity against enzyme [$IC_{50}$ (EGFRWT)/$IC_{50}$ (T790M/L858R)] |
|---|---|---|---|
| Z-17 | 23 | 218 | 9.5 |
| Z-18 | 16 | 197 | 12.3 |
| Z-19 | 3 | 28 | 9.3 |
| Z-89 | 4 | 228 | 57 |
| Z-55 | 2 | 21 | 10.5 |
| Z-90 | 8 | 102 | 12.75 |
| Z-91 | 25 | 195 | 7.8 |
| Z-93 | 11 | 42 | 3.8 |
| Z-94 | 2 | 20 | 10 |
| Z-95 | 16 | 328 | 20.5 |
| Z-96 | 2 | 41 | 20.5 |
| Z-97 | 14 | 341 | 24.4 |
| Z-98 | 15 | 407 | 27.1 |
| Z-99 | 4 | 38 | 9.5 |
| Z-100 | 11 | 297 | 27 |
| Z-101 | 7 | 112 | 16 |
| Z-102 | 2 | 62 | 31 |
| Z-105 | 3 | 7 | 2.3 |
| Z-106 | 2 | 4 | 2 |
| Z-107 | 4 | 16 | 4 |
| Z-109 | 6 | 28 | 4.7 |
| Z-110 | 7 | 40 | 5.7 |
| Z-112 | 7 | 22 | 3.1 |
| Z-113 | 15 | 121 | 8.1 |
| Z-114 | 14 | 116 | 8.3 |
| Z-115 | 6 | 22 | 3.7 |
| Z-116 | 6 | 37 | 6.2 |
| Z-117 | 2 | 8 | 4 |
| Z-118 | 2 | 6 | 3 |
| Z-121 | 3 | 14 | 4.7 |
| Z-122 | 5 | 25 | 5 |
| Z-123 | 1 | 3 | 3 |
| Z-124 | 4 | 13 | 3.25 |
| Z-125 | 2 | 14 | 7 |
| Z-126 | 2 | 7 | 3.5 |
| BIBW2992 | 5 | 1 | 0.2 |
| comparative compound 1 | 2 | 3 | 1.5 |

It can be seen from Table 1, Table 2 and Table 3 that the exemplary compounds of the invention showed strong inhibitory activities against EGFR mutant enzyme (T790M/L858R and L858R) but weak inhibitory activities against EGFR wild-type enzyme (T790M WT), the compounds of the present invention had significant selective inhibitory activities against EGFR mutant enzyme compared with the positive control BIBW2992 (afatinib), and selective inhibitory activities of the exemplary compounds of the invention against EGFR mutant enzyme were greater than that of the comparative compound 1 (specific structure was shown below, and can be found in WO2013014448A1). The highest selectivity was 18 times higher than that of the comparative compound 1.

comparative compound 1

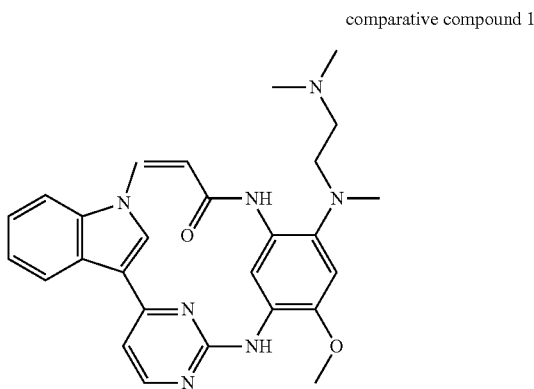 [SMILES: C=CC(=O)Nc1cc(Nc2nccc(-c3cn(C)c4ccccc34)n2)c(OC)cc1N(C)CCN(C)C]

Assay 2: Test of Cytostatic Activity by MTT (3-(4,5-dimethyl-thiazol-2)-2,5-diphenyl tetrazolium bromide) Method MTT assay used the method well known to those skilled in the art, and the reagents used in the method can be commercially obtained.

2.1 Test Method:

Firstly, the medium was removed and 0.25% trypsin/EDTA (Gibco, 25200-056) was added. After rinsed for one time, 1.5 ml trypsin/EDTA was added to digest the adherent cells until the cells detached, and then 3.5 ml of medium was added to terminate the trypsinization. The digested cell suspension was transferred to a 15 ml falcon tube, and spun at 1300 rpm for 3 min, the supernatant was discarded, and cells were suspended in fresh medium. The cells were then counted, and diluted to the following concentrations: $2.78 \times 10^4$ cells/ml (A431 and H1975), $3.33 \times 10^4$ cells/ml (NIH3T3). The cells were seeded in 96-well plates (BD 3072), 90 μl/well, and incubated overnight.

A431 cell culture medium: 10% FBS (Gibco, 10099-141) DMEM (Hyclone SH30243.01B);

NIH3T3 cell culture medium: 10% FBS (Gibco, 10099-141) DMEM (Hyclone SH30243.01B);

H1975 cell culture medium: 10% FBS (Gibco, 10099-141) RPMI-1640 (Hyclone SH30809.01B);

20 μl of 10 mM test compound was taken, and the test compound was diluted according to the following concentration gradient (2000, 666.67, 222.22, 74.07, 24.69, 8.23, 2.74, 0.91 μM), serum-free medium was then added (the final concentration: 10, 3.333, 1.111, 0.370, 0.123, 0.041, 0.014, 0.005 μM), and 10 μl of the test compound in each well was added into the cell culture plates, and the final concentration of DMSO was 0.5%.

The cells were added into the incubator after addition of the test compound, and incubated for 72 h, 10 μl of 5 mg/ml MTT (Sigma, M5655) solution was added to each well of the plate, and incubated the 96-well plates at 37° C. 5% $CO_2$ for 4 h in a incubator.

The plates were spun at 2000 rpm for 5 min. After the supernatant was removed, 150 μl DMSO was added to each well, and the plates was shaken on a shaker until the purple crystal completely dissolved (about 10-20 min). Finally, the absorbance at 492 nm was measured by using a microplate reader, and $IC_{50}$ was calculated with XLFIT 5.0 software (UK IDBS company). The inhibitory activity and selective inhibitory activity of the exemplary compounds against the cells were shown in Table 4 to Table 7.

TABLE 4

Inhibitory activity and selectivity of the compounds against the cell growth

| Compound | H1975 cells ($IC_{50}$/nM) | A431 cells ($IC_{50}$/nM) | selective inhibitory activity against the cell growth [$IC_{50}$ (A431 cells)/$IC_{50}$ (H1975 cells)] |
|---|---|---|---|
| Z-6 | 17 | 773 | 45.5 |
| Z-16 | 9 | 871 | 97 |
| Z-22 | 29 | 1899 | 65.5 |
| Z-27 | 49 | 2479 | 50.1 |
| Z-30 | 25 | 1111 | 44.4 |
| Z-39 | 16 | 918 | 57.4 |
| Z-44 | 32 | 1814 | 56.7 |
| Z-54 | 3 | 327 | 109 |
| comparative compound 1 | 13 | 478 | 36.77 |

TABLE 5

Results of cytotoxicity of the compounds against NIH3T3 cells

| Compound | $IC_{50}$/nM |
|---|---|
| Z-1 | 6587 |
| Z-3 | 8158 |
| Z-16 | >10000 |
| Z-25 | 6906 |
| Z-26 | >10000 |
| Z-27 | 7964 |
| Z-30 | 5793 |
| Z-32 | >10000 |
| Z-33 | >10000 |
| Z-38 | >10000 |
| Z-39 | 8887 |
| Z-41 | >10000 |
| Z-44 | 8877 |
| comparative compound 1 | 3552 |

TABLE 6

Inhibitory activity and selectivity of the compounds against the cell growth

| Compound No. | H1975 cells ($IC_{50}$/nM) | A431 cells ($IC_{50}$/nM) | selective inhibitory activity against the cell growth [$IC_{50}$ (A431 cells)/$IC_{50}$ (H1975 cells)] |
|---|---|---|---|
| Z-19 | 22 | 757 | 34.4 |
| Z-89 | 19 | 1730 | 91 |
| Z-55 | 7 | 660 | 94.3 |
| Z-90 | 17 | 2391 | 140.6 |
| Z-91 | 36 | 3609 | 100.3 |
| Z-94 | 8 | 645 | 80.6 |
| Z-95 | 45 | 5450 | 121.1 |
| Z-98 | 108 | 1641 | 15.2 |
| Z-99 | 40 | 1038 | 26 |
| Z-100 | 24 | 1226 | 51.1 |
| Z-101 | 43 | 2244 | 52.2 |
| Z-102 | 15 | 597 | 39.8 |
| Z-106 | 13 | 685 | 52.7 |
| Z-107 | 37 | 1412 | 38.2 |
| Z-108 | 77 | 2904 | 37.7 |
| Z-115 | 38 | 2495 | 66 |
| Z-117 | 19 | 1302 | 68.5 |
| Z-123 | 26 | 1044 | 40.2 |
| Z-124 | 38 | 1780 | 46.8 |
| Z-125 | 13 | 1316 | 101.2 |
| Z-126 | 10 | 495 | 49.5 |
| BIBW2992 | 88 | 29 | 0.33 |
| comparative compound 1 | 13 | 478 | 36.77 |

TABLE 6-continued

Inhibitory activity and selectivity of the compounds against the cell growth

| Compound No. | H1975 cells (IC$_{50}$/nM) | A431 cells (IC$_{50}$/nM) | selective inhibitory activity against the cell growth [IC$_{50}$ (A431 cells)/IC$_{50}$ (H1975 cells)] |
|---|---|---|---|
| comparative compound 2 | 277 | 6659 | 24 |
| comparative compound 3 | 437 | 2967 | 6.8 |

TABLE 7

Results of cytotoxicity of the compounds against NIH3T3 cells

| Compound No. | NIH3T3 cells MTT assay (IC$_{50}$/nM) | Compound No. | NIH3T3 cells MTT assay (IC$_{50}$/nM) |
|---|---|---|---|
| Z-19 | 4514 | Z-110 | 6835 |
| Z-89 | 4038 | Z-111 | 4012 |
| Z-55 | 5424 | Z-112 | >10000 |
| Z-90 | >10000 | Z-113 | 5321 |
| Z-91 | >10000 | Z-114 | 8282 |
| Z-93 | >10000 | Z-115 | >10000 |
| Z-94 | >10000 | Z-116 | >10000 |
| Z-95 | >10000 | Z-117 | >10000 |
| Z-98 | 4356 | Z-118 | 3325 |
| Z-99 | 5989 | Z-121 | 8531 |
| Z-100 | 3876 | Z-123 | 4737 |
| Z-101 | 3426 | Z-124 | 3244 |
| Z-105 | 9356 | Z-125 | 4656 |
| Z-108 | 3616 | Z-126 | 4907 |
| Z-109 | 6005 | BIBW2992 | 2750 |
| comparative compound 1 | 3552 | | |

It can be seen from Table 4 and Table 6 that the exemplary compounds of the invention showed strong inhibitory activities against EGFR mutant cells (H1975 cells) but weak inhibitory activities against EGFR wild-type cells (A431 cells), and the compounds of the present invention had significant selective inhibitory activities against EGFR mutant cell growth compared with the positive control BIBW2992 (afatinib). Selective inhibitory activities of most exemplary compounds against the EGFR mutant cell growth were greater than those of comparative compound 1, 2 and 3. The highest selectivity was nearly four times higher than that of the comparative compound 1. The study found that the activities against H1975 cell and selective inhibitory activities against cell growth significantly reduced after the ring A of the compound was changed to pyridine or quinoline.

It can be seen from Table 5 and Table 7 that the exemplary compounds of the invention possessed higher IC$_{50}$ values against NIH3T3 cells, and showed less toxicity.

Assay 3: ELISA Screening EGFR T790M Inhibitor for Cell Activity

The reagents, preparation methods of the solution, as well as the procedures of cell treatments and preparation of lysate, and the test steps of ELISA in the following method were conducted according to the instructions of R&D DYC3570, R&D DYC1095E and R&D DYC1095BE.

1, reagents and solutions
Cell lysis buffer: 1% NP-40, 20 mM Tris (pH 8.0), 137 mM NaCl, 10% glycerol, 1 mM NaVO$_3$, 2 mM EDTA.

Cell lysates: cell lysis buffer+10 μg/ml Aprotinin (Sigma), 10 μg/ml Leupeptin (Sigma). All reagents were prepared when using.

1×PBS buffer: NaCl: 0.137 M, KCl: 0.0027 M, Na$_2$PO$_4$-12H$_2$O: 0.01M, KH$_2$PO$_4$: 0.0015M, pH7.4.
Wash buffer: 0.05% Tween-20 in PBS.
IC Diluent: 20 mM Tris, 137 mM NaCl, 0.05% Tween-20, 0.1% BSA, pH 7.2-7.4.
Block Buffer: 1% BSA in PBS.
ELISA kits: R&D DYC3570, R&D DYC1095E and R&D DYC1095BE.

2, H1975 Cells
2.1 Treatment of H1975 Cells and Preparation of Lysates
(1) H1975 cells were innoculated into 96-well plate at 1×10$^4$ cells/well with 90 ul of 10% FBS, 1640 medium each well, and incubated at 37° C. with 5% CO$_2$ overnight.
(2) The test compounds were diluted according to the method in MTT assay, and 10 μl of diluted compound or DMSO was added to the corresponding plate well, and incubated at 37° C. with 5% CO$_2$ for 1 h. The final concentration of DMSO was 0.5%. Cell culture system merely treated with DMSO was used as cell control.
(3) 100 μl cell lysate was added after aspirating the medium, sealed and placed in a refrigerator at −80° C. overnight. Cell lysis buffer used as blank control.
2.2 ELISA Assay Procedure
The assay was operated according to the instructions of R&D DYC1095E or R&D DYC1095BE.
(1) R&D capture antibody ((DYC1095BE or DYC1095E)) was diluted with PBS by 1:180, and ELISA plate (Corning costar 42592) was coated with 100 μl/well of the diluted antibody, and incubated at 25° C. overnight under shaking;
(2) 360 μl of wash buffer was used for washing for three times;
(3) 300 μl of block buffer was added, incubated at 25° C. for 2 hours under shaking;
(4) 360 μl of wash buffer was used for washing for three times;
(5) 40 μl of cell lysis buffer and 60 μl of cell lysates were added, and incubated at 25° C. for 2 h under shaking;
(6) 360 μl of wash buffer was used for washing for three times;
(7) Detection antibody was diluted according to a predetermined ratio as stipulated in kit instructions by using IC diluent, and 100 μl of the diluted Detection Antibody was added to each well, and incubated at 25° C. for 1 h under shaking in darkness;
(8) 360 μl of wash buffer was used for washing for three times;
(9) reagent A and reagent B of TMB substrate (R & D DY999) were mixed with 1:1, and 100 μl of substrate was added to each well, and incubated at 25° C. for 20 minutes under shaking in darkness;
(10) 50 μl of 2N H$_2$SO$_4$ was added to each well;
(11) The OD450 values and OD570 values of the cell control, blank control and compound treatment were measured respectively by using microplate reader (Thermo Multiskan K3), and the corresponding OD570 values were subtracted from OD450 values of the same wells to get the OD$_{cell}$, OD$_{blank}$ and OD$_{compound\ treatment}$ respectively.
2.3 Data Analysis Inhibition ratio (%)=100%×(OD$_{cell}$−OD$_{compound\ treatment}$)(OD$_{cell}$−OD$_{blank}$)

2.4 IC$_{50}$ values were calculated with XLFIT 5.0 software from the calculated inhibition ratio and shown in Table 8.

3, A431 Cells 3.1 Treatment of A431 Cells and Assay Procedure (1) The A431 cells were innoculated into 96-well plate at $1\times10^4$ cells/well with 90 ul of 10% FBS, 1640 medium each well, and incubated at 37° C. with 5% $CO_2$ overnight.

(2) The medium of A431 cells was changed to 90 ul of DMEM FBS free medium, and incubated overnight.

(3) The test compounds were diluted according to the method in MTT assay, 10 μl of diluted compound or DMSO was added to the corresponding plate well, and incubated at 37° C. with 5% $CO_2$ for 1 h. The final concentration of DMSO was 0.5%. 10 μl of 2 μg/L EGF was then added to each well except the cell control well, 10 μl of FBS free DMEM was added to the well, and incubated for 45 minutes; the EGF-free and compound treatment-free cells were used as cell control, and the compound treatment-free but only EGF-treated cells were used as EGF control.

(4) 100 μl cell lysate was added after aspirating the medium, sealed and placed in refrigerator at −80° C. overnight.

3.2 ELISA Assay Procedure

The assay was operated according to the instructions of R&D DYC3570E.

(1) R&D capture antibody (DYC3570E) was diluted with PBS by 1:180, and the diluted antibody was added into ELISA plate (Corning costar 42592) at 100 μl/well, and incubated at 25° C. overnight under shaking;

(2) 360 μl of wash buffer was used for washing for three times;

(3) 200 μl of block buffer was added, and incubated at 25° C. for 2 hours under shaking;

(4) 360 μl of wash buffer was used for washing for three times;

(5) 40 μl of cell lysis buffer and 60 μl of cell lysates were added, and incubated at 25° C. for 2 h under shaking;

(6) 360 μl of wash buffer was used for washing for three times;

(7) Detection antibody was diluted according to a predetermined ratio of kit instruction by using IC dilution, and 100 μl of the diluted Detection Antibody was added to each well, and incubated at 25° C. for 1 h under shaking in darkness;

(8) 360 μl of wash buffer was used for washing for three times;

(9) reagent A and reagent B of TMB substrate (R & D DY999) were mixed at 1:1, 100 μl of substrate was added to each well, and incubated at 25° C. for 20 minutes under shaking in darkness;

(10) 50 μl of 2N $H_2SO_4$ was added to each well;

(11) The OD450 values and OD570 values of the cell control, blank control and compound treatment were measured respectively by using microplate reader (Thermo Multiskan K3), and the corresponding OD570 values were subtracted from OD450 values of the same wells to get the $OD_{EGF}$, $OD_{compound}$ and $OD_{cell}$ respectively.

3.3 Data Analysis

Inhibition ratio (%)=100%×($OD_{EGF}$−$OD_{compound}$)/($OD_{EGF}$−$OD_{cell}$)

3.4 $IC_{50}$ values were calculated with XLFIT 5.0 software from the calculated inhibition ratio and shown in Table 8.

TABLE 8

Results of cell activities measured by ELISA Assay

| Compound No. | H1975 cells ($IC_{50}$/nM) | A431 cells ($IC_{50}$/nM) | Selective inhibitory activities of target on cellular level [$IC_{50}$ (A431 cells)/$IC_{50}$ (H1975 cells)] |
|---|---|---|---|
| Z-1 | 30 | 471 | 15.7 |
| Z-6 | 34 | 194 | 5.7 |
| Z-16 | 10 | 153 | 15.3 |
| Z-20 | 22 | 167 | 7.6 |
| Z-21 | 11 | 113 | 10.3 |
| Z-22 | 23 | 1233 | 53.6 |
| Z-27 | 44 | 955 | 21.7 |
| Z-37 | 57 | 481 | 8.4 |
| Z-39 | 41 | 660 | 16.1 |
| Z-40 | 70 | 2138 | 30.5 |
| Z-41 | 31 | 954 | 30.8 |
| Z-54 | 4 | 18 | 4.5 |
| Z-87 | 31 | 210 | 6.8 |
| Z-88 | 18 | 449 | 24.9 |
| Z-17 | 77 | 3079 | 40 |
| Z-19 | 21 | 675 | 32.1 |
| Z-89 | 15 | 4790 | 319.3 |
| Z-55 | 15 | 200 | 13.3 |
| Z-90 | 34 | 1693 | 50 |
| Z-91 | 90 | 3277 | 36.4 |
| Z-93 | 77 | 821 | 10.7 |
| Z-94 | 16 | 372 | 23.3 |
| Z-95 | 41 | 4961 | 121 |
| Z-96 | 94 | 969 | 10.3 |
| Z-97 | 104 | 7503 | 72.1 |
| Z-99 | 57 | 663 | 11.6 |
| Z-100 | 24 | 8430 | 351.2 |
| Z-101 | 111 | 3619 | 32.6 |
| Z-102 | 11 | 1024 | 93.1 |
| Z-105 | 28 | 181 | 6.5 |
| Z-106 | 12 | 193 | 16.1 |
| Z-107 | 55 | 855 | 15.5 |
| Z-109 | 85 | 434 | 5.1 |
| Z-112 | 77 | 486 | 6.3 |
| Z-113 | 99 | 2254 | 22.8 |
| Z-115 | 90 | 469 | 5.2 |
| Z-117 | 18 | 164 | 9.1 |
| Z-125 | 47 | 291 | 6.2 |
| Z-126 | 20 | 229 | 11.5 |
| BIBW2992 | 21 | 5 | 0.24 |
| comparative compound 1 | 29 | 114 | 3.9 |
| comparative compound 2 | 241 | 199 | 0.83 |
| comparative compound 3 | 1139 | 3113 | 2.7 |

It can be seen from Table 8 that the exemplary compounds of the invention exhibit obvious selective inhibitory activities against target on cellular level compared with the positive control BIBW2992. The highest selective inhibitory activity against target on cellular level increased to 90 times compared with those of the comparative compounds 1, 2 and 3. The study found that the activities against H1975 cell and selective inhibitory activities against target on cellular level significantly reduced or even disappeared after the ring A of the compound was changed to pyridine or quinoline.

The enzyme and cell growth inhibition tests in vitro showed that the compounds of the invention exhibited strong inhibitory activities against EGFR mutant enzyme and cells but showed weak inhibitory activities against EGFR wild-type enzyme and cells, and thus possessed a better selectivity; in addition, the compounds showed very weak inhibitory effect on NIH-3T3 cells in cytotoxicity test, and thus exhibited lower toxicity. Therefore such compounds had better selective inhibitory activities against T790M mutations and lower cytotoxicity.

Assay 4: In Vivo Test of Rats or Mice

LC/MS/MS method was applied for the determination of the drug concentration in plasma at different times after the example compounds were orally and intravenously administered to rats or mice in order to study the pharmacokinetic behavior of the compounds of the invention in vivo in rats or mice and evaluate their pharmacokinetic characteristics.

Protocol:

Test Animals: healthy Adult male SD rats (weight 200-300 g, 6, fasted) or male CD1 mice (weight 20-30 g, 18, free access to water and food), provided by SLAC company;

Administration and Dosage: (1 mg/kg, 5 ml/kg, 5% DMAC (dimethylacetamide), 5% Solutol HS 15 (polyethylene glycol-15 hydroxystearate) and 90% saline was intravenously administered via foot dorsal vein and (20 mg/kg, 10 ml/kg, 0.5% CMC-Na solution) was administered via oral gavage to SD rats; (1 mg/kg, 5 ml/kg, 5% DMAC, 5% Solutol HS 15 and 90% Saline) was administered intravenously via tail vein and (5 mg/kg, 10 mL/kg, 0.5% CMC-Na aqueous solution) was administered via oral gavage to CD1 mice.

Blood collection: firstly, the animals which were selected to meet the test requirements prior to administration were weighed. The rats or mice were bound before the blood collection, blood from each administered rat was taken at predetermined time points (intravenous administration: blood was collected at 0.083, 0.25, 0.5, 1, 2, 4, 8, 24 h before and after administration respectively, 9 time points in total; gavage: blood was collected at 0.083, 0.25, 0.5, 1, 2, 4, 8, 24 h before and after administration respectively, 9 time points in total), about 150 µl of blood was collected via tail vein or heart (blood terminal). Blood from each administered mouse was taken blood at predetermined time points (tail vein: blood was collected at 0.083, 0.25, 0.5, 1, 2, 4, 8, 24 h, 8 time points in total; gavage: blood was collected at 0.25, 0.5, 1, 2, 4, 8, 24 h, 7 time points in total), about 150 µl of blood was collected via orbital or heart (blood terminal). Blood was transferred to a 1.5 ml tube to which $K_2EDTA$ was added previously. The collected blood sample was put on ice, and centrifuged to obtain plasma sample (2000 g, 5 min under 4° C.) within 15 minutes. All the plasma samples were stored at approximately −70° C. until analysis.

LC/MS/MS method was applied to determine the concentrations of the drug. At the same dose and administration, pharmacokinetic parameters of some example compounds of the invention in rats and mice were shown in Table 9:

It can be seen from Table 9 that the exemplary compounds of the present invention were well absorbed, and has obvious absorption effect while exhibiting excellent bioavailability.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

What we claim:

1. A compound of formula (I), or a pharmaceutically acceptable salt, stereoisomer, or a solvate thereof:

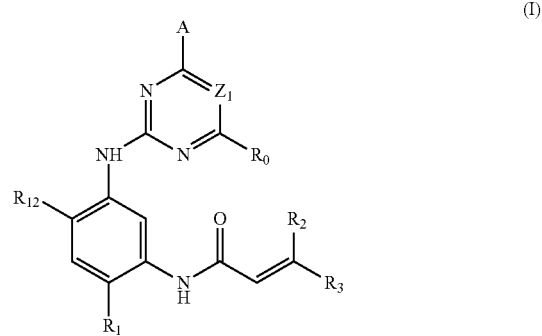

wherein,
A is

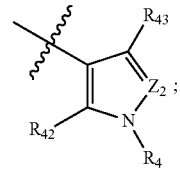

wherein $Z_2$ is $CR_5$ or N; $R_5$ is a hydrogen, halogen, trifluoromethyl or $C_{1-10}$ alkoxy;

each of $R_4$, $R_{42}$, $R_{43}$ is independently a hydrogen or $C_{1-10}$ alkyl, $C_{3-10}$ cycloalkyl, $C_{3-10}$ heterocycloalkyl, or $C_{1-10}$ haloalkyl;

TABLE 9

Pharmacokinetic parameters of compounds in rats and mice in vivo

| | Rats | | | Mice | | |
|---|---|---|---|---|---|---|
| | Z-89 | Z-90 | comparative compound 1 | Z-89 | Z-90 | comparative compound 1 |
| Clearance CL (ml/min/kg) | 43.5 | 43.9 | 54.3 | 47.7 | 65.5 | 89.0 |
| Half-life T½ (hr) | 7.05 (IV) | 7.02 (IV) | 8.28 (IV) | 4.43 (IV) | 4.65 (IV) | 1.99 (IV) |
| Oral relative bioavailability F | 102% | 92.6% | 18.5% | 59.7% | 66.4% | 30.2% |
| Maximum plasma concentration Cmax (ng/ml) | 437 | 408 | 118 | 85.3 | 90.6 | 67.9 |
| Area under the curve AUC (Hr * ng/ml) | 7190 | 6478 | 1119 | 1037 | 657 | 272 |

$R_0$ is a hydrogen, halogen, $C_{1-10}$ alkyl, —$NR_aR_b$ or —CO—$NR_aR_b$, wherein each of $R_a$, $R_b$ is independently $C_{1-10}$ alkyl;

$Z_1$ is $CR_6$; wherein $R_6$ is a hydrogen, halogen, trifluoromethyl, methoxy or —$CO_2C_{1-10}$ alkyl;

$R_1$ is a hydrogen, or any one selected from the group consisting of:

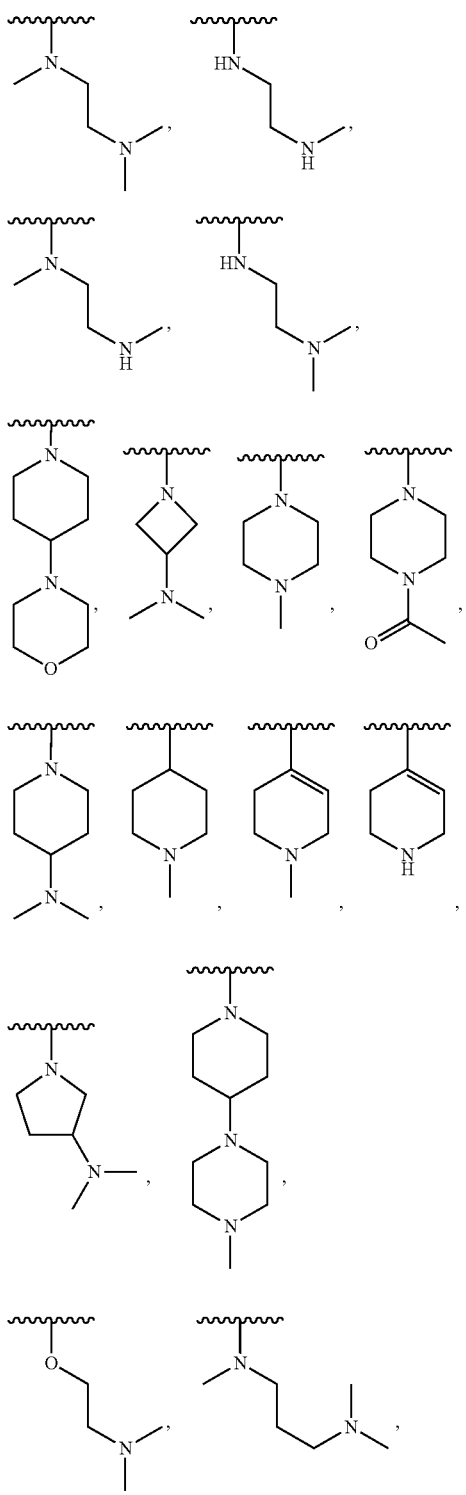

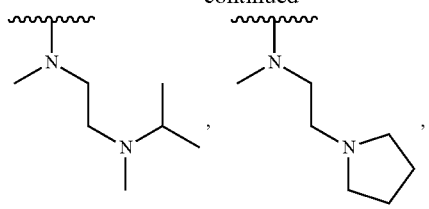

-continued

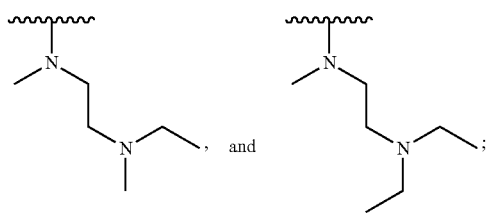

, and

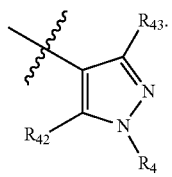

;

each of $R_2$ and $R_3$ is independently a hydrogen or —$CH_2NR_7R_8$; wherein (1) each of $R_7$, $R_8$ is independently a hydrogen or methyl; or (2) $R_7$ and $R_8$, together with the nitrogen atom to which they are attached, form a 5-6 membered nitrogen-containing saturated heterocyclic ring;

$R_{12}$ is a hydrogen, halogen, $C_{1-10}$ alkyl or $C_{1-10}$ alkoxy.

2. The compound of claim 1, or a pharmaceutically acceptable salt, stereoisomer, or a solvate thereof, wherein A is

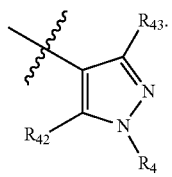

3. The compound of claim 1, or a pharmaceutically acceptable salt, stereoisomer, or a solvate thereof, wherein the compound of formula (I) is a compound represented by formula (IV-1):

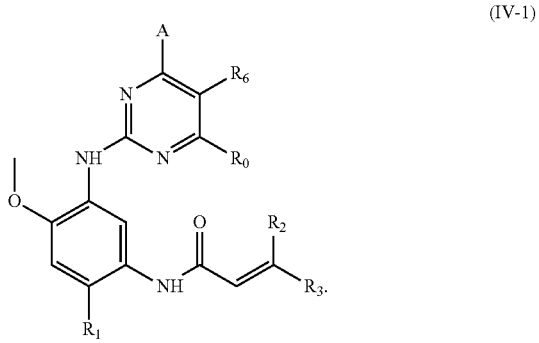

(IV-1)

4. The compound of claim 1 or a pharmaceutically acceptable salt, stereoisomer, or a solvate thereof, wherein the compound of formula (I) is a compound represented by formula (XI-1):

(XI-1)
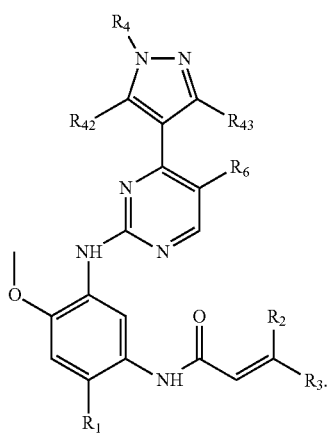
5. The compound of claim 1 or a pharmaceutically acceptable salt, stereoisomer, or a solvate thereof, wherein the compound of formula (I) is selected from the group consisting of:
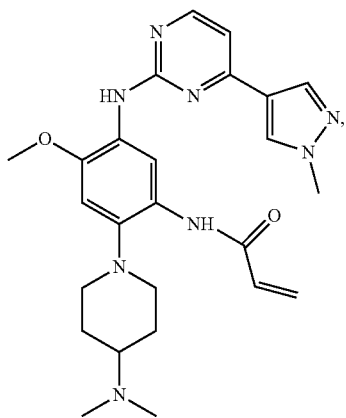
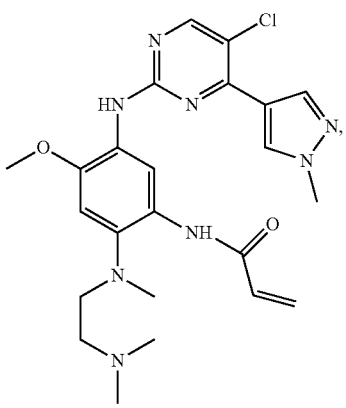
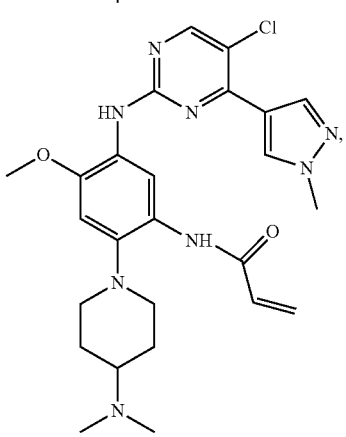
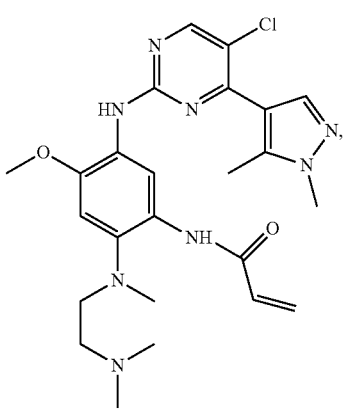
-continued
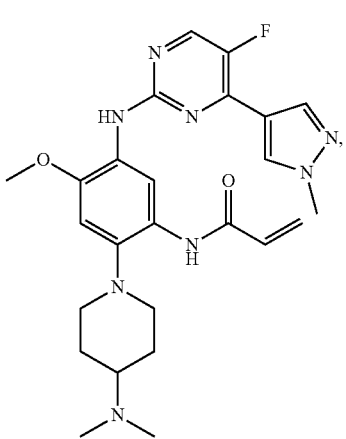

165
-continued
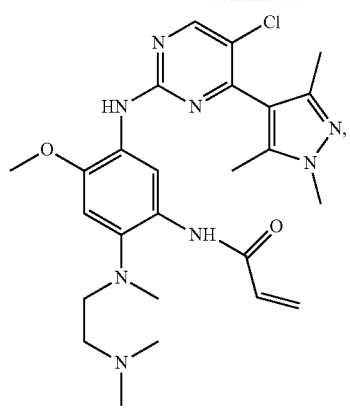
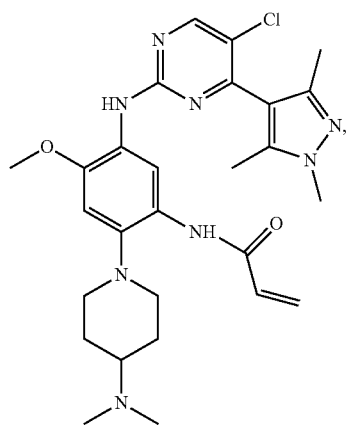
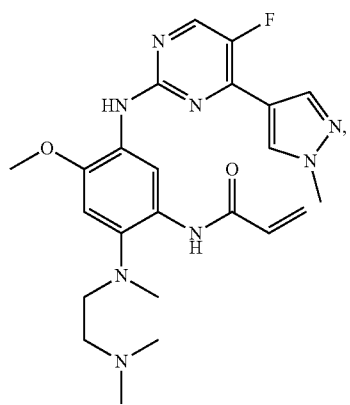
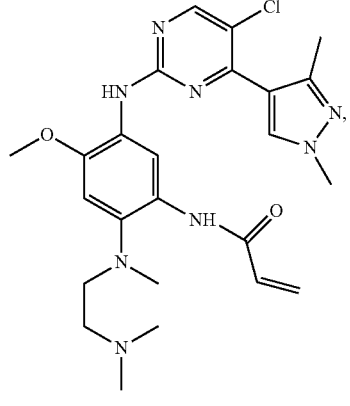
166
-continued
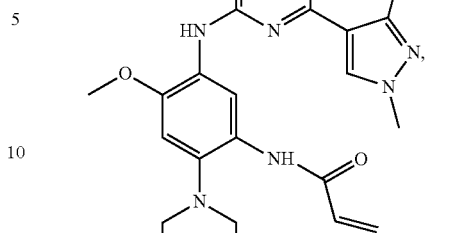
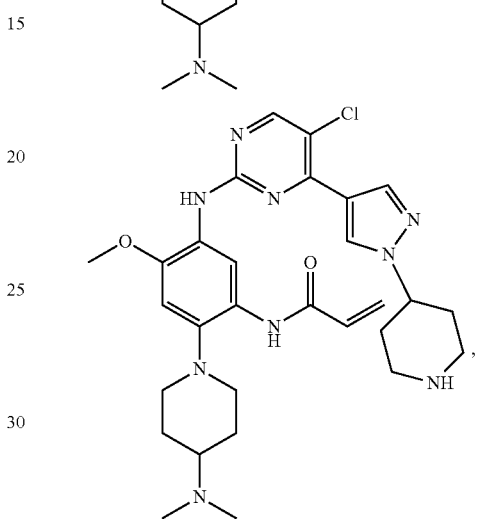
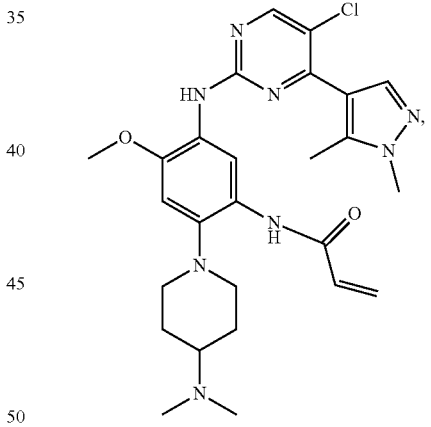
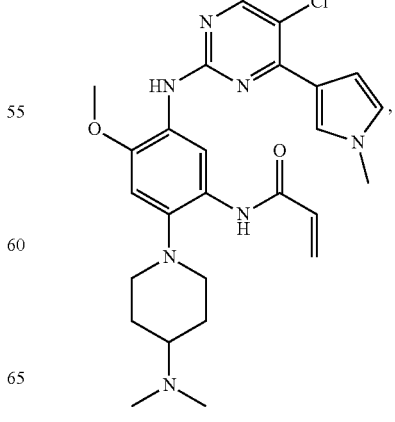

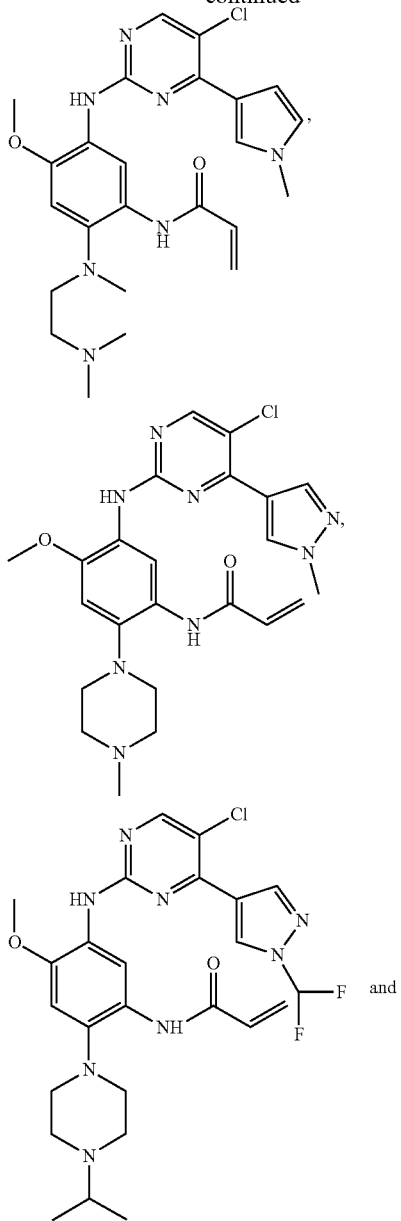

6. A pharmaceutical composition comprising a compound of claim 1, or a pharmaceutically acceptable salt, stereoisomer, or a solvate thereof, and a pharmaceutically acceptable carrier.

7. A method for adjusting EGFR tyrosine kinase activity or treating EGFR-related diseases by administering an effective amount of the compound of claim 1 or a pharmaceutically acceptable salt, stereoisomer, or a solvate thereof to a subject in need, wherein the EGFR-related disease is cancer, diabetes, immune system diseases, neurodegenerative diseases, cardiovascular diseases, or a disease that has acquired resistance during the treatment using EGFR modulators.

8. The method of claim 7, wherein the disease that has acquired resistance is caused by the T790 mutations encoded by EGFR exon 20.

9. A pharmaceutical composition comprising the compound of claim 1 or a pharmaceutically acceptable salt, stereoisomer, or a solvate thereof, and gefitinib.

* * * * *